US006531583B1

(12) United States Patent
Cassell et al.

(10) Patent No.: US 6,531,583 B1
(45) Date of Patent: Mar. 11, 2003

(54) **NUCLEIC ACID PROBES AND METHOD FOR DETECTING *UREAPLASMA UREALYTICUM***

(75) Inventors: Gail H. Cassell, Carmel, IN (US); Ellson Y. Chen, Burlingame, CA (US); Jennifer S. Glass, Indianapolis, IN (US); John I. Glass, Indianapolis, IN (US); Cheryl R. Heiner, La Honda, CA (US); Elliot Lefkowitz, Birmingham, AL (US)

(73) Assignee: UAB Research Foundation, The, Birmingham, AL (US)

( * ) Notice: Subject to any disclaimer, the term of this patent is extended or adjusted under 35 U.S.C. 154(b) by 0 days.

(21) Appl. No.: 09/601,198

(22) PCT Filed: Jan. 29, 1999

(86) PCT No.: PCT/US99/01972

§ 371 (c)(1),
(2), (4) Date: Dec. 8, 2000

(87) PCT Pub. No.: WO99/39007

PCT Pub. Date: Aug. 5, 1999

Related U.S. Application Data

(60) Provisional application No. 60/073,189, filed on Jan. 30, 1998.

(51) Int. Cl.[7] ................................................ C07H 19/00

(52) U.S. Cl. ........................... 536/22.1; 435/6; 435/7.1; 435/91.1; 435/91.2; 435/320.1; 536/23.1; 536/24.3; 536/24.31; 536/24.32; 536/24.33

(58) Field of Search ........................... 435/6, 7.1, 91.1, 435/91.2; 536/22.1, 23.1, 24.3, 24.31, 24.32, 24.33

(56) References Cited

U.S. PATENT DOCUMENTS 5,728,522 A * 3/1998 Del Vecchio et al. ........... 435/6
5,945,283 A * 8/1999 Kwok et al. .................. 435/6
6,093,538 A * 7/2000 Hogan et al. .................. 435/6
6,262,252 B1 * 7/2001 Wolff et al. .............. 536/25.32
6,265,158 B1 * 7/2001 Shiloh ........................... 435/6

OTHER PUBLICATIONS

Watson et al Recombinant DNA 2nd edition pp. 454–455 1992.*

* cited by examiner

*Primary Examiner*—Jeffery Siew

(57) ABSTRACT

A method of detecting a nucleic acid sequence in *Ureaplasma urealyticum* serovar 3 includes the steps of isolating a specimen containing nucleic acid; and analyzing the specimen with an assay such as in situ hybridization, Southern blotting, single strand conformational polymorphism, restriction endonuclease fingerprinting (REF), PCR amplification, 5' nuclease assay (TaqMan PCR), and DNA-chip analysis using the nucleic acid sequences SEQ ID Nos:1–181.

2 Claims, No Drawings

SEQUENCE LISTING

```
<160> NUMBER OF SEQ ID NOS: 181

<210> SEQ ID NO 1
<211> LENGTH: 561
<212> TYPE: DNA
<213> ORGANISM: Ureaplasma urealyticum

<400> SEQUENCE: 1

atgttaaata ttttaaataa tgtatctaat tcttcactat attcagccgc ttcaaatgct     60

actgcgcaaa ctggttcaaa tttgatcaat gatctagttc cagaaacatt aaccgcttca    120

ggaattagta tcgctatttc tgtttttagt gttataggta cgatcgttat tgctttgagt    180

gtattgccac aaacaattaa aactttacgt gaaaaagata cagcttcatt aagtttatta    240

ctattcttgc ttaatggtat tgctacagcc tttttaactc tatacggtat tggacttgtt    300

acagttcatc caaattcatt ttcattctta gtggatatta aaaacggaat gttcatttat    360

aatagagaag agtgagttgc tggatactta atctgcggta tcttcttaat tatgggtgaa    420

gcattatgtt cagtaacttc atttattgtt ctattctgca aagttaataa catgattaaa    480

gctaaaaaaa tgggaatgag cgaagaagaa tattatgaaa aacaaattaa accattccta    540

aaagtgaaag gagctaacta a                                              561


<210> SEQ ID NO 2
<211> LENGTH: 1068
```

-continued

<212> TYPE: DNA
<213> ORGANISM: Ureaplasma urealyticum

<400> SEQUENCE: 2

```
ttactttttt ctattattaa attttgatat tatattgttt agttcatttt tattttcatc     60
taattcgatt attttttctt ttaaaaataa aagtgcaaac ttggaaaact tatgtgtttt    120
attggttttt gatgttgtaa tttctaaatg atattttttc gattccttca ttttaaaata    180
tcaaataagt gcatataatt tttgaggtgt tatattaagt ttttcggcta attgtttttg    240
aatataggga taagtttcat ctaaattttc taatggaact ggaacttctt ctgccaaatt    300
tatatttcca gtaactttga ttactggtat tccttcattt tcactaaaac taccttcttt    360
tataaatttt gcttttttta gtaattttgc tataagattt ttttctaaaa caacatcaac    420
tccataagga gtggacaatt ttccgttatt ataatcaact attcctaaat tagtagcacc    480
attatttcta ataaattcaa aaaccttaaa taagctatct cgttcttgct tcattctaca    540
attaataatt tgttccattt ctgcatattt tattttttca gttctcgctc tataacgata    600
aaatatatca ccattaacaa ttttttctga actattattc ttttgtgcta tcactggttt    660
tatatttgat tcttcggtat aaattcaccc aataattttt tgaacaatga taacatcccc    720
attagaatta atttcttttt cttttaaaat aaatgagcct aattctcaat ttatagaagg    780
ggaaaataga ttattaatag aatctgtcaa atcttcttgt tgaatatttt caaaattact    840
attttgtaac ccaattatgg aacgaggtga atctttaata ccaaaaaataa tatatccacc    900
actgttatta gaaaatgctg ccatagtttt agcatatatt gcaatgttgc ctttattaaa    960
tgattgttta aattcaactt gagtattttc cctactacgc aaatttccat tttccatacg   1020
agcagataat atactcttta ctctttcttc atgttttgat ataagcat                1068
```

<210> SEQ ID NO 3
<211> LENGTH: 1308
<212> TYPE: DNA
<213> ORGANISM: Ureaplasma urealyticum

<400> SEQUENCE: 3

```
atgaataaaa ctaatcaaat tgtggattta ttaaccaata aacaaaataa ttcaattcaa     60
agacgcgata atctagtttt tgttaaaaat gaacaagaat tcaaagatat tttagattct    120
actattagct taagtaatgt ttatgatcct ttgttaggta atggttgtga acaagaaaaa    180
ataaaagaat taactatttt aaataatagt gttgatatta gcaaaattga agagtatact    240
aaaacattag aaagtaaagt agatgattta tacaataatg tttctaacca actaattcaa    300
gattatcaaa aaaatgagaa tacaagtgcg aataaatataa ttatgaaaaa tgaagaatta    360
ttaaattctc atttaaaaga agtcgaaaaa atttgtgaac agctaattga tgaatgaaaa    420
attgaaattt tagggggaagt taattttaaa tttcaacaac aattaataga aatcgatcaa    480
aaacaagaac ataaattgaa agtaaaatca ttaatcaatg aagatagttt tttaacaaaa    540
agacaagtta aaaacaaaaa taaaattctt actgaatttg aaaaacatcg ttcacaaatt    600
acacaaaatt atttaaataa acgtagtgat attctcaaga aagaatatga tgaattatta    660
aaagatgata aattatttga gttaagctca ggcgataatt gaaacaattt taaaaaaata    720
actttattta tttctaacga gatcggaatc attaatgatt tagaagatct attaaaccat    780
caagaattaa ttcggactcg aaattataca aaacgtgcta ttttaaatca acatcatatt    840
aatggtcact ttaaagatga aaaaaaatat ttgaaatctt tgtatgattt acgtgttaaa    900
```

-continued

```
tttatgtatg gtttaggttc agaaattgtt attttaaaat ttttaattga gcattataaa     960

aaattaaata gtttacgttt aagattagaa acattaaacc accctctttc aaattatgct    1020

gtttattttg atattttaaa ccgaattgaa aaacaaacac aattgttagc aaaaattgaa    1080

actttaaaat atgataatta tgattttaat gctgatgtta ttttagatga tttagaaagt    1140

aatatcacaa aaataaatga gattaaacat aattctaatg ttttaaataa aacaaaagtt    1200

attaaaacga ttattgagcc aaaatatgaa ttagaattaa tttcaaaaga tgataaagtt    1260

gatggtgtta aggtttacgt taacgatcaa gaaattcttt ctaaataa                 1308
```

<210> SEQ ID NO 4
<211> LENGTH: 1887
<212> TYPE: DNA
<213> ORGANISM: Ureaplasma urealyticum

<400> SEQUENCE: 4

```
atgattgaca agcaaaaaat taaacaacta atccaaaatc ctgtttatgg attttttgat      60

gaatttaaaa aaaatttaaa cagcgatctt gatcatgtaa ttttagaaca attaaaagat     120

caagataata atattgataa aattaatcat ttagtaaccg atattaataa tttaaaaaat     180

gatattaaac aacgcaaaaa agatgaaaaa attaaacaac ggactttttg taatattcta     240

atcgcagttt gttttgttat tattattggt ttgttttttt tacattttta tttgaaaaat     300

tccaaattta ttaaaaattt taaaaagtat gaaattgaaa aaaataatca aattaatata     360

tgtaacagcc aaaaaaataa atatatttat aatgttttat cacaaattaa ttcttataaa     420

atttcgcaag aaatttttgc taagaatggt ttatatttaa tgccagaaat tcaatatgaa     480

aatattaaac aaaccgattt attaatttca cgaaacgcaa aatttgttgg atttttttggt    540

ggtttagaag ttaaatttaa aagtacggat actttttttag tgtattataa ggaattttca    600

attaaagatg ttgtaacaag tggttgtatt caaatttctt atcgaaaagg agatcaaatg     660

gttagtgaaa cgatcgttgc tcatcataag gaaccaacac cgtttgttga tcttcacagt     720

aattttgttc ataaaactaa ttactctcca aactttaact tttcaacgta cgctcaaact     780

gttaattctc gttcaaaaac aattttttct aatttagaat tttctaagta ttatggctta     840

ggaattgcta ctcaaaattt agaatttgat acaaaaaatgc tagaattttt tacgcctttt    900

agtcaagaaa actatgaaaa ttttgctaaa tatttaaaac aagatgatat cacagttcct     960

atgtttacaa aaactgcgac atcccttatt attgatgatc aattattaaa agataataga    1020

aaaccattct ttataaattt attaacaaat aatagttatg taaaaacttg tgattttcta    1080

attgatacag atattaatgc ggacctacaa acgaatttaa atattttaaa atatgaatta    1140

gtaaaattat ttgaaaaata tattttatat ttaactacaa caagtttatc aagtgtaatt    1200

gcccgagaat gatatattaa taatgatact tataaaattg gtgataatta cgattatgaa    1260

agttattatt atactaatca aaatcaatta actccactat cagtttcgac aaaacttttt    1320

ttaaaaaacc aaatagcttt tgttaatgat tgtgaagtaa ttccttttgc tgaactagtt    1380

aataatcaaa cacgattcgg cattaataaa gcacagttta atattaaaag ttatcatgtt    1440

tataatcgtg tagataatgt accagtatat gcgcatggca gaacacacat tgttcctgta    1500

caatacaaag agtacatcga atatgaatat ccatttattt gtttatatgt tttaaaatat    1560

aaacagttaa cagaagaaat aggtttaaaa tattttacac gcccatttaa taatatttta    1620

ttaacaaatt ttgaagatca tagtgcttgt tctattgatg aaattcttga ttttaatgat    1680

aatgaatcca aaaataatag cgataatgat tttaaaattt atttaaaaga attagataca    1740
```

-continued

```
atcgtcacaa atgcgaattt aaataaaaat gaatttagct tcttaaaaga caatgatggt   1800

tatttcatta cgataagtaa taaaatagaa ttagacgaag aaactgaaca agaattatca   1860

acttgattaa gaaaagtaag cttatag                                        1887
```

<210> SEQ ID NO 5
<211> LENGTH: 576
<212> TYPE: DNA
<213> ORGANISM: Ureaplasma urealyticum

<400> SEQUENCE: 5

```
atgatagatc gtaaacaaat tcatgttaaa actagattaa caattaatga gttaaataag     60

ttttatactt taattagagt ccaaaaacaa agcttaaaag agattgaaga taaaatcaaa    120

aaacttgatt gaattaactt tagtgagatt aaaaatcaaa atttatttga tgaatttaaa    180

tttgattata aaaatatgac accatatgtt atttcacaag ttcaagatct ggttagtgtt    240

tatgatgtaa gacaaattag tgaaataatt cttgaattaa atcaagttaa tattcaaatt    300

caaactaaag atagtgagtt ttatattaaa aataataaaa aattaagttt aattagtagt    360

gaatttgaag attatcaatt aaaaaattat gatgcatatg aacattttaa aattacaatg    420

gatgaaccta aaattcatac tttaaatcat caaatgccat ttgattcaaa attaaacatc    480

aaaaccatca tttttatagt tttaacttct tgtttattat gtttattaat cgtcataatt    540

atatgtgcat tattaattgc aggagttatt aattaa                              576
```

<210> SEQ ID NO 6
<211> LENGTH: 288
<212> TYPE: DNA
<213> ORGANISM: Ureaplasma urealyticum

<400> SEQUENCE: 6

```
atgaattttg atattaattt aattaatgaa aatgattatg tttttagtgg atacattatt     60

ttaaaaaaac acaatgaaga aattatcgaa ttactaactt atttaggcga tgatcctatt    120

aatgatgaag ccaaaatcat aactttatat aataatgatc atattgatct aaaaaatctt    180

aatgatggag atttaattat tgtaaaagca agtttaatta taaataataa aaataacaaa    240

caattattgc ttaaagatat taataaacta gagttaagta ttaactaa                 288
```

<210> SEQ ID NO 7
<211> LENGTH: 915
<212> TYPE: DNA
<213> ORGANISM: Ureaplasma urealyticum

<400> SEQUENCE: 7

```
ttagtaaatg ttaatatctt gagtttgttg actttgatca atttctttat tattaatgtt     60

aattaaatta gttttttttat ttaaacaacc attttggtat tttgatttta gtgactctgc    120

tatttctttt tctataatga ttaaatctaa attatcaaaa tcttgtttaa ttactttttg    180

taattcaaaa attttttcat cactatccat atcaataacc ataatgatgt ttaattctgc    240

caaaccagaa taaatataat tcattattct cattaaatta taatcagcat tcatattaaa    300

aacaaaacga tggttatatt ctttgatccc ttcaataaat aatactttac gttttagtat    360

aaatttgaat gaattaatta aattcatcct tgcgatcaaa taatcttcta agctcatttt    420

attagttcta ggtctaattt ttttaatcat gtatatatat aaacaactaa aaaataaaaa    480

aaataggact aataaaatca atacaactac actaggactt gaaaaataag cttttcaaac    540
```

-continued

```
ttttggaatt aattctcatt gatcgacatt taagattgat gatccaccag ttaatccatt    600

aatattagaa ggagataaat ttttcataat aatctgtcca tcaataatta aatctccttt    660

aaattgacca cgacttaatg taattgattt gataacacag tcaataattg gccttgcaac    720

accagcgaga atacatacaa ttaatgcaac gatacaaaat aaaaaaaaga tttcgattaa    780

tcatgaacgt aaagaacgtt ttgcatgtga aatttcagga tttaatttat aatttgtagt    840

ttgaaatcat cattccatga aataaaatag aattttactt tttttcttaa tatgagcatc    900

aaagctttca cgcac                                                     915
```

<210> SEQ ID NO 8
<211> LENGTH: 1737
<212> TYPE: DNA
<213> ORGANISM: Ureaplasma urealyticum

<400> SEQUENCE: 8

```
atggtttatt ttttgtttaa agtagttgta tatttaatta ttataaatag agtaaggact     60

aatcatttta tgaagatgaa agctaagaaa tttttaatta caggattatt aggtgtagtt    120

agtttagcaa ctattaccac agtagctaca gcttgtacaa atggcaataa tcaaaaggct    180

aatacagtaa ataataagtc tgatttaaaa acaaatccaa atattaattt aactcaacaa    240

gatgtagaaa atttggaaaa acaaagacaa caatgaagtg aagatttaga tgtttatttt    300

aatggtgggt taagtaaaag tggcaaaaat tttgaccgta taaatacatt atcatcaaat    360

gcaacggaat gatttaagaa tcatcaaaaa ttagcggcaa cacgtgattc tggatcattg    420

gtacaagatg atgcagctta ttcatttgga attgcacccg attatgttca ttataaatga    480

gtttcaaaag atggtggcga cgtttctcca tcatatttaa aaccatattg aaataaaaat    540

ttaactgaag gtagaaactt ttcaaaatta gacccaaaga ctttggatga taatggaatc    600

ggtgttttat taatatctga tcaccattat ggtaaatgaa atgataattt tttaagcaaa    660

aaaactgttg gtggattaat tatgcaatca cgagtttctg gtttgccatc acactatcct    720

gctgttctaa caccaaaatt tttatttgat cctaatttaa atccaaattt aaaaaaatat    780

gcttctgcta attatgcgtt acctaattat tactctgacc cactagatgg gattatttta    840

acaggaaaaa ctttagatcg tatttatgat gctaaaaagt tttctaatgt ttataatgca    900

catgtagctg gcaaaacaca ttttgagaca ttcacagatt ttgcaaaggc aatggttgat    960

gaaacgcgtc gtggaatttc acaatgatct ttaaaaaatg ataaatgaaa agataaaaca   1020

gttttaatgg ttatgcctaa ctttactcca acagctaaaa tggtagatgt taattttaaa   1080

ccagaagact tagaattctt gagtaatgtt tgcattaatg aacctatgta ttgtccaaca   1140

atatatagtg atccaaatga taaatattta cctggattag gtgcaaaatt ccctattcca   1200

gtaaatcata tttcacaagt gcaaaattat attgatgatt atggacaaat tggtggaaaa   1260

gtattaaatg gtactggtaa tccagaagca tcaaaacaag ttggcccaac tttaggtgat   1320

gcttttaaag atacaagtga cgttgtagtt ttctgttata acgaatacgg tttattaaat   1380

tacaaacccg gaactgaaga aggcgaagct ttagtacaac aatttgaaaa gaatttaaca   1440

aattatgtta atggtttaac aaaagaaaca aaaaatcaat ttgtgccaac aaaagtttta   1500

aaagaaaaac cagtcgtggg taagaatttc tttattgaac gtaaaggtaa gttctatgat   1560

gcatgttatg gttttgctgg tcaagattta gtagttaata cattaaataa atgaacaagg   1620

ggagctaacg ctcaaaatat agatttaggg tatcctattt ttaataaaaa tacagttaaa   1680

cacattagag catttaagga ttctttaggt gttaaagttt tagacaaaca aaaatag      1737
```

-continued

<210> SEQ ID NO 9
<211> LENGTH: 1635
<212> TYPE: DNA
<213> ORGANISM: Ureaplasma urealyticum

<400> SEQUENCE: 9

```
atgaaatata aaaaaatttg aattacttca atagcttcta ttgcttttat aacaactatt     60

gtaagtacaa ctacagcttg tagtaaagtt aataatgaag ttaagtcttc aaatgacatt    120

tttaaacaaa tattaccaac taaagaagaa cttacaaatt taattaaaag acgtaaggat    180

tgagctaatg atttacaagt ttattttgag ggtggaaagt ctgcttcagg aaaagaattt    240

gagcgaattc aaactttagc aacaaatgca agtatatatt atcaaaagaa ccaaaaaatt    300

gctatgacgc gtgattctgg ctcattatgt caagatgatg ccgcatattc atttggaatt    360

gcaccagata tttctaatta tcgttgaaaa gcaggtgatg tagaagaagt tgtaccacat    420

tatttatctt acctttataa tcctaaatta actaaaggta tggaacttaa aggtgttaaa    480

gcagaaacat tagctgctga gaatgtaggt actttattta ttgcagattt taaatttgga    540

aattataaaa ctaatttttt agataaaaat aaaataggtg gaattgttat gcagtcacga    600

tcatcaggtt tgccttcaaa aacaccagct ttattcatgc ctaattggtt atttggtaaa    660

aataaccctt atttagagac tgacgttaac gcttcagctg gaattacaga tttttttgtt    720

gatccatatg atggcttaat ctttacaggt aaaaccttag atcgcattta tgatgcaaaa    780

aaatttgata atgttaataa agcggttatt gatggtaaaa gcaattttca aacatttaca    840

gattatgcaa aagcaattgt tagtgttgta cgaaagaatg tttcgaattg agctaaacaa    900

catagttatt gaaaaaataa aactgttgtt atgacaatgc caaacgtaat gaaaggagca    960

cgaattattg atcctaattt tagtaaagat gatttactat tcttaggtaa tatttttatt   1020

ccacaacctg tttattttcc aattttatat gcagaccaaa atgatgaata tacacctgga   1080

ttaggagcta aatttcctat tcctaaaaaa gatataaatg aagttcaacg ctatgtagat   1140

aattgaggtt gaataggtgg agcaatttta agtgatgcta ctaatcctga tgctgcaaaa   1200

cgtgttggtc caacattggg tgaagctttt gaaggaacgg ttgataaagt aatttattca   1260

tataatgaat atttaattaa aggatataaa ccaggaacag cagaaggtga agctataatt   1320

aaaaaattcg aagctaattt agcaaaatat gtaaatagtt tagatataaa tacaaaaaat   1380

agttttaatc ctacaaggat tttaaaagaa aagccagtgg taggtaaaaa ctttttttatc   1440

gaaagaaaag gtaatattta cgatgctaat tatggattta taggtcaaaa aactatggtt   1500

aatattttaa atcgttgaat gaatggtgaa aatagtccag aagttgattt gggtattcct   1560

aattttacta aggataatgt taaacattta cgtgctttta aagatgaatt aaatgttaaa   1620

aatactgatg aataa                                                    1635
```

<210> SEQ ID NO 10
<211> LENGTH: 1635
<212> TYPE: DNA
<213> ORGANISM: Ureaplasma urealyticum

<400> SEQUENCE: 10

```
atgaagttga agtttaaaaa aatcttatta tctatatcaa ctagtttaat aattttatca     60

tcaattatta caattgctgc atgtagcaat caagtaaaat ctaaaacaaa tttttcaaaa    120

acaacaccaa ctttagaaga attgactgag cttaaaaaaa gagaagaagc atgaaaagct    180
```

-continued

```
gatttagaag tttattttga aggtggagta agtaagtcag gaaaaaaatt taatcgaatt    240
gaaactttat catcaaaagc tagttcttat tatcaaaaaa accaaaaaat tgcggttact    300
aatgattcta gttcgttatg tcaagatgat gcactatatg catttggaat cgcacctgat    360
tattctggct ttcgttgaaa aacaagcgaa cttgaagaag tacatcctca ttatttaaat    420
tatttataca actctaaact aacaaaggga atgaatttca caggtaaagg agcattacca    480
gagaattttg ctaaattaaa tgtgggtaca ttatttattg ctgattttaa attcaataag    540
tataaagaaa atttttttaga taaaaatgaa attggtggtg tagcaatgca atcacgatca    600
tcaggtttgc cttcaaaaac accagcctta ttcatgccta gctggttgtt tggtaaaaat    660
aatccttatt tagaaactga tgttaatgct tcagctggaa ttacagattt ttttgttgat    720
ccatatgatg gcttaatctt tacaggtaaa accttagatc gcatttatga tgcaaaaaaa    780
tttgataatg ttaataaagc ggttattgat ggtaaaagca attttcaaac atttacagat    840
tatgctaatg ttgctgtaaa agctgttcga aaaagagttt cacaatgagc aaaacaaaat    900
aataaatgaa aagataaaac aacggttatg attagtcctg atgtaatgcc aaatggtcga    960
attgtagatc caaacattac taaagaagat ttattacatt taagtaattt ttttattacc   1020
caacccgttt atttaccaat tttatatgct gatcaaaatc atccttatac acctggaatg   1080
ggttgtaaat tccctattcc taaaaaacac ttagaagatg tacaaaaata tattgataat   1140
tgaggttgaa taggcggtgc aatattatca tctagtgcag aaaatcctga tgctgcaaaa   1200
cgtgttggtc caacattggg tgaagctttt gaaggaacgg ttgataaagt aatttattca   1260
tataatgaat atttaattaa aggatataaa ccaggaacag cagaaggaga agctgtaatt   1320
aaaaaattcg aagctaattt agcaaaatat gtaaatagtt tagatataaa tacaaaaaat   1380
agttttaatc ctacaaggat tttaaaagaa aagccagttg ttggtaaaaa tttctttatt   1440
gaacgtgaag gaacattctg cgatggttgt tatggtttta tgggtcaaaa aacaattgtt   1500
aatattttaa atcgttgaat gaatggtgaa aatagtccag aagttgattt gggtactcct   1560
aattttacta aggataatgt taaacattta cgtgctttta gagatgaatt aaatgttaaa   1620
aatactgatg aataa                                                     1635
```

<210> SEQ ID NO 11
<211> LENGTH: 525
<212> TYPE: DNA
<213> ORGANISM: Ureaplasma urealyticum

<400> SEQUENCE: 11

```
atgaaaaata agtattttag aaaaaataaa ttttggttat taataccaat aagttttgta     60
agtcttggaa gtattacatt agttgctact gcttgtgtaa agaaaaattt ttatcctaat    120
acatttgcag atgatcagat ttatatcact aagaataatg aaaaaactgt taagtttcgt    180
attagtcgta atgatgaaga aaataaaaag tattttaaag atgatcttaa atgaaatact    240
ttcattaata aacttaaaaa aacttatatt aatgttgaaa ctgttattcc aaaagaaaac    300
gcaaaacaaa atattaagca acaagattta tgcatgcgcg cattacctgt acaagtttta    360
agtaataata aatatgttga tatttacgta aagattcctg ttttattagc taatactaaa    420
atgttagttg ttggtgatga tttactaaaa tcattttatt ttgatacaga taacttaata    480
atgaatgcta aacattttca accaattcct atcaaaatgc tttag                    525
```

<210> SEQ ID NO 12
<211> LENGTH: 636

<212> TYPE: DNA
<213> ORGANISM: Ureaplasma urealyticum

<400> SEQUENCE: 12

```
ttattgctcg ttttttgctt ctagtttttg ttgcttttca agacgctttt gttcacgttg     60
acgtttcttt tcttcttgtt gttcatcaaa acgcttttca gcagcaacct tatcttgttg    120
agtttgtttt actaattcaa aaatctttca accagcatct gacataccat tattttttaa    180
acgacgatat ttaacgtatt tgccagattt aacaggtgtt tttggttctt tttcttcttt    240
aatactttct tgtttattaa cttgattatc ttggttaaca taaacaattt tctcaacaat    300
tttttcgatt ggcttttcaa cttcaataac tttttcaata taaacaggtt tttcaacttc    360
aacaattttt gtattgctta ggtttgttaa atcatttaaa tcaacacgta atttaacaat    420
ttgtgtttca tgatttaatg acacttcttg ttcataaaca ttattagttt caccatcatc    480
actatcataa ttttcgtgtt cacaataatg gttatattca attgttttta attttctttt    540
taaattatca actttattag ctaaatcacg aagctctaat aattcgctaa tttgtggatc    600
atatttttta ttagttgcag acatttgttc ctccac                              636
```

<210> SEQ ID NO 13
<211> LENGTH: 759
<212> TYPE: DNA
<213> ORGANISM: Ureaplasma urealyticum

<400> SEQUENCE: 13

```
ttatgttttt attttttgat agcctataat aagagcgcac attcttttga taaaatcttc     60
ataattattt aatattatag aattaccaaa taaatcatcg attttgtttg aataacttag    120
taagtcttca tcattcataa tttctttata acatcttatg taatcttttt tatttttaat    180
ttcctcacta atttctttca aactaagtaa aatgaagagc gttttatctg gtgtatgaaa    240
ataaacttta gggtcatcat ctgataattt taaatatttt tccaaattgt ggtttgaaat    300
attatcatat ttttgtaata caccatcact tttatagtat ggaactttat caaaaattat    360
aaaaatttga aaataaggaa ctgaattaga tcgtaaatta gctgtttcgc ctaacatatt    420
ctcaaaataa ttattactat tttgagaata attactcata acaaatttaa ttgctagtcc    480
agcaattgat tttccattat ttttaattgt tatatcaact tttttgttgt aatatctacc    540
atcaatacat tcttctttat catctctata accttgggat ttaatattgt attctttgcc    600
taacaattct tctaaatctt ttgctatact cccatgtaat gtttttaatt ttttagtact    660
tctagacgtt ccaacactca aataattatc aaaagattcc tttataatat ctaaatctaa    720
aaattttttg ttactcaaca ttttattaaa tttcctcat                           759
```

<210> SEQ ID NO 14
<211> LENGTH: 105
<212> TYPE: DNA
<213> ORGANISM: Ureaplasma urealyticum

<400> SEQUENCE: 14

```
ttaatttttt tcaacaactt cttctaaatt tttgctattg ttgcgtttta aaatttcttc     60
ataaaaaata tcagtaatga gatattcaag ttgttctctt gacat                    105
```

<210> SEQ ID NO 15
<211> LENGTH: 228
<212> TYPE: DNA
<213> ORGANISM: Ureaplasma urealyticum -continued

<400> SEQUENCE: 15

```
ttaccttttt ttggtagcct tgcctgtttg cgaatttata ttcataccta aattatagag     60

tttatatttg gttttaatta gttttaaact atatttattt agttgccttc cattactaat    120

ttcacaatat ttatatgata aaaattcttt agaaatatca taatttaaat attgttcata    180

tcaaaaaaat attgataatc attcatcttc tcttaattgt cttcccat                 228
```

<210> SEQ ID NO 16
<211> LENGTH: 729
<212> TYPE: DNA
<213> ORGANISM: Ureaplasma urealyticum

<400> SEQUENCE: 16

```
ttatttttgt gtttctatgt taacatttaa caatttagca ttggttaatt taacatcata     60

atttgcatta tttccattca ttttatcttt taaatcaatt tctaaaccat taagatttga    120

taattgattc tttgttaatg atttatgaac tacttgtaaa ctactatctt ttttaatttc    180

aatatcaaat gttaatatag gttgattttc ttctaaagaa tttaaaatat caaaattttg    240

taatttaaca ttaattttct tattttcttt gttgaatgtc ataaataatt ttgcattttt    300

aacatatgat tttaacaact cttcttcatt aaatttgact tctttaccat ttaaagttag    360

ttttgaaatt tcatagtcaa catttgaatt taaaccactt agtttaccgc ttaatgtttt    420

agatgcttca tcatatttta aatcacttgc ttgaattgga tttgtatcag ctttcttaat    480

aacttctaaa acaaaatctt ttttattagc atctgctaat tcaaatttac taaatgtaac    540

ttcaatagta gcagtattat ttttgacttc actaattttt acaccactag ctacaacatc    600

atcttttta gaattttctg gttgatcagc ttgctgttcg ctaccaccat tttcttttgg    660

ttcttcagtt tttggagctg gagtcggaga tggttgttgg cttggagctg aagctgcttc    720

aaagttcac                                                            729
```

<210> SEQ ID NO 17
<211> LENGTH: 1641
<212> TYPE: DNA
<213> ORGANISM: Ureaplasma urealyticum

<400> SEQUENCE: 17

```
atgaaaaaaa taaataaaaa gattttgttt tcttcattgt tatttggaac tgtagctatt     60

ggaactgttg cagttgcaac tgcatgtagt gacaataaga aaactaaaaa aacaatcaac    120

acaggcacta ctcaacccgg aagtagtaca ggaacaacaa gtaaatcatt aacgcaagaa    180

aaagtgttaa gaaatgaaat catttctgaa attttgaatg ctaaatctaa aaaaccagat    240

cgtgataaga tgtgagttaa ttgatgaaat agttcttttg aacaagcacg aaaactagca    300

agggaaatgg ataaagcagt tgatttaaca aaatcttcaa attttaaaaa attaattgct    360

gatggaaaat acaaatctac atttagtgca caaattgaag atattattac taaagttaaa    420

catgatatta aaatgtatgc agaatcacca ttttgaaaaa aatgacgtga tgaaaaaaag    480

actgttatta cattagtaaa taacaacgct cctcgtgaag atttaggagc tatgaatgta    540

acatcaattg atttacctgc tgattttcca attatttatt caaaacctga ttatgatggt    600

attcctggat taggtgcacg ttttccaaca cctaaatcaa aagtagctcc tgaaaaatta    660

ttagatgatg gtttctcatt tggagatatt attgttgaag atggttcaga tactcaaaaa    720

gcaaatctac ctggtcaatt aattgaatca tttgaaaaga cagctgataa agtaatttac    780

ttatactatg attcaggttt accagaagcg tttaaaaaca atcaacgtca acctgaaaaa    840
```

-continued

```
attaaacaat ttgaagactg aatgaagagt caaaatgcta atgatttcgt tgcaaaacgc    900
atgttaaaaa atccaaataa taaggacgat ttaattgtta tgccaatgag tagtttatga    960
tatgcaagtt atggtatttt aggagttaat tattcattac atgccctttc agaagcattt   1020
ggtatgccaa aatctgaatt agatgcttta aaagctaaag aagaatttaa agtgccaaaa   1080
caattagtta cattagttaa ccaagctaca gatttaaaag aagataaaca aacaattaaa   1140
gatgaatgcg atccttttaa atcacaccgt gatccaaatc ataaaattga ctgaaaagtt   1200
tgagcaacaa attcacaagt tttagatatt gctattactt taggactaaa acctgattta   1260
ttagtaaatg gtgaattatc aacaagtgga catgaagaaa atcaattagc tttatattta   1320
tcagattata ttaatggaca actaaaagat tgtagaacaa ttactccaaa tgatggaatt   1380
cgttgagaaa caacatcatt aactaaaatt aaagatttaa atgttaattt gattctagct   1440
ggaattcatg ggaagctgc aacaaaaatg tttggtgcat taatgaaaga acataaagaa   1500
attgccaatt ttgcaattac taaccgccga tttaatgatg aaacaagaaa agtagttgct   1560
cctcaagatc gcgataaata ctctcaaaat gcagctcttg ttgattgaga agattactta   1620
aaaacaaaag atttacatta a                                               1641
```

<210> SEQ ID NO 18
<211> LENGTH: 1182
<212> TYPE: DNA
<213> ORGANISM: Ureaplasma urealyticum

<400> SEQUENCE: 18

```
atgaacaaac caatgtgttt gcttcgttta gataattatt attttacatt gttggtattt     60
atttataatg atgtaactaa agttaatgat ttaattttta taaaatctat tccaaacaat    120
aatcaaaata attatgaatc atcaaatttt ttgcaaacag atttaaaaat ccaacttaat    180
acattgatta actgttttaa aaaagaattg cacattaatt ttattgatga aattattgtt    240
agttatggtt ttagtagctt tcaaactaca catactactt tttataacta taatgaattt    300
atgaaattaa gatcaaattt taataatgaa cacagtgaat tattaagttc agatcaaaaa    360
agttatatag cagttgattt tggaataagc cactattcta aagaaaatag ttataagttg    420
atttcatatt atattttgaa atatgattat caattaataa ttgatttgtg ccaatcattt    480
aatttaaaaa ttaagcaatt tatagtttca caagctcatt taaacggttt aaaatttgat    540
aatgaagata ataaaacttc attattatta gaattagaaa attttaaaat aaattttaga    600
acttataatg aatataattt aattagtaat gttattagtg agacaaaaaa ccacttttgc    660
ctggctgata tcattactca aacagcacaa tcattaaata ttaatcctaa aaagattgag    720
agctacttta atgatattaa ttataataat aaaaaagtta ttgaaattaa tattgatcct    780
aaagagttgt ttacttatag ttttatttgt ggtgcggata ttgaaaatac ttttttaaaa    840
atttttaaag aacattttga aaaaagtatt ttatctcaat ttgatcatcc attactagat    900
tttaatccaa agaatttagc ctttcttttt attaacactc ctttcaataa tttaaataag    960
atattttatt attttttag ttcatatttt aaagaagtta aaattgaagt tttcaaaat   1020
aaatttttta tttattcaaa ttgttatgaa tatagtaata gtcaagccct agctaagcaa   1080
gatttttaca atgtacataa catgaaaaat tttgatagct ttagcaatga aaatatccta   1140
acaaagatgc atgatcaaac aataaacata aaaaattttt aa                       1182
```

<210> SEQ ID NO 19

<211> LENGTH: 876
<212> TYPE: DNA
<213> ORGANISM: Ureaplasma urealyticum

<400> SEQUENCE: 19

```
atggcgttaa gtaaacacag tattggtttg attaaaaatt taaagaataa aggattgact     60
attaaaaata aagaaaaatt cattagtttc ttgtttaatt atggagtcat aagagttata    120
gatggttatt catttttttt aaaaaaagat aatcaatatg taaaaggctt aaaaagtaag    180
gatttaatta attttgtttt attagatcgt aaaattgcta atttaatggg tgattgtatt    240
atgctatttg aacaacaatt aaatgctatt gttgttcaaa attttttaaa gatcaataat    300
ttaaattcaa aatatgttat agatatgcga acagatcctt ttataaaatt tgaatcacca    360
aaacattatg aaatattatc agaaaatatt tacacatatg ctaattcttc taatttgtta    420
agtcaattta atactaacgc acaagaaatt cctttaatta atttagcatt atcatgaaca    480
ttaaatacca ctattggctt ttatcgtgca gttgataata atgttcaaat tagtgtttta    540
gagtattttc aattaaatca tattacacca ttagaattta ttgatatttt acatatcata    600
aaacattttc gtaatagtat ttctcataac gatatggtaa ttactaatag tttcaatgat    660
aacgtaggtg catttgctaa atcattaaaa ttaaaaagta ttaaaaaagt agtgggattt    720
ttagatgttg cggctttttt aacggcgttt acaaacgata aatttcatgt tttaaatggt    780
aatttacaca tcaaaatttt acaagcaatt aaaaaagcaa aattcaaagg cgttgtttta    840
gaacatatta ataatttatt aggagttgaa gattaa                              876
```

<210> SEQ ID NO 20
<211> LENGTH: 816
<212> TYPE: DNA
<213> ORGANISM: Ureaplasma urealyticum

<400> SEQUENCE: 20

```
ttgaatttaa agtcatttga atttttaaaa ggtgatgcaa ttgttgataa ccaaataaaa     60
aaagctatta atactagttt gattaaagca tcattttcat gtgcaattat gtgtatatta    120
gttcttattt ttggtttttt aatgcgaaaa tatttatttt atttttcaga tgcatctagt    180
ttaattatta gctctcgttt gatttttcaa ataattacaa tcattgttgc tactttatca    240
attgtctatt ttattgttca tttaatcatt tactttagac aaagaaataa ttttttagct    300
cctaaatttg catgatcaat catattgtat ctattggatg gtattacaat gtgttttatg    360
attagttatg tagcggcgat tgtaggatta gatttgacgt taatagccat tggaattagt    420
ttatcaatca ttgtcgcaat gggaatacta ggttttatta tgaatcataa aattgctttt    480
aaattaggca ttgctaatat cgttttattt actattgcta caattggttc aattatttta    540
ttgattgtat tttttacaac gagatataac catactggtt ttaacaaagg tgttattatt    600
gctgacattg tattaagtat tatttgattg ctcgctttaa gtattggttt tgcttcgacg    660
atttacatta ttaaagtaat ggccgaacat cataatttag ataataaaaa aataatgcgt    720
gattttacaa cttgaaatag ttatttacta tttgcttcat tcaatcgtat tttattatat    780
gtaattcgtt tgtttttatt gtttaaaaga gtataa                              816
```

<210> SEQ ID NO 21
<211> LENGTH: 1784
<212> TYPE: DNA
<213> ORGANISM: Ureaplasma urealyticum

<400> SEQUENCE: 21

-continued

```
atgttaaaaa attattttca atcaagttga ttatatacaa cctttttatc acgtttggta     60
ctttttaaaa aaagcacata ttttttagta ggaattagct tatttgttaa tttaattttt    120
ataattataa atggtttaaa tattgctaat aatataaaaa cgtatttgat tttattttat    180
ctttttacta gtattaattc acttttaaca atagtcttta gcactattaa agctattaat    240
ttattcaaag atttaaagga tgaaggaatt gaaattttag tcttttcaaa aagtatttca    300
cgtaaaaaca ttatttttac taaaataggt tttttaatat taaatattgt tttttgaagt    360
ttaataactt atattttaaa tattattttt tacgtagtaa atataaagaa taataacggt    420
attaattttt tttatttata tgcttttttt aattattatt tctgtggatt aatttttgct    480
agtattgctg ctttaattgt tagtcgttga tcaaataaag ttgctatgat tattccaatt    540
agttgttttc tcccctttttt aattgctggt ggtgttgcta atttgtattc aacatctaaa    600
attaatcaag tagccaaata catgaatatt aattatgata aatatgatag taatacaatt    660
ttagatgtag aaaaatttta tttaaataat cataatgatg aagtttattt aatcactaaa    720
aatttaaata atccacaatt tagtaaacgt cagaattatt ttttgaaagc agcgtttgat    780
cacgcaaaaa atgcatcgac attttttcat gtcttatctt gattatctgt tccttatcaa    840
ttaaataata gtttttataa gaatgatatt gatcctttta gtgttaatag ccaacacgaa    900
aattatttag ataaatattt taattatcat ggtttagaat caaaattata tgattataaa    960
cttaacaaac accctcattt accacaattt aatattaatg aaaatcaaaa agaatatttt   1020
gttcctggag ctttaaaaaa tacgagtcaa ttcccaacac ttgagaatcg taatttaatt   1080
tatgcgagag aaaatgtaga tcgttttgac gttaatttca ttgaggatga taatttattt   1140
tcatcaacta atgattttgt tggtgaatta aaatgagcgg ttattagaaa tacattagaa   1200
tcaaaagttt tcaataactt tgccaaaaaa ttttatgata attttgatga agatattgat   1260
aaaccacaaa ttattgctgc ttataatgat gtaattaatg aacaatcatc aataaatttt   1320
tcaacaatcg ttgatgaaaa tagtattcta tttgctaaaa agataaataa ttattatgtt   1380
aaaaatcttg ttgaaaagaa aatttatttc attgtagctt taatgtatta tttatatttt   1440
aatgaggaac gttgaaatct tttagaaaaa ttattaaaaa acgataaagt tattaatttt   1500
tatcgtccat catcaataag aatcaatgta aataattatg catatgatat ggagggattg   1560
gaagttatga attaatgaaa aaagtagtta ataacaaaac tttatatcgt taccaactac   1620
aaaaaagtaa taattatgtt tttcaaacag caaaagaagt ttattctatt aaacgtgctg   1680
atcaaattgt taataaaaat tattattgat taatttgaat tttatttagt acgattttaa   1740
ttataagctt ggctttaatt tatttaaaac gagattataa ataa                    1784
```

<210> SEQ ID NO 22
<211> LENGTH: 300
<212> TYPE: DNA
<213> ORGANISM: Ureaplasma urealyticum

<400> SEQUENCE: 22

```
ttatttcctt accggacgtt tctctcaaac atcaaaagtg cttttttat caacaacttt     60
ttctaaaaga tcaataaaat tatttagtga tgttgtgtat tcacgttctt tttcgaattt    120
tcttttatat tcattaagtt cttctatttt taatattgca tttttatgtt catttataaa    180
tatttctaat tcattaatta attcgtctaa aaaaacatct acactttcag gatcgtaacc    240
aactttgtta gcaacaaatt ttttattttt atactcatta attttattat catttaccat    300
```

<210> SEQ ID NO 23
<211> LENGTH: 282
<212> TYPE: DNA
<213> ORGANISM: Ureaplasma urealyticum

<400> SEQUENCE: 23
ttaagaattt aaataataaa tattcatata gggaatttta ggaccaacta ttgtactcat 60
atctacatta attgtttcta ttttaatcga atctatatct tgtgaatcgt ggttttgttg 120
tgatgaacta gccattacaa tatttgttat gcctccaatc atagaaatag ctgtattagc 180
aataattgtc ccaaataaca ttttatttca aaaacctaat gctccagaaa caagtggcat 240
aaatcctcca taaatcatgt ttttattaat tattctttgc at 282

<210> SEQ ID NO 24
<211> LENGTH: 267
<212> TYPE: DNA
<213> ORGANISM: Ureaplasma urealyticum

<400> SEQUENCE: 24
ttatcaattt ctataccatg tataaatgtt tctaattgtt ttttttaact caattaaatc 60
attattattt ataagataat ctttgcaata tctatcaact atataagtta aaaattgccc 120
atctccacaa ctattatcaa ttacatgttt tttatttata tttccattaa tataatgccc 180
tttatcaagt attatattta ctaaataatc aggtgtataa acttttccat agcgtttaac 240
cttagtcaat ctcaataatt ctttcat 267

<210> SEQ ID NO 25
<211> LENGTH: 279
<212> TYPE: DNA
<213> ORGANISM: Ureaplasma urealyticum

<400> SEQUENCE: 25
ttaaaaaaat ggagttccta aactaatcgt tgaattcatt ggtttttgtg cgattcttgc 60
ataagtgcga gcaacagagt tatcgatcat ttgttgagga ttaaattttg gttgagggtt 120
aaaagcataa actaattgtg aaatcattcc taagaatcca acaactgttt gacctaacat 180
tgatgaaatt aaagcgttat ttcacatata attaaaagag ttagaagttg aaaaaccacc 240
ataataaact tttttaaaat tatcagatat tttttgcat 279

<210> SEQ ID NO 26
<211> LENGTH: 606
<212> TYPE: DNA
<213> ORGANISM: Ureaplasma urealyticum

<400> SEQUENCE: 26
atgaaattta agaagtttga tagtaaaaaa tcgattttac gttttttaca agttgatgaa 60
acaaaacgtg aaattaattt gtcttttaat gacacaactg attttatttt ttttctaaaa 120
gaaattgctg aagatcctaa tattgctaaa aagaatgcta aaaaattaac tagcttatac 180
attgaaatta gtaataaact gggtaatgat gacaacactg atttaagcgt ttatgaaaca 240
aaatgtaata atttaattga agcctgtgtt attgatgaag caatctattt agttaatatg 300
gcaaagaaca tagtcatttt cttagctcat aacaaacttg atcttttaca aaaagatttt 360
tttgataaat tattattaat agaatcgcat tttaattttg atcaaaatct tacttattca 420
tatattaaaa actcatcaat tgcgttattg atatttcatt taaagcaatt tattaacatt 480
tatgatgaat ttttaaacaa ttttgaaaat gttattaatc atagtttaga aaattcaatt 540

```
tcaactaaaa ataaattaac ccaacaaatc aatcatttta atactataaa acgtcgtcct    600

tcataa                                                                606
```

<210> SEQ ID NO 27
<211> LENGTH: 1606
<212> TYPE: DNA
<213> ORGANISM: Ureaplasma urealyticum

<400> SEQUENCE: 27

```
ttatttttgt ttattttctt ttgctggatc tgttcaactt acaacttttg ttccttcaac      60

agattgtaat gtgtttgttg tacgatcata gaattcaaaa ttaattggtg aacgagaatt     120

atttgaatcg ccacgttcag taggaacagc ttttggtatt gcattgccaa taagagtttt     180

aaaagaacgg ttaatatgag aattattacc acctagagca tataaattca taccagcaac     240

tttttgagca tcaccagtga aatctttaaa ttcggttttt gtttcatcta ctaaatcagc     300

taaaaatcct ggtagtttag tatatgtttt tccttttttct ttaacgaatg aagcatagtc    360

tggttgaatt cccaatgcca cacaatgatc tcataaatta tagaatcaga ttgcaaattt     420

attatgatca ttattagaat tttttggacg aatgtgtttt aatgtttgtt ttgatggcat     480

agttcaatca agactaacac ttgctaattc actatcactt acccctaatc ttttagcaag     540

tgattgaact aaacgtactg ttccaatagg tcctcaaatt gaagaatatt caaattgaaa     600

atcaactgga ataattttgt tattattaac agttttctta aagaattttt caaaatttga     660

ttttaaaatc tctccatctt cattgccttc aagattgttt gagtcataat taaagaaaac     720

ataatccgca gttccataaa aagcttcttg cattgatagc attcaatcat agtcattttt     780

tgacgcatta ttttgggatg caccaattcc atgtcagtta tcaaaatatt tatcagcatt     840

atggtttttt ggtttaggaa aacgtaaacc aaacccagga acatttgaat catctggttg     900

agaatacaat aaagggaata aatcttcttg ttggaaatag tataaatcta atttagatgc     960

atctgaacta ttaaaacttt gtgttgattc tgctcataaa acagttgtat tattatctct    1020

taattttttta atagttggta aattagcaac ttttctaaca tattcacgaa tcttattatt   1080

aagttcttta gcatactcta aaaaacttgt tttaccgcta tttttcaaag gttcatgtga    1140

tgtaatttca taacctgcat catccaatga ttttgcaaac atttcaaaac atttataagg    1200

gtctgttagt gaattaaaaa aagtactact attattaaca tcacttaaga tatatttttc    1260

actagattta gttgcatttt gttttggagc ttttttttgaa attaacttat taagtgttgt   1320

ttttccttcc tctttaacgt tattgtcttt tcttgcacat gctgtagcag caaccgcaat    1380

acttgaaatt aaaacagttg aaaaacctac tagcaatact gctaaagatt ttttattttt    1440

cttaaacata tttttattat cctcattttt aaaataatat tgttttgttt tgacaaacaa    1500

tttcattcta atagtaaaaa gaaaatattc tatgatttat ataccaaaaa atccactttt    1560

tgatgtccaa tattagtttt agaaacaatt ccaccgccaa tgcaat                   1606
```

<210> SEQ ID NO 28
<211> LENGTH: 450
<212> TYPE: DNA
<213> ORGANISM: Ureaplasma urealyticum

<400> SEQUENCE: 28

```
ttattccttt ttttcatgat gttcatgatg acaaggtttg cataaatcca ttttattcat      60

atataaatta attgttttgt aatttaattt aacattatat tgtgtttcaa gaatttttttg    120
```

-continued

```
aattttacga caaccaatat aatgcttatg acttttacaa attttttcaa ttaaatccat    180

atttcttttt ttaattggac aaacttgatc tatttttaag tcttctagtc atttataata    240

accagaaatt gatacatcaa acaacggaat taatttcgtt aaatgcattt ggtggttttt    300

aatcaattca tgaatcattt taaatttttc ttttttgat tcatgatgac gataagcatt    360

aattacctta ataatatgat tttgttctca ttcttcataa tgattaattc ttaatgcatt    420

gatatcaatg ttatcgacaa tttttgacat                                      450
```

<210> SEQ ID NO 29
<211> LENGTH: 213
<212> TYPE: DNA
<213> ORGANISM: Ureaplasma urealyticum

<400> SEQUENCE: 29

```
ttataaattt tgttgtttct ctttaataat ttttttgatc ttttcacgtg ttttcttatc     60

aatttttca tattctaaga tatatgataa ttcttcaatc gaatgttctt cgtacggttt    120

ttgttcatca atatcattaa tatcgaaaat agatgtttct tgtacttttg aacgctcaaa    180

taacttttca aaatcacttt ttttatcact cat                                 213
```

<210> SEQ ID NO 30
<211> LENGTH: 504
<212> TYPE: DNA
<213> ORGANISM: Ureaplasma urealyticum

<400> SEQUENCE: 30

```
atgaacatta aaaaaattaa acgtgaattt aatactcatt acgaattgat taaaaaagaa     60

attaaaaact taaatgaata taaaaaagaa ttagaattct taattgcaac aatttatttt    120

aattctaaaa tggtttttaa agaaatatca ttagatagtt gaaaaaaatt tagcgattat    180

gtttatcgat ttttttaat aattaataaa aataatcaat cacaaaattt tgatttagat    240

tgttgatact tagaaattaa agaattaata aaagtactaa atattagtaa ttttttattg    300

aataagcaat tggaacaaat atatttgaaa tacataattt tttattggta taacattaat    360

attccaataa attatgaaat tgatgatttt aatattattt gtttacgcaa taaagcattt    420

gtagattgta tgcaaatttt acaagaatat tatcatatta atgttgatat tttaattaat    480

ttagttatca aacaaattag ataa                                           504
```

<210> SEQ ID NO 31
<211> LENGTH: 810
<212> TYPE: DNA
<213> ORGANISM: Ureaplasma urealyticum

<400> SEQUENCE: 31

```
atggtttgca tcattttaaa aataaaaaag ggaatgttaa agataatgaa taataataaa     60

agctacatta aaaaatattt tgatgatatt ttaatacagg ctaaacaggt tttaaaaaaa    120

catgattatg cgtatgcata tgatttaatt tctaatgaat ttaataatcc attaattgat    180

ttaaaaactt tacaagaatt tgaagcattt gctatagaaa ttaaaaaaag tgccgaactt    240

aactttattg atgaaaatga ggcaaaatta gctaaaacag atttttattg taaaattcat    300

gatccaaaaa caacttatgt tagtttagca tatttagaaa cttttttaat gcgtttcatt    360

aatgaaatgg atgaattaga tattacattt ttaaatagct tgctaacaaa taaattaatt    420

aatggatcaa caaaattaga tattttagat ttattagcaa ctaataatat tgatcaaaat    480

tttaattttt acaataaata tttaaaacaa acaaaaaatg ttaaccctgt taattttaat    540
```

```
aaccattacc aagaaattga ccaaattcaa aattatctaa ataagtattt agctaaaaat    600

ccttctttat tacatttagc caataaatta ttaatgatgt acattacata ttattttcca    660

tttaaatttg cacataatca taatttaatt gctaaaacaa ttattgatta tgtaaaaaat    720

gctatggaaa atcatgtttg tcagtatagt gaagaacaaa aagctattgt ggcttgtatt    780

aataaaattt tagaagaaga gcaagtataa                                      810
```

```
<210> SEQ ID NO 32
<211> LENGTH: 975
<212> TYPE: DNA
<213> ORGANISM: Ureaplasma urealyticum

<400> SEQUENCE: 32

aaacaaattc ttgattcagc aaaaaacaaa aatccaactt ttcacatcaa cgagtgaaat     60

gcatcatttg catatttaca acaatttaat gcaataattg gtgaaataga agctaaaaaa    120

gacaatttaa ataatcaaaa tttttctaaa gctaaaacta ataaaattat tacttttgtt    180

ccttatattg aacttgattc taataaatat ttaacaaacc aagcaatttc taaggataca    240

agagttaatt gaatatctgt tattaaccaa tatgcgaata ataatgaaca taatttaatg    300

gcaactagca atgatttact aatttattct aatttaaaac aaacacctaa ataccaaata    360

gataataaaa aactaaaaga agattttgtt aaaaataata attgactaag cgaaaatgtt    420

gattatcatt taagtatttt taaagatatt aaatatgatt tttatctaag ccattggtgt    480

tatcaatatt gaattgatca aaatcgttta gatgttattt taaaactaat ttataatgct    540

aataaaataa ttttataccc gaatggaaat gctgaattat attatgttgc aaattattac    600

gcacaggcaa ttaaaaattt aattagggaa gatccccatt tatcaaaaca aaagattaat    660

gatcatttaa ataattttat taatatgaaa tcatttttag aagcaaaaaa ttattttagt    720

tcacaattaa ataataataa agattgatta acagtttttg tcttaaataa gttgtttaaa    780

atttttacaa ttggtgaaag ttgagtcgat tctaagtact ttagttttaa taaggaacta    840

atgcctaaat cttataaaat tcgcacaaat tatgcaagcg tactaaattc actaaattta    900

tcattagatg ctaaaaatca atttaaaaaa aaaattttga gcacactttt agaatataca    960

ataaaacatt tttag                                                      975
```

```
<210> SEQ ID NO 33
<211> LENGTH: 552
<212> TYPE: DNA
<213> ORGANISM: Ureaplasma urealyticum

<400> SEQUENCE: 33

atgggttctt cactatttaa aaataatgtt ttaaaagatc gtaaaattgc taaacaagaa     60

ttacaacaat gagcactaaa aattaaaaac aaatatccta atgctaatta ctttttttaaa   120

ttacacccta tttataatca aaatcaagta ttagattaca ttcaagaaat cactaatgga    180

atctttaaac caattatttt agatgcaaaa acaccatgag aaaatatctt attaaaagat    240

tatttatcaa ttaaaaataa caaagcagtt ttatttaaaa acaaaaacac acctaatttt    300

tcattatggg gttttcaacc aacaacatca gcacttctaa cgagttttga ttttattcgt    360

aataatacta aactaacaaa tgatgaagcc caatcaatta taggttttga taatttttta    420

cttggtaaaa attatgacat tttaagacgt gattatgaac caaataaaga ttatacaaac    480

gaaaatttgc aaattttaga aagaatatat ggacaattaa tttttgctaa aattttaaaa    540
```

-continued

```
aaattctttt aa                                                         552


<210> SEQ ID NO 34
<211> LENGTH: 252
<212> TYPE: DNA
<213> ORGANISM: Ureaplasma urealyticum

<400> SEQUENCE: 34

atgatttata aagaaattgt acgtaatatt attaaacatc cattaatttt accagatgga      60

aaacactatc atctacacaa aatcttaact tcaaaagatg aattacgtaa aggcgaagta     120

actttagttg cagaaaatgg caaagaatat acagttgatt tatctgcctt tgttgatcta     180

ttagttgatg gtgattgcat ctttgatgat aaccactcat tagttgcatt atattttgat     240

gatgcaaaat aa                                                         252


<210> SEQ ID NO 35
<211> LENGTH: 417
<212> TYPE: DNA
<213> ORGANISM: Ureaplasma urealyticum

<400> SEQUENCE: 35

atgtctccaa ttagtattga attaataatt caaataagta ttggattaag tgctagccta      60

attttattgt ttgctttctt accacaaaca cttttaacta ttaaaactaa aaatactgct     120

gcattaacaa ttagtatgtt tattatttgt tttattgcac gtttatgttt tagtttaagt     180

gctattctaa caattatcgt ctatattcat aatcagaatt atggtttatc tttatatgcg     240

cttacacttc ctgttttaat atgtcatggt attaatatgt tattaaattt aattattgct     300

tttataaaaa tcaataatgt ttataaagcc aaaatccata aaatgaatga gaatgaatat     360

attatttttg cttatgctca aaaattaaag gaaaaagtat cgataaaaaa taaataa        417


<210> SEQ ID NO 36
<211> LENGTH: 1500
<212> TYPE: DNA
<213> ORGANISM: Ureaplasma urealyticum

<400> SEQUENCE: 36

ttatttagta gacaaataag ttgatcataa ataaaattca ctaacactaa aatctgctaa      60

ttctttagca tcatcaataa tacccatttt tactaagtat tgtaaaaatt cgttttttat     120

attttgcatt cgggttttta atgattcatt tttagttttt aattgattaa tttcttcatt     180

atttttatct ttgttaatac taatttgtca ttcgttttca tataactgtt ttaataagtt     240

taaataacga tcttcatagt gtgaatttat aggattagtt tctattaatt catctttttt     300

agctttaatg taatcagtaa tatcataatc tcgtcaaagc atgttaataa tactaaaacg     360

aattttatca ttcattaatt tagtattaga tgtactaatc gaataatatt tattatcata     420

tcaatatgca tttacaaata aattgaactt attaagttga tcattaatgt tttcaaaaaa     480

tcgttttaat tcatttttttg tacttgaata ttctttgtta tttaaaaatg atttttctaa     540

aaagatatta aaatctaatt tattagttat ttcataattt tgatcgatta aattttcttg     600

ttttaaatac ttaataatta aatttttatt ttcatcattg ctttgattaa gtttttttaaa     660

cgctaaaaat aaagtgttga ttcttgtttt atcatatgtt tttattttaa ataatatacg     720

attaacgtta gagaaataat acctatcatt tttataaata cgacttattg gatagctatg     780

attaatatat ttacttggaa gatctaaatt aaatttttga ttgtaatact tgtataattc     840

tctagcattg taataatgat ttatatgagc aaaataaatg aaattgtatc aagaataaaa     900
```

-continued ataatcttta ttattagaac ttaatttatt aggatgataa tattttttaa atattcttgt 960
tgcttcatca aaataatgtt ctggatctct taaactaata tacttaatag aatttgctaa 1020
aaattttggt ttattatcaa taaaatatgt cacatttaaa aacatataat aatcaattaa 1080
tcatttaaat caaggtttgt tttggttatt tttaactaat tcaaaatcaa ctaaattact 1140
tatatgttgg tcaatgtatg ctagtaattt attaacaaat tctaaatcat aggtttgttt 1200
ttggtcatct caaactttac catcataaac aaagctttta atattattag catataaaac 1260
tttgtaataa tcattttttg gaatatcaat tattggtgat agttctttag tttttggttt 1320
ttcttgttgt ttattttctt tgatttctat ttgctttgac aatttattag aattattgga 1380
ttttgattta ttagttgtac aaccaataat caaaggtgca attaaaaata atgataataa 1440
gctagtttta atgaatagct ttttctttaa tgaatgtgta actaaatgac gtttgttcat 1500

<210> SEQ ID NO 37
<211> LENGTH: 1353
<212> TYPE: DNA
<213> ORGANISM: Ureaplasma urealyticum

<400> SEQUENCE: 37
ttaatgaata gctttttctt taatgaatgt gtaactaaat gacgtttgtt catttcttac 60
ttctcctttt tgataaacta aaattttgta ttcgccttta tttagatttg gtgctctaat 120
taattcaaca ttcgaatctg attctgaacg ataaatgttt atagttctta aaatttcgcc 180
aaagttatca aaattttgat aatcaatatt ttttagatct tcatttttaa ctaaatagat 240
atcataattg tcatttttaa aatatgttag ttttttatat tcgttgtata cactattata 300
atcatgtttt tttgaaaaac tatttgatgt tggcttaaat aatcatgata aagcaaaatt 360
gaaattagtt tgatcattat caatacttat atccatttct ttaactagtt gtttatcttt 420
gtgtttcgtt aaaatttttg tttgttttgc gtttttatat gcttctattg ctcttttaaa 480
atctaaatga ccagcaccat ataaatgact aaaactattt ttataaaaat cataattttc 540
attatttttt aaaggaattg atgaagcagc taaaattgag cgaatatgtg ttagtggaat 600
tgttttatta gcgttattaa ccatataata agattgcaat aaactaatcg caccagtgac 660
aataggcgca gaaaaactag tacctagatt tatattttta tctcctttat ttttaataaa 720
ctttgtaatt attgaagtgt cataaatacc ttctccagga gcaactaaaa atggcatcaa 780
taaatctcca tatttatttt taacatcatt caagtgatgt cgatctgaaa aattacttac 840
tttttcatta tttttattag tagatcctac atatattgaa ttttgattaa atctatccat 900
aaaactatat ttagatatat caaatcaatt aatttctaaa atatgtccat ttttatttct 960
atatcgtatt tcatcattat aagaatttcc agctgaaaaa atatttataa tatcaaaata 1020
atatgatatg aaatcataaa tataattttt aaatttatat ttattaatag tattattaac 1080
aatatcatcc ttattcaatg tatctatata tttttttaac tctcttttaa aatctttatc 1140
atcgtttatt tctttaccat taataaaatt ataaaaacca atatttaaaa aatcatttgg 1200
acttcatcca taactatggt taataatttt tacgtcattt tgtattaatc aatctaactc 1260
ttttcaaatt ttaatatgac tattttctga tgtttcatcc tttgcattaa tatctagtga 1320
ataaagatgg actttctcaa ttttcacgat cat 1353

<210> SEQ ID NO 38
<211> LENGTH: 1251
<212> TYPE: DNA

-continued

<213> ORGANISM: Ureaplasma urealyticum

<400> SEQUENCE: 38
ttaatatcta gtgaataaag atggactttc tcaattttca cgatcattta aattcattaa 60
ctttatttca attgattcat ctttatttat attattaaaa ttaggattta atgataaagt 120
taaactttgt gaagtacttt cttcttgtgg tttattaaaa tgagcatcaa aataaacttt 180
tgaaattaaa tcatgaacag taatgttgtt attaaaaact acttgcattt gataatattg 240
ttcattatga ttgattaatt cctcaaaaac tcaaatttta ttttctttat ctcaatactc 300
aataccagta aatcgataat tccctgaata caattcttca aattttaaat cttcatgatt 360
taagaatgtt agggcattaa caggtaatgt tttaattact ttaccatgtt catgttgata 420
cactaatcgc attattttat actgtaatcc agattttttt gataacaaac tttcaaaatc 480
atcttttata ggattggttt taattaataa atgatcattg ggcgttggag tttgttcaaa 540
taaattagta ttatcataaa aatctgcaaa aaactcatca cttaaacgat cttctacatt 600
ttcaataaat tcttctctta attcaagcaa atcttttgaa taaactggtt caaaacttgt 660
tccactactt gaatcgattt gacaaaattc tccaacatct tgatcaaatc ctcattcatt 720
ttttaaaact aaatttttac actcaccaaa tacagccatt ggtttttgat caatcttttt 780
attaaataaa ataaatttaa ttttattaat aattacttga ttaataaaat cactatttga 840
taatgattca agttgtttta agtccaattt attattaaaa ataattaaat ccataaaagg 900
taaataatca aattcattat attgatctac acctgatatt tttgcatttt taattcaagt 960
tttaattttt aaatgttgct caaaaatttc tgtttttgaa gcttttgttg tattaaaaat 1020
caaacgaata attaatttat ctttaaaata atctttattg ctttcatcaa tttcaataac 1080
actataacta attttgtttt gattttgatt gtcaaccaaa ttaacttgtt ggtttagttt 1140
cgaactaatt gtttgttgac ttttattttt tgctaacaaa ctaaacgatc ctaaaaccat 1200
cgaacttaaa cttattgtcg acaataatat tgctttcttt ttaaatttca t 1251

<210> SEQ ID NO 39
<211> LENGTH: 1887
<212> TYPE: DNA
<213> ORGANISM: Ureaplasma urealyticum

<400> SEQUENCE: 39
ttatttacta ttattttcaa tcttttgcga agttccattt tgtatttttt taacttcttc 60
aattagtttt tttagttttt tattataaag atctaacgta taagaagaca cattattatt 120
gttaattcct tgttcaacaa atttagtaaa tttttttaat ctttctactt tagattcgtt 180
atttgttttt ccattttttg tttcagtaat tttcttactt tcttcaatta attctttagc 240
ttcaggaata tataattttt tatcaacaat cgtaaaaatc ttaacactaa aattttcaat 300
atcttttgtg aacacccttt cttgattatt atctaatttt aaatagttaa ttaactcttt 360
tggttttaat aaaaaatcat tagaataagc taaatcaata ttttctagat tatcaattgt 420
taatgtttga tttgcactaa gttttaaact gactttagta tttattcaag gatcattttt 480
ataactattt aaaacatctt gaattgtttg ggttttatta gttttctttg cttgatcatt 540
ttcactatta actttagtat taaattcttt tagatgttta atgaaatctt tgaataaata 600
agttttttta aagtttgata gaattgtttg tttgatttga tcaacaattg aactaatttt 660
agtattagca tcttcaaatt ttttagttaa ttcattatta agattatttg cactatcaat 720
cgttaagcta tttgtattaa agctaaataa actaataatt gattgtaaat tttcaatttg 780

-continued

```
attttctaaa ccattatatg tagcttttga actattgttt ttgtcttttt ggatattttg    840

ttgtttttca atactatagt aaggattgta atcgtctggt tttaatgatt gaataatact    900

aattaattta ttaatactat tttcactatc taatgcaatt gtatttaaac cttgtaaata    960

attttgtaaa tcatttaata atttattagt taaagattta atttgttcaa tatctaatga   1020

ttttttaaca ttaacaatat tagtgatatt cttgtttaga ttttgtttta aattagttaa   1080

ttttaattga tcaaatcata aaaaactata attttgttgg taaatagtat taataacatt   1140

aacaatatca tctaattttt taataaaagg taaagctttt agttctttgt taattaaatc   1200

attaatatca tttaatttag tgtaaattaa tttaaaatct tcatatagtt ttttaaaatt   1260

agcttttgtg ttattattaa ctaatttttg aatatcactt tcaatctcga caatattttt   1320

atttgatcca gatgttttaa ttaaattttt aattttatta gctaaatcta aaattgtttt   1380

ttgaattaaa gctttagtgt gcaatctttt ttgatgagca tcagatttta gtttatcaat   1440

tattgtagta tcaacacttg cttgattaag taatttttca tattgattta aaaaatcttg   1500

taattgtttt ttagtgtttt ctaattcaac aacatctatt aaatcactca tgtttttgat   1560

tgaatctaat tcatttaaaa cactaacttg tgtaattaaa tttttaattg tttgttgttc   1620

ttgttttaat ttttgctctg ataatttatt aatgttttct aaatttgatt taagagtttg   1680

attatatatc tttttaaaat cttcataaga tgattgatca actatttctt ttaataaaac   1740

agctttattt aaacttgatt gtaattcttc tttagctttt tgttttgtat caacttttgc   1800

acaagctgta attattgttg ctaacaaagg tatagcacta atcatactta gttttaatca   1860

aattcatttg tatttttgt gtttcat                                         1887
```

<210> SEQ ID NO 40
<211> LENGTH: 177
<212> TYPE: DNA
<213> ORGANISM: Ureaplasma urealyticum

<400> SEQUENCE: 40

```
ttaaagtaac aaatctaata aatgtttaat gtcaataata aattttactt tattcgcaac     60

tagttgttct agagttttgt taatacttgt gttttttaaa agatcaaaat taacttttt    120

atttaaaaca gcatttgaac tagctccata aaaataaaaa tctttttgat ttttcat       177
```

<210> SEQ ID NO 41
<211> LENGTH: 426
<212> TYPE: DNA
<213> ORGANISM: Ureaplasma urealyticum

<400> SEQUENCE: 41

```
ttattttaaa ataaaatcag ggtatgaatt acttatttga ccatcttcat taaaatattg     60

atattttaat ccatgaaaaa caggattttt agtccaaagt tcaacattat ttttaatttt    120

atcattatca tttgataatg aaagaaaacg atttgcaaat ttagattcag ttgaagaatc    180

aaaatagtga ttttgttctt taagatcttt atatgcatac ttatcacaaa tgtttaaatc    240

taacatgttt tcacattttt tatatttttc aataggaata aaaatttcat tttgattagg    300

taaattttta ttattttgta atttaaaaag taattcatga ttatcttttt tcatttgttc    360

taatgaattt ttatataatt gttcaaattg atcaagatat tttttgataa taacatatca    420

atacat                                                               426
```

<210> SEQ ID NO 42

-continued

<211> LENGTH: 1017
<212> TYPE: DNA
<213> ORGANISM: Ureaplasma urealyticum

<400> SEQUENCE: 42

```
ttactttttt gatgatttgt ttgctgattc agtttctcat catgtttttt tcgaaattgg     60
atcactttga aattcttctt caattaatac tgtttttaat aataattgtt gtttttttatc   120
taaaccatta ttaatgggta aaacatcatc aattgctttt tctatttgtt cttttccatt    180
ttttttaaca attaaatcat ggccacgatg atgacgttgc gctttatgtt tattatggtg    240
attatctgga tcaatatgtt catattcttc ttctataaag tattcattat taggaaatac    300
tgaactttga ggtgctaata aacattcatc ataaactagt tgtgctagtt cagcttcatc    360
acgtttattt caaacactta catactttga taaccaacta aaatcatttt gatcatcatt    420
aattaaactt tctttttcag aaaataaaga ttctaaaaat aaattttcag catacacttt    480
ttggtttgaa taaatatttt caaaaacagg ttcttcaaat tcaaaagaaa caggagtaaa    540
aggtgtatgt tcttttactg aattatcaac ttcatcaact ggagctacaa tattctcctg    600
tataaattct tcattgcttt gattttcgtt ctttataggc tcaggttcaa cttcttcatg    660
taatggttca ataggtgtag attcatgttc gttaacaata tcatcttctt ggttattaac    720
tggagctgat gatagatcat tgcaatcttg taaaatttgt ggttcatcca ttacaggtat    780
ttgttcttgt tggatgtttg ttaaagctaa attacgtaaa cttttaatcg tttttgtgta    840
atcaactcac ataaaaaacgc cacaattttt gcatcttact ttaacttttt tagtaacaat   900
agtttcatca tataattgat aaatatcttt gttattatct aaaacatcag taatatttat    960
atttttatct tcagttaact tttgatttaa tttatttttc ttactaaata atcccat      1017
```

<210> SEQ ID NO 43
<211> LENGTH: 3399
<212> TYPE: DNA
<213> ORGANISM: Ureaplasma urealyticum

<400> SEQUENCE: 43

```
atggagtttg atatgaaatt taaaaaaatt cttttaacaa gcacattaag tgttttaggg     60
gttatttcaa ttgcaagttt agctacaaat tgttcacaaa cgaaaacaaa aattaaccag    120
tataaaataa ctataaataa attagatagt ctaaatttaa caagtaattt aactacaaaa    180
caagctttaa aagatgtttt attctcaaaa gaaggacaaa atgaattttt attatcaaat    240
gttaaaaaag tggtttatga ttgagcaaaa aacaataatg atccaaaatt agctcatgat    300
gttagtgaat ataatacaca attagatgaa caattaaaga gaattaaaga aaatgtaaaa    360
aaatcatacc caaatgattg acaatctgtt ttacaaagcg aactatatga tactgaaggt    420
ggtagtgaaa aatcatgaaa agaagctaag ttaattgatc aagcatacaa atcaattact    480
tcttcaattt ttgatgataa tgataattga attagtgtat taaatgatca aaatcaacta    540
attgatgcct attcaaatga tgctactaag ttgttagaga atgaaagtac ttttaaatca    600
actaaaattg gagatagaaa caaaattgtt gctaagacaa ataatttttt acaaaaagga    660
tacgctaatt tatttaattt cttaattgat gattatatta aatataacct gcctttatca    720
tttgccaaca ttgaatttaa atatgatgat ttaaaaaatc aaaacattta taataaagat    780
ttttttacaa aaataccaac ttctggcaca tcacctaatt ttccttgatt tgatcctaaa    840
ccaactgata ataaatcaac taacactaca actaattatc tagaagtagc taaattatta    900
aaagaaaata aatacttaga ttcaaaagat gatacgaata atattgacaa aaaattcaac    960
```

-continued

```
aacaataatg atattaataa atatttaagc ttaaatgatt ttattactca agacaacaca   1020
aatttaacat taagtgtcgg tttattagct aaatttttat cattatttgg aaatgaaaat   1080
tttggtattt atcaattaga taatttagat gaaaataata ttttaaacaa ttttattagt   1140
aagaatcaaa gtaatgcaaa cacaaataat gttgatttat tttatccttt agttaaaaaa   1200
gataaaacag ctttttttaaa tgattttaag gatgttaaag ctatccgtca aattaatgat   1260
ttaaaaaatg gatatactct attacgtaat gaaaacagtg ttgatttatg aggtattaac   1320
aattttaaaa gacttcaaca agcagctaaa ataggtttga acgctctatt aacagagtta   1380
aaaaatgatt ttttatacaa tggtgcacta tacttaaatt cacgcaaatc aaatagtgtt   1440
aaaaaacaag gctatgatat taaagctaaa attaaagatt actttaataa caataaagag   1500
cgcttattag cactatatat tgctacacat caaaacgata gtgatttttt gtttaaatca   1560
aacttaaaaa atgattcaaa agtttttgca tttgatcaaa gaacaattaa tattattaaa   1620
gaaaacaatg aaattcattt attaaattac tatgataatt taattgataa gttaaatgat   1680
aaattaatta aatttaataa aaaaacattt attattccta gtgttgatag tttatatgat   1740
aatggaatta atacaccaat ttacttaatt aaagaccaaa atcaacaaat tagtttattt   1800
caaactttaa aaataaaact agtgggtaat aaaaatctta tagatgaaaa tcaaaaatta   1860
tctacaatga ttaatgatta tgttgaaaac tttgatataa aaaaacacct tgttgctaat   1920
aataaaaact cccaatcaat tgtttttgac gattatgtta taaataaagt atttagtaaa   1980
ggaataaaca gtgtttttgc aaatattatt aaacaagaac aaattaaaaa aagtgtagca   2040
aaattctttg aatttaatga ttttaatttt aaaaataatt ttcttgaaaa ccaagaatta   2100
ttagcagcat ttaaccaaat tattaagaat acaagtgttt tggaaacaac acaaactaat   2160
aattttagta attttgataa cttaaaaaaa gtttatgaac aagctttgaa attatgaaac   2220
gataattata ctaaaaatgg ccttttttaat cagttatcaa tcaattatca aaaataccaa   2280
gcattatttg aaacactcgc tattattaat tacttgttag attttaaaga tggtaaacca   2340
acatatcaaa atttaattaa ttacttgtta aaaaaaactg ctaatcatca accattattt   2400
attggttgaa aagctttaaa tgatgtaact aaaattccta attttggaaa agattctaaa   2460
gaagatttta gtttcaagaa ataccaaatt aatttatata atggacttga cctataccaa   2520
ttaaaaaaag ctgatgttta tgaaattgac caaaatagtc aagaagttaa attcaaaaaa   2580
acttttatag atgcattaac atacactaac gataaaaatt attgaaactc aaccgttaat   2640
aaagatggtt cagtttataa taattttatt ggcttaattg atcaaaataa tcaaaaagat   2700
aaattaggta aagcttttga aaaaatcgac ttgtttgata aattagttta cgctaataac   2760
ccaagtaaac aatttaaagg tgcactatat ggttatggta gtagagaatt attaattaaa   2820
acattagatg gttttgtgtc ttatcatgac taccaaacac ttgcacaatt actttatgat   2880
ctaaatttta atgcagaagc taatgctgaa tttaaaacta ttttagataa ccaaaaacaa   2940
attattcctg gcaatcaaaa agatagtaaa ataaaaaata ttgatttagc aactaatgaa   3000
attaaaacaa ttatgattaa aggaattaat aaaatccccc aaactgcctt tcaaagatta   3060
gatttagatt tagtttataa caaattagac aaaaatgcta caccattagt taataaagaa   3120
gataatgcta atttaaaata tattttatta gtttcacaat ttaatgcaaa tgatgtgcaa   3180
aatttagtta ttaacaatca attaaatcaa agtgcaacag gatatttagg attgtcaaaa   3240
agccaatttt ataacttatt atttgattta gcattaaatg atcaaacttt aaaaattgaa   3300
```

-continued

```
gcttttagtc aaattgaaaa cgaacataaa attaaagttt acgataaacg tttagctaat   3360

aatagtaatt taaaaggttg aatcataaat aatctataa                          3399
```

<210> SEQ ID NO 44
<211> LENGTH: 471
<212> TYPE: DNA
<213> ORGANISM: Ureaplasma urealyticum

<400> SEQUENCE: 44

```
ttactcgctt tcttttttag tatcttcttg ttgatcttta atcacttttt gatcttcttt     60

attatttttt tgaaaattac gaaaccaatt cttaactaat tttttatctt ttaattctgg    120

aatataaacg tttgaataag atcaataagc aaaaatatta atattaataa taataattaa    180

aaacgaactt attccaagaa ttgaaccata tttaaatatt ttaatttggt tataaggaga    240

atctaaatga aaatttttgg ttttaaaaat tttaataata ttttgttttc attcgttata    300

ttcatcaatt cgcgcataat aatctttgat atagtatgat aaacgaacag ccgatcagat    360

taaaattgct aataaaattg ctacaaaaac atatgaaata atcgtaataa ttttaaaacc    420

ctcgattgtt tttaaaaaat cataaaattt tttacctttt ttgttattca t             471
```

<210> SEQ ID NO 45
<211> LENGTH: 819
<212> TYPE: DNA
<213> ORGANISM: Ureaplasma urealyticum

<400> SEQUENCE: 45

```
ttattttcct ttttgatcat cttcaacttt atattttatt cgttcatttg ctttattacg     60

ctttttttaat tctaaacgtt ttttgttaaa ttcattataa tattgttctg aatctttaag    120

ttcattgtat agatctgcag catatgtctc aaaatgtttt gagcgattca taatagcatt    180

tgtaattttt gtcatgataa aaattggtaa aataaaagca actactaaaa ttaaaaatcg    240

tactaaatat cctcaaattt gactaggaat aaatccagaa ataattaaaa taaacattcc    300

aaatcaacat gaaactactg gcgtaagaat gtctcaacga atctttggcg tactaaaagc    360

aaatataata catacaataa ctgctaatcc taaagttgaa aacattgcaa ctcaaactgg    420

atatgaacta attatatttg taccaaattc aacaccatga ttgtattgat tagtaatttc    480

attaactaat ttttgcattc tttcaatcat aagaggaccc ggttttggtt ttaattgatc    540

atatacaata ggatttcaat gataaaaatc tttaactcct acaatccatt gttggttttc    600

atctaattta aaaccttttc catatcaacg accattaaca ccaattattc cattaaaacc    660

taaaagattg atttcaccat ataaaataaa aaaaacaatc attggaatga caacaaaaaa    720

tgatgtaatt aaaaatttat ataaaagagg tgatttaaaa cgtgtattag tttcaaaggg    780

ttttctaaat caagtagttt ttgaatgcct taaattcat                           819
```

<210> SEQ ID NO 46
<211> LENGTH: 2349
<212> TYPE: DNA
<213> ORGANISM: Ureaplasma urealyticum

<400> SEQUENCE: 46

```
atgaaattta ttaaacgtaa aacaaaatta ttaacgatta caattggtgc agttgctgtt     60

agttcaatct tattaggagg aattttttat ggtacaagtc aaaaaagtcc ctcaagtttt    120

ggtattgctt ctattgatca aaaagaaaat tttattaata aagacaattt agattaccaa    180

aaagcaagac catcaattaa agatagtaac ttaaaagaaa ttcccaaacc taaacctcaa    240
```

-continued

```
ccaaaaccta agcctcaacc aactccattt ccagatccca tcccaacacc tccaaaaaaa    300
gaagagctaa aaaaaccaga tattaaacca gaagaaccta aaaaacctga aattaaacca    360
gaaccaaaac ctgagcctat tcctcaacca gcccctccta ttgaaacaaa accaaaagaa    420
gaattattac cacccaaccc tccgcctcca aaagaagaac caaaaccaga accaaatccg    480
caaccacagc cacaacaggt tccaaacaat agtaattcac gaattataga aattaatggt    540
gtaagagtgg aagctgaagt tgaagtccct ccccctcgtg atattgctga atatgataaa    600
caaaataatc tggttaaccc taatccatac attaatgata gtgttggtaa aattaaaaac    660
gtaaaggtta ccgatgaatt gcgaaaagca acaggtaaat tggtccaagg aaatttagga    720
cgttgagatt acaaacattt aattaatgat ttattaactc ttaaaccaga ggaaatagaa    780
aaatatgtaa aaaacgataa aagcggttat tatgcaaaag tttgatatcg tttttcaaga    840
ttatttgaat ctgaaaatgt tgttaatttt ttaactgaac aaggtaaaaa agaatatcct    900
gaaatgaagt ctaaatttgt ttcaaaagac cataaatatg catggcttta tcaacattta    960
gacttaacaa agtttacaca attatcaaat gaatcagaat cttatttaaa agaaggctat   1020
acacctgatc ctgataatgc atatgttgat gaaaatggaa aaattagttc tcacgcatat   1080
tcacctgcca aggttataa ttcggtaaca agtcgaatgg aaaatgataa ttgaaatcgg    1140
cgtgttttcg gttataaaag ttggtatgga cgtactcctg gaaatttagt tgaaggtaat   1200
tatcctggtt gaaagaaaac aaatgtaacc caagaattcc atcaatatgg cgttagcgat   1260
ggtgatggaa ttacagttaa taaattaact cgtgaaaaaa ctgaagatgg tcgtttaaat   1320
gaaggatatg ttattgatat tgatgctgat aatccacaag gttatgaaaa aacaaaaaaa   1380
ttaattcaaa ctttaaaaga aaaaaatatc aatatcacag ggtatagaat tcataatatg   1440
gggaaatcag attcaagtca aaaatttgtt gatattctaa aaacattacc aaatcaattg   1500
cctttattag aattgttttt ctccgctggt tcgcataata cctcttcatt aatcgcactg   1560
aaggataaaa aaattaaaga attaggtttg ttcacactag gaaattcatt attagatgaa   1620
tgatcaatta atcctaatgc cttacgaaat gttgaatgaa ttaattcaaa cgattataat   1680
gtttcattta attataaaca aggtgcagat atcgctactc gtattacttt tgatacttta   1740
gcttttgatg aaagtgatta taatgacaat gcatctgaca ttaaatcaaa attaaaacaa   1800
attaatgatg gtttacgaat ggtttattga acaagaaata atgaaccaat ttttcagggt   1860
agttttggac ctggtttaga tcctgaccac aaagaatcag gcaacagtta tccacaagga   1920
ttagatttta gtcgtgtccc tcaaattcgc tcattacggg gtttaatatt taaagatgaa   1980
caaaaaacat caaataataa agatcgtaaa ttacgaagaa ttaattttta caataacagc   2040
acaacttata aaatgtctat tgaggactta aatgaagccg gatttaacga acatattgta   2100
agtggtgaac ctggtgaaaa aagtaaaatt acttttagca atggttctgg tacaactaaa   2160
atccaaattg atggtgatca agaattgtca gcaaatggaa ttagtaactt atcagcaatg   2220
tttaattttg ctgaaagttt acaacggaca attgttgtaa ataataccaa ctcaccactt   2280
gcaaatcaac taagaaatgc gggatatagt gttgaatcaa caactaacgc tggactaata   2340
gatatttaa                                                           2349
```

<210> SEQ ID NO 47
<211> LENGTH: 192
<212> TYPE: DNA
<213> ORGANISM: Ureaplasma urealyticum -continued

<400> SEQUENCE: 47

```
atggaattag cagctattgc tcatgtatgc acgcgtatgt taacaccact agtaagtatt     60
aaattagtta gtgatcatat tactcttccc aattccaatc aagaacagtt taataaaaac    120
ttatcactaa ttgataaatg atttaatgag catttaccat ccattattga agcaatttta    180
gagatctact aa                                                         192
```

<210> SEQ ID NO 48
<211> LENGTH: 252
<212> TYPE: DNA
<213> ORGANISM: Ureaplasma urealyticum

<400> SEQUENCE: 48

```
atgatttata aagaaattgt tcgtaatatt atcaagcatc cattaatctt accagaagga     60
aaacattacc atttacataa aattctaact tcaaaagatg aattacgtaa gggtgaagtt    120
agtttagttg cagaaaatgg caaagaatac actgttgatt tatctgcatt tgttgactta    180
ttagttgatg gtgattgcat tattgatgat aatcattcac ttgttgcttt atactttgat    240
gaaagtaaat aa                                                         252
```

<210> SEQ ID NO 49
<211> LENGTH: 2328
<212> TYPE: DNA
<213> ORGANISM: Ureaplasma urealyticum

<400> SEQUENCE: 49

```
atgaaatcaa ataataaaaa ttacaaattt ttgaacataa aaaaacggaa atatcgcatt     60
ttttttatgt tgtgttcttt aaatttaata tgagcaggcg ttattatagc tattgttctg    120
cgtttaaaaa atattgataa acgctttagt gaaaatgacc ataaaattgc tcgtccaact    180
tgagagtatg ataatgatgg aaatttagag attcacactc aattagcaaa tgatttaaat    240
gatgatttaa aacaaaaagc tttaaataat gcaaatgtca aaggaattgt tgttgaccaa    300
aatggtgtag aacatgagat agatgtaagt attgatgcta atggtaaggt tattattcca    360
acaaaagatt tagtaaataa tgacccaact aaacctaata tatacacact taaaaaagtc    420
gttttaaaac aacataatca accaaatatt gatctaatta gtgaagagca attaagtggt    480
gataatcata tttcatttaa aaaaccaaca gtggttgctc aaattaatga taacaatgat    540
tatataatgc attttacgaa tcctaattta gttaacaaga aaattaaatt aacatttaaa    600
gttgatgatc aagatgatca tacaaaaacc attgaagcta tcattggatt agatggaaag    660
gctattttta aaacaagtga tgatgcaatt tttgcaccag atcataaata tacactaaca    720
aaaattgaag ctaataacaa aaaagttgct aacattgatg aaattccatt aaaaaataga    780
atcgttgata aaaatccaat taaaagaatt aacttaacac aactaaaagt tgctaaagat    840
ttaattcttt gaaataatac aaaccaaaac caattcataa ctgctacttt taaaaatata    900
aataacgatt ttgatgatta tattgttaaa ttaatttatg aatacaatta tcgtggagaa    960
atgaaagaaa ttgcatcaca acctttcaaa ttagaaaaaa ataaaacaac atacaacaat   1020
atccttttgc caattagtat tccaaatcgc ttatatcatt ttaaaaaagt agtaattcaa   1080
aaattaaatc aaccaaataa atctattgat ttagatcatg atccaaattt aaaatctttt   1140
tttattgttg gtcctggtaa aacagatttt gcatgaaaaa aaccaaatga tgatcaaatt   1200
acatatgatg gtttaaagag attaaatatt gaaattactt ctcaagatta tgcattacaa   1260
aatggtaaaa aagttatggt ttggtttaaa tcagatgccg aaccaaataa tgattcactt   1320
```

-continued

```
aaatttatag gcgaattatc tcaaactaac gccaatggaa cagctgctgt cattaataat   1380
ttaaataatt tatacggtat gaaagaacaa acagagtatt acatctataa aattcagttc   1440
atagatgaat tagaatattc aaaattacca ccaaaccgta ataacattgt ttatgaatat   1500
aataaaaata ttgcacgtaa ttatgcattc cgaactaaaa ctgccccttt aattttagaa   1560
aaaatagaaa aagatgataa tggtagcatt ggaggacaaa atttttattt ttacctaaat   1620
aaagctagtg atgatcctag tacaatcaag caagttacta tatattgtcg tgataataat   1680
aatgaattat atacttctga tgatcaagaa atagattctg ttgatcttgt atatcattct   1740
tgaattcatg atttaaaatg aaatcgtgaa tatgtttttg atcatgctga aatacaaaca   1800
acatatcctg atgatcctga atatggtggt gaaacaaatg atttagaaat taaaagagga   1860
ttaactttca agttttatac accaccaagt aaaacagaaa tacagtgaaa acatcctata   1920
aaaataacta ataatggggc aattttagat attcaattac aatcaaaaga tcgggcattt   1980
gaagataagc aaaaatatcg agtgacatta gttgaagctg aaaatcaaaa caatgctgtt   2040
gttggtgact tttacttgc tggcacttct attaataaaa atgatagccc aattggtgat   2100
aataatgata agaacaaaga tatagcaact ttgagctgta attttgaaaa caaattaaaa   2160
aaagggacta aatacttatt aaaagaagtt cgatttattg ctaatccaaa tgaagaaatt   2220
agtgctaaac ctactagagc tgctagacca tttaataatg ataatattat ttatagtttg   2280
aatctacgaa taaatgatcc ctatgacttt acaactttaa aaaattag                2328
```

<210> SEQ ID NO 50
<211> LENGTH: 3942
<212> TYPE: DNA
<213> ORGANISM: Ureaplasma urealyticum

<400> SEQUENCE: 50

```
atgaaagtaa ataaaataat tatgaaaaaa agagttaata aaatatataa acacaatatg     60
tttattttgc tagctacttt aaatttagtg tgagcaggcg ttatcacagg aattgtttta    120
agactaaaaa gtaaagatta ctcaaagcat actatcttaa aaaaatatta ttcatttgat    180
aaaaacggca atttaattct taaaggttat ttaaaaccac atgataatac taattatgtt    240
tttgggattt ttagcgatga aagcaatcaa gaacataaaa ttcaagcact tgttaatgat    300
aaaaaaggat ttgaatttaa cactaaatca ttaccactaa accatagtta caaacttaaa    360
aaagttacaa gtattaatga ctataaccat gttttattaa caaatgatga tttagttagt    420
cagcaaaaaa tttgttttag taagccagtt gatgcaaaag ttaactttat taataataaa    480
aaagtttatc aagttaaact aaacacgtta ttaaaaaaca ctttaattca attaacacta    540
aaagacttag agcataacgt atataaaatt acagccaaat caaatgatat gggagaagtt    600
agttttgatg tttcacaatt aaaaaataat aatttatatg aggtaattgc tttacaaaca    660
caagaccaaa ctaaaatcgt taatgttaat gagattgaat acaacaataa gatcataaat    720
aatttaaata ttgatgaatt aaatacacca taccaatata gcaaaaatgg tcatcttaac    780
ttaattgcta agataccatt acgctatgct aatgaacaag tctatggtgt ttttgaagac    840
caaaataacc aaaaacattt aattcctgcc gtaaataaaa atgatggaac aataatgttt    900
gatactcaag ttttaactaa aaatcccaat aaaaaatatc atttacaaaa agttgtttta    960
gcaaaaaatc aaaatcaaat tttaatacat aattttgatt tagtaagtaa tcaaaaacaa   1020
gatatcttct taaaagaata taaagttatt agtattagtg ctctagaaaa tgatgctgat   1080
```

-continued

```
aaaactaaaa gagaaatcaa tttaaaacta tctaacataa aaaatgactg agttaataag   1140
caaattaaag ttatttattc aagttcagat ggttcagatg ttcaaactca acctttagtt   1200
ttagaaaaaa atcaaacaaa ctatgtatta aaactaaata atttaaaagc aaatcgttta   1260
tatacactaa aggcggttga attaataaat aacaatggta aaactaattt accattagat   1320
actaacttaa ctaatagttt tatggttgaa agaactagtg ctgtattagc aacaagtatt   1380
agtgaaataa gtaatcgttt gggaactgct ttaacgaatg cacaagttaa aatcacttta   1440
aaagatgtgg ataatgtttt attagctaat caaaaagcga ttattaacta tggtaataat   1500
caaaagagtg aagcaactgt tattgttaac aatggtgtta agtatctaat agcaacctta   1560
actaaattaa cattaaatac gcctacaata attaaatcca ttacatttga acaaaaacca   1620
acatgtgcta ttgaaaatat tgggttagat aaaacaaata acattattta tcaaaataca   1680
catgaagcag caattccttt agtaattaat aataattttg aaatcaatgg gccattagca   1740
tcaagtcatg aaagtttaaa aagtattaat gcatctgatg ctaaaaaggt aaatgcaatt   1800
aatttaaccc ttgactttaa taccaatgaa catatttata aaaatttatt ttttaaacta   1860
aaatatgtcc ctattgacga tcaaggtaat gaaaatattt atgacgcatc agaagcaatt   1920
tatagtgatg ttttaagtgc aaataatata attgctaata aaatccaatt tagtttaggt   1980
aatttacaaa ctaatcgtaa atataaatta aaaacaattt attatttaac atcaaaaaca   2040
acacctttag atgatcataa cgttgtaatg atcaaaccaa atgttaaatc cgaaattatt   2100
gttgccccta atgatagtac gattgtaaaa tatggtaatt gaaatcaaga ttcaattact   2160
aatggatcaa aggctatttt taaaattaat tgtaatgatg gtgatatttt aagtgaggat   2220
ttaagtgcta cacttgttta tgaatctaat gatcctcatg atttacaatc atacactaca   2280
aaactaaaaa aagttaacaa tgattgggtg attgatttta atttaaataa tttaaaacca   2340
caaaccactt accatttaaa atcaataaca atagcaaaac caaataaagc atatactaat   2400
ttaaaaattc aatcacttcc acaagtggat attaaaacgc aattacctaa tttaatcttg   2460
catgatttaa aagccacaag tgcggtttta aaatgggatt ctactaacaa tggtaaaaac   2520
aatcaccaaa caattcaagc aactttttct catgtaagtg ctaattatga taatcttaat   2580
gttaaattgg tttatgaata taattatcgg ggtgatatca aagcagttga atctgattta   2640
attactctta aaaaagacca aaatgtttat caaataaatt taccaatcag cgttcctaac   2700
cgaaaatata cttttaagaa agttttaatt caagaacgca ataatttaaa caactatgtg   2760
gatttaaata aaaagataaa cttaacagat tcatttgtag ttagccctgg aaaaacaaca   2820
tttgaatgaa cacaaccaac tagtgatcaa attagtcaaa caaccctaaa agcattaaaa   2880
attaaaattc tttcagaaga taaaacgctt gataataatg ttaaggttat tgtgtgattt   2940
aaatcccata cagattcaaa tgatgcactt aaatgaacac ggggaacttg ggaggttaat   3000
agtgatggat cagaagcgat tattaatcaa ttaaataact taagtggatt taaagcagga   3060
acgcaatact atctttataa aattgcattt gttgataatc tacaatatgg aaatacgcaa   3120
gcgaatgata ataaagtaat ttatgaatga aaagccaatg atactaaaga atatgaattt   3180
acaatgaaaa atgcaccaac aattttacaa tcaataaaat ttgaaaattg tgatgctaat   3240
ggtgtaatta ataatgaagc ggaaggaatt gcagaatttt caatgacaac aaacaaggtt   3300
aatgatgatt ttgctaaccg aaaagttaaa ttcatatatc atgacaataa caatgttgct   3360
tatgaaactg atggttttcc attaagcaga tcagaaacaa gtcttcattt ttctttatca   3420
aacatcccta acaaccgcga ctatactttt gaccatgctg aaattgaaac tagtcctaat   3480
```

agtaataaat atgaaatttg acattctcaa aacaagataa tatctaagtt caaacttaaa 3540
ccagctcaaa cttctgtaaa atatattgat aaacaagaaa gaaataataa taatgtagat 3600
tttgagcttc atttaggttc aagagactgt gcatttgaaa ataaccaaaa atatcgtgtt 3660
acactagtgt cagtagacgc actccaaacc gaaatttcta aggaattttt actttctgat 3720
gttaaattag attatcaaga tggtaatatt ggaatattaa aatgccattt tgataactta 3780
ataccaaaca ccggatatac attaaaagaa attaaatttc ttgctaaccc aaatgaacaa 3840
caaagtgcaa aaccacataa ggtaattaaa ccttttaatg atgataacaa tgttattatc 3900
gataaaaatt attcttgaaa atgatatatt tatccttcat aa 3942

<210> SEQ ID NO 51
<211> LENGTH: 1851
<212> TYPE: DNA
<213> ORGANISM: Ureaplasma urealyticum

<400> SEQUENCE: 51
ttaatgctgt ggtttttaa tttcttcaat cagttttgtt aatctttgaa tataaagatt 60
aagagtataa gaagaaacat tttcattact tattccttgt tcaacaaaac tagtgaattt 120
ttctaatcgt tgtaattttg ctttattatt tgtatgttca ttttttgttt gaataatttt 180
tttgctttca tcaattaatt ctttagcttt gggaatataa agtttttat caatgatagt 240 aaaaactcta acactaagat tttcaagttc tttgctaaat tctctttctt gattattatt 300
taattctaaa taagcgatta attcttgtgg tttttgcagc gaatcagaag catatgttaa 360
atcaattttt tcaagattat ttactgttaa tacttcgttt ggagcaagtt ttaaattaat 420
tttagtattt aaaaataaat ccttttcata actttttaag acttcttgaa tggtttgaat 480
tcgattagct ttttttattg gatcgttttc attatttaat tcaatattaa actcttttaa 540
atgtttaatg aagtacttaa ataaataaat ttgtttaaaa tttgataaaa tggtttgttt 600
aattttaatc acaacatcat taatttgtga attagctttt tgaaattttt taattaattc 660
atcattaaga ttatagattg catcaattga taaattagta atgttaaaat caaataagtt 720
aatgattgat tttaaacttt taatttggtg ttctaaacca ttatatgttg cttgagaatt 780
gttttcatct ttttgcttat tttcttgttt ttcaatacta tagtaaggat tataatcatc 840
tggttgtaat gattcaataa tactgattaa tttgttaaca ctattttcac tttctaacgc 900
aatcattttt aaaccttcta agtaattttg aaggtcaacc aaaagttgat tagttaaagt 960
tttaatttct ttgatctcta atgtcttttt aacatttaat acatgattta tattctttat 1020
taaaatttgt cttaaatttg ttaatttagt ttgatcaaat catagaaaat gatgattttg 1080
ttcataaata gtattaataa cattaactat atcatctaat tttttaataa aaggtaaagc 1140
ttttagttct ttgttaatta agtcattaat atcatttaat ttagtgtaaa ttaatttaaa 1200
atcttcatat agtttttaa aattagcttt tgtgtcatta ttaactaatt tttgaatatc 1260
attttcaagc tcaacaatgt ttttatttaa tccagatgtt ttaattaggc ttttaatttt 1320
attagctaaa tctaaaattg ttttttgaat taaagctttg gtgtctaatc ttttttgatg 1380
agcatcagat tttagtttat caattattgt agtatcaaca cttgcttgat taagtaattt 1440
ttcatattga tttaaaaaat cttgtaattg ttttttagtg ttttctaatt caacaacatc 1500
tattaaatca ctcatgtttt tgattgaatc taattcattt aaaacactaa cttgtgtaat 1560
taaattttta attgtttgtt gttcttgttt taatttttgc tctgataatt tattaatgtt 1620

-continued

```
ttctaaattt gatttaagag tttgattata tatcttttta aaatcttcat aagatgattg   1680

atcaactatt tcttttaata aaacagcttt atttaaactt gattgtaatt cttctttagc   1740

tttttgtttt gtatcaactt ttgcacaagt tgtaattatt gttgctaaca aaggtatagc   1800

actaatcata cttagtttca atcaaattga tttgtatttt ttgtgtttca t            1851
```

```
<210> SEQ ID NO 52
<211> LENGTH: 2478
<212> TYPE: DNA
<213> ORGANISM: Ureaplasma urealyticum

<400> SEQUENCE: 52

ttaaagtaag aaatctaata aatgtttaat gtcaataata aattttgctt tattcgcaac     60

tagttgttct ggagttttgt taatacttgt ctttttttaaa agatcaaaat taactttttt    120

atttaaaaca tcatttgaac tagctccata aaaataaaaa tctttttgat tttcatattt    180

aatataacaa actaaaatcg taatttctgc tttgtctaat tcatctaata ttaaattatc    240

gttattgttt ttattttcaa tatatcgttg atatgattca attaataatt ttgttttttc    300

ataatcataa tcactatata aatttttttac ttcaatatat aaataatgat ctttttgatc    360

atgtgttttt atttttaaaa taaaatcagg gtatgaatta cttatttgac catcttcatt    420

aaaatattga tattttaatc catgaaaaac aggattttta gtccaaagtt caacattatt    480

tttaatttta tcattatcat ttgataatga aaggaaacga tttgcaaatt tagattcagt    540

taaagaatca aaatagtgat tttgttcttt aagatcttta tatgcatact tatcacaaac    600

atttaaatct aacatgtttt cacatttttt atatttttca atgggaataa aaatttcatt    660

ttgattaggt aaatttttat tattttgcaa tttaaaaagt aattcatgat tatctttttt    720

catttgttct aatgaatttt tatatatttt ttcaatttga tcaagatatt ctttaataat    780

aacatatcaa tacatgttga tgcttatgtt taattttcat cttttttctc actcattaaa    840

cttcgtttca agaaaatcaa taattttttg aggaaataga tgtttgtatt ttcttaattg    900

ttcaataata taaagttcaa gttcgattga atttttaatt ttagtataaa cacgtgtttt    960

accttcaatt tttgaagttt cgccttctaa gtattgattt tttacaaaat tttcacgata   1020

ttcctcatta acatagtatt caaaattact aattgaatct tcaaacttct ctactatttc   1080

ttctttataa gtttctccat ttaaatagtt attaattttc tcttgattaa tttcgccata   1140

aaaaaatcta tcatttttat atttgtcttt taaaatcaaa gtttgacgaa ttttatcttc   1200

tgaaataata ttagaataaa taaaatattg atttgatatg gaattatagc taatttcgtt   1260

tttgtcaaag ctaggatttg gaaaacgctt aattcttcca attgtttgta ctgataaatt   1320

ttttgaagaa acgtttcgca attgtactaa catgcaagca cgcggaatat ttcaaccagt   1380

tgcaggacca attttaaaca aaattacatc cacatttgaa gtctttttag aaatttcttt   1440

tagagaaatt ttattatttt ttttattaat taaaatatta gtttgaacct ctttatcatt   1500

agaaaagtat ttaactcatg ataaattatg tttttctaaa attttaataa tttttttcaat   1560

tttatctaaa aattcgcttt tttgtggttc tttattaggt tcattttcaa cttgaattaa   1620

catggctgga cgaatatttt ttaactcttt tgcttttgaa tattgctctt tgatttttaa   1680

aaattgctca caagcagttg ttaataatag ttcatcatca atgttttctt cttttagttc   1740

tttaatttct agattataaa catgttcatc ttttaacaat tttgtatcat catccattaa   1800

atctttttca tcaatgaata ctaatttatg aattccttta ggagttgctg tcattttaat   1860

aataaaagat gctgcttctt gaattttata ttcaaatcgt gtttcttctt ttttaaaaga   1920
```

-continued

```
atttttgtgt attttttcat caaaatcttc aaatattttt gttttattaa cattaccgcc   1980

atgatgagct tcatcacgga tataaactaa tgtatatcct tgtgatttaa tttcatctaa   2040

aaaagcatct aaaattcctt cttctgtaat aattcttcct ttaccaaatg aagaagaccc   2100

aaaaataatt actttatttt cttcagctaa aatattgtaa gaactatctt ttttagcact   2160

tttagaagat ggtgattctt taagttcgac atcaaataaa ccattaatat aatatttata   2220

ctcattcata ttttgttcta attgaaatgg taaatcagct gatgataaag tcgcaattac   2280

aaaaattaat ttttgaggac taccattagc tttgtttgtc ttaataattt cattaatagt   2340

attggtaata ataaaggttt taccagatcc tgttggtgct tgaaaatcaa taatttcttt   2400

tttattgtta ttcacgcttt ctaaataaca attaactaat tgactaacag ctttttgttg   2460

tgatttggtt aatttcat                                                 2478
```

<210> SEQ ID NO 53
<211> LENGTH: 351
<212> TYPE: DNA
<213> ORGANISM: Ureaplasma urealyticum

<400> SEQUENCE: 53

```
ctagtctctc tctctctctc tctctaacac taataaattc tttagtacat catagttttc     60

accaatgatt aaactattag tatcattttt aaataaatta tgtgcatcat tcatgaaaga    120

taattgctca tttttagcta atatcgcaat ttgagtttgg tgcacgcttg gagcaacatc    180

aaaactaaat cctattttaa cacgttgaat taataattga aacacattat ctaaatcctg    240

gggatcagtt ttttctaaaa tttttttaat taattgtttt tgatcctcat ttaatgaact    300

cttactcatt tcatcaatgt cttttaaata actatttaaa tctttaatca t             351
```

<210> SEQ ID NO 54
<211> LENGTH: 3078
<212> TYPE: DNA
<213> ORGANISM: Ureaplasma urealyticum

<400> SEQUENCE: 54

```
ttaattagtt gttgtaaatg aataatcatt gtgttgagga ttatcttttt ttgcttgatt     60

acggttataa atttcgttat tgttattagc aaaatttcat ttataagtta aataatttgg    120

cttttcacta aagtaaatac gattgatata gtattttgta ttcggttcta aattattaat    180

tttattttct gatattaatc atgatgttaa acctgtttgt aattcttgat gtttattagg    240

gtcaatatga tttttaatta atccatcaaa ttctttatct gttttcgaaa gtgtgatttg    300

ataaggtcct ttaatatttc ctttatcatc aattaattct aaattagcaa ctaaaccatc    360

atgaaaagct tggtcgtggg aaattaattc taaattaaga ttaacttggg ttggtgaaat    420

gtttttaata tacttatttt ctttattttc attaaaatca cttgcagttg ttaaaatcgt    480

gttttgactt ggacgacaac gaattgttat agagctttga ttaaaaattg ttcaagtatt    540

atcatcgttt aaaacttcta ttcgttcaaa attatattct cgattagcaa ttggtaatgg    600

aattttaaca tacatacggt tttttaattt aaataaaaga ttttctctat taattatttg    660

atcactacta ccaatatcat tgctataagc cataaactct ttttttgtgc catcaactgt    720

tgtataagaa aaaacaaaac gtgctttttt atttactaat caaggatatt taacatttaa    780

aataaataat ttcacttcac aaactggatg attagttttt ttatcaacat caagtgtgtt    840

ttttagatat ttttccacca aagctattga taaaggattt tgtaattcaa aattataagt    900
```

-continued

```
aatttgattt aatttatgtt tttcatctaa attatttgga ttatttttat ctaaataata    960
aatattatct agttcatata atgtagcagt tttaatgtca tcaaacttta aattaaattc   1020
gatcattcac ttatttattt catttttaat tggtgtacaa ctaatagcgt tagttttaat   1080
tttttgaca atcttgttgt ctttgtattt aaaagttgca gcaaatgtaa ggttttttag   1140
aatattagag ttggctttta attcaacttt taatttaata ttagcttcat ttttacgttg   1200
aaaataatct tcttggtttt ctaatggtaa taatgcaaaa ttattattga ttgtcaaagg   1260
ttgatttttt tcttcttttg tatcatcata aataatatta gtatctaaat aaccaatatt   1320
tacaattgct ttaggcggct tttgatcaaa ttcaatttta ttaataaaag atgttttatt   1380
taattctaaa ttatctaatc gagctgttaa atatttttta ttattttcag ccactacatg   1440
agcttttgta attttattat catcataatt aatagttgca ctcatatttg tatttaaaac   1500
attggcttca tcactaattt caaactttat atttgttgaa ttaatactat ttggtgatcg   1560
cggttcttca actagtgaac ttgttaaaac tttaactaag ggttttttaa taatcacttt   1620
gttaatttct aaaatatcat ctaaattcgc aatattgtta ttgactgtta gtttattatc   1680
aacaattcca attaatgtat atttatgatt tggcgcaaat aaagtattat catttgtctt   1740
tagtgttatt tttttattaa catctactat tgcttgtatt gtttttattt cattggtatt   1800
atcaattttg aatctaagtt caatcttttt attaattaaa tttgcatcgt taaaatttat   1860
tgtataatcc ccgtttttta aataattaac cactatattt ggtctattaa gagtttgttt   1920
ttgattgcta gataaatcaa aattgtgtac gaattcaata ttttcatcac tagcagaaac   1980
aatttttttct aatcgatact ggtttggttt tactaatttt ccaatatcaa aacaaatctg   2040
accatcatta tcaactttag ctaataattt atgtaattta tgattttgat ctttaaaaat   2100
cccatatact tgttggttaa cataatatgg cgctacttta gcaattaaat taatatcacc   2160
attttttgta tactgatatg gttggtttaa actattaaca tttaaattgt taatagtttt   2220
attatgatat gcgatattaa ctggattaat aactttaact aaaggatgcg tgttattttt   2280
ataaatgtta actaattcat agaagttatt atttgctaat ttacttacat caaaatcaac   2340
atttccttct acatctactt tagcatcaat actataaatt tgattattta aatcttttag   2400
ttgcaaacta agagaagaat taaataatca ctttcctaca tttattcggt atatttttttg  2460
attattttgg ttaataaaag aagctgtttt aggtggttta ctaatcataa tttgatgttc   2520
aatcgctaac tcattttgtt gaattaaaac gtgattgtaa tcagttttgt caagaatttt   2580
tactaaacga taatcatgat tatttgctaa ttttgatgta ttaaaataag caactttatc   2640
tttaatagtt ggttgtatgt aatgatattg atgcttttca tcaacaaaaa cacccataat   2700
ttgcggattc tttttagctt tgttttttaa attaacttta ataacaatat caccagtatt   2760
tgaatattca ttggttttat ctatcttaga taaagttaaa ccaattatgg aattagacaa   2820
tttatttttt tgtaatcgat aaacattacc ctgtggtaaa tgggtattaa tctcggtttt   2880
aagatctttt ttattatgaa tttttaatca ataggaatca ttattttgat ctacaaaaat   2940
aattgaattc tccttatcat aaagtcttaa aacaattcca actatgacag ctgatcaaca   3000
tagatttaaa catattaaaa aagaagcaat tttaatatgc ttttttcaaa gtattttctt   3060
attattttc attttcat                                                  3078
```

<210> SEQ ID NO 55
<211> LENGTH: 3057
<212> TYPE: DNA
<213> ORGANISM: Ureaplasma urealyticum

<400> SEQUENCE: 55

```
ttacaatcaa attatttttg tttttttatc atttgggact aatgcaattt ttgcattatc     60
ttttttatca tttgctcttc aatatttaat accataaaat tgatatcttg aagattttgg    120
cattttatct aaaagtagtt gaaattggcc aggagtatta taatttttgt taacattatt    180
ttcaattatt ccaactgttg tattataaat ttgaccatta tctaaatttt tgtacataac    240
ttcaccaaaa atagaatcat tttgattatt catattatta aaaataagtt ttctaacact    300
tccactaaaa ctaacataag tataacttgt attatttgta gtataaatgt tatgatcaac    360
attcgtaata tctactattc cagcataatt acttgtatta gaacttttgt atataactga    420
accattttta ttagtatcat aaaaaatatt atctcaatca ttatttatgt ttttatatag    480
gtaagaattt ggtttatttt caaattttac aattcttaat ttatattcat tattttgatc    540
atttatatta atattgttaa tatgaatttg taatttaggt ttaccattgt catttacaat    600
tttaattatt ggattatcat caattttatt ggttgataaa ttttccacaa tagcacgaat    660
tttatatgaa tttaataatg attgagaaaa tcactcatca tcattagtaa tattaaattc    720
cattattctt gatcaaattt gtttttttc atcaaaattt gtaatatttt taaaattagt    780
taattttgtc acacttggtt caacaacaaa tgttttatca tttaatttac taatatctat    840
tgaagtaata ttattagtat tatgatttat tttaataata ttttttaaag tatattcacg    900
attataagtt aaattttcaa tattaacgct ataatcttct tgatttttat ttaaagttaa    960
gcttacttct tttttagaag ttgaattatt gtatctatac tctaatacta atctatcacc   1020
atcattgtaa tcttttatat ccttaatttt taatttaata attcttcttc ttaaatcatt   1080
agttttttca taagtaattg attcgatata tggatcaata cctttagtta aaattttatt   1140
ttgattttgt tcaataatgt taatgtttgt gtttaattct gtatcaaata gatcattgcc   1200
tgttggtctt gataatttta ttgtagataa aatgtattct gtatttggct ctaaattaga   1260
tatttctcct tcaagaatcc atttattatc ttttcttact aaattaattg tttgtataaa   1320
tgtcttggta ctatcactaa ctttttaaa taccaattgg aatttagaat ttgtatttaa   1380
cattgttcca tcattagtag ttgtaatttc aaaagcatac tttgcactat taattgttgg   1440
ttgatcccaa tttccgtatt tttttgcatt atatattgct caatttgttt taaaattagt   1500
attctctaac gttcttcttt gtgcatcatt aattggtgaa ataattttat taccatttac   1560
atcttcataa gctttgtttg gttttttaat cattcttatt tcttttatgt aatattcact   1620
tccttcatca agatttacta aatcatgttt aatatttgcg tataatccat catttcttga   1680
atcaatgatt gacattgtat aaactttcat tttatcttga ttgtttggat atttttttatt   1740
agcaaaagtt acaactatct tatcgccatt ttctaaaatt ttatctaatg attctaaacc   1800
taatctaaat ttagcagtag ttatgccaat atttgatttt cacaattgat tttcatcgcc   1860
ttctgtttta aatgttactg cagttggtgc atgatgatat ataaatgaat cagcaatatt   1920
atttgaattt agcaattctt caaagatatt attatttgaa attaaaatct ttttgaaaga   1980
atattttcta ttaggagtta gtttactaat atcaaaatta taactagttt tattgtttga   2040
taaagttagt tcattagttt ctcattcttg atgattgtta tcttcatata ctaatttaat   2100
ttttttgtta atgtaattag aattaattct tgaaaattct gcttttattg ttcctatcac   2160
tctattagga ttaacagcat tttcttgtat attgtaataa atatcattat ttgattctaa   2220
tttcaataat tttagtttat caactaatgt tttgaattta gtatctagat tacctccata   2280
```

-continued

```
tattacatta tttttattta ttgttaacat tcatttagct aaatctggct tatttttaaa   2340

tttagctgat gtgaatctat attctgtttc tggttttaaa tcagttaaat ttcatttaat   2400

tttagcacta tttttatttg cacttacttc acttaataca ccatcaattt ttttaatttc   2460

tgatggattt gatgtagata caaatgtagc ttcaacaatt tgattatttt caaaaacttg   2520

atcagttgaa ttaactttta catttatagt agcactattc tcagttaaat ttgttaccca   2580

attagaataa tcgatagata aatttgtatt ataaggatta ataccaaatt tatgactaac   2640

accattaata cttaaatcat taaacactgt attagtatct tttgaatcag taatttgagc   2700

tttaaataat ttatattcac gattagtaat caaatcctta tcaagaacta aatcgtaaat   2760

ctttttatta ttttccaatg taacttcttt tgttcaaaca atttgctcat tattatcctt   2820

ataagctaat ttaatttttc taccagcata attatcatta acaccagaaa cggttaattt   2880

aattgtttgg gttgtattat taatattatc gtttgaagta atatttacaa tagttgttgg   2940

tcctgatatc gttctgaatt tataattttc attattatta ataataatat ttccaggtaa   3000

taaattttca tatgctaaac gtggtttttg aacaaattca acttttaata atttata      3057
```

```
<210> SEQ ID NO 56
<211> LENGTH: 14066
<212> TYPE: DNA
<213> ORGANISM: Ureaplasma urealyticum

<400> SEQUENCE: 56

ttagtttcaa atatttgatt caacagattt taattttata tttaactcag cactattata     60

cgtaatattt aatggagtgc tccattcgat gcttgttgtt gatgggtttc gtttaaaact    120

attatttaca gtattttgtt tttttaaatc aatatattga gaattatttt tatcatcatt    180

aatttgtatt ttaataaaag tgtaatttct attagctatc agaccactta gagtaaaatt    240

atatttttgc atacctttttt ttaaattaac tatattgctt tcatataatt cgttattttg    300

atcacgataa attaatttta ctcgacgccc attatattga tcatttactc cagaaaatgt    360

tgcattaatt gtttgagaat caacattaat ttcatttgtt gataacaatt catttaaaat    420

tgaaggccca aattgggttg taaatgaaat atttctttta ttttcaatag aaacatctaa    480

atcttcataa acattgcttg gttttgtaat attaattgaa tttaatacgt atgttgaatt    540

tggttctaaa ttatttattt tacctttaat taatcatttc ccattttctt ttaataagtt    600

aacatttact tgttttaaag taccaccatt tttattaaat gttaccgttg ctgttgcatt    660

tgcatctaat tctccatcat tatcatctgt ttttagaaga aaattaaatt cagcacttgt    720

atctgaagga tttgatcatt cgccattttt agaaattata gtgtgtgatt tgtttatttt    780

aatttgataa ttaatgttat ttaattttgg taatttatta ctttcaacaa ttgtatttga    840

attattattt actaaataat acacatcaac taatgaatat aacttattag cttttaaatt    900

atttaaagta aatctaattg atgtctttcc gtcattattt actaaagatg acccattaat    960

aacattagtt tcaataatat cattatttgt tgatttgaat ttagctataa atcttaaatt   1020

atgtgctatt ttaggattaa tttgcaatcc aagatctaca tcgatattgt ttttttgatt   1080

agcgttttta acaactattt ctttatttat tggaccatta acaataatat cgttattaat   1140

ttctaattta ggtattgaat cattattata aatgatatta ttagatttat caattccaat   1200

attttcagct gctatacttg gtttattatt aaaactaata tttactatat ttactttatc   1260

attaaaattt aaatcaacta aagtagcagt taaatatttg atattaccac ttacagtaat   1320

aaatcccatt gcttgtttat tattaccata aacaatagta gcttgatctt tatctctaag   1380
```

-continued

```
tacattatct ggatcgttta aattaatttt aataatagta gattttaaat tagttgaggc   1440
tcgattacta atttcttcaa tattcaatac atttatggcg cttgttcttg ttgtaataaa   1500
actatttgtt aaattacctt cttttgggaa atctgaaaca ttattattat caatcaattt   1560
tacatcaatt aaggtatatg tccgattacg ttttaaatta tttaacaata tattatattg   1620
tgttttatta gattcaatta atacctcatt agtatgaatt gattcactag tatcatttga   1680
tttataactt agttttattt tctttccaac tcatgatttt ttaactccac taagtgtaaa   1740
attaattgtt tgcgaatttg tgttaacgtt attacttgat gtaatattta ttaatttgtg   1800
gtcgccaact ttcgttgtaa attcataatt tgaattaata gaatttgtgt tatctaaaat   1860
aacattattt tcactattat tgatattatt tttggctttt gttggtttgt taacaaattg   1920
gattttaact aatttataag ttgtttcttc tttaaaatta acactattac ttaaatcatg   1980
cgctcaagtt ccttctttga aatcactagt tacatctttt aatggtcttg tgtattgtaa   2040
ccatgtatta gtatctctaa ttgtttcttt aggagcaaat catgcaacta cttgttgatt   2100
attttctaaa attttatctt ctgatttaat tttgaaatta aaattaacac cacgcgtccc   2160
aacaattgta gcactactat catttcattg aactgtagta ttttttgttt gagtaataaa   2220
tgtatttgac acaccattta atttttcaag atcttcaaaa ttattagtat tagaaatatg   2280
atttatttca atttttttcaa acctatattc tcgatttgaa tttaaatttg ataacaataa   2340
ttgatagtca tttttacctt tttgtaatgt aattaaagaa ctttcataga taacattatt   2400
attatcttta taaactactt taatctgacg tccattatat ttagagttaa ctcctgataa   2460
cgttacatta atagtttgtt gagtatcatt aatagtatca ttttgagttt gaataacttt   2520
taaaaccgga tttccagttt cagtaattaa acttatattt tctttatcat taatcgatac   2580
agataaatta gtgtgagttt ttaatggttt acttaattca atattttcta atttatattt   2640
agtttctgga tttaaattat cgatttgacc tttgattaat caatcattat tttctttaat   2700
tatacgaact attttttgct taatattatt atgttcatct ttaaatttaa cagttgcatc   2760
aatgttattt aaaacatcat tatcatcttg agtttcaatt ttaaattcaa aattagctgt   2820
tgtatctgta ggtgattttc aatttccatg tttactaatc attgtaacac ctggattaat   2880
ttcaatttcc ttagatacat tatggtcttt aaatattttt cttgtttcat caatattttg   2940
atgaatatta tctaaataat aaacatcaac taatttatat aattgatttg attttaaccc   3000
cttaacacta aaaagaactt cttgtttgcc tgttttatta atattattac catcaattaa   3060
ttcgctatat acttcatgac caaattcatt tctaaattta agcttaaatt taagattttt   3120
agctatatgt ttgtttattg taaattcaat tgatgaatta atgctttctt tatcattata   3180
atttttaatt tcaagatgta aattattaga tgataatgga ccacttattc taaaatcatt   3240
gttaattttt aattttctag tttcttctat taaatttgtt aattcataaa ttttattcga   3300
attattaatg ccaacactat caactgcctt attaggacga gttataaatt caattttatt   3360
gataattgta tcatgattaa attcaagatt agataaacta acttctaggt atttctcatt   3420
atttactgta ataacttttg catttgtttt tttatttgta tcatatgtta tttcagcaat   3480
ttcgttgtta cttaatacat cctcaggatc atttaatgaa aattgaattt ttgctacatt   3540
taaattattt attactcgat cactaatctc atttagctta ttgacactaa ttggtgtttt   3600
tcctttaata ataaatgaat tttgaagatt ttgcttattt ggaaaatcaa ttcaattttg   3660
accatcaaat cattttatgg atttcaaagt atatttgcga ttgtatttta aattattaaa   3720
```

-continued

```
attaaaaaca taatttaatt tattttcctc taaattaact ttcgcctcta cttcatcatt   3780
tgtattagat atatatacta atttagcttc tttgttaaat cattcactac gaattccatc   3840
aattgtaaca tttacatttt gcgaatttgt tagtgtttga tttgattcaa tatttataat   3900
tccataatta ccaggttttg ttttaaatga aatattagtt ggattaatag ttttaagatt   3960
agagttagca tttagtggct tagttaatac aatagacttt aactcatact ctgtttctgg   4020
ttttaaatta tttactatac cttcaataaa ccaaatgttt ccttcttttt ttaattttac   4080
attgttaaca aattttgtat cattttgatt tgattttgat gaaaagataa catcagccat   4140
aacattatta tctaatatgt cttcatcatc agattcaact tgtaatttaa aatttacact   4200
gtttgaattg atctgccatt caacattatt ttttttaaaa gttgtattac cgggtttaac   4260
ttcaatttca ttaacaacat tattagatct tattaattta ttattatcta taagatcttt   4320
atcgtcttga tttaataaat aatataaatt atcaaagtga tataaacgat ttgattttag   4380
atttggaatt ctaagttcaa taatttgttt tttaccttct tttttgattg aactataaga   4440
aacaatactt gattttacgg tttcattatt ttgatcttta aatgttgcta taaagtataa   4500
attttgcaaa atattatcat tagcttttaa ttctaaatta acttttacat tagttttatt   4560
attatattcc aaagtaatac gtttattagt atcactttga acaggaccaa tgacactaaa   4620
attattatca atttttaatg gatttatatt gtttgtattg ttatatattt tattgctatt   4680
atctattcca atattcgtag cagcttttat tggtttatta ataaaagtaa tactgttaat   4740
aatagtatct tggtttaatg ctagattatt gaatgttgtt tctaaatatt tttgactccc   4800
tacaatttta acttttgctt ttacagataa attctcacca taattaatga ttgcttcttc   4860
ttcattactt aaaacattat caggatcatt taatataaat ctaatttgtg ttgattgtaa   4920
attatttttc gctcttgcaa ttggctcaat tattgaactt atactaatcg attgtgtttt   4980
attaacaata aatcaatcag ctattccatt ttttaaatgg aaaattattg atgttttatt   5040
atcatcatta ataattctta cttcttttag tgtatattta cgattatgtt ttaaattaga   5100
caattcgaaa ctatagtggt tattagccca aagcaatgtt ttttgatcac ttaaaatttc   5160
ttcaccgtca tttgaagtat ataccaattg aattttttta ttaattcaag ttcgttgaat   5220
tccatcaata tcaatattaa ctgtttgtgt tgtagtattt atagaatcat tagaactaac   5280
atttgttact ttatgatcaa caattaaggt tttaaaatta taattcgaat tattgtcttc   5340
aaaaatgaca ttattagcat cattattaat attagtgtaa gctaatgttg gttttctaac   5400
aaagccaact tttattagtt tataatttgc ttcttctttt agtgtttgat cagtattaaa   5460
actaactgtt gcctcacttc catcactact tatacttgtg atagtttttg tatatgatat   5520
ttcttgacgt tcatcatcat tagatttcaa ataagtaata atgctatcac ctacttgaaa   5580
tacgtgatct ttagatttta atttatatgt aattgttgca cttgtgcttg ttatatttgt   5640
tgctaaatta gtattatcaa tgactatttg tgtctttgat gcatttacat taaaactatt   5700
cgtaacattt gttgaattat taagtgtttc aaaattatta ttagaagtct ttatttttat   5760
ttctttaaaa gaatattgac gattagcaac actaattggc agtgtaaaaa tatattgtgt   5820
ttgatctttt tgaagagtta gttcatttga ttcaactaaa ctttttttgat tattacttct   5880
atattcatag actaacttaa tcttacgatt attatataaa tcattaaccc ctgatacttt   5940
agcggtaatt gtttgttgat ttgatgcatt aggttgatca tttcacatta aatcatgaga   6000
tgtaatgcta actaattgtg ttggtccact ttgagttgta aaactaattt gttctttatt   6060
ttcaatttgg atttttaaat tagcaaaagc attcattggt ttagtaattg agatgtcatc   6120
```

-continued

```
taatttgtat gtatcattat aagccaaatc actaatagta tcttcaatat accattgatt   6180
atctttttgt tttagttttg ttgtaattgt ttttttagta tcatgttggt cactaaaagt   6240
gatagttgca tctagatcag tactaaaatc aacattttca tctgaattaa tattaaactt   6300
aaatttttga gcatttggtt gtgggaatgt tcaattacca tttttttgaa tcgtagtaat   6360
cgttggttta acagttattt tataatcaac gtttgaattc ttttcaaatt tattattttc   6420
atcaatatta gtttgatttg atgaatttac ataatatagt cctttgaaaa tatattgacg   6480
atttgatgtt aaattagtta aattaaatgt taattctttt ttattattgt tattatttgt   6540
aacaatttta tctgcagcaa ttgggtttgt taaaacactc tgaccatcgt tactgtcaaa   6600
ttttgcaata aaatataagt ttttactaat atgattattt gtatctaatt ctaatgaaac   6660
tgaaatattt gttttattat tagcttcaaa ctcttttagt gtatgaagtg ggccagtgat   6720
ttttaaatca ttattaatta ttaaattagt agcatcataa ataacattag tatcattaat   6780
accaatattc ttacttgcat ttttaggttt tgtattaaat tcaattttat taatgatagt   6840
atctttgttt aagactaaat tactaaaagt tgcttctaaa tatttttgat tttgatcagt   6900
aattactttt gcactagtag tttgattatt attataagta atagttgctt gttcatcatt   6960
acttaaaaca ttatctaaat catttaattc aaaccgaatt tttgcactat ttaaatgatt   7020
tacatctcta tcttgaattt caataatatt accaactcca acttggttat tacttaaaac   7080
aataaattta tcttgaatcg aatcactttt attaaatggt gttttagtgt tattatcatt   7140
aattaattca attttagtaa atgtataagt tcggtttttc tctaaattag ttaattcaaa   7200
ctcatattct aatttatttt tttctaattt aattatagcg gtttttgttg agttatcgtt   7260
tgcactataa gttatttcta attgtttttc atttcatgca ttttgtatac catcaagttt   7320
taacttaatt ctttgttttg tatctactgt tgatggattt tgtgatttaa tttgaataac   7380
tttataatta ccagcttgcg tttgaaatga aatatcgtct ttatttaata tttcaactac   7440
taatggcttc tttgttttat ttggtttagc taatagaatt gattcaagta catacctgtt   7500
ttctggttct aaattagtaa tttgaccctt aattaaatat ttattattct gcttaataat   7560
attaacttta actggtgtta gtagagtttg accttttttta aaactaattg ttgcttctaa   7620
attatctaaa acttcattac catcatcact attaattaca aactcaaatt gtgaacttgt   7680
tgatgtagta tttcaagtat tatttgattt gctaattgtt gttttaccag gtgcaatgtc   7740
aattattcga gtaacattat ttgcttttgg tactttgttt ttgtcattaa tagtatcatt   7800
attatcatca atataataaa catcaactaa tctatataat tgatttgatt ttaaattatc   7860
taaagtaaaa ttaattacgt ttttattgtt attaactata attgaactat tagttaaaat   7920
tggactataa acaacttcac cattgatatt ttgaaattta agtttaaatt tcaaattctt   7980
actaatatgt ggattaactt taaaatctag tgttgaagaa attacgtgtt tattattagc   8040
cactatattt tgtgtactat taacatcagt tgataatgga ccaatgattt ggaaatcatt   8100
attaataatt aatttattta aattactttc gtcataaatt acatttgtat tatttttgcc   8160
aactttaata aaggtttgag ataaattttt aaattcaatt tttttaataa ttacattttt   8220
attaaatacc aaatttgtta ttattgcttc taaatatttt tgattttgtg cattagtttt   8280
tacaatagca tcaacttttt gttcgttatc ataagtaatt gttgcaatat catttgtttt   8340
taaaatatca ttgtcatctt ttaaattaat tttaatagtt gtttgattta atttatcagg   8400
agcacgatca ttaatttctt ctacgcttga tgctgtaatt tcgctttgta aattaacatc   8460
```

-continued

```
aaatgaatta tttacattga tttcttttac aaattcgtga tcttggccat tgtcaacttc   8520
tttaatatta attttcttta aactataacg tcgacctggt tttaaattat ttaatactaa   8580
attatattct tttttatcaa aacttagatg aacactattg ttgttattat caactgttgt   8640
tttaatttca ggatcaccta aaatgtttga ttcataaact aattcaagct ttttattatt   8700
tcaagctcgc tgaataccat caattttaac agtaatttct tgttgtgttg tatttgttga   8760
tgtgcttgac actacatcaa taactttatg ttcaaatttt tgtgtcgtga attcatatgc   8820
ttgtgaacca tttttatact caaaaataac accattttta tttaataact catatgcttt   8880
atttggttta tttttaaatg ttactttgat taaacgatat gtcgtttctt ctcttaaacc   8940
gcttaaatta aattctaatt caccttcatt aaatgaatta gttacattat ttaattttgc   9000
ttcaactact ttttgatcat ttaaattatt agttggagca aaaactgctt cgacaatttg   9060
atcgttttct aatgcttcat catttgtttt aagcttaaaa tgtacttgag cattatgtgc   9120
actaactgtt ttaatagcat tattagtatc ataattaatt gttgttaatg atggttcaaa   9180
ttcaattttt ggtttatgaa tctttgaatt aaaactaatt tgattatttg tcatatcatt   9240
cactgaattt tgatcatcaa aataatacaa accttctatt cataagcacg attatgaatt   9300
aaattagaaa gtttaaaact aattttagca ttattattga ataagatcgg atcagttcaa   9360
acagttttat tatcgtttaa ctgctttaat tttaaacgta aatattggtt tgctaataat   9420
tgtttatcaa cttgaagatc aacatcaata tttactgatt tatcattctt gttaattgtt   9480
tggggtttat aagatgttgg attaatatta tttgataaac taattttatt ttgttcatca   9540
tatgaataaa caatgttatt agttttatta ttagtaaaat taaaatatgc attagttggt   9600
tttgaattaa aactaatttc tttaataaca taattttgat taatttttaa actaactaaa   9660
tcgaatttta aaaatttttt attgttttct acaacaactt gggcattagt tgctaatttt   9720
aaattattat tggcatcatt actattttct aattgataaa caatatttgg tttatcagct   9780
gtatttaaaa cattatcaat gtcatcaact tcaatctttg ctgaaattaa tgattggtca   9840
ttattaacta atatacgttt tgtgatttca atattagtgt tattttttaa agaaactgca   9900
ttattacttg gattaatgct aaattgatga gttaacgtgt ctaacttatg taatgtttga   9960
ttattagttt cataaacaat tttagaaaaa gtatataaac gattcttaat taaatttgaa  10020
aattcgaatt gataatttct ttgtcctttg attaaagtaa ctgcttttga tttaatctct  10080
ttgttatcat ttgatacata aattaattta acttgttgat tatcttgaaa atcatcacct  10140
atattaattt tggcatttat tataggagtt tgatcattat ttcaattatc aattgaattt  10200
agacccacta gtgttgtgtt tttattagat gtactaaaat tagtatttgg atctagtaaa  10260
tcaaattcac tattaacaat actgcttgca ctcttattta aagcttcaag tttttttaata  10320
acatatgttg ttttttcttt taaaccaacc aaattgaatt taattttatt atttgcaaca  10380
acttttccat atccaatttg tagttcgttt ttagtgttat caatattttg ataataaatt  10440
ttaacatctt cattaattcg taatttttga tcataatctt tataatcaat aaataaatta  10500
gcatggtctg caaaaaatatc ttgttctaca gcgcttttat taaatgataa attgatctta  10560
tgagggtttg taataaaatg ttgttcatat tttgtaacat catttttaaa taaatacacc  10620
ttttggtttt ggtcatttaa ataatataag tttttaatac tatatttact atttcctttt  10680
aaatcaagac cattaattga agcgatttta ttagttttac taaaattaac taaagggtta  10740
ataacatctg tatctaataa atcatcatcc attaaagcta actgtgcata gatttttttga  10800
tcattttttta aaatattatc tttatcatca atttcaaagg tgatagttgt atcattatta  10860
```

-continued

```
gttttaacaa ccacatcaaa tttagttcaa attggtggat taatagtagt tgctgagctt  10920
gttgtgaatt caaaatttaa aacatcatct ttaattaatt ttattggttt ttctttgttg  10980
tttaattcta gtaattcaac atcaacaact ttatattttg tgtttgcatc taagtgtgta  11040
aaatcaaaat ttagtttata gttgttagtt tttggatcat aagttgcaat gtatttttgt  11100
gtatcattta aatcattaac tttagcaatt gttagtgcaa attgacgatt ataagatagt  11160
ttatttaaat caaataagtt tacttggaaa ttaatagcat ttactgttac gttagaaact  11220
gctggtgctt ttaaaacaag cttacgagct tgatcgacac catcattaat tgcactaaca  11280
tctttgttaa tactatttct atctaatatt gttttgtttg gatattcatt taaatctaca  11340
atcttatcaa aatcatagat tttgttagga tcaaataaat tattgtttgg attaacaata  11400
acttttccct tatcatcagt tttgattgga acatgaattt cattgttatt tttatcttta  11460
taaacagcag ttaaatcttt attttttga tctggtattt taaactcatg cttattatca  11520
gcattaacat taccattttt ttgtttatta actattcgat ctaatggtga aatttcatca  11580
atattagcaa ctttttatt atcagcttca atttttgtta gtgtatattt atgatctggt  11640
gcaaaaattg catcatcact tgttttaaaa atagcttttc catctaaacc aatactagct  11700
tcaaccgttt ttgtattagt attattatca tcggttttaa atgttaattt aattttttta  11760
tttgctaaac taggatttga aaaactaatt tcataatcat cattttcttt agttttagca  11820
gttattgttg gttttttaaa tgaaatatga ttatcaccac ttaattgctc ttcactaatt  11880
agatcaatat ttggttgatt attttgtttt aaaacgactt ttttaagtgt gtatatatta  11940
ggtttagttg ggtcattatt tgctaaattt tttgttggaa taataacctt gccattagca  12000
tcaatactta catctatctc atgttctata ccatcttgat caacaacaat tcctttgaca  12060
tttgcattat ttaaagcttt ttgttttaaa tcatcattta aatcatttgc taattgagtg  12120
tgaatttcta aatttccatc attatcgtac gtaaaatctg gatgtgaatc taataaattc  12180
aaatctcgtt tatcaattat tttatctttt agttcaaaat cattaagatt aatgacttta  12240
tttaaatcgt tattttcaac tttagctaaa tgataaatat atccttttgg taaatcatta  12300
ctatcaaaaa taattttatt attttgatcc acattagcaa ctactttata ttctttatca  12360
ttattatcaa caaaagttgc tactaatttc tgattaatta aatcattatt taaattttct  12420
aaaatttggg tttttttagt tgaatcaaca cttgcattag cagctggctt tttaattaat  12480
tgtttttgtt ttgaagttaa atcaaaattt gaaaccaaaa cattttgtgg gtttgaaact  12540
gaaacaattt tgtctagtga ataattactg ttattattta atgcacctgt atcaaatgct  12600
atggttccat ctttttaac ttttgctaaa atttggtgtt cttgattatt ttgatcttta  12660
aaaattccat atacttgttg gttaacataa tatggcgcta ctttagcaat taaattaata  12720
tcaccatttt ttgtatattg atatggggta tttaatgcgt ttgaatttaa attattaatt  12780
gatcgattat ggtatggaat ctgtttaaga ttaacaacat caacttcatt agtttttta  12840
ataccaataa cttcatataa attattatca cctaaagatg aaatatcaaa aacagctcgt  12900
ccttttcat ctgtttttgc attaatttta tatgtttgat gatttagatc ttctaaggta  12960
agttcaagag gagtgttttt taattgaaca cctaaatcaa cttcatatac tttttgtta  13020
tcaataaaat taactttagc ttttgttggt ttatttacac taactttatg ttcaagcatt  13080
aattcattat ttggcactaa aacatcattt aattcattat tgttaacaat tcggtttaat  13140
tcatatttgt gatttaaagg tagtttttta gtattaaaat acccaacatt attttttaca  13200
```

-continued

```
ctcaacgctg gtattaaata ttctttatta ttttcatctt taaaaactgc tgttggcaag  13260

gcttggtttt tagttttatt tgttaaatca acttttaaaa caagattacc ttcattatca  13320

taagtatgtg ttttatcaat ttttttaaac tgttcatcaa tatcattaac atttacaact  13380

tttgttaatg gatttgaatc ttttaaaatt agatctttta aataataaac attgccatct  13440

tttaaactac ttgtatcaat atcaattttt tgatctaatc caacatgtgc ttcaatacta  13500

taaacttcat tattttgatt tacaaatttt gcgactaaaa ttttattagc aagtatttta  13560

tttaccttta attgaatgtg cttttcgttt ttttgatcct catatacatt agttggaact  13620

ggttttaaaa cttcaatttt ctgttcaggt tttagcttct cattttcacg aacaatgtta  13680

ttatttaaat caataattcg atttagctta tatttacctg tttttggtaa atacttagta  13740

tcaaattcaa attttgcata agaatcaatt tgagttttta ttttatattc ttgattgttt  13800

tcatcaacaa aaacaccata aacatctttg ttaatataag tttttggtaa ttgaccttta  13860

atgattaagt caccatcatc attaaaacta taaaaatcat tattacttaa ttcattattg  13920

ttttttgaat gtaaaacaat cccaataatt gctcctgctc acgctaaatt tagcgttgca  13980

agcaataaga aaagacgttg cttacgactt tttttattat tatcgttttt tattgtttgg  14040

attttttac ttttttttatt attcat                                       14066
```

<210> SEQ ID NO 57
<211> LENGTH: 2376
<212> TYPE: DNA
<213> ORGANISM: Ureaplasma urealyticum

<400> SEQUENCE: 57

```
atgaaattta ttaaacgtaa aacaaaatta ttaacgatta caattggtgc agttgctgtg    60

agttcaattt tattaggagg aattttttat ggtacaagtc aaaaaagtcc ttcaagtttt   120

ggtattgctt ctattgatca aaaagaaaat tttattaata aagacaattt agattaccaa   180

aaagcaagac catcaattaa agataataac ttaaaagaaa ttcccaaacc aaaacctcag   240

ccaaaaccag aaccacaacc aacaccattt ccagatccca tcccaacacc tccaaaaaaa   300

gaagagttaa aaaaaccaga gattaaacca gaagagccta aaaagcctga aattaaacca   360

gaaccaattc ctaaaccaaa acctcagcct attcctcaac caacacctcc tgttgaaact   420

aaaccaaaag aagaattatt accaccaagc ccaccacctc caaaagaaga accaaaacca   480

gaaccagatc cacaaccaca accacaacaa attcctaacc aaagtactgt tagaaaaatt   540

gaattgaatg gtgttttagt ggacgctgaa gttgaagttc caccccctcg tcaaactttt   600

aaatatgatc aggataatgg attatcaaat cttaatccct atacaaatat aagtgttggg   660

aaaattaaaa aagtttttgt aacagatgag ttgcggcaca aatcagcaga tttagtgcgc   720

gggaatttaa agcgtggcga ttatcaaagt ttagttaaag atttattaga tccaaatata   780

aaaccagagg aaattgatag ttatatcgca atggttgata aaagtggata tcacgctaaa   840

ttatgaagta aatttaaaaa actatttgat acagacaatg ttgttaattt tctgaatgaa   900

caaggtaaaa aagaatatcc taatatgaaa acaaaatttg tttctgatgc gcacaagtat   960

gcttgattat atgctcattt agatttttca aaattcacta aactttcagc caattctgaa  1020

aagtatttac aagaaggttt aacgcctgat ccagataatt catatgttaa tgaaaacggc  1080

gaattagact catatgctta ttcacctgct aaagaatata atacagtaac aagccgttta  1140

gcaaatgata atgctaaccg aagggtgttt gggtataacg aatgatacaa tcgtagtcca  1200

aatggtttag ctaatggtga ttatcctggt tgaaataaat cagatgcaac agctgagttc  1260
```

-continued

```
aaacagtatg gcattaaaga tggtgatggt attaaagttt ataaactaga gcgccaaaaa   1320
ccacaagaag gtaaattaaa tactggatat attgttgata ttgatgctga taatcctgat   1380
ggataccaaa aaacaaaaga attaattcaa aaattaaata atcaaaacaa aaaaattaca   1440
ggatatcgaa ttcgtaacat ggggaaatca gattcaggac aaaagttctc tgatattcta   1500
aaagccttac caaatgaatt gccattgctt gaattgttct tttctgctgg ttcacataat   1560
acgtcagcac tttctgctct tgaaactaaa catattaaag aacttgggtt gtatacatta   1620
ggtaattcat tattagatga atgatcaatt aatccaaatg cgcttcgaaa agtagaatga   1680
attaattcta atgattataa tgtttcgtca gaatataaac aaggatcaga tattgctaca   1740
cgaattactt ttgatactct ttcttttgat aaaaatgatt tcaatgataa tgcaaatgat   1800
cttcgaacaa aattaaaacg tattaatgat ggattacgaa tggtttattg aacaagaaat   1860
aatgaaccat tctttcaagg tggatttggt ccaggattag atcctgatca taaagaggtg   1920
ggaaatagtt atccccaagg tttagacttt agtcgtgtcc ctcaaattcg ctcattacgg   1980
ggtttaatat ttaaagacga acaaaaagct tcaaacaatc gtgaacgtaa attaagaaga   2040
gttaatttct ttaatgataa agaaaattat gaaatgtcaa ttaatgattt aaatgaagct   2100
ggttttagtg aacatattgt gactaatgaa ccaatgcctc ctaaaagtaa aattactttt   2160
agtaatggta atgctacaaa acgtatttac attaaaggca atggtagtct aactgcaagt   2220
ggtattcaaa atttagctac attatttaat ctagcagaaa gtttagattc taaatctgtt   2280
gttgttgatt ctaataattc agaattaaag tcacaattag aaggtttagg atataaagta   2340
agtgatgctt ctgacgctaa ctatattgat atttaa                              2376
```

<210> SEQ ID NO 58
<211> LENGTH: 3312
<212> TYPE: DNA
<213> ORGANISM: Ureaplasma urealyticum

<400> SEQUENCE: 58

```
ttagtttact ttaggaattt tatgaccatt aattttaata ctctttaaaa attgtgtaga     60
gatctgattt gaatcaagat ttgagcatat atcttttaaa tcatttaatc aataacaatt    120
ttcattagtt agtgtaattt caacactttt attattattt ttattaattt ttgcaactat    180
ttttgactct aaagtatccc catcgctatt gttatataca taatttaatt caatattaca    240
ttctttatct tgggataaat tacttaaaaa tatatcttga tcaaaagtaa tattaatttt    300
tggatcagat ccattaactt catatttaat attatctact tttcatttta aattgggatt    360
taagattcca ggaaaattaa aatagcgttg gttatctact caagttaaat ctaaattttt    420
atcattcaat tgaattgaat taattcgata tttaatatca ggctttaaat attttaattc    480
aaattcaatt gtttggtgct catagtcgat ttttaattgg ttatgagcat ttaaatcaat    540
acattcttgt tggttgtttt catcttctaa cactaatgac attttatggg cgtttttatc    600
tttaaagatg aaatcgctaa aatgcaactt gaatttaatg tttttttgtt gttggttaat    660
ttcatgatca attttatcta agtaaaattg atcaaagccg taatctaaag ttttaaaagt    720
cttattattg atattttta aattaatctg ttgcttatca ataaaaagtt cactaatttc    780
ataatcagta ttaatgttta agttatctaa tttagttgag atttggtgtg ttttttttatc   840
aaaataaaaa tctgttttaa ataaatacaa cagcttgttt gtttttttat tttttaaaat    900
aacatcaact ctttttggca tatttataac tgcttggttt agtgttaatt ttaaagtact    960
```

-continued

```
atttgtattt ttaatatcat taaattctaa atttaataat aaatgtggag atgattcatt   1020
aagtgtttta actgtaatat tattagttaa ataattgtca tcatctattt caaaagaaat   1080
aagtttaaat gtttgatttt tatctaaagc aaaaagatgt aaaataatgt tttttgttgc   1140
attaagttga gtagtttctg attttgataa gtttttaaca aacttatatt tattatgatt   1200
ttcatcttct aaagtatatt ttattttatg ctcaatacta tcagcatatt gattgtcttg   1260
taaatcaaca tttagatcgg ttgaagttga ttttgtattt gtgaatgaaa aaacagcttt   1320
tttgaactca tttgttttaa atttaagaaa tgaaagatcc aagtgaaatg gatgagaatc   1380
aaaaaaatct cctatataaa catttacatt aaaattatca ctatggtaat taccatcaac   1440
atcttctaag ataaaactta caaattcata attaatatga ttatctaaat ttaataattt   1500
aattttaatt gttttttgat cttcatcaat actcatgaag caatttttat cttcaaaact   1560
aaactcctta tatgctcatt catttggatt atttaatgga tgatatctta atttaatttt   1620
gggttttaaa gaattttctt ttcttaaaag taatttttca catttaatat taataatcgc   1680
actattttta gtaatatccg aaatgaaaag gtgttcttta taatcttttt ttacttcttt   1740
tgatctttca ttatcatctt ttttagaaac tgataaatat caaaaccaac tattaaaagc   1800
actatagtaa gaattataga atgatttatc tttaaaaatt tcaatacttg atcgatcagg   1860
acgtatttta aatgttttgt taataggtcc ataatatcca cctgcatagt catcatcatt   1920
agggaaagat actggtttac cgtttagtaa aatattatca atttcataag ttttgtcaac   1980
atctaaacca ttaattacag cagttaataa acgttcttgt tcatcgtatt taacttctga   2040
gaattcaatt gggttttgat cattttcttt tctaattaaa aatttaaaat tatgaatatt   2100
aggattgtag aaagcaagat cttcagataa ttttacttta attgtaactg cttttgtaat   2160
tttatcaaca gctgtttcat aatcaatagc ttcaacttta gcataatcgc cttttgttgt   2220
aaaatcatgt gtttgattat ttaaatttaa aacttgatca ttaatcttaa tttgtttaat   2280
atcataatga gttcctcttt ctaattcatc aacataaaca ataattctct tgtttaattt   2340
atcaataaaa aaatgcttct tattaagctc taattgacct tttttataaa ctctattata   2400
tgctaaacta atgtggatat tatttaaagc ttcatcacta tcatctttta tttttaactc   2460
tttaaaattt aaagttaaat tagcaccatt atcattaatc tttgtaattt ctagattttt   2520
taaaagatta tcactatcat caagggtttt aaaagtgtgg tttggaattg aagttaattg   2580
aatttttga ttattaaaat taagtttatc taataaatat tcacaatcag atgttaaatt   2640
ataaacggta gcatcaattt cattttttg cttattgaaa acagcatcac tagtaatgat   2700
ttggtgatta gtttttttga taattttaa actaaaatta tgaatagcat cgtctttaaa   2760
agaaactgtt tttaacttaa tctttatatc aacttggttt tgtttaatat ttgtaaacga   2820
aatattatta atttctaaat gatcaatctt tggtgtatta ggaagtgatg gttgtaaatt   2880
taaatcttca ttaatatctt gttcgataaa atttaaatta tgatcaaaaa ttaaatgtag   2940
tgcaggaaat gcatcatttg aaaaattagt gataaaatga tcattaattt ttggtttacg   3000
agctagtctt aaataaattt tgttattaat aatcaaagga tgaatatttt ctaaacggtc   3060
aacttttta tttaacaatg gattaaaaag attggtgttt aaagttaaat tcttataaat   3120
accttgcgaa gtatttagtt cattaacttc ataaacaaca taataatggt cactcttggt   3180
atgaattata tctttcatta aaacattaac atttaacttt gatttattgc tacaagatgc   3240
aagtgctgta gcaacaatag gaactaaagc agctgtaaat aaaaataata actttttctt   3300
aattaatttc at                                                        3312
```

<210> SEQ ID NO 59
<211> LENGTH: 2118
<212> TYPE: DNA
<213> ORGANISM: Ureaplasma urealyticum

<400> SEQUENCE: 59

```
ttattcatga tagtcagcac tatgaataat agaaaaatac ttatctaatg atttgttaaa     60
ttcaatattt tgattattta ctttaacatc aacaaaatca taaacaattt ggtcctcaat    120
attttcaaat tttgctatta aagttttctt atttacatca tattccaaag tttttgggct    180
tatcagatta gtagtgtatc ctgttcgttt tttaattgta aatgtaaaat tattagatga    240
agtgggattt gtgggaatat tatcaaattt taatttgatt gttgttaatt tagtttcttt    300
attataagat ttactaattt catttacatt aaatttagtt ttataatcac tatttttagt    360
atcaaaatca agcgggatat taaaaggatg gttatgatga tttgtatttt tttttaaaaa    420
ttcaggtttg tttaataatt gtttattttt ataatcatta ataacaaagt caataacttc    480
atatgattta tttgattcta aatcattaat tgttacattc aatatgtggt tatgaaccaa    540
accctcaaca gtattattag tagtatcaat actattagat gatggtttta gtctatattt    600
gacactaact ttatcaccat caactaaatc aaaatcatct tctaaatgaa actctaattt    660
agcggattta tcggttgaac tataagaaat ctttttgatt ttaatttttg cttgaggtgt    720
attaaaacta ccatttaatc cttgagtatt tacttctaaa gcttgttttt cactaaaatc    780
ttgtagatca tcaaaaacta gtttagaaaa agtgtatttt cggtttgata aaactttatc    840
gaaactaaat tcgtactctt tttttgtggg atcaaataaa acaggttttg atacaatgat    900
gttatttgca ttatccatgt atactaattt taaatattta ttttttaaat aattaacgtt    960
attttcaaaa tataatttaa tcttaacact caaattttca tcattaaatc aaaaatcact   1020
gctttcatgt tctaagttct ctaatctttg aacagtagtt aattttgtag aggttaaaat   1080
atttaaatct aaattagcta atgatattgg ctgtccatta agagttaatg aatttaatga   1140
gtattttgta ctagtttgta aacccgttaa attaaatgat aaggtctttt tagagttatt   1200
gtaaacataa ttttcaaaac taaaagtatt tgatggttgg tgtgctgaaa ctaattttaa   1260
aacaaatttt tgattattta aatcacctaa cttattatct ttaaaataaa aaatcaattt   1320
tgcactagta tcataaattt ctttttcaat tttggtgatg tttaaatctt taataatcgg   1380
gtttgagttt tgcttattag tattagataa tactaaattt tggttactaa aaactaactc   1440
tttattattt aaaacaatcc tatgaatttg gtatttagcg ttgttttcta attgagtaaa   1500
attaaatgtt atcgatggcg aatttggttg ataattaaac ttaaattttg taatttgttg   1560
ggtttgtaaa tttaataaac taatctcaaa aatattttgg ttttcgttcg ctaaaaaata   1620
ttttgtaaat tctaaattta aatcagcact attattagta atattttttc aatcaatttt   1680
ttttatacta aattgatcta cattttcttg tgttaatgta cttgttataa aatctagttt   1740
agttattagc tgtttttgat tattaattaa taaatctact aattcataac ccatatttgg   1800
ttttaattca ttaataatta atttattaag atcattatcc ttaactaatt ttaaattatt   1860
aattgttttt aaatcaccag ttgctttttc ttttaaaaca acactgtatg aatgtgatgc   1920
taaaactgca ctaccttcta aaaataactc aatactatta gtagttgttt taaatttttt   1980
tattttaaaa agcacttgtt tatcatcaac cttacttttt gatttagtgc atgcaccaat   2040
taagcaagat aaaccaataa ttaaagtact acaagttaaa attgtaatta ttttagttaa   2100
```

-continued

```
atgtttttta gttatcat                                          2118

<210> SEQ ID NO 60
<211> LENGTH: 15016
<212> TYPE: DNA
<213> ORGANISM: Ureaplasma urealyticum

<400> SEQUENCE: 60

ttaaaattgg ttttcgttat ttgtatccat agcatcatta ttcgttgtac caaaactatc      60

agtgtagtgt ttgtgttgat catcaatttt aaagattgat gcttttggtt ctcctgaata     120

atatgtagcg tttgaactat ttggaagatt tggattaatt cgtggttcat atcacacttt     180

accaatatca attgtatttt ttaaactatc tgaatttctt cgaaggtaat ttgctaatgt     240

acaactgctt gataacacgt tagcacttgt tggtcgtgaa gctctttcaa aatctgttag     300

taatgaagta tcttcacctt cattaatacc atcaatatca tagcctttaa aagctaaatt     360

atttgtatta tgttgataaa ttcgagcata aacaccaagt gatttagcta atcctaaatc     420

aaagattgtt ttacgataac caccaaaacc tgtaaatggt cctttaaggg ataaagcaac     480

ttgatatctt caagtaaagt tatttcttcc atgaccaaat tttcatactt ttcaatcgac     540

tgatttggta ctaaatgcat tttttaaact atagcccata tctttagctg aaattgtatt     600

tgatgcttga tagtgtaaga ctttaactat attataattt tggtttggaa ttaattgaat     660

atttttaaat tctaaacaat tattatgtgc aacaattgaa acaatcacgt aatctttttt     720

aatatcatag tttagatgat tatcaatctt attttcataa tcacgtgtat taaatggatc     780

atctcatgtt gataaaacta cattataagt ttgtccttca acaaaagtat ttgcttcttt     840

acctttaat ttaaaattaa ccactgatgc tgggtaacca ccagaatcac cttttgtaaa      900

gacaatatcg tttttaacaa ctgtagtttg atcaaattca atttgagccc ctacggtttt     960

aatgtgatat tttgatgaat tataattatt agttgtgtaa ataatttgat tatcagcatt    1020

atttattgat ccaataattc tattaatacc tttattaaca aatgaaatac ttttaatata    1080

ataatcttga ttaaaattta aattgttaaa atctgcattg aaatatcaaa atgggtcatt    1140

attatttttc ttaaataatt tacatgctcc agtactaaaa ctagcttcat tatcaggttg    1200

atcttttcgt ttgtattcaa tatttataga aaaatcacca tttaaaattt ggtttaaaac    1260

tgtactatca ttttttccaa ctaatttaaa ttgttttgaa attccatctt taaattgcgc    1320

aagattttgc acttcattaa catcaatatg aatacctgtt ttaatagttt ttgttatgcg    1380

attatcaata ttaattattt tgagattatc gatcatataa atttgctttt caatctcatt    1440

tttatttgga tgagtttgct tttcattata ataaacacct aaaaattgat attcactatt    1500

ttcttctaaa gccccattat taggtaaatc aaattctaat tttgaataat tattagtatt    1560

taattgaatt ggtttagatc aaacttctgc atttgtttta gtgttagtaa ataaagcaaa    1620

catgtattta ttataaagat gttcatcttt attgttaaat gtcacagttg attttagtgt    1680

tagattttta ttatctaatt tatttttcac actttttact tcataaggat tttggttttc    1740

ttcaatttta atacttgagt attgactatt gtctaattca aaagttactt tatccttata    1800

catttttgtt tgtggatttt catacattaa tttatttaaa tccttatggg atagtgtctt    1860

aggttcataa actaaatcaa tgctaataag ttgatataaa ttacctggtt taaaatgatc    1920

atcattatta tcaatattaa attcaatgat ttttttcttg ttatcaactt caccaactaa    1980

tggagggttc aaaggtattt gttttctttt atttggcagt aaaatttttt ctatacctat    2040

tctttgcccc ataaataaac tgtcatctgg atcgtcatat cgaatttgaa atgtcatttt    2100
```

-continued

```
tttatgattt ttattataaa caatcttagg ggttgcaaca tatcatttaa ttgttgttgc   2160
gtcagtacta aatgatagtg cattactatt tacatttttg aatgcttcac tatcagtatc   2220
tttagatatt agtttttat ggtgtttatc ttgagaaaaa ctaggatctg ctcattcaat   2280
tcctaatatt ttatattcac gattaccctt aaaatattca ttatgatctt taatgatttg   2340
aactaaatag tctttttgac ccgctttaaa atttattggt tcagaataga ttagttgttt   2400
atcattagat tctcaattat tattcttttc atcccacaca tcactttttc tttttgaaga   2460
ttcgtaaatt aatctgaatg gtttaccaat ataagttcca tcatgctgta attttaaatc   2520
aaaacttata ccatcattag tttgatcttt tttaactaaa ctaataattt ttggttcaac   2580
agttttagtt ttgaatgaaa tattaggttg tgtcttatca ttagtatttt cataaattac   2640
attgttatta gcttttgaat ttaaattagc ataggcctta gttggttttt gctcaaatca   2700
cattttagta attttatatt taatattagg ctctaaatta tttaaagata aaagtacaat   2760
tgcactatta gaatttccat ttaatgtgta tgtacgttca aatactggaa tattttctgc   2820
tggaatatct tttttattaa tatcttcatt aaatggtgta atttgaatat gtaatacttg   2880
tttatcaaat acttgatctt ttgattctaa ttgaaatcaa actgttgcag catcagttgt   2940
agctggtgtt ttaatatttt gaattcgtac accatcggtt ggcactaata aatttgctgg   3000
gtataaactt agtaaatatg tagcattacc ttgttcaaaa tcactttgtt gatttccaaa   3060
atataaacca tttaaattat aataacgatt tgtagttaaa ttatcaatct cagcttgata   3120
aagaatttga ttattatcat tagttgttat taaacggggt ttagttcatt ttgtttcccc   3180
attattatca acatatgctg cactaattca tttattagct aataattttg gagcttgtgt   3240
aattgtaata tcaaccttac ctttattatt aacaacatca cctgtttttg atggacgttc   3300
cttagttgac aaatcattat tttctaatag aattttaaat ttatattgat tatcatcatt   3360
tgttgaattt tgataaatag atgaatagtt gtttttatca ttattattga tgttttcacc   3420
cattctagct ggttttgtta acaacattag ttcacaaact ttataatctt gatttagatc   3480
aattccacta atatgaaatt taactatttt tttattttct ttaatttcaa catgtgcact   3540
agctgaaacg ctttgtttta gattatttaa cattgcgtat ttaatactaa attgatcttg   3600
attagttaat atattacttg gatcattcaa ctcaaaacat aagtctaaag cccctaatgc   3660
ttttttaact ttatttccat tttcattaac ttcttgtgtt aatagtgaat aattagttgg   3720
agtttgcatt tgattaatac taatacgttg agcatttggt gttttaatat ttcctttagc   3780
agttttttct aatgctaatc atgttcattt actatcatca gtggctttat tatcatcccc   3840
atatccaata cgtaatgtat aagatgaatt tcataataaa tcactaccaa aatctttttt   3900
tcaatttaaa ttattaagat ctaatgaaga tattggaata gtgtaataaa gtggtttagt   3960
atttggatca ctattattta attttcactc aaaacgaata tattgacttt tactaaatac   4020
acttaaatcc ccatttagtt taagatcaat tgtagcgttt ggagtattat ttacaaaatt   4080
aatcgttgca gtttcaacat aagcactttt cattgtttta aacactattt gatcagaatc   4140
aacatttaaa ttatcaactg ctgttacctt gttaaatttc ttcaattctt cttcattaaa   4200
tattaattta gcatctttta gttcatattg catatcttca gttaagttat caaaaacaat   4260
ttcatctaaa acaatttcat tatttactat tttagttttt agttttttag taattcatga   4320
attagatgat tgattatttt ttactccaaa acgtaattca agctcataat ttaaattttt   4380
taaaacacta tcttggtctt caagttttag atttagtttt gcatgatgtg ctttgatttc   4440
```

-continued

```
actaacattt acttgcttaa tttttaaagg tttacttgca cgaactgtaa attgatctaa   4500
atcatctgtt ttctttgtta gataaccctt ttctaattta tattttttaa aatcagtatt   4560
atcactcaca ttatttttg ctaaacccac tcatttaatt gtatattgca ttccccatgt   4620
taaattatta aggtcaaaag taaagtattt aacagcatta ttatcttgat ttttatctgt   4680
atctttatgt gattttgtat aattaaactc ttcgttttta ttatttacta ataataaacg   4740
taaataccct tgtttaataa attcagaata atcaccatct aaagttaatt ttagggtata   4800
actgttttct tgagcttttt tgttaatctc aattttatta ataaacaagt gttttatagt   4860
tgcaaaatga acattgttaa tttcaaaatg aggttttgaa gaaatataag tttctttttg   4920
acttcaattt tcttgattta aactaaccgt ttttagttca tattctgtat tttcacttaa   4980
tccgctaaga tctacatcat ttaaaattac ttcattattt tgaatttctt taacgctaac   5040
atgtatgttt ttttgttttg gagtagttgg atttattttt gtattaaaca caagatctaa   5100
ttcatcgcca actttaaaaa tatggtcagg atcattaagt gttaatttta attttgctgt   5160
gttatcacta agattactaa tcttatcatt tgcattaata taacttatag tattgattgc   5220
atttgttagt actttattt gtggtggatt taaatttgtg atattattag caacaaaaac   5280
ttctttgttt tgatcatcaa cacaataaac accaacataa ctatatatgt gatttttagc   5340
taaatttgta aatgtaaaat ctaaatcgtc atgaatattt tcgtcgattt taattttagt   5400
tgaagatcaa actaattcgt tagtatcatt acgtttatat tttaatgcta aatatttacc   5460
tttaaaagca ctcttcatgt tattttgcat tttaacatga actgtcgtat tactatcagt   5520
tggagttgaa gggtgtgcaa cattaatact attaacttta aatatgtttc ctacaagata   5580
attttgattt ttaatatctt tattataaat aaaattatca taaccgtgat ttgtcttgtg   5640
aatatcaaat ttcgcttttg ctggtttttt attaactgat acagccccaa cttcaaattc   5700
ttggttattt aaactaccaa cacttaatca aacttcagtg tatcatttat tttcttgttg   5760
gtcaaaatga ataggtcaat catgagatac tcatacattg tttgtatttg gataaactaa   5820
cttaacatta acattatcat tatcattaaa gatttgatct tgatttaagt cattaaaata   5880
aattctaaat ttaacatcgt tttgtgttct ttttgaatca tcttcaacaa tttttgcaat   5940
actaattggt gtaggttcaa cattaaattg gtcaacaaga ttattcttat ttaattcaca   6000
ccattggtta tgttcattta aatataaaat tttatctaaa tgatattcac ggttaccaat   6060
aattgaattt gaagcgtttt tatcaaaact aaacacataa tcatgtgtat ttgtgctaac   6120
taataatggt tgagtttcaa aggtttcgtt attattttgt gattgataaa ctaattttag   6180
ttttttagca tttaaatatg gatcaatttt attaaattta gcgttaactt taatttcttc   6240
tttatttgat gcgtaagtat tttttatagt tttaatacta ttaatttcaa aaataggtgt   6300
acttgttgta aaaataattg aatgtgtttg atcatttgaa taaaactgat cattatattt   6360
gttattaata tgtttataag cattatttgg ttgttgttta aattcaacac taactaatat   6420
atatttagta tttggttcta aattatttaa cgtaaagcta agttttgttt ggttatttac   6480
attcgcaaca acaccattag ctacaaaagt cttagttaaa tcatcacctt tagcaaaatg   6540
acctataatt tgtgaatttg gtttaaaaat atcaccatca tttgtactta tagaacaatt   6600
aatatcagct gatgttgaag taatattttt aacttcatgt gaactaattg ttgttgctga   6660
tggatttata actattttt tatttgtaat tgatgaatta attggaattt gatttgtgtt   6720
tgtgcatgca aaatcattat tttggtctga gaaataaata gcttggattt cataagcctt   6780
attagcaatt aatttgtcat gaccaatctc cacactagct ttattattag taattttaaa   6840
```

-continued

```
agcactacta aattggtcat cttgtttaaa cttatgacca cttacactat atttaacacg   6900
aatgtactta ttgtttaata aattagaact taattcaatc ggtcaactaa tcttggtgtt   6960
ttgatcataa tcaagatctt gtttattaat tgtaacttta ttaacttcac aatctaaagc   7020
aatttttga tttatatctt gattattagt acttaaaaga gctaaaggat gttgggtatc   7080
attaatttta gcaaatgcgg catgaattgg tttattagca aaactaattt caaaaatacc   7140
ataatcttga tttaaagtta aattatcaat atcaaattca caatagaatt gtttattttg   7200
ttgatcatat ttaattgtaa tattgttaat taaattagca ttttgcgttt gattaaataa   7260
agcatattta acatttaata attcttttga gcaatcagtt gaatttaaaa taccatcagg   7320
atcattaatt atatatttaa catgtgcact aacagattga ttatcttgaa cttttgtaat   7380
tgtaattgtt ggtttttgca catccatttt atttggcgct aaccctaaag ctaatgatag   7440
atgattttca tttaaatctt ttttaatttc attgtttgca cccttgtttt taattgcaca   7500
aatttcactc aactcatatt gatgattagg tgtaatttgt gattttaaca attcaaattc   7560
ataaacttga tttgaatttg aattaatgtt attagagctt ttaatttcaa tagctggttt   7620
gttaggattt gttttatcta caaatttagc ataaatttca tatccttcaa gttcatggcc   7680
ttctttatgt aaaccaacac taaatttaac attttcgtct tttgcacatt cataaactcc   7740
atttactaat ttagagtttg atgctaattt aaaatcttta atgaaattat gagcaacctt   7800
agttgttaaa tctagttttt ctaattgttt tttagtagtt tcattatatt gaattggtga   7860
tgtttttaca ttaggtgaat gaacatgtgt tgtgctaata gcaccaattt cataagttgt   7920
atttggtgtt aaatccttta atgtaacatt aattttatga tttttaacac taacttcacc   7980
agcttttgaa cttgttcaag cttgttcacc tttttttgcga tatgtaattg taatttggtc   8040
attatcaact aaattatgat cttgatcatc ataatcgaat gatagatgga tttcatcata   8100
cgtatttgat ccactttgaa taacattatt aacactaata ggtgtaggtt cgatactaaa   8160
tttagcatca tctttattaa aattaggtgt taaatcaagt gtattagcgt ttttaaaatc   8220
agcagtatca ctaatgatta acttaacaaa ttcaaaatca cgattagcaa ctaagctagt   8280
ttgattatta ttaaaactaa attctttatt aaatggtttt gtagttgtat ctgaattcaa   8340
caatacagga tctgattcaa tttgttggtt attattatct ttataaacta atttcgcata   8400
tttgttttct aaactagaac ctgttttatt aaaaccaacc attaacttaa ttgattcatt   8460
cttgttaaag tttgtttttg ttggtttaac actatttaaa gttgattttt ctaaagtttt   8520
taaatcaata ttagtattat gattattaat tggataaact atattgtcct tattaacgcc   8580
attatagata gtatcacttg gtttgcttgt gaaccaaact tttttcactc gatatttagt   8640
attaggtttt aaattaatca gttgggtttt taataatcat tcattatttt ctttttctaa   8700
tgttaaatca taatcatgcg ttgttgaatt aattatttga tcatgtgcat caagttcatc   8760
aatactgatt ttagcgattt ttagatggtt attcttatct tcaaaaattt ggtcatttga   8820
atgtaacaat aaacttaaag tgattttatt ttcatctgca ttttgtgctt ttaaatcaac   8880
atacgtactt gatggtttag tgcttattgt ttgtgggttt acattatttt taataactac   8940
catatttgca tgattttcat caacattaac atcttttgaa tagtataaag cagcaaaagt   9000
gtataaacga tttgaaataa gttggttttg gtttaattca aaatttaaag caatattatt   9060
tttattatta cctatattag ttggcgcagg gattgtatta gttcaaacga cacgattatc   9120
attactaata tattttgctt taaaatgata tccttgaatt gtttcaactc gtgaatctaa   9180
```

-continued

```
attaatacta atattttgtt tatttgctac atcaacatca gttaagttat tactaaaact   9240
tgcaatagca aatttatttg taaatacgta tgtttgtgtt gtattaacac tagcatcata   9300
aacaacattg tttggttctt tataatcatt tttaaaatta attttataaa caccattacc   9360
aacatcttgg ttttcatcaa agtagatttt ataaacttta tattctttgt taactttaat   9420
gttattaaga ttagcaacaa agaatttttg cccatcaata atttctactt taccttcatg   9480
ttcgctaatc tcatttaaat tagcaccatt attttcattt ggttgaatat taaacttaaa   9540
ggtttgattt tcttttaaaa catcatcaaa atcattgata gcaaatttta gttgtacttt   9600
tgcaccatta tcactaattt ctttaattgg tgcaccaata atccctaatg gtttagttgg   9660
taataattta aaagttttat taagattttc atatattcat agatcaatat aatcactttc   9720
actaacgttg ctttgattaa aatctttatt tttaagataa acgacacgct ctaaagtgta   9780
ttcgcgatta cgtaataaat ctttaaattc tcattcataa tttgcgtcat ttgctgatgt   9840
aactttatga ataaatgaaa tttgcttacc atcattttta cgtttgaaaa taaatttgat   9900
atctttatta aataaagaag cgccaatgtt ttcgattcgt aaatttattt ttaaatctgc   9960
tgtgttttta ttttcatgat aaacaggatc catacttaga cttgttattt taaaaacagg  10020
ggcaagagta taaaaaccaa ttggtcctga tggtagttca aaaatgatag gagaaacatt  10080
cttggttttt tgattcttaa ttgtaacact cacaatttca taatcaagac cagcaattaa  10140
attagttgcc atacattttg tatatctttt atcttgatca ctaattgtag ctggggttga  10200
aataatattt tgtgttcctt taatacgata attgatatta atttcatcac cgctatgtag  10260
ttgattatca ctatcatcta aaattaattt aatcaaggcc tggttttgtc atacatcaat  10320
agcgtttttg ctaactttaa tttttgctgg cgtagtacta aagcttgaat taactaaaga  10380
gggatttaaa gctaaaatat ttttttgttc attaatagca tcaaaatttt gttcatcacc  10440
ataaacaact tttaataaac gataaaggtg atttggtttt aaattactaa aactaaaatt  10500
ttgtaaacta attaaattag tttggtctaa tttattaact aaaagatcgt ttgtacttat  10560
tagttggtgt tcattgtcct caaatactac tttaacatat ttattattaa gcttattatt  10620
gttcttaata atattaatat tgaatttaac atcatatatg ccattattat tttttggata  10680
agcatctgct aaattactaa tttcattaac aattgatttt gataatgtat gaatagtttt  10740
ttgattatct tcaatattgt ttaaaagaat ttcattatta ttgttgttat taatattaac  10800
attagctaat tgtggttttt gttttaaact aacacttgtt aaacgataag tatgatctgc  10860
taataaatta gtaattaccc ctgaagcact aaaactatgt tcatcttttt taactaatgt  10920
tgtttgtgtt tttaaaactg gttggttttt atctactaaa ttttcaaaac ataattcaac  10980
aagcattcca ggttctaaaa cttgatcatc attattaatg ttaaaatcat aattaaattg  11040
atcttcatca acattgtgtg ttttaaattc taatagttgg gtagttgaag ctaaagtact  11100
aaaatcataa gtttttgaat gctcttttac aaaaatcttc ttaccttggg tttcatcatt  11160
attttgattt tgatcattaa aataataaat tcctgcaaaa ttgtatttac gattaggtgt  11220
taaatgattg aaatttaaat taatatgtgc taaatcaaca ttatttacac tagcataatc  11280
acttcaaatt ttttggtggt tattatcaat atataaagct cgtaaatatt ggtcttttaa  11340
taagttttga ctagatttta attcaacatc aatgcttgca gtaggattta aatttgtatt  11400
aggttgatta acattaatgt tgttaacaaa taattcgttt gtaaaactta gaattttact  11460
tggatttgaa ctagcatcat aaatactatt tttattagaa ttattactaa tagcattggc  11520
aggttgaatt ttattttttg ttgcataatt aatattatca acaatgtatt tatgatttgg  11580
```

-continued

```
ttgaatttta aatgtgttag tgttttctac actaaattca agtgttttat tattattagc  11640
gtcaacattg attttaccaa taacattatg agttgtttta tctttttcat catggaatgt  11700
aatttctaaa atactatctt gttctaaaaa atcattagga tcatttattt gaagttttaa  11760
attaatttta tttaaatttg aatctggttt gcgaactagt ttagtatcta ttgttaattg  11820
ctcgttaact gatgctgttt taaaagtgtt tgtaattttt tgattattta aaaaactaaa  11880
tttataatca ttttgattag gttcagtata aatcagtttt ttaaatgaat aaatacgatt  11940
atgttttaaa tcatctaaat taaaatcata ttcattaaca ccataattta aaacaacaaa  12000
gttattagat actaaatcat gttccccatc gttatacaca attttagctt tacaattatt  12060
taaacttgtt ccatcattat taataacaat atgaacacta ttagttttta cattcgcatc  12120
tactacatca cttgcagtaa cactaactaa atcaaaactt gcttttggag tactaaaacc  12180
tggtgttttt tgtgaatcaa ttaatacatg attatcatca ctattattaa cattaaaagc  12240
acctaatact ggtttttgtc taaatttaac agatttgatc tgataattaa cttctgggct  12300
taaattattt gcatgaattt taacgcctca cgtttttgtt atatcatcat attctaaatt  12360
agatgtaaac attaaatcat ttttcgtatt atctttattg ccaatagtaa catcaataac  12420
ttgatctttt gcaaaaatat catcggttga cactaatggt aaataaatcc gcactagcag  12480
gagtgatgtt attaatagtt acttttggtg aattaagatt gatttttgaa gctgtttgaa  12540
tttgtaaagg tgttatattg ttcatattaa ccttattagc tgatgttatc ttaacagtat  12600
taacatcttt gaaataatat aacccatcaa atttataaat acggtttgat tttaatgcat  12660
ttttgtctgg taaattaaat tcatattcat tattaacatt attaattgaa acaggatcag  12720
atcaaacaac atcaccatta ttatcaatat actttagttt taaatagtat tcattcatta  12780
aattcaatga acgtttaagg gttaatttaa ctttataatt taaaacattt gtttttacat  12840
ctgttatatt tggctcataa ttataagtat taactaataa ttcattacca aattcactca  12900
attgtggttg agaattattt aactcataaa cttgttcatg attttcattt tgattaaaag  12960
cagcgttgat tggtttatta atcaacgtga tattgttaat atgatattta tggtttaatg  13020
aaacattagg aacatcaaac tctaaattac gattcccgtt ttgatcaatc actatttttt  13080
gattatctgc atcaaaaaga ttattaggat catctaaatc actaatttta atagtaaatg  13140
aactaccatc actgtcaact aagacatgat cattatcaac taatggaatt gataatctaa  13200
tactatcatc agtacgttta attacttgta aactattatt ttttaaacta ataattcctg  13260
ttggttctgt tttaaaacca tgacttaaat cagtgctatt ttttatcacc gcatcagtgc  13320
tttgtaaatc attttgatct tgtgcatata ttaatttaac aaatttataa acacgatttg  13380
ataaaaaacc atttggttta ttatttgtta atgtgaattt atagttacta ttgccaacat  13440
ttaataataa aggttgagat aaacaaactt cattatcttt actaatataa actaattggg  13500
ctcaaacgtt atttaatgtt ttatcttttt gtgagaaaac aatttttaca ttaacatcaa  13560
gtttattttc atctttttta attacttcat ttgaactaat tgattcaata tatgttccaa  13620
ttaatttcgt actaaattga ttatgttttt gatcaaaagg ggcaaataca actttttgat  13680
acgcatcatt tgctaaacct aaggccttta attctaacaa ttcataatta ttattagata  13740
ctaaattatt aagttcaaat tctaacgtac cacttttgtt ggttttgtta attcctttaa  13800
catacccatat tgttttataa acttgttgat tattcttatt taaataagtt aattcaactg  13860
ggttaccaat tcttaatttt tgatcttgat ctacaaaatc aattgctatt cgtgcatctt  13920
```

-continued

```
gtgatttaat aatttgttta ggattgttaa catcaaaatt aactatagta gcatgtggag  13980

ttgtaccaaa aattaatgga gttttaattg gagttgaata atgaatttta ttgttgtttt  14040

catcattaaa acccaacaat aaatatttac tattgccttt taaattttgc aaatgtgcta  14100

cataattttt tttcactaaa tcataattta ggttagcaac taaatctggt tctaatgcgt  14160

tattattttc atctaataaa cgataagtaa ttgttttggg gtgcttatta gttgtactaa  14220

tatttaaatt taatttagtt gcattaggat cagtatcata ttgatgataa tcctctaata  14280

ccaatgtatt agtagaaaaa attctaaatg tataaccaat aacttgatct ttaataatat  14340

tgattttagt ttgactatga gcttcagcgt ttaaatcagt aagatttaaa ttattatttt  14400

taaaaactaa atttttaatg taataagcag tatctgtttg taaatgatta aaatcaaaaa  14460

ctaaactatt atttttataa tcaattaagc cataagcact aacacaatgt tttggatcgt  14520

tttttaaagc aagtgttaat tttaatcgtt catttaaagc taatttatta gggtcattaa  14580

ctgttaaaat taaagttgtg ggtttgtttt gaataacact aggattttta acaataattt  14640

tacggcccag atcaacttca ttatttaatg ttttaactga attatcaaca tcatctgaac  14700

taataattgt ttctttagga atgtgatatt catcttctat gctaattgaa tcaaaatgat  14760

aaatcttatc ttttgtaaaa ttagggttgt ttgatagatc aatttgtagt tggtgtttat  14820

tattaacaat tgcaggaatt tttatcaaat taccatcaac atcttggtaa ttaacaaaaa  14880

cgtcttcgcc ttcttcaaca ttttttggca catcaaaaac taattggtta ttaacaattt  14940

taccaatatt tagtttgtta acaataattt gtttttgatc caaatcagca acattaatta  15000

ctttttttgac catcat                                                15016
```

```
<210> SEQ ID NO 61
<211> LENGTH: 2418
<212> TYPE: DNA
<213> ORGANISM: Ureaplasma urealyticum

<400> SEQUENCE: 61

ttaattactt ttttgaccat catatttaag agcaattagt tgatatttat gatggttagg    60

taaaacctca tcactagtta taaatcgtgt ttgacctaat gaatcaataa tagtttttgc   120

tttaacatga tattcttttt gattttcatc aataaaagtt gcatctaatg aacgattaaa   180

caaattctta tcaaaagtta gtaggtttaa atttttattt gcatcttgtt taataattgc   240

aagtggttta ataatgctaa ttctgtttaa aggattaatt tcgtttgaat ttaataaaat   300

ttgctcatgc ttgtttttat caacaatatt taacaattga tagtggtggt ttgcatctaa   360

atcttttgtg ttaatactta ttttattctt atttaaatca actttagtag gaacaaaata   420

atctttatta ttttcatcaa taaaatgagc aacagcatct tgagttgtta ttttatttaa   480

attatcatta atgtcaataa ttaaatttcc taaatcatca taggtgtatg tatttaattg   540

ttgtaattta tttacatcga ctttttctaa taatctatct tttctatcta aatcattaac   600

attaacgatt ggttgattat taacattagt aattttagtc aatgtataag tgtgattatt   660

aggtagtaaa tgatcatcat ttgttcttaa aattaattct tgttgatcat ttaatttacc   720

agttaattga taaggatgat gattttcatc ttcaaaagtt aagacaacag acttattagc   780

taaatcaggg tttaaaagtt gaattttata attattatct tctaatgccc caacaatcgc   840

agctggttta ctaaactttg tttttgatt aattgcaagt tcataatcat ttaaaacatt   900

tgtttctggc tcttctaaac taataacatg ttttagttta tatgtatgat ttaagtttaa   960

atcagaagtg ttaattacaa tattgccatt tagatcaacc tttgtcaaca ctttatgttc  1020
```

```
attatttttt tcatcaataa acacggcttc aacttgatca ttagcgaatt gtttagaatc   1080
tactttagca ttaaaaatta aattcccttt atcatcataa tgatatggat catttaatgc   1140
attagtgttt aatttattaa tagttttagc actttcattt aaatcatcta agttagcaac   1200
gcgttttgct ggagaggtat tattaatgct aatattatct agtttatata agtgtccatc   1260
ttttaaattg tttaaatcta cagtaatttc accattatta accttagcaa taatattggt   1320
tttatcgtgg ttttcgtttt caaaactaag tgttaataat cgatcattta aacttgaatc   1380
aacttgaata tgaagtgctt tttgtaaacc atttttatca gtttcaattt ttattttatt   1440
tggtttatgg acaatatttt gatgtgccgc atctaattta ttaggtttta taacatcatg   1500
attatcctta tcaacaattt gaattagttt ataatcatgg tgattttcta aatcttttgt   1560
taataaacgc acaagaccat cagtaccaac tattgccttt aaagtgtgta attggtgttt   1620
ttcatcttca aataaggcat taatattttg attagctaaa ttttgtgaaa cacgtgcgtt   1680
aataataacg tttccttgat catcaaaact gcgtgtttta tcaataccac gaatgggttc   1740
actaatttca tctaaattaa caatttttgt gtttttatta tcttctttta aagttaaacc   1800
tacgaattta taaaaatttc ctaaaggtag ttgtttagtt ccaacaatta cattaccatt   1860
atgatcaacc tgaatatttt gaatatattt agcattattt tgattaataa aatgcgcagt   1920
caaatactga ttactcaatt catggtttaa tttaatttca aaaaatttat cgccttcttt   1980
attaaaatta actttaaaga cattaggacg atcgacaagt atttttttgtt gccataccaa   2040
ctcattatta ttgattaatg tattattatt ttcatcaaca atacgatcta aaactcaaga   2100
attattcaaa cctaaactcg ttgtgtcaat tcgtgctact tctttatttc ttgtaattaa   2160
aactgaagtt tccttgccta atttatcttt aaaaatcgca taaatctttt ggttaatatc   2220
attatctctt gtaaataaac gaaccttaat aattaaatta ccatcttttg tatattcata   2280
gtatttacta aaaatttgat tggaatgctg atttgcgaaa cgtaatacaa ttcctgtaat   2340
tacaccagct caaattaaag aactaattgt aagtccagta gctattttgg cattacgttt   2400
tttattttta ttattcat                                                 2418
```

<210> SEQ ID NO 62
<211> LENGTH: 1134
<212> TYPE: DNA
<213> ORGANISM: Ureaplasma urealyticum

<400> SEQUENCE: 62

```
atgaaaaaaa acacacataa gaaacttttg cctttaattt ctatttttgt tttaatccct     60
ttgagttcac ttgttgtaat gtgttcaaaa actaaaacaa aaatagtaaa agaacaaaag    120
caaattactg cttcatcgtt aagatctact gatattgatt taacatcaat taaccttgaa    180
atctattttg ctaaatttga tgttaatgat attttagtta aaaaattcag cattgaatta    240
gaagatgata agggaaataa gataaatgtt gatataaatc ccgaatataa caaaaattta    300
caaatgctaa gttttaaatt agaaaactta aaaccaaaca ctacatataa aattacaaag    360
tttaatatca caggacatga ggttgatcta actcaaataa aagattcatt attcactact    420
aaagctgaga atcttttacc tgatatccct aatttaccta atagtgttgg tattgaaatt    480
aaagatatta aaactaattc acttagcaat gatgcaacaa aagtgaatgt taatgtcaat    540
ttagaaatta accaatcaac attagaaaat caatatgccc gattagttta taaaagcaat    600
gataattctt gaaagctatc aaatacttta aaaattgctg aaattaaaaa tagtaatttt    660
```

-continued

```
gttttagatg gtttaatatc aaaccgtaaa tatcttttta aagaattaat tattggaagc    720

caaagtgatt taaatttaac taatgcgcaa actaaaataa ctactaataa tgagctaagt    780

ttcactacag ctccaaaacc tgttgaaata aaaagtgttt taattgatac aaaatttgat    840

aatcatccaa gtagtttaat taatttgaag tttaatgata gtgagaataa tttaaaagaa    900

aatgatattt taaaaattaa atataaaaaa gtaggaccaa atgaagtcat ctttgaaaaa    960

acagttcgat tagctaataa ttttgaacta ttatttgaaa ttgaaaatac aaaaaagaat   1020

gaaaaatatg aaatcttaag tttagaatca aacactaaac atggatataa tgttgcacca   1080

agtatattta attttatttc taatgattta cgcacttttg aaatcaaagg ttaa         1134
```

<210> SEQ ID NO 63
<211> LENGTH: 1692
<212> TYPE: DNA
<213> ORGANISM: Ureaplasma urealyticum

<400> SEQUENCE: 63

```
atgtctttaa tttatcttct aataggtttt attttattat ttttacttat ttactctact     60

tttgcattat tggacatttg aacacttaga aaatataaca cattccgtca aaattttttt    120

aattttgatc aattagtcaa tacaaaattt aatgatattt atactcatac agataatatc    180

tatgcacgta caagtaaaca aaaaataaca attattaata aatacctaat tgcaattaat    240

aatgaattag attttcataa aaaaagtcta attaaattac aagattatct tgaaaatcat    300

aaattattct cttatttatc acttattaag tttattaaag caaatgaaat taaaattaaa    360

aataatgtag atgaatttgt agatttaatt caatcttttt gaaatgattt tattattatt    420

gatcaacaag aaagaaaaat tgaagatacc cataagaaat tagatttaat gtataaagat    480

cttataagta aatatagtat tccaaattta aattatcaaa aagcaattaa ttgaactact    540

gattcattta ataatttaat tgaaactaaa attagtatga attattcaaa gtataattat    600

tttttagttc aattaattca tcgtattaaa aataaagttc atttattaaa aaatatcatt    660

gtagttttaa attcaatcaa aattattgaa gaagctaata aaaatagctt acaaaaagtg    720

caagaaatca cctttttgac tgatgacaaa attaaagaat taagacaatt taaccatgat    780

tttaatgatt ttattaataa ccaattagct gattttattt ataattcaaa atttgttaat    840

ttaaataacc tttatttaaa tagttattat caacaagcct taaattgact taatattagt    900

tcgcaaaaca atattggtgg ggctgttttt gataaatata aaaaacgttt ttatgatgat    960

tttagcttca ttaatagcac tattattaaa gtaaataata ttttagaaaa aataaagagc   1020

acttcaaaaa actatcaatt aaaccaatta aaccaattaa ttttagactt agatcaagct   1080

aatcaaaaaa ttattaattc taaaattgat aaaaatgata tcaaacaaaa tattgatttc   1140

attatttcaa cacaattatt ctatgataat ttaaaaaatt tattgtttta tttaaatgat   1200

ttaaatgtta agttagcaaa ttggaatcac cactgaaata cactagttaa aaaaactatc   1260

actatttata ataaaaaaat cgaacttgaa tcttatatta aaaacaaaga tatatttttt   1320

aatttatcta atgaaatttt tttagatgat ttcgaatata ttgaaaatat atttcaaaaa   1380

ataaatgctt caaatagttt tgatccccaa attttaacca atcatgagtt aattattcac   1440

caattaaatt taattaatga acgttttgat tatcttattg aatatattaa ccaaacccaa   1500

ttatggatgc caaaaatcta tgatttgctt tataataaaa taaattatta tggtatcaac   1560

tatgaatgaa taaaaaaaga atttcaaaat ttaaattgaa acaatgtgcc tcaagcatct   1620

aaattattaa atgaatttat tgataatatt attattgctg atcacgcttt aaaacgttta   1680
```

aaatttaatt aa 1692

<210> SEQ ID NO 64
<211> LENGTH: 822
<212> TYPE: DNA
<213> ORGANISM: Ureaplasma urealyticum

<400> SEQUENCE: 64
ttatatttta tctagttctt gaattaaatt atcgattttt tgaatctcaa cttcacgttt 60
tgttttatgt ttaggcgctt gttttggttt ctcataatgc atccataata aaacaacttt 120
tgctacttga tcatgtaaag cacgtttttt tgaattcata aacatgtgaa ttacaataat 180
acaactaact aaacccataa ttgaatatag acttttaact aaaatactta aaatagccat 240
agttgtagta ttggtgaaat tatcattaat ttttaaagat aaaattgact gcacataagc 300
ttttaaatct ttaatttgat gataatactc ttttagctca gtctcattca tagcttgaat 360
tgatttaaaa cttgcatcag caaaaacaaa acaaaatccc atcgctaata aattaattat 420
ggtaaaaatt aatcaagtta ataaactatg tttaattaaa gcaataaata aaattttttt 480
atcgttttgt tttactaaac taatcattct aatcgaaaat gctcatcgaa ataaagtata 540
agatttacaa aataaaggaa taataatgta gtatgtagaa taaacaaaaa aagcaattat 600
tcccattaag aataaacgtc aaggttcagg agcaagctca tcattattaa caaaaatatc 660
actaatttta aaattactat taataaaaac taataaagat aataaaaaag caataatgga 720
aataaaaata taatctaaaa cactagcgct agcacgcctt agtgcaccaa caacgggata 780
ttcgatcgta ttttcttgtt ttaatgttga cttatcactc at 822

<210> SEQ ID NO 65
<211> LENGTH: 1164
<212> TYPE: DNA
<213> ORGANISM: Ureaplasma urealyticum

<400> SEQUENCE: 65
atgaaaaaga aggtgataaa aatgatcaat aattcaccaa acattaatta ttatttacaa 60
gataaaaaat atattccaaa atatgcttac tatgttaata aaaaacaaaa acctatcgag 120
ctatttgcac gatataaagg acgtcctgct ctttttattc gtgaaaatac catgattaat 180
acttcattaa attcaaatgt attaaattta gactttgaat ttgaagttgc aggagatttt 240
aaattaccta ttaattactt ttttatggat ataaaaagtg atataggtga atttcgtaat 300
ttagaagttt atgaaactaa acactctttg tatgaaatcg gaggagtgat ttatgactta 360
tacacttata aaaccaattt aaaaattaat cttaatcaag ctggttttgt taataagaac 420
actttaagta aaaaaattaa ttttgctttt tttcttcgta ttaatgatga taaacgaatt 480
catgaacaaa ttaattatac atgtgaaaaa agtttgtttt ttgaggcagt acaaaaagaa 540
tttcaagatc ttaattttga ttatttttac aaaaatacat ttttattaaa taaacacgaa 600
aaagttaatc ctactaattt ttgagaaaca attccattat tttgaattca agataaagaa 660
cttgataatg aaataaaaat caaaaataat aagcgttata tatttaatac aaaatttagt 720
ttaaatgatg ataattcatg aaataatcgt cctacgaaag aaacgtttga attgattaaa 780
tactccttag aatacgtaaa tttagctaaa gaaaataaaa aaattgaatg aattgaagat 840
tatcaaaata ttaatattac atatgattat taccaaagac ctattgattt tttattaaaa 900
atgaaaacaa aattcttgta tgattttaaa aacgatcaat tatctattaa taataattat 960

-continued

```
ggttttaatg gtatttgatt accaaataaa caaatagcaa aattaaaaat tacagttatt   1020

aataattatc taacaccaca aaaatttgta attaatcaat taattaacat cgaaaatgat   1080

tttaattcta tcaataaaca aaaaattagt gtacagaaag caataattga aaattatgaa   1140

aattttaaat cacttgaaaa ttaa                                          1164


<210> SEQ ID NO 66
<211> LENGTH: 861
<212> TYPE: DNA
<213> ORGANISM: Ureaplasma urealyticum

<400> SEQUENCE: 66

atgaaaattt taaatcactt gaaaattaat tggcgtagtc ataaaaataaa ggtgattgtt    60

ggtggaatta ttagtttatt aattgtaatt actgctatta ttttaggtgt tattctatca    120

actcaaaata caaataaaat tagtaaaaaa gaacccttaa ctcaaattga agataatatt    180

aataataaaa aacaagatgc acataaggtt aatgaaaata taacaattat tgataaaaaa    240

ggtggtataa tccataaaaa gacagacatt acaaaaatta accaaataaa tcaacaaaaa    300

gaaattttaa aggattattt aaaaaataaa gaagaaaaaa ataaggatca aataaataat    360

actaacgaaa atctaaataa accaataatt aatgttaaaa atgtagatga taaaaacaaa    420

caagaaaatt caactaaatt aaaaaataat gattttattt ctaataatga taaaaacaat    480

aaaatcaacg aaaataataa tataagttat gaagaaaaac cttttaaact aaaacgcttc    540

aatattatta atgtaattgc gaaaaataaa gatttatacc aattattaga tttcaaaact    600

tatttttcta atgaaaacat taataatgat attaaattta atgaaaagtt gtttattaaa    660

aatatctatg aaatagtcaa atctgctata agtagttttc aagaattttg taatatcatg    720

cagtatatta aaattgatat caaatataaa tttaataaag atgcaaaaaa cataattgtt    780

attgctaatt gattattcga taattataat attaaaaatg aaacaagata ttatgaagag    840

tttgttttaa gtattaatta a                                              861


<210> SEQ ID NO 67
<211> LENGTH: 1794
<212> TYPE: DNA
<213> ORGANISM: Ureaplasma urealyticum

<400> SEQUENCE: 67

ctattttcat aaaatatggc ggattcattt aaatgaatat tgattagtaa tttgattatc    60

tttataatcg tttttattta aatacttgta gtagacaatc gtaaacatta ataaagaaat    120

aattaaaatt acagcactag atattgataa tggcattgat cacgccaata atccagcaaa    180

cttaacacta ctttggtaat caacaccaaa accaacaaca aaagcaatta ctaaaacttg    240

caataataat gttggaaaag gtgattgttg ctttttagca attagatcac gataacgcat    300

taatgttaat gacaatgagt aaaaaattgc aaatattgtt aaatgaatat atgtattatc    360

accaattaat aattttttaa ctacctctgc tgaaatttgc acaaaagatg tggtaattgg    420

attatcaata ccatataaat atttaaagtt aggccctgct gctcaaattg gagttattaa    480

ttgtttaata acaacttttc atacctcagg attatggttt gttaagtgtg ctaaaatcaa    540

tcttggatca atatgggctt gtgcccctaa aaagtatact aatcgaggat tatttaaaat    600

tccttgacga attgacatat aaaaatgatc tggtatttct gcatctaaat taatatatgc    660

ttcattttgt tctttagcat aaacgactga tagaggtttg attgaaaaac caaaaataat    720

tgctgcaatc attaaataaa caaacaataa accaaaaaca caaataaata attggcgcga    780
```

-continued

```
atggtaacga cgatcacgaa tagtttgttt ttgaaaaata taaaataggt aatcagtaaa    840
acctaatcca atcccttgaa taaacaacat cgcatgatat cataaaattc gaccagtttg    900
tagatttaaa ggaacagaat ttgtcatttt ttgattaatt aaatgatata aagctaatag    960
aacaaacatt tttataattg aactaaaaat cgaaattaaa gtttgatttc aaatttgttt   1020
aatgctaatt tttaataaat ttaatgataa acctaattta gatatccttc aatctttact   1080
aaatttaata atactaatgg caattgttga aataatataa ccaattgaca atcctaaacc   1140
atacccacta taagctaaaa tactatattt acctaataaa aaacttgtca ctaaacaaat   1200
tgttcatgtg gcaaaatcta aaataatagt taatagaatt ttacgacgat catttgttca   1260
aatagaaatt aaaaaataat tatgaactgg tgctaaaacg ataatcccca aacttgatca   1320
tatgtattgt tcaccaaata gttgagcaaa caaggtattt tcatgaatgt ttgcataaag   1380
attataagta taagatgtcg ccaaataaac acccaacatt attaaaccga atgaaaatgc   1440
ataaaaactt gctaagttag ttgttgaatg tgatggaaca aacttgtgtt tacttccatc   1500
atatagtttt ttagctcata aggctaaaac tacacctata tttccaccta attgtataaa   1560
actaaattgg aaaacaacaa tatagctaac acttgtcgca gcaaatgcac cactaaaatt   1620
atgtaacgct attattattg taattaataa taaagctaac gatgagaaca aacttgaagc   1680
tataaacgat gagctatctt ttatgacttc tcataatgtt gtaaaaatgc cataatgttt   1740
tttaaaaaca tgacgtttaa ttacaagggg cgtttttca atcgatgatg tcat          1794
```

<210> SEQ ID NO 68
<211> LENGTH: 1505
<212> TYPE: DNA
<213> ORGANISM: Ureaplasma urealyticum

<400> SEQUENCE: 68

```
atgatgaata caaaaacatt tacttccgtt aatagagtaa tttatgatga taactattcg     60
ctaaagcaac aacaaaaaag tagctttatc aatcaatttt taaaaggatt gttatctgct    120
attactttat tattctttat tttactttta atctttgctg aaaatacgtt gtttggttta    180
ggttttggtg atgagaataa atcaatgatg atttcaaaat cgctaaatgc tttttttgat    240
ttacacagcc ctaaatattt acaacttaac tttttaattg tatttcgctt ttttatttta    300
agttttacac tgttttatac cttaatcaaa aatttcacaa atctttattg gcatcgagca    360
accattaaaa aatacttacc atgattcgtt ttatatttag tgattgcaac aattagtttc    420
ttactatttt ttactttttt tagtgtttga ccaaaagaag tttttaattt agtattttta    480
ctattagtgt tatttttatt aaatttaagt tatgaaatat ttaattattt tatttctaaa    540
aaaactaacc ctttattata cgataattat aaaaatttaa ttattgccat ggtttttcaa    600
gcgttattac tattatttgt aataattacc ccccttgtat gaattaatac aggtaaaagt    660
cctaactttt tatttgttga taatcgtttc tacacacgca tagttgatat cttcactgtt    720
caatcaggta aaaattttat tattttaatt gctttcttct tctttttaat tacatttatt    780
gttttagcaa atactaattt tttcgcttta gtaattaata aacgttacga tcgtaattat    840
gttaagaata atttatgatt tattttactt ttatttagtg ctatatttat ttgattatta    900
agagtttttg catataagca cgaaaatgaa aatctaccgg ttggtaacaa ccatttatta    960
tgagtttata ttttacaaag tttttttgca ataatcatat taatactata tatggtattc   1020
actttaaaaa aacgcttaag cgtaaagagt agtttaaata ctttattaaa tttagtagtc   1080
```

-continued actcaaacaa ttctaagttt aagcttgttt ttagtaacat tatttaattc taagagtgtg 1140
gtttctttaa ttaatgtttt tattacaatt actgtacaaa tgagtgtgtt tggaatctac 1200
atatttcaaa ataaaaacat ttcaactaaa ttattggtgc tattaaaggt tattatgatt 1260
ttaattattt taaccgcagc aattgtaggt tttgattatt tattaacatc tgatcatcat 1320
aataactatt tattctcaaa cattcaaccg aaaatgaatt tagtacaaat catgttgtta 1380
ttaaatttta gtttgaattt tactttaatt agttatttaa caattaaatt tgcaatggta 1440
atttttaaaa tcaataagct aaataaggag ttaaacaatg aaaaaaaata aatctaatct 1500
gacac 1505

<210> SEQ ID NO 69
<211> LENGTH: 1836
<212> TYPE: DNA
<213> ORGANISM: Ureaplasma urealyticum

<400> SEQUENCE: 69
ttaattttga cgaaccttaa tttgttgttc taattgtttt ttaggcataa ttgataattt 60
ttcatcattg tacttatgat tctttaaata tttacgataa atacgtaaaa ttttataagt 120
gctatatcct aaaataaaaa tacttgatat aaataaagga aatgatcaag ccattaaacc 180
aatgaaatgt ggatctgatt ggtgtgttaa cccaaatcca gaagtaaacg caaccataac 240
taattgaata acaatcatta catatggagg acgttgtcgt cgggcaatta atcctacata 300
acgacttaaa atagaagaaa aagaaaagaa tgtacaaaag aatgataata aaatataagc 360
attattttta attaaataac tataaatatt tgaagctgaa atatcaacaa atcgatgtgt 420
aaaaggattt ttcatttgat atatcgtttc aaatttatca cctagttttc atattggatc 480
aatcactttt tgcgccattg gtaatcaaat atttttatca tttgatgata aagcattaac 540
aacttcttgg cgaccaatat tcacatgact agtaataata tctaataatt tttcatcatt 600
aattaaaatt tttcttaaag attgatagaa atgttcggga acttgctttt ctaaaaatat 660
ataagatgga ctttgttcac ttgtatacaa ttggactaat tgttttacag aaaaaccaaa 720
aataactgaa gtaattaaag caaataaaat acctaatata aaaactcaaa aaaataattg 780
tcttgaatga taacgacagt ctctgacttc ttgtttttga tataaataaa ataaaaaatc 840
tgacaatcct aaatttaaca tttgtatgaa aatcattgat tggtacatta gaattctcgt 900
tgattgaaaa tctaataatg atgaaccaac tacacgtgag ttaattacca caaatgtaat 960
taacaaaata aacattttac caactgattt taatgatgat aaaatcgttt gaattcataa 1020
taatttaata cttaaaacaa ataatctttt tgaaatatat aatggacgta aaacaatttg 1080
ggctttttca attgtagtca taccaataat aatagttcaa aaaacaaaac caattgacat 1140
accaaggcca tagccccaat aatttaaaac actataacta cctaataaaa aagctgcaat 1200
taatgcggtt gttcatgtac aaaaatctaa aacaattgct aataaaacat taatggactt 1260
ggttgatctt attaacatca ataaatagtt tcgcaaaggt gctaaaccaa caactgctaa 1320
tcctgaaaca atatatgcac tacctacact ttgattaatc actgtatttt ggtgatcatt 1380
tgcaaaatga ttataaatgt aagaggttgt aaaataaatt aataaaacta ctaaaccaaa 1440
gataaatgaa taaaaactag cagcatttac tgtatcattt gtaggttcaa acttatactt 1500
accatcttta aatgatcttt ttgaccaaat cgcaaaaaca atgccaaagg ttgttcctaa 1560
ttgtaaaaaa cttaactgaa agatagttaa ataactaata ctagttgctg cataagcacc 1620
aatatcttta tgatgagcaa caattacaac aattaaaatt aatgatagtc ctgtaaaaac 1680

-continued

```
acttgcagcg ataaatggcg agctttcttt taaaagttct aaaagtgttc taaaaacggt   1740

aagatttttt ttaaaataag aatcggattt tttaataact ttcatttgtt tctgttcttc   1800

caaattaaat ctcccccttt tatataaaaa caccat                             1836
```

<210> SEQ ID NO 70
<211> LENGTH: 2427
<212> TYPE: DNA
<213> ORGANISM: Ureaplasma urealyticum

<400> SEQUENCE: 70

```
atgaaaaaaa tgtttctatt aatgaagaat atgatgcgtt tattctttaa aaataaaact     60

ttagtaactc aactttcaat tttaatgatt gtttcaacag ttgttattgt tgcaacaacg    120

attacagtac aacgtttgca aaaatcacaa agcgatatta aaaaaattgg tttacaaagt    180

gattttttaa ttgatacaaa agagcaagat aatattaatt tcaacgaaat tgacgttagc    240

aacaatcttg taaaacataa tgaaaaatta attcaattag caacttttaa tcaaaatatt    300

ttaaaaaatt caaataatta tttacaacta gttgataatg catttcataa tcataacctt    360

ttttggccaa ctaatgtaaa caatcaaaaa atagatgtac taaatcttga aggaaatatc    420

gattgaaata aaattaatca attaaaatta caaactgttt tttgatttga aaacaataaa    480

gaaaataatc aaaattttgc taacaattat gatgatttgg tttatgaata tcataattct    540

aaaaatcaat tagtaggatt tcaaaattta gatggtgggc atattttatt taaaacaccg    600

gcgttaaaat cagcaaacgg taattatgaa acaacattta aaattaatgc tgcaattgtc    660

caaaaaaata aaccatttaa atcttttttt aactttgata aatataaaga attaggattt    720

aagaataaat cttattttac aaatcctgta ttaattaaaa atatagatct ttattcaaaa    780

caagttgttc aaacactaaa cgatcgttca aatcaatcaa ttgattttaa agactatcaa    840

agcacatttc aagccattgt tgatacactt gaaactaaca cgataaataa agatttttat    900

agtgtgaatt tacatgttga ttttaacaca ctatcaacaa aatacctact atttgctaat    960

tatttaaaaa atgaaggtat tgataaaaac cgttatataa atgaattaaa aatcgataac   1020

tataaacaga agtatttaga tttatttcaa aaccaagttt taattccaaa agaattaatt   1080

gacgatccaa aaaaaataga agaagtgcaa aaaattattg caaaagccaa agccttgtta   1140

attgctaaaa ttcgtgaaga aacaaatatt ttttatgaaa actcacaaaa atcagctctt   1200

gaaaataaaa ataagattcg tgattatgag atgcaattaa aacaaataaa tattgctcta   1260

caaaattcga attattctaa taacgaactt attcaattaa aaaatgaaca aaaagtatta   1320

gcagcaaatc tcgatcaagc aaaatttaaa cactttttat ataatgattt aattaaacaa   1380

gatttccgtt cgattttaaa taattataat atttattatc gcaaacatga atcagcaatt   1440

tataatgatg ttaaaagtga ttcaaatttt attgtcacaa atgcaagcaa tccaacatat   1500

acacaaaacg gtttaattgc accaagaaat caatgaattg ataatatggt gcaaattaat   1560

gaaaaaaata aaaatagtca aaatccaaat aaaaaattta agcgaatttt tattaatgat   1620

gataattcaa ataaaattaa taacttttat gacctttatt caaattacat taaagtcatt   1680

caaattttaa aaaatagtta tgaaaaagat ccagatactg ataaagattt actagttgaa   1740

gagcgtgatt atactccttg aattaataca tcactaatta atatatatca acttccacaa   1800

ttttttaata tcttatttaa tcaatctgaa tgattattat caattcaata tctaaaagaa   1860

atgagtgatt ataaaaaata tttactacaa atttttgaac catatcaaga taaagaatgg   1920
```

-continued

```
atttttaatt taaaacataa agattgacaa gatggcgaac aagtggttgc tatttataaa   1980

aatgcagata gtaatagcga ccaaaaagaa tattatttta acggctatgt taaaaatcaa   2040

cgagcttata ttaatgttaa atataataaa aatctgccaa cacgtttaaa attaattaat   2100

attattaaac aaaatcaaat aaatcaaaaa aacaatttag ttaatgtttt agatcaagat   2160

ttaaatgatt atgcaaagat tattaatttt aaaaaaggta ttaaagatat taatacaaac   2220

cagcaatcag tttatgatca gtgagcttta aataatccac aagattatgc tatgtttaaa   2280

atttgattat caaaaatcat taaacgttat tattttctac gcttcagcaa tcaccttatg   2340

gatatacaat tcaagcacaa aacgttttat caaaagcttt gttattgccg tttacaatta   2400

atattattaa tcgtagttca gatctag                                       2427
```

<210> SEQ ID NO 71
<211> LENGTH: 285
<212> TYPE: DNA
<213> ORGANISM: Ureaplasma urealyticum

<400> SEQUENCE: 71

```
ttatttttca ttttttaata ccccataatg atcgattact tttaggcaat tatttagaac     60

ttcttcgcta ttattaccta cacaagaatt aatttcatct tctcgtaaaa aattatcaaa    120

ggatttatta ataatttcaa aaggtgttat attttgtaaa ttaaaaagct caaaaacttt    180

aatttcatta aataaattat ttaaacgatt ttcaacctgt ttaatttcat catcagttaa    240

tataaacatg catgatgaca ttaatttttg taaattataa ctcat                    285
```

<210> SEQ ID NO 72
<211> LENGTH: 1767
<212> TYPE: DNA
<213> ORGANISM: Ureaplasma urealyticum

<400> SEQUENCE: 72

```
ttatgaattc ttttcatttc atttgctata gttaacattt acacttttaa tttcattaag     60

gttaaaaaga tattttctaa aattattctt agcagcttta aaactagtca aattatgaat    120

attagcatcc ttattttcta aagcaatcat tgctaattgc gaatatgatt gttttgataa    180

aatttggttg ttttcagggt tagtaacagg taaaatagta cgagaattgt tagatgcttt    240

aattgcttca acaaatttgc gtgatttgat gaaatcatct atttttaatt cattgatctt    300

tttttcacct aagaaagcat atggataaac accatttaga ccacgatcat gttcataata    360

ttgtcagtct tcaagttttt tatcttcaac atactctttt ttattaactt tagcttcgtt    420

ttttaattct tgttttaaat cgcggcccaa aatactaaac gcatgaattt tagataatgt    480

acctgtgtag tattcattat aaacagttgt acgtttttttc tctgtctcag ttaaccctgt    540

tttttgattt ttaattttta aaaaatttc ttgaagagtt tgtgttgctt tttgattaat    600

attagcagaa cgcattgttg atggtgcaaa attaactacc atatctttta atggaatttc    660

ataaactaaa ttacgaattt ctggtttgtg atcatcatga atttcagcat aagttttttt    720

atcaacactt gataaagcag cgttaattga actaagtgca tttagttgac taccattaga    780

actagcttcc ataaatgatc cagctttttt gtttgaagag ttatatcaag catattgtaa    840

tttaatattt tttaaacgta caagaacatt ttttaaactt ggattaacta ataattcatc    900

atttacttta acaccaaaat taggtttatt aatacttaaa cctgtaattg catctacata    960

ttctcaatca aaactaaaat tatataaagc aagtttgtat gtatgtttac ctgcacctac   1020

accttgtact aaagctaata aaaattcttt agcaacttcg ttttttaacc ctttaaaaag   1080
```

```
ttcaaaatct ttatttgaat ggttattaaa tgcatgttct gctaatcatt ttattaattg   1140

atctgtcata gaggtaatat aagtatacaa tccatcacta ataactaaag agttgattaa   1200

ttcactaacc ttatttattt ttgttaattc atcacttgaa tatagttttt ggttaaaaac   1260

agtttgtttt tttgtttggt caagaatttc taaattatta gcatatttac ttgttgaatc   1320

aaaatttaac ttattaccaa ttaaacgaat caattcattt tgcaaaatac tcaaatcaat   1380

tggtgttagt ttagttgaac ttgataaact ttttgttcaa acttcttttt tgggaaccaa   1440

ataaccaaat tgatcgattt ctttattgtt tttatcaaag cgtttattat ctttaacact   1500

cgtataagtt aaatcacctg ccgcataata aacatcatct aataaatttt gattctcaaa   1560

aatcatttca tgtttttgat tcttaccttc aaaggctcga attttaattt taccaatatt   1620

attagttgta gcattagcac taacataatg aacattaact tgaggatgag cagctgctga   1680

acacgatgca gcaacaattg gcgttaatcc aataaaacta attcctaata ttgaaaaaat   1740

tagcttttta cttttgtttt ttttcat                                        1767
```

<210> SEQ ID NO 73
<211> LENGTH: 489
<212> TYPE: DNA
<213> ORGANISM: Ureaplasma urealyticum

<400> SEQUENCE: 73

```
ttaataagcc gagatatatt cttcttgtaa agtgtgactt ttttttcgat ttcaattaaa     60

tactttatca tacacaactg ttaataaaat tgatgagaca tagtgtatga aaggaattaa    120

tgaaataatt aaagcttttt taactttcgt tttattttca ttaaaatcat ttaaatactt    180

aattaaaatg cgaatattaa caactaagct aattaaatat gttaatgttc ataaaactaa    240

aaataggcca aaaaaaccaa ttgataaacg aatttgttct ttttgtgata aataaacttc    300

taaatcttta ggatttaaca tgttaattaa ttctttttca tgatttaggg tatatgcatc    360

aaataaatta tgacgcacta attcatgacc aattcaagct cctacacaaa caaataacgc    420

agctgcaaat aaaagtaaaa ctcaattttg aattgaaata aactttaatc ttttaaaaat    480

taaatccat                                                            489
```

<210> SEQ ID NO 74
<211> LENGTH: 3396
<212> TYPE: DNA
<213> ORGANISM: Ureaplasma urealyticum

<400> SEQUENCE: 74

```
ttaattatcc ccttctgctt gtggtgatgt tggtaaacca ggacgtggag gtcttcgata     60

atcataagca aattgtaaat aatatgtaaa gttatttttc ataccaccaa gtgatgaaat    120

cgttcagttt gtatcaattt ccataatagg cacaattgct gcttcatcac gtaaaatttt    180

ttctaaattt aaaattgttc taaagatact atcatcatct tctcaacctg gacgattccc    240

tgaaaagaaa tcaataattc ttttacgttg atcaacaact gtttctaatt ttgtcatata    300

aatttcatta ttaactttat cagatatttc attattctca tttcttaagt acttacttaa    360

taatggtttt aaatcattta tgtaagataa gttgattact tgatatgatc caattggtaa    420

ttttttaata gaaaatttgt atttaaatcg ttttttgaaa ttaatttcat caatattttc    480

tttattataa tattttgcat aatcttcttt tgtagcttga acatattgat ttgttttttt    540

atcgataact ggttgaattt gtagcgttgt aaattgacct gttacattat tttgcaatac    600
```

-continued

```
tagtaaaaac ggtttatttt cacgttttgg atcgtgttta tttaagaact cttctgataa    660
ataaaattca cgttcttgca ttgtatcaat ttcgttctgt agattattag cttctttttc    720
tcacgttgat ttcgaactac ttgtaggctc atttttaatt ttttgattta atttattaat    780
ttggtgttct aaatcatgaa tgatcttagc gtcatattca gaataattaa catcaaacat    840
tggaatggct ttatctttta attttaattt acgtaaatca gctctatttg ttaggtgttg    900
tggattataa acttcacttg ttttaatatt tgttggcgtt accaattcac gaataatatc    960
agcgtcttct tcactaatat gtaaacgttt caaagcgtaa tctaattctg ctttattttt   1020
ataacgatca aaaaagtttt ttggcgttca agatcctgtt ggatttaatt cataacctga   1080
gcttttatta ttttttaaat caattccatc aggtgttaaa aataatccta atgctgagtc   1140
ataagtacta ccagcatatt tatcaaagtt ttgataagaa atatcaaatt taccactatt   1200
tgcaaatgtc acaaatgtgt ttggcggtaa tgcttgtaac tctaatttta cataaccatt   1260
cagattacgg tcaattaaat ctttaatagc aattacagct tttccaatat cagctggttc   1320
ggtaggataa acaaatttta aaacaacttg ttttttatct ggatgttttt tcttatattt   1380
atctaaataa aatttagcaa cttgtggatc aaaaccagta tcttttcggt taatattttc   1440
aaatgttgaa tttttagcag caacgtggtc actaaaatca ttattttgga ttaaaaaaga   1500
acggttttgt tttcttgttt catgtgtttt ttcatcttta atagtatcaa tgtattcact   1560
atcaaaacgt ttattatcaa atcaatattc taaattacgc ccttttgaat ctttaattct   1620
ttgaaatgat gttcaagttg taactggaaa agatgaagtt caaccagata attttaatat   1680
gttttctctg ttaatagcaa aagcaattgc acgtcgtaaa tcaggatcta ggattggaat   1740
gtccttatta ggatttttta aatattcttg ataactatca taacgtgatt gacgatctaa   1800
attaaattgc attgcaaccg ttccagcccc tgcttgtttt ttcattaaat cacgcatttt   1860
actttgcgct cagaatttta attgatatga tggtggaaca gtagttgatg aaatcatccc   1920
ttgttcaaat caaagtgatg taacttcatt tttagaatta aaataaattt taatcttatc   1980
gctaattgtt caattagctg aaaaataatc tttatttttt tctaatgtca tataaccttg   2040
aggtcctaaa acaacatcag caatattaaa tggaccgctt caaacaaaat tttcaagagt   2100
agaaccgaat ttttcaattc caccatgtgt ttcaataaaa cgacgattaa ctggtagtaa   2160
agcttggttt cctaaaatat cagtcaataa aacactaaat gaaggttttg gagcataagt   2220
ctcaaattcc attagtaaat caaaacgtga agttggtaat gatttaaatt taaataaatc   2280
ttttgaatta gctaaagttt gtaaatcatc acttgccaac ttttgacgat gattaaacga   2340
agggttttca attaaattaa taacaatttt ttcaggtgtg tttttatctg gttttttatg   2400
atcatattta ggattaaaaa ttgttaaagt ttttgactca tgaaatttga aatccttatt   2460
ttcaggtaat tttaaagctt cttttaattc tttatttgaa atattagtat aggcttgacc   2520
tgtacttaat ccaatttcat aagctgcttt tttaattgcc gcaatttcta gatcatcaac   2580
agggtgacca tttttatcaa aagtttggtt ttggtatgga acaaaattag gatcttcttc   2640
tcattgacct gtttgcttat ttaaaatata tggagcacga ccaaaagggt ttttataagg   2700
aacgccatgt ttacgaatat attcttcttg agcatcatta aaagcgtttg ttcctttgat   2760
gttaaaacgt aataagtgtg aacgtaattg actaccagta tttaagtcta aaatatactg   2820
aattgcatca atgaaatctt gtgcattaac ttctttacca tcacttcatt tcgaagcgcc   2880
aaaattagtt gtaaattttg ttgcaacaat acgattattt gaattgttat aaaaaactca   2940
tgttggatca tcttcactaa ctgttggtgc taacgctcca gaattaattc caaaagatga   3000
```

```
taaatcaaca tatgatggtg atattctcat accttctaat tgtgcatcag tcatattatt   3060

aaaacctgca tcaactggat ttttatattg atttaaaaac aactttgata ttcctaataa   3120

gttaccgatt gttgaatttg ttgatggcgc ttcttttatt aaaccatcta ctagtgaaaa   3180

tacaatttta cgaagcgatg caaattttac ataattcaat gtgttgattg catccattgc   3240

caaaccaaaa ttactaccat cttctaaata tggactaatt ttattttgtt ctttagtggt   3300

cttagttcta gcacaagaag caataatcgc agcaacggga attaaaccaa caattccaat   3360

agataaaaat ataattttct tatttatttt tttcat                             3396
```

<210> SEQ ID NO 75
<211> LENGTH: 5652
<212> TYPE: DNA
<213> ORGANISM: Ureaplasma urealyticum

<400> SEQUENCE: 75

```
ctaaactgag aattggtttg aaattctaat aattgtacga tttttatctt ttgtattttc     60

gtttcttgca taaactggtg aaacagtata tgatttaccg ttttcagcaa catatttgcg    120

tgaacctaaa gtcattaaac tttttgggtt ttttggatca cttaaatcca taacttcttt    180

tagatcttta tccacaaaat atatttcaaa ttcacttcct ttggcattaa ttgaatcata    240

accaattaat tggttagtga aattagataa aattgcataa tcacttgttc atgaaacata    300

accttcatct tctaatgttc atttagaatt aatgtctgat tgacgtttta gataaaataa    360

attatttgta ttatctgtgt gaacatcgat atattctatt ttgccattat ttttattttt    420

tattgcaatt tttttaactt tatccttata ttcttttttta aagaaaccat acattaaaat    480

agaatctttt tctttatttc gataaatttg agctaatgtt cgatcaccaa taccttttga    540

tcttaatata tatagtcaca ttgctcgagc acgatctgtt acttttgttt tattatctaa    600

ttccaaaata tttaaatgat catctttaat tggttcacga ttgtcatcat aaatctctca    660

atcaataatt tttcttaatc aacggtcttt gaaaaaacca ttatttgtta atcttgtttt    720

accgatatat gaattagatt taggacttaa acgtgttaga aaagaatatg aattcaaatt    780

atttaaaaca tcactatcat gagtttttgt caatgctaaa aagttagcat tagataaaaa    840

gctttcctta actttattaa aattactttc taattcttgt ggttttgtta gataatcatc    900

aaataactgt tgattttttt gataaacatt taaagcctga tttgctaaaa cattttgaat    960

tttttcgtaa ttatttgttg caaataaggt atttaatgcg attgtatttg atacacttaa   1020

gaaattattt actggaatta aacgctcgtt tcattgtttt gtattatcac cactaaagac   1080

atattcattc cctgtattaa aatcacttaa acctgaaata taatttggta ggttatctaa   1140

ctcattttgt gaaggaataa atacagtttg tacataatca cgtgttaata cctcagcaat   1200

attaaataca taatccccaa aaatttcgtt taatttttct tgaacacgtt ttttatttaa   1260

tgttacataa tctgatgaaa caacagttcc atcagcattt ggaatttcag acgattgaga   1320

aatcccaaaa aatgatccta atcaaccata aatatctttt gaaccaccag gtatatcagt   1380

ataaattgta aatccaaaag catattgtaa taattgacca aagtttaaag tgttattctc   1440

acggtgtttt cgttcaattt caagttgaat tcctttaata attgaatcaa cagtacgtac   1500

atttttttgg tttggttttg cttttcaaac attctgtgga ttaccagcaa aattatatgt   1560

atcaagtggc tctccatatg gtgagcctgg tctttcatat ttattaccaa aacttctaaa   1620

tccatataaa cctagtttgc catcaaacac ttgtttgtat ttatctaatt cagatgggtt   1680
```

-continued

```
aaaatctttt gatttataaa atttaaaaat atcattagat tctgtaaatc catcaaataa   1740
taaacctgtc agattttgtt taaactcttc tagtgttaga tttttatatg cttcttgttt   1800
ttttattact tcattgaaaa atttatcaac atcataacgt tcttttaaat attcataatc   1860
tcatttacga acattttcat gacttgagct taaagcattt tccacaattg tatatttagc   1920
tggatccaca gacataaatt caattaaaga aggaatatct ttaaatttaa ttgtgtagaa   1980
ttttgatcca ttattttcaa gtgtaagagg agtgaatgat ccattatttg attttagata   2040
atcaaaatta attgcttgtg cttcagcagg cgttaaaatc attaatgggt aaatttcttt   2100
ttctgttaat tcgtcaagct tttttaaatg tttattatct tttccatcac ctctatcaac   2160
aatcaactta atagttccaa attcatttaa atttatcatg cttttattaa ataattgttc   2220
atatgaagta attttatttt gtgtaagata gctaggacgg ataccaataa ttgattcaac   2280
tgattctttt gtttttgttc ttaaaatatt ttgatatagt tctttttctt ttggtttaac   2340
aaaatattta taaccattat taccttcaat tccagcgtca aaataattaa ataatgttgt   2400
ttgagcaact acattaacat ttttaacacc gaaacgatca aactgtttgt cataatattt   2460
tttaatttct attaattctg gatcaagttt gctgacttct tctttagatt tattatctca   2520
aatttttgat gcattgtatt gtaaagttaa taaagcatat ttaaattggt caaaggtttt   2580
atttgtaata tcttcgccaa taatttgcga aagaactttt ttataaatatg gaacagatga   2640
tgcattcgct tttcatctta attttaaaga tttgctaatg ttaaaatcag ggtatttaaa   2700
catcgcatca gtaattcgtt cagctcattt tcgtttttca tttgaagtaa acattgggtg   2760
atcaaaatat gtttttaaat taaacattga tgtatcaaaa ttaccgtttt catctcaacc   2820
accattatag taatttttaa cgattaggct attaattgaa tcttgtatct ctctcacttt   2880
ttcattaagt tttcttgtgt taattgtccc atctgatttt aaacaagttg ataaatcaat   2940
tactggtgta ttgtttttgg ttttaattaa aatttcaata tcatcttttt tgtatggatg   3000
ttttttcttg tgaagtttat aaacaattgc tctaccatct ttactaaatt taattggtgt   3060
tcccatacca tcttttaaaa taccatcata ttttgaaagt cctggttttt caataacact   3120
accaaattta aaattatcat ttttttgttc ttgactattt tgatcattat aaaaataata   3180
ttcagctttt aaacgacttg gatctttaat gtcagggcca aatgatgggt taacagttgc   3240
agattcatga tcaaatgaat tcataataaa taaatcatat ggtttaacat tacgtaattt   3300
tgccgcctca aataattcat cgtatttttg taaaaaacga cgttttttat tatagaaaaa   3360
ggctttagga tcatcagcat taacggaacc aaaaatatct tttgtgtttt ctcaaactgg   3420
atttttagga tcgttattta atgaaaaatt aaagaatgac ccatcttttg ttggattata   3480
atcaacatca gtttttctaa aggtaattcc gctagaacgt gcatttaaat aatcttgtaa   3540
tgccttacca tttacatatg attcatcact aactcccgat ctagaatcaa ttcctccacc   3600
aataactgaa tcattactat cactaatatc tttcatgtct tgtaatgttt ggtgatgtcc   3660
atattcgtgt gtacttacat attttaaata gttaatacct gttgttttaa atgcaggatc   3720
agattgagca actaatgata aataaggaat tcgatcagtt acataaatac cttcgtattc   3780
accattaaca actttatatg tatttttacc atatttatct tgaacaactt ctgtatgaat   3840
accattaatt ttttgtaata aatgacgatt tttatttaaa accttatcta ataaaccgct   3900
atatgcatca acataaatag tataagtttt aataattttg ccgttaacaa atttacttcc   3960
ttgtttaatc aaacgaggtg taaaaacatc aaaataatta gccgcaactt taagagtgtt   4020
gaaagcatca tcaaaacttg aatcataatt ataacctttt ggattatttt taggtgattc   4080
```

```
taaaattaaa tctttatcat cttttgttgt taaaattagt ttatttaaac cttcgacttt   4140

tgttttagta atagttacca atgaaacttt tttctcatca tagttaacta attcagattc   4200

taataatgat tcttttgatt tataaaaatg ggattttta ccattaccat caatatcata    4260

aatataaaat tgtttatttt taaatgtaga ttcaacatca taaacatttt taaaattttg   4320

tttttgatca atataatcat taaaattttt agtaattatt tcacgtaaac ttgatgctaa   4380

aatactatta tcattttgaa taaattcatc atttgaactt gatttagtag tgaattcatc   4440

cttaaacatg tagtatttaa ttttttgttg ttggccacca atggttgcat caattagtaa   4500

ataattttga ttaccacttg atttaccaat tgattcaaga tcaagcgaac caccaaaagg   4560

agatgaagca ctagcattaa attccaaaaa ttcattaatt ttaattttat taatttcatc   4620

cattttaacg tcgattttag gattaaattt tttatctttt ggaattaacc ctttaacaaa   4680

ttgtaattcg tttaaatatg cttgtacttt ttgttttgct tgttgttcgt tttgagcata   4740

aaaaagataa tttaatgttc gatcacttgc tttaagattt tttaaattag gaaaatttag   4800

tggatctttt gttaaatcaa agtacttatc agcattaaat aaataagtat tttttgcgtt   4860

ttttaggaca tcaattaatt taacaccacc aaaactatgg ctattatatg ctgaaatcat   4920

taaaggaatt ttttgatgat attcttctaa ttcttctaat gtcatagcat ctttattaac   4980

ttgtcgtgct aatgaatcat aagcattgcc ggggccagca ttaatattat aaattggtaa   5040

tgaaccaaaa aaagcatctg ggaagaattc aattactgtt ctttctcttg taccactatg   5100

taaccctagt gtaattgcgt taccattttg ttgaattcca cgacttaatt taaattcttt   5160

caaagtcaac aaatccggtc ctcaagaaac atttttaaag aatcaattag taaactcaat   5220

gaattcgtct ggagaaatac tattgatata attgttattg aaaacaattg ggcccacttc   5280

taatcttaaa tttggtaagt tgttgttatt taaattaaca aaattatcta aaaattcaag   5340

ataagaaatt ttctgacctt ttttatattt tccaaaatca attaataatg ttacttgtgt   5400

attattacct ttttttgctt taaaatcata atcagcaact ggtttgccaa attgatccat   5460

taataaagca cgatctactt gacgattagg aattgtcgta tcaaaactac tgttaacttg   5520

taatgtttga cgtccaagtc caccagtaga aacagcatat aatttcataa aaccaacaac   5580

agcaccagca aatgcaccaa ctgatgcaaa agcaattgca attttagctg ataattttaa   5640

cctttttttc at                                                       5652
```

<210> SEQ ID NO 76
<211> LENGTH: 441
<212> TYPE: DNA
<213> ORGANISM: Ureaplasma urealyticum

<400> SEQUENCE: 76

```
ttaagtaatt gattgtgtgg ttttaataat ataagcaatc atacaagcta atgcataaat     60

aaaactaggt aaaatgataa ttgtaattaa aatatttaag cgaattgtgg cataatcaat    120

agatcgtaat tcatatttag cattgatata aaaacgatca actaatttca tttctcacga    180

actaagttta tactcattat attttcttaa tttaactgct caacggcgac gataaacttg    240

gcgcgagaag ataatatata agaaaactac cataaagata catgtataag ctataaaaac    300

attcatacgg tattggtgat aatctttaat taattcaaca attaagtgac taataaccat    360

caatattaat aatgcaatta aaacaataat gcttttataa tttaataaac gattcggaaa    420

cgattgtttt tttatactca t                                              441
```

<210> SEQ ID NO 77
<211> LENGTH: 1194
<212> TYPE: DNA
<213> ORGANISM: Ureaplasma urealyticum

<400> SEQUENCE: 77

```
ttaatgacaa aaaccatcag catggcaatg atgaatacta cctggttttt taggttcaag      60
tgttaaatca aaataactat acatactata aataacatac attcctttaa ttagagcatt     120
attgtttttt tgcccctgaa ttagaagatt ttcatataaa ttatctaaat actctttatt     180
tgtttttaaa ttaaaaggtg taattttttt accattcttt ttaatgaatg ttggtgctaa     240
aaatgcaatt ggtgaaaagt aaaaatcatc taatttatta tttcaaatat tggtataaac     300
aagatcacgt tcgggtttaa tagatgtttg tgcaggacga tcaacaataa aaatttgttt     360
taaaacaaga tcatttaaat taaataattt aacatcgtta tcaatattta aatcattaat     420
tttactaatc atataacgga ctttgttttg attatcatcg gttggtatag cttgtttaac     480
tcaacgatat aaactaccac cagttattgt atatccttca taatgttctt tgctatctgg     540
atatttaata atcgaatgat aaattttgac atttgaataa ttaatttgca tgctaatagc     600
ttcattaaaa taatcaatta ttgctttttt tgaaccaaat caaaaacgtt taattttctt     660
agtaaagtga taatcatcat ttctcacttt tttgtcaggt ggaattggct cataaaattg     720
aggtttagtt tgtatattaa tatcaccaat gtcatcaata actaagccta atttataatt     780
aatatcaaaa gtaccattat ttgaattttt atctgtattg taaattaaac taaaatcatt     840
taacttaaca tgatattttg cattatataa atttagtaaa gcaaaattat aagaataata     900
taaatacaag gagcgtttaa ttgtttgatc aaaataatct tttaaactct catagaggtt     960
tagaaaaatt ttagtttctt tattttgaga ttgatttaat atttgttttt catttgcaag    1020
attaatatta ttatttgtga ttgattgaaa cttgatttgc gtatcttgat taattgttac    1080
tttttagat  ttttttgttg aacaactagt taataaaact aaactaataa tagttgttaa    1140
taatatacta ataaagatta ttaatcttgc tttgagatta ctttttgttt tcat          1194
```

<210> SEQ ID NO 78
<211> LENGTH: 1736
<212> TYPE: DNA
<213> ORGANISM: Ureaplasma urealyticum

<400> SEQUENCE: 78

```
tgagaaataa tttatctgat ttggaaatcg aaaaattgac caaaacatta gtatcaaaaa      60
acaaaagagt tgtagcttta tatggcgttc ccgaaaacac ttcttataaa ctaatgaacg     120
atctaattag tttaatggat gtagaaattc ctaattgatc atcaatttca agcgcaactg     180
aagaccaatg tattaatgat attaaaaatt ttttactgtc aaatgcaagt ttagaaaact     240
ttaaaaactt gccttctaat aaccctttaa ttaattggtg gaaaagacgc cgtttaaata     300
ctgttgttaa aaagattgaa gaaatcaact cagcgttcgc agaccgtgaa ataacatctc     360
gttcaaaaat ctttttgatg cctgttttaa cagcatttag tactttagga actacactag     420
ctgttccttt aatatctgtt acttttttac ggggtgatgc aattattaat ttgtggggta     480
aagatggata tattgctttc ttaagtttac tattttcttt agttgttgct gttattattt     540
cagcttttgt cgctttattt agtagtttaa aaaataataa acgtaattat attgtttcaa     600
acatgaccaa aggtcttaaa agaatatatg ataaatattt tatcgaaagt aattctcaag     660
aaaagattaa tgctaaagta actttttatt cacgcttttt agaacgttct aaattcgttg     720
```

```
ttcaaaataa ttacacattt ttttatgatg ttgtagatat taatagtgat caatatccta    780

aaatattaaa atatttcaaa accttaaacc aattaaataa tacagtaatc ttcgatgcta    840

gtggttttaa atatttagac gaacgtaaaa ttttccgtaa cattatcgat ttagagaaaa    900

caaatgttgt ccgtttggat cgttataaaa caaaaacaag cggacgtcgc ttaatgagtt    960

ttattttcta tcaattatca atcattgcta atgttaatac acgaaaactt ttacaaaaat   1020

ttcctttctt tgtcaactct ttatatcgtt ttttagatta cagcgaaaaa aatactgagt   1080

tattaacact tttattagac attaaaaaac acgcttcaaa aacagaaatt ccattaaacg   1140

atgaatcaca attatttttt gtagactttt ttacattcgt ggtttttaaa gctttggatg   1200

aattaggatt tgagacgcta atgaatgatt taacagtcta tggtcgtcca tctgaaatca   1260

ctaagaaaaa tataacttat aattcattaa aattggatta catcattaat cgtaatgcgc   1320

gtaattttgg acaacaagca ttattgttta acttattaga ttattttgat gagacagtaa   1380

ataaaaatat ctttaacgaa ttaggaaata gtaataaaaa catgattttt tctaaaaatc   1440

atcaattaaa tttagccaat gaagctttaa gtaaaaaagg ttttacaaag cgtgaaattg   1500

atttaaataa tcattgatat gatgctttat attctaatct tcatgatgat gaagacatgt   1560

ttgttaaaat tattgaaatt aaagataatg ttgatatctt aaatgtatta gatgaactct   1620

ttgttcgtgc tcaaaatgat ggtgttaaaa atttattaat ttatgttttt aatgtaaaaa   1680

tgttatattc attaatagat aatgaatacg agttggttaa tgagtcaatt atttaa       1736
```

<210> SEQ ID NO 79
<211> LENGTH: 516
<212> TYPE: DNA
<213> ORGANISM: Ureaplasma urealyticum

<400> SEQUENCE: 79

```
atgaaaaaaa ataaatctaa tctgacacct acaacaaatt attttgatgt atttaatact     60

tataaagaga aaaaagcaag tgttgattta attacatatg aagaattaat ggcatcagtt    120

ttatttgata ataaattagg ttttgaatca gaggtttatt tagattttgt taaaaaattt    180

acattagctt ttgaaaaaaa actagatatt tgatttgaaa attttattat taatttcaat    240

ttaaatttaa aattttcaac aactattatg attccaatat tagtaactaa agctaattct    300

acaactgatg caattaattt tagaaatgat caaaatcctg tttataataa tttttttaatt   360

tcatataacc aaaaaattaa aaaattatta cttcaaaatc atcctgttca aattcttcct    420

catttgattt tatttaaatc aaatcttaat ggtagtttag tgctcgtatt tagtgaaaaa    480

attatcgctt caattgaaca aaaatcagga aattaa                              516
```

<210> SEQ ID NO 80
<211> LENGTH: 1581
<212> TYPE: DNA
<213> ORGANISM: Ureaplasma urealyticum

<400> SEQUENCE: 80

```
atgaaaagaa agaataaaat aataacatca tcattagctt tattgtttac aggagtaata     60

gcaacgataa gtattgccgc ttgctcaaaa caaaataatc aaaaaacaaa aaattttaat    120

tcacaagaac aagcaaataa gattattgag gctatattaa ataaaaaaga aggtaaggat    180

aattttatcg attgagttca ttgatgaaat agtccatttc aacaagcacg caaacttgca    240

aaagatttag ataaatatat tgatttaaca aaatctaaaa attttaaatc aatgattgat    300
```

-continued

```
aaaaatgaat ataagtcaac ttttagtgca caaattgaaa atgtaattag gatcattaaa     360

gatgatatta aaatgtatgc taattcacca ttttgaaaaa aatgacgcca gcaaaagaaa     420

acagcactat ttttaattaa ttatgcacct attcaaaaag atgatagcca aattaatgct     480

ccaggtattt tattacctgc tgaataccca ttattatatt ctaaacctga ttttgaagaa     540

ctaccaggat tcggtgcatt ttttcctaca ccaaaatcta tggatgcagt cgatctttta     600

gatacttgaa aatcgtttgg atcattaatt tcatctaaag gtaattctgt tgaaaaaagc     660

gttttagcat ctaaattaca aaattcattt gcaaaaacag cagataaagt tgtttacatt     720

tatgatgatg ctattgtccc taatatttat gataagaatg gcaatcgtaa tttaaaaatt     780

acacaagaat ttgctaattg aatgattaac caaaattata aaggttattt agctcgtgaa     840

tttttaaaaa taaatcaaaa aaatgattta attcctttac caatgagtat tgtttgacac     900

gcaagttatg gtatcatcgg aatgcatcgt atgttatata ctttatcaaa agcttttgga     960

atgccaaaag atgaattaga acatttgaaa gcacaagaaa aatttaaaat tccaacttta    1020

aaaaaattac taacaaatga tgaattagaa ttgaaaaatg gtatacaaac gattaaaaca    1080

ggcattgatt cgccatttaa atatcatcgc gatcaaaacc gtgatgattg aaaaatttga    1140

gcaactaatt cccaagtttt agatatttgt attgctttgg gtttaaaacc agatttatta    1200

gttaaaggcg aactatcaac tagtgtccat gaagatccta acttagctta ttatttaaat    1260

gatgtaataa aaaaccaatt aagtgatata gaacaaatta gtattaaaaa aaaccacatt    1320

aattgaacag caacaaatta tgaacctatt aaaaatttaa atgttaattt aattttaatg    1380

ggtgtgcatg gcttaattaa aaattcagct tttaaaaaaa tgatggatga aggtaaacaa    1440

attaaaaatt gggcctttac tgaccgcaga tttagcgatg aaacacgcca atatgttaaa    1500

aaaggtgaag aagatttata tagccaaaac gcatcaattc ttggttgaga tgagttttta    1560

aaaacgaaga acaatcaata a                                               1581
```

<210> SEQ ID NO 81
<211> LENGTH: 501
<212> TYPE: DNA
<213> ORGANISM: Ureaplasma urealyticum

<400> SEQUENCE: 81

```
atggttaatg acaaaaaaca aaaatcaaat aaatatttaa cgtaccaaga tcaagaatat      60

gaacgtaatc ttttattaga aaaagaacgt aaacaacaaa aaaagatttt ggcacaacaa     120

gcatatcaac aattagatct taataaaaaa ttaattaaaa aagctaaaaa tgatcaaaaa     180

cttattttaa gactactaaa agaagataaa tcaatttcaa aaacacaatt taatacccac     240

cgtttagaat taaaaaatac aattgatcaa atggttgatg aatattatga attattagaa     300

caatatagtg tagattttga aaaaataagt tttaaattaa aacgttggct ctatggcatt     360

aataaagaaa tcagacgtac tacttgggct tctaaacgtt ctgttattat cagtttaatc     420

attgtaattg ttattgtttt aattcttgct gcaatatttt ttggtattga tacaggtttt     480

tataaattat cagcaaaata a                                               501
```

<210> SEQ ID NO 82
<211> LENGTH: 720
<212> TYPE: DNA
<213> ORGANISM: Ureaplasma urealyticum

<400> SEQUENCE: 82

```
ttaatttatt aattttgaat ttttaataaa ttgataaata cgattaatgt atttgggata      60
```

aattgtgttt tgcttagcta attttttatc taataacacc aaatctaatt ggcaatcttt 120
atatttatta aaaagataat catctatttg atataactca ttaacacata aaatatggtc 180
gcttgaagcg catgcaagac gttttaaatc ctgtgtaatt ttattactat tgtaatcttt 240
tggaatttca gatattacac taacattgca gtaacttaag tatttaatgt ttttagaact 300
atagattccc tcatctgtga tgatacatat tctagcttta agagaaatta aacgattgat 360
aagtgtgtcc aaaacaacac tatcataata aataacaaat ccatatcctg cttttatcaa 420
ggttagtata tcataatttg atattgcatt ttcataatct attaaccaaa tatttttttt 480
atcaagtcat tcaactgttg ttgaataata taaaataaaa ggaggttggt taattttttt 540
atatttatta ggatattttt catcagttaa atcaatagct ttaacttttt cgtaatcttc 600
tttttctaaa aataaatatt cattttgatc ttcatgattt attaatgcta aataaatttt 660
tgatcaatcc cctttatact tcaaactgaa atagtgtgtt aaataattca atggtatcac 720

<210> SEQ ID NO 83
<211> LENGTH: 441
<212> TYPE: DNA
<213> ORGANISM: Ureaplasma urealyticum

<400> SEQUENCE: 83
ctacacatac tcattaaaag atattaaata tttataaatt tgtttttgtt gatattgaat 60
tttttgtctt atattaaatg tataataagc taatctaaaa aaaataaaag gaagattttt 120
gatcggtttt ttcggtgggt atttattgat ttttaaaatt aaatatcttg ctgtgctatt 180
atgacaattg atccataaaa gataaattat tgtaataaat aacattaaaa aactaataca 240
tgttaaaatt gtaaaatcta aatatttttt ataatttaat aatttttcat tatatccata 300
atttaaagct aaaattaaat ttgtgataaa agaaattaat caaccagcta aaaatatact 360
aataaaaact ccaataaatt tatatttaaa atataattta cctatcaaat aatcttttaa 420
ttcttctaaa actattttca a 441

<210> SEQ ID NO 84
<211> LENGTH: 513
<212> TYPE: DNA
<213> ORGANISM: Ureaplasma urealyticum

<400> SEQUENCE: 84
ttatttttct tcttcaactt tcatttgctt taaatattta cgaatggcat attcaacttg 60
caaattatta gtagcatttt caaagaaatc atggatggta cgaacatcat caaaatcttt 120
aataccatca tcaacaaatc attttacaaa actaaatgtt tcaaaatcat tttcttccaa 180
acatactttt gccatattgg ctacatgctt acgaactttt aattctgtat ctaaaatgtg 240
ttttattaat tccttaggat tcgctggctt aaaattaaca tctacactaa atttagtgtg 300
taatggaatt tcaactttac gagcatattc agaaattaaa ttcttgtgaa cacctaattt 360
atcattgctt aaatcagcaa taaattttgc taaaaaaggc atactgaatt ggtcatcagc 420
aatatgagca tattgtgcat aaatactacc tagttctaaa tttaaattat aatgtgtatt 480
taaaacatct ataacttttt gagatttaac cat 513

<210> SEQ ID NO 85
<211> LENGTH: 864
<212> TYPE: DNA
<213> ORGANISM: Ureaplasma urealyticum

<400> SEQUENCE: 85

```
ttatggtttt cgtaaaatta aaggtttttt attgaataat tttcttctaa aataatcatg     60
agcaacagca ttaatttttt caacatgata ataagtatta gctaaaactc gtaatcccaa    120
accaggaata tccatacgtg atacaccaaa tatcatatcc atgtcaggat atttttcctt    180
aactaaatca cgaattttaa taacatcatc ttcaataact tgttgattaa ttacaatcat    240
ggttccacaa taatgatagc catccatgat tccaaatgct gattcatcat ttttacgtgg    300
ttgaaatttt aaattatcaa ataaaaccaa tttatcatca taatatattt tagtatttaa    360
atacattttt tcgtattgat aagcagaccc atgtggcgat caaccagggc caaaacattc    420
tgtgtaaatt aaagtagcac ttgaatccat tttaaaatta ttaaattgtg cgaactttcc    480
atcttcataa acaattacgt tatcacttat atattctaaa atactatttt ttcctaacgt    540
gatatttgta tgttgctcag aagtttttcc atcaaccgtt ttataagctt tagctgagga    600
ttgtgttgta atgatacaac gagcatcatc attaatttca aaatcagaac gataaatttc    660
acctgaaaca tatccaccac ccatactaat tgtttgaaaa caggggttga ttggatcttc    720
ttcatctaaa aataaaggtt tagatgaacg ataaaaattc gtaaaataga cagtatgtgc    780
catttttgaa tgagcttgat catatgctac tttaatgtat aaataagcag cataattttt    840
aatttttctt ttatttaaaa tcat                                           864
```

<210> SEQ ID NO 86
<211> LENGTH: 621
<212> TYPE: DNA
<213> ORGANISM: Ureaplasma urealyticum

<400> SEQUENCE: 86

```
ttattcttct agtaaagcta attgcaaacg cttttcaatt caatcagcaa cagattttaa     60
accttcatct gtttttaaat tcgttacaaa gaaatcttta ttaccacgtg attttaatgt    120
atcggctttc attacttcta cattagcacc aacataagga gctaaatcaa ctttattaat    180
aataaataag tctgatttaa tcattccttg accaccctta cgaggaattt tttctccttg    240
tgcaacatca atgatataaa ttgaaaaatc aactaaatct ggactaaatg ttgcagataa    300
attatcccca ccagattcta aaaataataa ttgtaaatca gggtgtttat cacacatttc    360
ttcaattgca gcaaagttca ttgaagcatc ttcacgaatt gctgtatgtg gacatcctcc    420
tgtttcaaca ccagcaatac gatcagctgg taaaacagaa gtatttaata aaattctagc    480
atcttcttta gtgtaaatat cattagtaat tgctgccata ctataacctt ttgttgaaag    540
gtatcttgtt aatctttcga ttagcattgt tttacctgct cctacaggtc cacctacacc    600
aataattaat ggtcttttca t                                              621
```

<210> SEQ ID NO 87
<211> LENGTH: 753
<212> TYPE: DNA
<213> ORGANISM: Ureaplasma urealyticum

<400> SEQUENCE: 87

```
ttatgacatg aataatcgaa caggtgtgtc ttcgtgttcc atttgtgcaa tttcaaggcc     60
tggtatattt ttgcaaaaat ctgttttaaa atccaatgta aagactttat taacaatatc    120
atcaaaataa acatgtttaa gttgataaat tattttttgt cccttaactt gtcctaatgg    180
aattgcacgt acacagtttt gcgttaatgc agcaactgta gagtaaagat gcgtatataa    240
agcagttttt aaatctattt ttaaatgcat agctaataaa gcaaacgcaa cagcaggatt    300
```

```
tccataagat tttttatttt ttattctttc agcatattca actaaaagtt cacaattaaa    360

aagttcatta tatatcttta ccatttgttg tccaattcga cgttgacctt cacgagtctc    420

tcttgctaaa ccttgaaagt ttatcatttg atcaatttct caaattgcat ttattttttg    480

ttttggcaat agtttaaaaa tttgataaat tgccaataaa tcaccatgta acaattgttc    540

attcatatac agaagtaacg ctttaattaa tgattctcca tcaaaaacaa tatcttttct    600

aatataagtt tcaactccaa aagaatgact aaatgttcca attggaaagt ttgcgttagt    660

gatctgcatt aggtctaata aatttaaata gtcactattt agcgtcacta cagtgtttaa    720

atgcttcttt aagtttaatt ttttttcttt cat                                 753
```

<210> SEQ ID NO 88
<211> LENGTH: 450
<212> TYPE: DNA
<213> ORGANISM: Ureaplasma urealyticum

<400> SEQUENCE: 88

```
ctatttagcg tcactacagt gtttaaatgc ttctttaagt ttaatttttt ttctttcata     60

tagggcttta ttatcttgaa ggtattcttc tactaaatag tcgtagggaa cgatcatttg    120

tgtttcagta aattgagccg gcatatgacg attacctaaa ttatgggcaa tttttgccat    180

ttcaccaatt gtgtgtgctg taataattaa tacatctgat aactctaatc taataacaac    240

tagtttataa tcatccttgt ataagatgtc accatccatt aatttttttgt cctcttctaa    300

acgaattcca tattcaacat tttgatctga tgaaatgata attacacgtt ttaaaacgtc    360

gtcgcttgtt aaatgaatgt tctcaatttg ataactttca acatttttaa tgttagcaat    420

attatctaaa atttctttaa atacagtcaa                                     450
```

<210> SEQ ID NO 89
<211> LENGTH: 1797
<212> TYPE: DNA
<213> ORGANISM: Ureaplasma urealyticum

<400> SEQUENCE: 89

```
ttaaaataag aaatatcttt gtgctaatgg cgcttctgtt aaaggttcag catcaagtat     60

atatttgcca cttgaagtct tttttaattt tttagctaat tcagaagctg attgttctag    120

tcaattttct aaatcattaa aatcaacagc agcatcaaaa gtttgcggat caacttctaa    180

atttggagtc gcagagtttc atttcatact ctttttattt actgaacggc aatttttaac    240

tggtaataat tctttttcta atttatattc ctctttaatg ccattttcta acccaatttt    300

tgaaacaaaa cttactgatg tattagttaa caaacgtcca taagttccaa attggtcacg    360

cataattaca ggttcgcatg ttggaattga agcatttgga tcacctgcta cacaacgagc    420

gattacaccc atttttacaa cataataagg ttttgcacca aagaatttag gttctcaagc    480

aacaatatca gctaatttac caacttctag tgaaccaata taagaatcaa caccatgtgc    540

aatagctggg ttaattgtat atttagaaat ataacgtttt acacgattgt tatcactgaa    600

ttcactatca ccttttaatg atccaaattg tgctttcatt ttgtgagcca tttgtcatgt    660

acgagttgca acttcgccaa tacgtcccat agctaatgta tctgatgaca taattgaaat    720

tgcacccata tcgtgcaata agtcttcagc tgcaattgtt tggctacgaa tacgtgaatc    780

agcaaaagca acatcttctg gaaccttagg atttaagtgg tgacatacca ttaacatatc    840

taaatgttca gcaattgtat ttactgtata aggaattgtt gggtttgtag aagctggtaa    900
```

-continued

```
aatatgggca tatttaacag tttctagaat atctggagca tgccctccac cagcaccttc    960

tgtatgataa gcatgaattg ttcgcccttt catagctgca attgtatgtt ctacaaatcc   1020

agcttcattt aatgtatctg tatgaatagc aacagctaca tcagttttat cagcaactgt   1080

taatgctaaa tcaatcgcat ttcctgttgc ccctcagtct tcatggattt taagtccaca   1140

agctccagca gcaatttgct caaaaattgg atcttccata ccttgacctt tagctaaaaa   1200

accggcatta attgataatc catcagctgc ttgtaaagct gatttaactc aaaatttacc   1260

aggtgaaaca gttgtggctt ttgtaccatc attcatacct gtaccaccag caataacagt   1320

tgtaatacca ccatctaatg caacaggaac tatttctggt tctagtcagt gaacgtgagt   1380

atctaaacca ccagctgtat aaattttacc ctcaccagct gaaatttcag ttgagatacc   1440

cacaatcata tcaacattat ctgttaaatg tggatttcca gatttaccaa tcgcagcaat   1500

ttttccattt ttaataccaa tatctgcttt ataaatacct gtataatcaa caattagtgc   1560

atttgtaata actaaatcca ttacttcagc attacctaat ttatcatcta acttcatagt   1620

agaattcatt cccatacctt cacgtagggt ttttccacca ccaaaaacag attcttcacc   1680

ataagtagtt aagtcttttt caactttaac tcaaagattt gtatctccta atctaacgct   1740

atcaccagtt gtaataccgt ataaatctga ataatttttt cttgaaattt taaacat      1797
```

<210> SEQ ID NO 90
<211> LENGTH: 915
<212> TYPE: DNA
<213> ORGANISM: Ureaplasma urealyticum

<400> SEQUENCE: 90

```
atgcaattaa aagatttaat taataaaaaa aagaatttaa ataatattaa tttaaaagtg     60

agtaacgaac gtaatatttt tttaattaat attatgaaac taaatcagcg attaactttt    120

tttagtaaaa atgcttttga aataaaagaa tcaattctaa gtttaaagcg tatttataat    180

attaaacatg atatgttaag acatgaggaa cgaaagattt ttaagttttt aaataaaatt    240

aatgatcgtg ttttatggat ttatttaact gaagagcaaa aatatagtac tgattcatat    300

tcgcgttatg aacaaaaaat cttaaaaacg attaaatcaa atcgtgatga ttttattttg    360

atcggtcaag gagcaattga atttggtaag aatcataatt taaatgttct gcaaacattt    420

aatgactcaa atattaaaaa tttaactaca caattaacta aaatgattat gattttatat    480

acttttgata attataaaaa agttaatttt gttattaatt ctaataaaaa ctatgatgga    540

cactttacta tattaccaat gaatgaattt agttttgata aatttattaa tttacaaaaa    600

tgcgattcta atattattga ttttcaaaaa gtaaaaattt atccaaattt aaatgaattt    660

attaatgtcc aaattaatgt tttcttagtt aatattatta atactttaat tactgaatca    720

tctttttata aaacaaaaaa tggactagta gctactaata atatcctaaa agaactagat    780

gataaccttt caaaaattca acgtaaaatt acacgtgtaa agacagagtt gcaaattgaa    840

gaaataaatt tattagcaag acaaaatatg aatgaagatg ataatgataa cgatggtggt    900

gtttatgaat cataa                                                     915
```

<210> SEQ ID NO 91
<211> LENGTH: 375
<212> TYPE: DNA
<213> ORGANISM: Ureaplasma urealyticum

<400> SEQUENCE: 91

```
ttatttttta agttttccat taactaagcc atttacacct caaacttcgc gtgttccggc     60
```

```
taaatcaata attgaaactt cttttttatc tcctggttca aaacgaatag cagtacctga    120

tggaatatcg aaacgtcgtc cataagcaac tttgcgttct ttatcttcat ttcctttttc    180

atcaaaaaat actaatgcac tattcacttc aaacaagtga aaatgtgatc caacttgtat    240

aggacggtcc ccagtatttt taatactaat tacttttgcc tctctacctt cattcatcac    300

aatttcacca ctagcgaaat taattgcccc tggtactaat ttacctggac taaattgact    360

tgatgatcct gacat                                                     375


<210> SEQ ID NO 92
<211> LENGTH: 306
<212> TYPE: DNA
<213> ORGANISM: Ureaplasma urealyticum

<400> SEQUENCE: 92

ttatttgtaa attggatcgt gtacagaaac tagtttagta ccatcaggga aagtaacttc     60

aacttgaatt atactaacca ttgtatctac accttccata acttgatcaa cacgtagtac    120

ttcacgagca gattgcatta ggtcagcaac tagcttacca tctcttgccc cttccattac    180

atgatcagta attaaagcaa cagcttctga atagtttaat tttaaacctc tagctaaacg    240

tcttcttgca acgtcagcag caactgttat caataatttt tggacttctc ttaatgatag    300

attcat                                                               306


<210> SEQ ID NO 93
<211> LENGTH: 513
<212> TYPE: DNA
<213> ORGANISM: Ureaplasma urealyticum

<400> SEQUENCE: 93

atgaagatga taatgataac gatggtggtg tttatgaatc ataattataa tattcaaatt     60

acattacttg aaaacaaaaa gtttaatatt gataatggtt tattatatgt aaatgttaat    120

gaagaaaata catgacaaaa aattgaaaac aacaccgttt tagcctatga aataatctta    180

ttaaaaatag ttgatgatga ttataaaaaa actttttatt tatttctaaa aaacacacat    240

atttctgttt taaataacat cgttaaaatt caagcattaa atgatttaca tttctttatt    300

aaagatggat taaacaaaaa aaataatcat aaaaaagagt tggtagataa atataaaaat    360

attactaata atattttaga acttgaagct aaacaacaat taggattaac tctaagtgaa    420

tttttagatc ttgataatct aaaacaagaa caatatataa ctaatatgca aattagatta    480

aatttagtgg agtataaaaa agatgagaaa taa                                 513


<210> SEQ ID NO 94
<211> LENGTH: 477
<212> TYPE: DNA
<213> ORGANISM: Ureaplasma urealyticum

<400> SEQUENCE: 94

atgaatttca cttcattatt gcaagatggt atatatgaag ttggtaatgg tgcaatcgtt     60

actgaccaat caccatattt aggaattaca cctgattatc agggtgcata tggtttccca    120

acacaccctt gaggtatttt ctttcaagtt gttggagcta ttttagtttt tggtgcttat    180

ttacctgctg ttattaaagt actaatttca aaaagaactg aaaatttggc tattggtatg    240

tgaattattt caattgctgg tttaggatta ttagcgatat ttgcttgatt aggtgtttct    300

gtaaaccctg gaggatttat tcttgtagct ctaagtgaaa cactatcttg cattgcaagt    360
```

-continued

```
ataattgtgt ttgctttaaa aattgcaaat aaagctaaag ctaaagccgc tggtatgact    420

gaattagaat actgcaactt acactatcca attgttaaaa aattacctaa aagataa       477
```

```
<210> SEQ ID NO 95
<211> LENGTH: 2166
<212> TYPE: DNA
<213> ORGANISM: Ureaplasma urealyticum

<400> SEQUENCE: 95

atgagaaata aattgaaaat aaaattaaaa tttttagctt cactagcaac aataccaatt     60

gtagcttcac cattaatttt ttctgttgca gctaatgagg atggtaaaca agaaaacaat    120

aatggtaata atcatgatcc taatcaacaa aaaaaaccaa aaattcctaa aaacgatcct    180

aattttaata cttttaaaac tgatgctgat aaaactgtta aagatagttt agaaaaagga    240

attaatgctg ctattgttta tgtaaaatca cgtcaagaag aaattttaga aaataaagaa    300

attgagttta agaaaaaaat tcaacaacta atttatttaa aaaatctgca gtcatatctt    360

gagaaaaata aagaaaacat cttaaaaaat cctaatgatt atggttttta tttaaatact    420

cctcaaattt taggaactct taaaaattat gatattaaag atattgagtt taatggagaa    480

acatataagc aaatcaaagt tggcaaaact gatcctttaa attatcaaaa agccgttgct    540

ccaaaaggaa aaattagtga tgtacaaagt gatcaaatta atgatgttga agaaacaaaa    600

tacaaagata cgttaaaaaa atatgaatct gaatttttaa aagaaattaa taaattaatt    660

tatgatgaaa atgatgttcc acaaattaac aaagatgttg agttaacacg tgatgaaaaa    720

ggacaattta atacaacttt acctaaaggt tataatgatt gaaacgctta ttttatttct    780

aaaataaaag atcgtgttac agcatttgat ttaaaacaaa atcaacaaac aaacgaagat    840

aaacaagaag aacagccaaa tgagcaaaaa gatcccgata caccaccacc attaccacca    900

ccattagtag aaggcgatca taatgaaata gatcttcccc caacacaagc taatgctatt    960

atttcttctt taccactatt attaccttat attagtccta tatattcaaa tgaatcatta   1020

agtggattaa aatcaaaatt tgatagttta aaaccagagc ttaaacaaac attattttat   1080

tttaataacc caattaacac acgttatctt tatagtgtat tagattttgg cgttaatggt   1140

agtagtatga ttaatattaa agttaaaatt attgatcaag ttaatcctaa actacaacgt   1200

acatatatta ttaataaata tgatccaatt ttagatatta attttaatag tctaaaatta   1260

aatgaagtta atgctattaa acaaattttt gttaacttgt ataaacattt aggactagat   1320

gagaaaattg attataagaa attacgtaac ttttatatta gaaatgcttt atttacaatg   1380

attgaagctg ctcaaaaact tattttgcga ttcaatcaaa ttgataaaga taataaaatt   1440

attggtcaaa aaacttttgc aacattacaa aatgaatatt tagaaaaata caaacaaaaa   1500

cttgtaaaca acaccgatga taaggaaaga ttattaaatg agtttaataa tttaacaaaa   1560

gaaaatttct ttcgttattt aaataacact ttaatcaata atgattatta ttgatatcaa   1620

ctagttggtg cttataaaca agttagctta cagtttagtg aagttcttcg attaaataaa   1680

gataaaatta aagctaatat tgcaagtatt aaaggtgatg aaaacaccat tgcaaattta   1740

tataaattaa ataaccaatt aatttatcaa ttatcggcga ttgttgcaca acgtagtttt   1800

aattctcaac aatgatatca gtcatattta aatgttttac aaccgattaa agaaaatttt   1860

gatttaatgt ctatattaac aaatcaaacc gatattaaaa caaataagga caaagctaag   1920

gattttaaaa atgcatatga tagtgcttta aaatctcttg aaagacaaaa acaagtaaat   1980

aaacaaattc gtcgtaagat tggaattgcg tttatagtaa ttagcttact ggttttaata   2040
```

attaatttaa ttatttatgg attgattaaa aaactaaaaa ataaaaaagt tattctaatt 2100
attaatagtg tgataatggt gttgacaatc attgttttaa taatgggaat tattctaata 2160
atttag 2166

<210> SEQ ID NO 96
<211> LENGTH: 225
<212> TYPE: DNA
<213> ORGANISM: Ureaplasma urealyticum

<400> SEQUENCE: 96
atggcattaa caattgtttt aatcttgttt agtgttctag ctttaataat aggtttatta 60
ttatcaagaa cttcaccatc tggtggattg tcaagtttaa atggacaaga tctagaaatt 120
tttaaaaaaa caaaagaccg tggttgaatt aaaggtttac aagtctttat gtttttatta 180
acaattgtta tgattttaat aataattttt tatagagtga gctag 225

<210> SEQ ID NO 97
<211> LENGTH: 477
<212> TYPE: DNA
<213> ORGANISM: Ureaplasma urealyticum

<400> SEQUENCE: 97
ttattttttt aattctatta ataaatgatt aagtaaatct gtaaaattag taaaatattg 60
gcaatgtgat aatatcatac catctaaaaa cttgtttaaa acttcattgc ggtgtttgtg 120
aactcttcaa tcagtattta aaatataaat ttttaacgtt ggtttaacgt gtttttgaag 180
tgctacaaaa taacccattt cagccatggt gccatcatca gtgttatcaa tatctataat 240
tgcgatatca gtttgatcaa taaatttaat atctgattca taaaaaaaga tatttggttt 300
atgtgcatta gcacctaatt cgtcgttaac ttcgatcgga ttaaaaagat caagttcata 360
atttggtaat tcatctttaa atgtttttct aattaaacta gcttgttgtt ttcgatcatt 420
aatttcagct aaggtgaata aaggaccagc taaataaatt ttgatttttt tactcat 477

<210> SEQ ID NO 98
<211> LENGTH: 267
<212> TYPE: DNA
<213> ORGANISM: Ureaplasma urealyticum

<400> SEQUENCE: 98
ttacaataat gaaatttcta ttttattaat ttcgtggttt aattctttgg tttttaattc 60
caatgatttt ctttttttgat ttaaactaat aattcttgat aaatttatta ttaaataaaa 120
tagccctact atggttaaaa aaaagattaa aataacggct atgattattt tcatcataaa 180
ttcattttta attttatcta attcaaactc aagatcatta actttttgct tcaattctat 240
taatttagtt ttttgttcgt cactcat 267

<210> SEQ ID NO 99
<211> LENGTH: 615
<212> TYPE: DNA
<213> ORGANISM: Ureaplasma urealyticum

<400> SEQUENCE: 99
ttaattaata attaatttat tagtctcttc ataatcaaaa tattctttgc taatgtgtgt 60
taaaattaat aattctactt ttaatgatga tgaagttaat ttatttaaaa taattggtgt 120
gttaaattta atattttcat cttctaaaat tgattttaat aaattaatat tctcataatt 180

-continued

```
aatttgtgtt tttacattaa aaaaatcatc aaaaccagaa agaattaatt gtttactaat    240

attaatgtta ttagtatcga attgttctaa atccatatta tttggtgtta tatagtatga    300

tactgcaatt attttttat ttttaattaa actaaattta gtgattgaat taaacttatt    360

accatgatat tcaaaatcaa ttagaaattg ttcgtattta atattatcaa tggttttgta    420

taaattagca aaagccttgt tagtaaagtg atcaatactt gaataaacat aataaccact    480

tcctttgatt gttgttacaa tgcctaaaac ttttaatact tcataagcat tatgaatagt    540

gattcgtcca caattaaaat aacttgctag tttatactca ctaggaatca attcatttat    600

tttatattga tccat                                                     615
```

<210> SEQ ID NO 100
<211> LENGTH: 1968
<212> TYPE: DNA
<213> ORGANISM: Ureaplasma urealyticum

<400> SEQUENCE: 100

```
ttatttttgg ttaacaaatg tttttcaata tgaaccccaa tcattagctt cttttaacaa     60

ttgtttattt tgttggatta attgcggatc aattgtttta ttaataattt taatcacaga    120

atctaaaatc atattatatc caataggtga tttaattcca tcatttcata attcataatt    180

atcatcaaaa atacgcttcg ctggatcatc ataatctgat ttaattaatg acatgattaa    240

ttctttttgt ggtcttgata aattattact atgaaaatct tctaagtttt gataactaat    300

tttaattaaa tagtcgaact ctgaattaaa tttagcaaag ttactagcac ttaatgatcc    360

ctctcctaaa tttcatcatc aaccattatc atccatatta aatagagaac caacaatgtt    420

tttatcaatt tgtgtcccat cttgattatc accaccaaaa caatgaattt gtccatttcc    480

gtgtctatga cataataatt gtttgccgtt aacatcttct aataattcag tccattcgtc    540

ctttttaag attggtttag gtgctttaaa ccctaaatca taatataaaa aaccgtattt    600

agattgagtt tgtaaagttg aagaaccact attttgtgat gtagttaata agcctaaagt    660

tttggaatta gtattatcaa attgttttat attaggatta taatttttat caacaacgcc    720

aattgcttga aaatacaaac gcattttgtt taagcgatta attaaattat tagcaatttg    780

attagcatta aataacgctt tttttaatgg ttctaatttt gctaaattat ctttaaaatc    840

aatttttgct tcttctgagt atgcatattt tgttgttgca taagcaatat catataaata    900

aagcaatgaa tcgcgcattg ttcctaaata aacctgtgta cctccatctc atcgcatatt    960

ttgttcataa ataggatggt gttgtagaat tgatgtaaca taactatctt gttttgtagt   1020

tgataaaaaa ggatcataat ttaatttatt taatcctgat tccctaactt tttttgttaa   1080

cacaactgtt ttaaatgctt cataaatttt tgaatttaat gatttaggat cttttcattt   1140

tgtttcagta taaaaaatag gtatatcatt accttctaaa attctttttt taaaagctga   1200

attattaaaa ttaataccat caaatgtttc agcattaaaa tagtttttgt ttaatttatc   1260

agcaaaatag gaataattat aaagttcgtt taattcacct tttctttat ccttatactc   1320

taaacctaac aatagacttt tacgtaataa tgagttagga tcgtttttaa aatttaaaat   1380

gtcattttta tttaaggtta aataaaaatc acgactcatt ttaaaatcaa caggaatagc   1440

agtttttga tttgatatcg ggccaccatg tgcaactaat gttttttttg cacgttcaaa   1500

atgactatta tcaatcaaat aacgatcata ataaacaagt ttgcctttat ttttatttca   1560

atactcttca cttacacctt cgccataagt attgccacta aagcttcatc atgtagttcc   1620

atattgttta atattttttt ctaaattaat taatttttct ttaaatttat tagcaaaatc   1680
```

-continued

```
gtctttttca taaaatcatt tttgataatt tggtttttgg ggatttaaat aatcataagg   1740
tgaatttttc tttcaataca tttgttgagg ataataatca ggtgtaattc ctaacgctaa   1800
taaattatca gcctgagaag tataagttgg cattatatcg tatttgattt gctcttgaac   1860
gtttgcagat gtttttttg tacatgaact aataattgtt gttgtaccaa ttacaataga    1920
aattgttgcc aacatactaa ttaaatattt ttttgttttc ttatgcat                1968
```

<210> SEQ ID NO 101
<211> LENGTH: 1788
<212> TYPE: DNA
<213> ORGANISM: Ureaplasma urealyticum

<400> SEQUENCE: 101

```
atgaataaaa aaataaattt gaacagcagt ttagcttata ttggtttttt aacacgcctt     60
attattgtaa aaaaaacaac atatctttta ccgatcataa ctttattaat tacattaatt    120
ataggaattg ttgtcggctg tgttgttaag caaaaaacac aatttttgat aatttcatat    180
gtaatgatca tgtttaattt attaatgaca acaattttg cttcactaaa agcattaaat     240
atttttaagg attttagtga agatggtatt gatattttag taatttctaa accaattagc    300
cgtaaaaaca ttgtttgatc aaaaattttt ttcttcgtcc taacaggtat tgtttgaagt    360
ctagttagtt ttttaggact attaattttt tatttaatta gctttaattt tgctaaaaat    420
gttaattatt attgaatctt aagttatata agtcctttta tttgttattt aatttttggg    480
ttaataacaa gccttttagc tttaaaatta aatgcaaaaa taagtatttt aattcctttt    540
gttagtttta ttcccttact tactattgga attattgcga acttagttag tcaagtccaa    600
tcacaagcct ttttaagatt attaaaacaa aaatcaacaa acaatattga ggctttttat    660
ttaaataata atttagatca atattattta attaacacag gttttttaa tcataaattt     720
aatgaaaatc aaaatttaga aattatgaac gcttatttaa aaactagaag tttagcaact    780
ttttgacaag taagtagttg aattcttcct gtttatcaat tagctgatgt ttttaataaa    840
agtgattatg agccatttag tgattttatt aaaaatcaag tagatcagat tttatatgcc    900
aataatttag catcaaaaca atttaattat cagttagaaa aaaatagtaa ttcattaatc    960
aattttagta ttaataatga taaaagtttt ttaattccaa gtttgttaaa aaacgattct   1020
caaaatttaa ttaacaataa cttaaatcaa gaagtaattt atgcaattga caattgaaaa   1080
gatcaaacga tcgaatatca aaaaaacagt tatacacaat taagtagtga tgatattgtt   1140
ggttcgctta aatgaatgat tattaaagag gtattaaacg taagatcgtt taatacatat   1200
gctaataatt tatttaaaac acttgatcaa aaagcaaatc aaaaacaaat cttagattta   1260
atttcaaata gtgtacaaaa atttgatttc aataaatgaa acgatgagaa tgctgattta   1320
tttaaaaagg attttaataa attattaatt aaatcaaaaa ctgaacaaca aatatattta   1380
gcagttagtt taatttatta tctatatttc aatccacact atacgaattt actaaaaatt   1440
ttattagttg atcatcaaaa taatttacaa tataaaacac aattaaaaat aaatttaaat   1500
aataaaaatt atttaattgg cggttttaaa agctacttac ttcatcagat attgcctcaa   1560
gaaaatgacg atggcataga tgaattaaaa aaagataaaa agattcgtta cagatatagt   1620
ttagaacaag gcggaaatta tttattcgat tatgtccaac aaaattatag ttttaaaaga   1680
aagcaacaaa ttgtttataa agaagcttac tgcgtaattt gattaatatt aatttttagt   1740
ttattaattg gtacatatta tggctataaa agaaaggact atcgttaa                1788
```

<210> SEQ ID NO 102
<211> LENGTH: 3165
<212> TYPE: DNA
<213> ORGANISM: Ureaplasma urealyticum

<400> SEQUENCE: 102

```
atgtttaaaa aaagaagttc aagtcgtaaa tgatttataa tctgtacttc attatcaata     60

agtagtattg ctgtagtttc attaagtgca tgtgctaaca caaataataa aatagtaaac    120

gcaggtttta tttataatgg atcaacaacc aacgacgcaa ttactggttt tgatgtaaac    180

gattacataa ttaaagcgcc agaaaatgat actaatttaa atcaacaaat tttgagaaat    240

aataattatg aacaaaaacc aattctttga aatgattatt taaaagaata tgatagtgtt    300

aaaaaacaac acgatcaaca aatcaagaat ttttatgaat atatttgaat taatgaagca    360

tcaaaatata aaaatttaaa taaagttatt gatattaatg acccctattt tataaattga    420

tttttaaaat taacgcctaa tacattaaaa aatgatcttt ataattttat taataatatt    480

cgtaaagaca acactaaacc atcacttgtt ttttcatcaa gtgaaccaca aattaaagtt    540

tgaaaagatt taggaaataa tcaaaaacaa gttttaaatc ccaatcaagc catttttgaa    600

ccactaacag aacaagatat taaaaataat attaatcttt tagaaaagaa taaggcgtta    660

agagttagca ttagtttttg gtatgcttta acaaatcaaa gtagtgctaa tattttaatc    720

aatgatccat tttataaaaa accttctggg attgcttcaa atactagtga aaaatatttt    780

attaggattg aagcatcacc gatcgcttta gattttagcc aaaccgatcg attagaacgc    840

gataaatata gtgcacaaac cacatcaatt aaaaacacat ataaaatgcg ttattatttt    900

aataatattc gtgttgaaaa acaagttaca aaggttaaaa acaatgctaa acgtggagac    960

caaaacgcag aagaaaattt tccaaaagaa ttttatttcg gtgctaatag taatgaaaaa   1020

tttagctttg gtacacactc atacacatta aataatgaaa tcacacaagc ttcatatgaa   1080

caagatattt ttagtttaga tcataaaatt aaaaacgaat taaaaaaatt aaatgaacaa   1140

caaattttaa aagatattga atatgcattt actagtggtt atgatgtagc aattgattcc   1200

attggtagta tttttaacat tttaaaaggt gttgctaatg atttaaattt aaaagaattg   1260

tttttacaat catcacaaga ttttagaaat ttaacttata acattacaca acagaataat   1320

ttgactaatt taatcacttt aattacatca aatcaatcat tagggatggt tattgatggt   1380

tttaaaccaa ttttaaaaga aattatttat aataatccaa gtattgacca atcagttaaa   1440

aatacaattt gatcaaaaat tgattcaatg gattttaaaa ataatttaat tgctgaaatt   1500

ggacaaatta gaaccttact tgatagtatc tcattaactg aaattaaaac ctataaacca   1560

attattaata aattattaga attaatttct ttaattgaag cacgttctaa aaaagaccct   1620

aaaaattatg gatttattga tggtttggac gaactatttt ccttcttttt aaatttaaaa   1680

caaaatgatc taccaagtag tattaatttt aaaattggtg atcaaaatta tactttatat   1740

gatttaatta ctgaagttaa aaaaattgca aataacttaa ttccgcatga aaaccaatat   1800

gaccctaaag accaacaaat tatcagtacc aattattttt taacaaaaat taaaatttta   1860

gatttgattt ctttaaacaa aaatgaccaa cttgattatc ataagggtgt tgaaatgatt   1920

tttagtttat taaaaaaatt tcaaatagca attcccgaat ttatttataa aattattgat   1980

gaattactaa ttcaaaatac taattgaaat aaagaaaata ttaaaaaact tttagatgct   2040

attttatatc caaaaattac atctaatgat ccttcaatta atgatttaaa atcatatttt   2100

aaatatggga ttagcaagcc tgaaatcaca agtaaagaac ttgaatatga tcaaaacaat   2160
```

-continued

```
ttattaatta agaaactaaa tattaaatat cgttataaag ttttagctaa tgcagaattt   2220
gatattaaac ctttatttga tttattacca caaaaaccat taagttttat tgatcttggt   2280
ggattatgag aacaaatcaa aaaagaattt ccttataaaa ttgttttagc aaaaaacgat   2340
tatgttgatc atacaattag cattagtcaa ccacaagagt taacaacttt aatttttaaa   2400
gaccgtagtg atcatgataa atataaaatt ggttatgttt tttatccaac acacacagtt   2460
caaacccata tgcctaattc tatgaaagca atcattgaaa atatatcatt aagaaacgat   2520
cgtttattac ctaataaata tgttgctcaa ttattaaatt ggttatttta taaaaaatga   2580
gtattcataa atccactagc gatttatgaa acttttgaag gtgataaaaa gattcctaat   2640
gacaaaaatg ttaaatattt aatcaaagat aatttaaaca agtatttaaa aaactatgat   2700
tcaaatacat attgtgaagg ctttgatttc aaacattttt ctaataattt agaaaataaa   2760
gttggtaatc aaacaattcg taacttaatt ttagctaaaa ttaaaactat taaaacagat   2820
ggtcaagaat tatatcaaga cgcattagga cgaaaaatca ttgcaactag tgcttatgat   2880
caaattaatt taacgcttca agaactaatt gattataaat tgcttggatt tgggaaaaaa   2940
gttgatttaa aaaaagatgt ttatttgagt gcagttgcat ttaattttgg tttaaacact   3000
aacgatagtg atcaaacaaa cgtcttaaat aataatgatg aaattaaata caatctaaat   3060
attttaaaaa aagtagttat cacattacac tttactaagc caatgttaga tttaagtgat   3120
cctaatcgca ctaaattagt taattcttat acttttgttg tttag                  3165
```

<210> SEQ ID NO 103
<211> LENGTH: 567
<212> TYPE: DNA
<213> ORGANISM: Ureaplasma urealyticum

<400> SEQUENCE: 103

```
ttaatgttgg tgactgtgat gatgatggtg ttcatgttcg tgaccaccac agcaatcatc     60
tttagttcca ccacaacatt cttcttgggt ttctgatgtt tttgtttccg agtcacagca    120
aacttcatgt tcatgttcgt gaccaccaca acaatcatct ttagctccgc cacagcattc    180
ttcttcaact tttacttctg aattacaaca agcttcattt tcttcatcgc tacagcattc    240
atcttcacaa cagcaatctt cttcataatc atcatcttca ctaaaatgaa tatctaagaa    300
aacttctgat aaatctaata ctgtatcatt agaaattaaa aaagcatcaa tttttgcttg    360
taactcttct tttttaagat caaataaaat gtttgttgat tcaaaatcag cataattaat    420
atacaactct gatcctagat cgcttgtttt ataagcttca tctccaccaa gttctaaata    480
tgaatcaata tcttctggaa gaatattaat tgtacgtgcg ttgtctaaat taatgtaaga    540
aacacctgtt ttaatgtatt tagccat                                        567
```

<210> SEQ ID NO 104
<211> LENGTH: 1665
<212> TYPE: DNA
<213> ORGANISM: Ureaplasma urealyticum

<400> SEQUENCE: 104

```
atgaaacata agacaaaaaa aataacgctt ttaatagcag gaattacttt aacttcatta     60
tgtacaattt ttgctattac agcttgtagt aagcaaaaat cacaaccaaa tccaaaaata    120
aaacccaata aaattattga gaaaattgat caagcatttt ttaatgaatt taaaacaaaa    180
attgaacaaa aacgcacact tccaaatatt aaaatcactt caacctttaa aattcctttt    240
```

-continued

```
gagaaaaacg aaaacacttt aaaatcccca ctttttaaaa ttggtgagaa atcggttttt    300

gatttaaaac aaaatgaaat tccaataaca tgagttcaag atttaaaaga ttatttttta    360

tcgcaaaaaa ccattttaac ttattattca ttagcaaatt taaaactaac aggcaatgat    420

gctaaagatg catatttttt agaatttatt caatatattc aaaatatgca acaaaaagga    480

attatatcag aagattttta tcaacaatta tgatatttaa ttagtgaaat tagtgactat    540

gatatgcaaa atggtatttt acgttcagta tatcgtatcg ctaatcctaa acttgcaatc    600

aaggattttt accttgatgg ttcgctttat ggatttaaaa aagaaaaaag taaatacatg    660

aattttacaa gtttgtttca atgaccgaat gcagaagaaa aagcaacttt tgatgttgtt    720

tttaaaaata aaaacagcgc tcagtcttat acaaaaaaga ttgaactgat ttattctaaa    780

gaaaaaaaat ttattttaga ttcattaatt aattatagtg agtttactcc aggtgaatat    840

gaattagtat caattaaaaa acatgatgat atgaatgcca agaatttgat taatcccaac    900

aaccctaata ttgcaaaaat ttttaaaatt aaagttttta aagaaaacga aaaatttaaa    960

ccaataacct taacgtcaat taatcaacaa gaagcggatg aatatgatcg acaaagaaat   1020

caaattattc ataaaaataa ttcagaaatt gggatattag atgattcaaa taaaattaaa   1080

gagttaggaa ctttttttata ttttaaaaaa cctttatctg aaattacaat caacgatttt   1140

gatcgttatt ttagaactta ttttatttgt ccagagcaag attttaatga ttttagtcgt   1200

caatataaaa ttactaaaat tgataaacaa aaacaaataa tagaactaag tatattacat   1260

attaataata aaacaaatga aatttatagt tcaccaatta attttaagtt ttattacaaa   1320

aaaatatatg atattaacaa aaacactgat gcacgattag atttaagttt tgatgaatct   1380

aaaaaagaac aaaaacaaaa actacaagag ttagttaata aattaaattt tgataaactt   1440

acttataatg atttaagtga attagctgtt gtgatgtttg aggatgtgga tttagaaaac   1500

actaaaattt atgttgaaat gattaaaaat aaagatcgtt caattacttt aaaagctttt   1560

gttgataaag cttttaaaaa tggaaaatta aaggtaagta ataaaccaga tattttaata   1620

aaagagttta aaataaacta ttttatgcct aattacttta aataa                   1665
```

<210> SEQ ID NO 105
<211> LENGTH: 1550
<212> TYPE: DNA
<213> ORGANISM: Ureaplasma urealyticum

<400> SEQUENCE: 105

```
tataattgtg gaatcttaat tccatgtttt gcatagaatt cttttagacc gttgtacgta     60

ttttcagaat atccaccatc ttttactttt gctcctgcat aagataaaag caacccaatt    120

aatgcttgtt tttcatcatt tgatttagta ttatcccata tttctttaaa tttctttgaa    180

gatgtgttag aaatatatgt agatttggca acaggataga aataatatgt acctttagct    240

gatttataaa aagttccgcc atttactctt ggatcaatcg ttttattatt taataaagat    300

gcttcattat ctgtttcttt tttaacatct aaataaccat caacaactgg tttttttatca   360

agtgttttaa ataaatcatc attagtgatt ttattaacta attcatcata tgtgcttact    420

ttatcacttt gatttgtttg tgctaaatta aatgcatcaa ttacataatg ataagctgat    480

ggtgaaatac caactacacc atctgataaa ttaccaacag tattaactcc taatttatat    540

ttatcttttg gatcaatttc gctaccaata acaatctggt cagatttttt agataatgat    600

tctcccttaa ttgcattttc taataatttt atcgttgctg tgtctaaacg ttttgtaatt    660

gaaaaacgaa taacaccgtt tttatttccg cttagatgtg tgttaataaa tttatctgtt    720
```

-continued

```
tttttattga ttgcttgatc gttttcaatt tctacgtcaa caccaataac tcctacattg    780
tgtgaagttg ttgcaattgc ttcagtaaca gctattccaa cttgaggaat agctactggt    840
aaaattaaat cagcaccttt agtaattaat tcctgaataa tttttttagc attagcacta    900
tcagattgga aacctccagc actactttct gaagcataaa cttgttcaac attaatccat    960
ttttttgttt cttgtgttcc ttcttgttta atgtttttat cttttaattt ttcattagct   1020
catttaacac ctaaatcaaa acctgctaag taattggttg tatttttagc atttatacct   1080
acatacccac ctcaagttaa tttattatct gcaccaaaaa ctgcttgatt tgagtttaac   1140
atataagctg cagcaatacc tcctaaaaaa gcggcttcat caactttaaa ataaacatca   1200
gcaacacgat ctgctccctt ataaaactca gctttattgt cattattata aactccatct   1260
aaaattaaag cgattaaatt aggatcaaat ttatcattta ctaaagcatt ttgtaatctt   1320
tcaggatgtt gataaccagg cattaataaa gctcgtttac catcactagc catactttta   1380
tattttgttt gaaaaccttc atcatcatca cttgttggtg aagtccaata aaattgacta   1440
tagtttaatg tagattttg tgtacatgat gttgctacag taataattgt acctaaagca    1500
aaaacgctac caattgctaa aaatagaact tttttattta actttttcat              1550
```

<210> SEQ ID NO 106
<211> LENGTH: 603
<212> TYPE: DNA
<213> ORGANISM: Ureaplasma urealyticum

<400> SEQUENCE: 106

```
atgaattata aatatagtgc tgaagaaaaa caaattattt ataactatat tttaagagaa     60
tatgggcaag tggaccacat tatattttta tcaaatgaac atatacgtgt tccgattgaa    120
tatgatattt tagttattaa aaaacaaaac ttacaaatat taatgacttt tggactaggt    180
gcttttaaat cacataatca cgaagaaaat acgcaagagc gtgctgagat ttttttagaa    240
ttacctgttg attgagattt taataaacat gaaaacatgt gaccagttca ttttttaatt    300
aatatcgtta aatattctta ttcaaatcat ttaacactaa aatgattaca aaccttcatt    360
aatccctctt attttaataa atcaaataaa attgctgggt ttttagattt atcttgatat    420
ggcgagaatt ctttagagtg taaaattaat aatgattttt ttgtaagttt ttatcaaatt    480
ttaattattg atgatgaaga attattctat gcaaaaacaa atggaattcg tgctttaagt    540
aaattctttg atgatggtaa atcaagaatt gttgatttaa atcgaaaatc atttgttaaa    600
taa                                                                  603
```

<210> SEQ ID NO 107
<211> LENGTH: 1128
<212> TYPE: DNA
<213> ORGANISM: Ureaplasma urealyticum

<400> SEQUENCE: 107

```
atgaaaatat gtgataatat tagtgaaata aatgatgatc aggatttagt ctttattgat     60
attgaagcaa cagatagtaa gggcgaacaa cgaattattc agtttagcgg ataccgttta    120
aatattaaaa aaaataaaat ttttaatttt aataaaaaat tcaatcctga acaagaaatt    180
aattcacgta ttaaaacctt gctgaacttt aataaaaatt ttaataatat tgaacaaatg    240
ccaaaattag ataagcaagc agcaagagaa atttattgtt ttgttaaaaa tgcgattgtc    300
attactttca cagattttga tattaaaaaa atgcacgagc tttttacata ttataatttc    360
```

-continued

```
gattttgaaa aaatcgttta ttttgatgtt tataagtttt ttgaaaaaaa attacaaact    420
aaatcagttc ctagtttatt ttcattagga attctaagtg gaattaaaat taattttttc    480
aaattacata atgcgctata tgatgctttt attttaaaag aaatttttat gtgtattcgt    540
cataaaacga acgaagaatt atatgaaatg tatcgttatt atgaattttt gccaaaaatt    600
atttcttctt catattttgt tactaatgaa caagaaaaaa acaggggaat tattaaaaaa    660
gaaattaagt atgtaatgta tattaaagaa tttgatttct caaataaatt taatttagac    720
tttgttgttt ataaaaaaga tcatcatttt tattcaaaac caatttatga tagtagttta    780
gaattgcaaa caatttcttc actaacttcc aaatctaatt ttatgaaagt taaattagca    840
aacatctttt ttaattattt aagtaaaagt gctgttttta gtataaaaaa actatcaata    900
aaacaaagtg aaaaattctt aaaattttat aaaacacaga ctaataaaag aaaggttatt    960
aaagttttaa atttaaatct taaaaaagaa attaaacctg agaattttgt cataaaagct   1020
caaataattt gtgaaatact ttttaaaaac ccaataattc atcattttgt acatgaatat   1080
ttaaaaattt ttcaaaatat attttctcaa gaagaaaaag ataattaa                1128
```

<210> SEQ ID NO 108
<211> LENGTH: 3255
<212> TYPE: DNA
<213> ORGANISM: Ureaplasma urealyticum

<400> SEQUENCE: 108

```
ctatttataa atatcttcat atttttctgg atataaatag gctaattgtt tgatttgttg     60
aattaaagat gtacgattag cgaaattgtt tttatctcca aaaaatccag aaattagaga    120
atcaaaaaca atcatacctc cggctgtaaa ttttgcattt tcatgggcgc caaaagaaat    180
cattccaact aaatcaccat tttcatcata aactactgat cctgatgaac cagaaccaac    240
atcaaaatat tgattactaa ttttagttgt ccctactgtt gataagtaat tattagtagt    300
aataatattt tcttggattt tatcatattt attaatttca tattcacgat agcgtggaag    360
tttgccagca ttaaattcat taattgtctc tgttctaggg aaagttgaca agtatcattt    420
tacattttga ttatcatcga aatacttagt ttgattactt aatttcaaag gttttagatc    480
cttaaaatta attatatgtc taataacact ctgttgttct tttgttaaat cattaaaagc    540
aggtgaattt tctaattgac catatttttg aaaaaaaggt tttaaattaa tggtaattaa    600
tgaaaaatct aaacttgcat taggattaaa aaaacctaaa gcgttaacat gaggggataa    660
tttatttttt acttgatgat caaaattaat gatcgattcg atactaattt tttcaggaaa    720
atttaaaaat tgaaattgat tttgattagc ttcaagtttg ccattttttt caagtgcatt    780
gtaataagga tttttttat catttaatgt ttcattttca tgaataattt ggggaactag    840
tggatcaaaa tctccattag aactattact tgattcaaag agatctttat tacctgtttt    900
gttaattgat ttaaaagctt gcgtactatt taaaacatga gcacaactaa ttagataata    960
gcgataatca tcatcatcat taggtttaac cttccctaga acatttcatg taccatcttg   1020
aattaaactt aatgaaatta cacgatcacg agcattttta attggtaaaa aattctgttc   1080
attgttttta taaattcttg ttgtatattg attattagat ttatcatctt ccattatatc   1140
tatagtagta ttatttaaat aataaatatt aaaattagcc tttgttaaaa aataagatga   1200
atctattgaa gaattatgtt ctcaaatatt atcaaaaaca ctaatgttat ttttagaaat   1260
aattttaatt tttaattcat catttatata agatatttga aaacgaaaat cttgcttaat   1320
ttttttgtag agttcatatt cgtactcttg atttccaata ccataattta aaacaaattc   1380
```

```
agcatcttca ataacttttt tattttttaa agttttataa gggactgcta atgaaatttg   1440

agaccttaac ataaggtttt ttcacaggtt agtttctttg atgagatttg gatctaaacc   1500

aaaagtaata ttaaaaacta aattttttc atttacaaga tttaaatttt taatcttatt   1560

tattttttt gttaattgaa aataattatc tttatctttt ttaaagatca aatctggatt   1620

atcttttaat gtagttttat gtaaattttt gatttcatta ttatttacaa gtataaaatc   1680

agctttttta gttatgaaat cataaaaacc ttcgtttgtt ttattttgat aaaataagta   1740

ggtattttca tattgaacta atgaaataaa atttcgcaat gaataatcta aatataaatt   1800

attttgatta gatgctcaaa gtttatataa gtcatttaaa gttaaatttt tattctttaa   1860

agtttgatat tttgttgaaa aaaactgatt attattgtaa tacaaatcaa taattttacg   1920

atcattatat attatatttt ttacaaaaaa agtacttgta tttaattctt ttactttaac   1980

aaaagcaaaa ggcgttaaac tattattatc acgaacacta attctgttta atttgtataa   2040

atatccatta tataaatgag ggattttgaa ttttcatagc gatttaaaag gaacacgaac   2100

atactgaatt ggtggagtat attttgcaat taaactttga ttttttttag cttcgctata   2160

attttcgtct agagtaaact caaataaaaa aatcttgttc ttatataatt ttaaagtttg   2220

ttcattaaaa tcaaaaaatg ctgatccata tacttcattt tcttgcaaat agaaattaag   2280

ttttttgagt gttaactctt cttcaatttg attatataaa aataaatttt ttaaatcacg   2340

tcctagtgat tctacaacat catcatactg aatatgagta atgataaatt ttgttaatga   2400

tttaggaaaa tcttttagtg aaaagcgtaa ttgattatta ttaatttttt catatgaaat   2460

aattttgcta aaaggattgg ttcaatcaaa atttttaatc aaaagacgtt tatttgtcgc   2520

atttaatatt ttttgtattg tttgtgaatc agaatcatga ctaaaactaa ctgttgcaat   2580

ttggttttgc ttatctattt caatttttc aaatttaaag ttagtgtgat gatctgttag   2640

ttggttttgt tttgttaaga gcgttgcttg attaaagggt agttgtttaa aattatcttc   2700

attttgaata aaattaaaat aattattaaa ttcttggtta tttttctgca ttgttattaa   2760

agaaagatca ctagtttttt ttatgttttg cggtgaagat aataattgtt ttaatgcaaa   2820

aggacgataa tcattattta ttaattcatc attaatatat tttgtttcaa taacactttg   2880

cttcttattg atttctaagt tttgtgtata ttctttagtt tggttatgca aactgagttg   2940

gtattgaaca aaaaaattat ttgacttttg ttcaataaata actttttaa ttattatttt   3000

agcttgcccc aagtcaccca caactttaat tttattaatt ttaattattt gctcatcttc   3060

attttcaaaa atatcatatt taaatttaat gtttttttgct attatgtcta aatttttagt   3120

atcttgattc gtaattgtag aagacgaaaa tgttttttttg ttataagaac aattagataa   3180

tgatatagtt attgaaccaa gaattattgt tgatacaaca cctattgata agttttttaa   3240

tattttttt tgcat                                                     3255
```

<210> SEQ ID NO 109
<211> LENGTH: 306
<212> TYPE: DNA
<213> ORGANISM: Ureaplasma urealyticum

<400> SEQUENCE: 109

```
ttaaatcttt ttgttaatta ctttcttttc tttaatcttt gttattacta ttattataat     60

tggtgttatg aatattaaaa agcaaataat tgttaaaaca attacaccaa ttaatgctga    120

ttcataatga tttgagtatt caaatgaatt atcaatttta ttatattggt gtaatttatc    180
```

-continued

```
taaaaaatta agatatttca aataatcacc ttgatgataa taatcaattt cgattccaaa    240

aataattgca aaagccaaaa gaatgcaaaa aactattcct aaaaaagctg acccaataat    300

cttcat                                                                306


<210> SEQ ID NO 110
<211> LENGTH: 807
<212> TYPE: DNA
<213> ORGANISM: Ureaplasma urealyticum

<400> SEQUENCE: 110

ctagtttgcc tctaaattta aatttatttg ttgtaaagaa ttatttaatt ttttagcctt     60

tttttgattt ttaacttcaa gttttgcaag tttataagct tgtttttctt cagcactttt    120

tttaggtgaa aatacagtcg ctagtttaac aacaataatt ataaaagtaa tcatttgtgg    180

catcataaat acaataaata ctcaattata tgcaatataa tttggatttt gatattgtat    240

aatggttgat aattttgcaa gagattttat tccttgagct gctaatacag gattttgtga    300

gttagctaat tgtgagaata attgattata tttgtaaaat caactatttt ctcaatcact    360

taatactttt gttacaaatc ctcatgttcc attatgatta ataaatttac tatgcgcatg    420

ataatgaaga gcttcatata attttggatc gttattttta ttagtattat taattaatga    480

ctccattgtt tttccattaa tcaattgatc gtgaattgtt ttatacaatt cttgataatt    540

agcgtgttga tcataaccta atcatgacat taaagaatga ttatcaccac taacatcagc    600

tactttacca ataatttgac cttgatcatt aactaatgct cttgcatttt caaaaccttc    660

atttaataaa ccaaccattg taaacgctat tgttaatcct actataaata taactaatgc    720

tgctataaat caaggcgtaa agacttgttt aatttttgga agtttgctga attcagcaaa    780

gcttttattc attttaattt gattcat                                        807


<210> SEQ ID NO 111
<211> LENGTH: 711
<212> TYPE: DNA
<213> ORGANISM: Ureaplasma urealyticum

<400> SEQUENCE: 111

atggatgaac aaatttttat tcaattatta gaaaacaatc taacaaattc aaaatcatat     60

gtgactcaac caataatatt agaatttaaa acggatgttt ttttgattat aaatcaaatt    120

ttaaaacaat ataaaaaagg taaaattatc aaaaataata caaatgaaat tattttagaa    180

attgataata aattaatttc tataacaaat ttagatatca ataaatttca ttcgtatcaa    240

attgttaata ttaatgaaaa taaaaatatt tataacgaaa ggaatagttt aattttattt    300

gatttagtaa attatatcat tgaaaaaaat caaaattcta tcagacacat taatttttga    360

acgattcaaa tgagtgtagt taattgaatt tattttatta cttataattt taacaattca    420

tatttaattg atccaaattg aaaaaaatat gtttttaaaa ttaaaaaaga tgaatctaaa    480

ggtgtaatta gtaccaattt attacataat tatggttttg tggattttgt tgtacagtct    540

aaatcacaga attttttaaa agcttatcgt gttcaagatg aaattctaaa atctgtttta    600

aatttaggcg ataacttaaa taatgaattt ttagaagaaa tcatgagaaa atatgataca    660

tacaaaataa ttgatagaga tcataaatat ttagtgatca atattgaata a             711


<210> SEQ ID NO 112
<211> LENGTH: 732
<212> TYPE: DNA
<213> ORGANISM: Ureaplasma urealyticum
```

<400> SEQUENCE: 112
ttatttttta tttactacat tatctaattc aataaaattt ttaataatgt ctcttccttt 60
ataatctatt ccaacaattt gtttagcaat tgctgtagct acttttatag cagattcttt 120
tgtcttttta attttttcat cattggcttg tttattatca ttaaagtcga ttggattttg 180
ctctagatca attggaaaat cagcattaac attgaattgt ttatttaaat atggtaataa 240
ttgttggtta aaggcgatat tagccatatg atacttagca tttttgttta atttttttac 300
aaaagaaaca atagatgaat tcattaattg tgatttttta atttcaacaa ctgaaatttt 360
tgttttatct gttggtgcag caagattgtt ttctactttt tgatctttat tatattcgta 420
gaaagttaaa cgtaaaattg ttggatcaga tatatcaatt aatttattag tattagtgtc 480
taacttttta aatgcaatat tttttagttt ttcagatata tcaaaaccta atccaattga 540
aaatttagct tctactttat cattagaatt tttaatatca ttggttgata gatgtcgaaa 600
tgaaatatga ttttgttcaa tattattaac attatcatta tttaatgcaa tatttgcaat 660
tttaacatta gtcaatttaa catcataatc acgattatta aactttatgt atatggtttt 720
atggagcgac aa 732

<210> SEQ ID NO 113
<211> LENGTH: 627
<212> TYPE: DNA
<213> ORGANISM: Ureaplasma urealyticum

<400> SEQUENCE: 113
atgataaata atatttttaa taaaaagttg ttagtttaca acgaaaaaga tcaacgttgg 60
tataacaaat ttgatagaac taaaccttta ttttcaccaa gtagactatt aagttttaaa 120
aattacattt ttgaaaaaat accagcaaaa aatctagaat atccaattga gtttggaact 180
agtttaatgc aaatcattca atactatttt gaaaatcaat caaaattaga tgtcatttta 240
aatagtatta atgaagaaaa attaaaagaa gtctttttat tgtttttaga ctatttaaaa 300
acaaatgatt attcactaat cgctgttgaa ttacatttat ttagtccaaa actaaaccat 360
tactgacatg gttttgctga tgttgttgtt aaaaccaaag atgataagta taaagtactt 420
gaaatcaaaa cacacaacga aatccaatca gtgccatctt gaaagtttca agctggtgta 480
tatgattaca tcatcagcca agaattaagc aattacgaac catcagctat actagcattt 540
agtcgtaaac aagcaaagtt aagcgtttat gaaaatgatt cattagattt aagttttatt 600
aataaaatca atgaactata ttcttaa 627

<210> SEQ ID NO 114
<211> LENGTH: 174
<212> TYPE: DNA
<213> ORGANISM: Ureaplasma urealyticum

<400> SEQUENCE: 114
atgaactata ttcttaataa aaacaaaaaa gtaagcttaa ctgaactaat gaatcaacaa 60
ccacattgat acttagaaga actacaagaa catttaatta aatatcttga tacaaacgga 120
ctaaacgaca ctaaaaaact aattaaacaa acaattaaag aatggaaaaa ataa 174

<210> SEQ ID NO 115
<211> LENGTH: 342
<212> TYPE: DNA
<213> ORGANISM: Ureaplasma urealyticum

<400> SEQUENCE: 115

```
atggataaaa ttaaaaatta tctagaaaaa ttacaagcgt tttataagtt atattctctt     60

aatttaactc aaggaacaga aattttaatt attcaaatca ttgataaagg taatttaatt    120

tttgattcca ttgaaaaagg taaaacattt aacgaaagta aaataataga accactttta    180

ttcattttta aaaaaataaa tacaatttta gctatcttaa aattaacttt tactaaagat    240

gatttaattg gaattctaca atcattagaa gagcatatat cagaatttat tattgcaaat    300

tataaatatg attttgaaat cgaagaagat gatgaagatt aa                       342
```

<210> SEQ ID NO 116
<211> LENGTH: 1413
<212> TYPE: DNA
<213> ORGANISM: Ureaplasma urealyticum

<400> SEQUENCE: 116

```
ttaaaaatct gatttagccg tgttgattct tgttttaaat tgggttttgg gatcattaat     60

tccttgtgta ctactaatta ttcaagatcc tgtattttta atcataatta atttattcat    120

tgagtttaat aaatgggatg ggcccatata aattgcaaaa tttttatcaa caaattccgc    180

tttttcacta tcattaggag ccttattaat tttttctaat ttatcataat taatcaactc    240

ttttaaataa ttaccaacac cttgggtttt taaattaata ttattaaaac tttcataatc    300

aactattgca tcaggtttta aaccgaatga aattaaatga tcaatactat ctgctcatgt    360

cccaacaatt ttataaccat aagttagctt aaaattttta tttatataat gaggtttaat    420

tattaaatta cgctctttaa tagttggttt gtgatcaaat aaatttatta attcttcttt    480

attaaatggg agataacttc attgtttttt tattgttttt ttatttgtga aaatttttaa    540

taattcttta ataattagtg attgcccaac cattgtaaaa gaacctcatc aaaacaatga    600

acgatcaata aaaataattt ttgaacgaga attgcgtaag aatttatgag cataaaaatt    660

tttgtttgat aaaatttctt taaataaatc ttcacgtttt tgaccatctg ttttgtattt    720

attattagta aataaattag aatcatacat ataaaaaaca taatcagctg ttttataaaa    780

tgaagatgtt tgttttaaga ctgattcgag cgggtttgtt cttaatgcat tataaccaat    840

tgattgataa cgatcaataa tatcactaat atcattatta attggttttg gaaaattcaa    900

tcccaatcct ggaacttctg tataaggatt agaatagatt agtggaaaat ctgaaggtgt    960

tagaatagaa aatttattat aattttcttt attattaact aattcattac gattttctat   1020

aactaaaaca gttgctttat gattgcgcat tttttggatg ctatcgagca ttgctacatt   1080

attaatatca ttttttaata aacgtgcgat ctttagactt cattcagtaa atgaatgtac   1140

attttgcatt ggttttggta gacgtttttt taattcatta aaatttaaaa cattatctaa   1200

ttggcgagca aattctaaat gaattttata aggatcacga aaaaaattat tcaatctcca   1260

atttttattt ttgaataatc aattagtatc atacggtttt tgttgttgaa gatttttaca   1320

tgaacttaat gttgtaaaaa taatacttaa tccaagcatt gaaattacat taattaatct   1380

aaatttaaaa ctaattttca ttattaaaac cat                                1413
```

<210> SEQ ID NO 117
<211> LENGTH: 297
<212> TYPE: DNA
<213> ORGANISM: Ureaplasma urealyticum

<400> SEQUENCE: 117

```
atggaaaaaa tagttggctt tattgtgaac ataattaatg ttcaaaaaca aatgataaaa     60
```

gacttaaaag aactaaaaaa tcataaagac atcatggtaa aagaccatga aaaattaaat 120
gatatgttaa atagtatgat agatgaagca gttaaaaatt acaaaattgc attaaaaaac 180
ataacagaaa ttctaaacgt tcatttaaac tgtgttttat ataatcacaa tcttaaatgt 240
ggcgtaaaag atgaaaaatt attattacca ctatttaaaa gaaagaaagc gagttaa 297

<210> SEQ ID NO 118
<211> LENGTH: 237
<212> TYPE: DNA
<213> ORGANISM: Ureaplasma urealyticum

<400> SEQUENCE: 118
atggcaatgc tttgtatgtg tgatgaatgc caagcaatta ttaattatta tgttgtacaa 60
attgaacaat tgtgtaacga aattgtaaaa acaagaaaaa gagttgaacc atataaaaaa 120
ttgggtaaat tgttttttga aattattcaa aatgatttat ttgaagcaat agctgaagaa 180
gtgtttagaa tagatgaaaa accaaaacga aaaacaaata aaagagtatg taaataa 237

<210> SEQ ID NO 119
<211> LENGTH: 183
<212> TYPE: DNA
<213> ORGANISM: Ureaplasma urealyticum

<400> SEQUENCE: 119
atgaaaaacc aaaacgaaaa acaaataaaa gagtatgtaa ataaatttaa agatttgcgt 60
aatcaactaa caaaaaacaa tgacgttaaa aaagtttgcg atttaattaa tgatttgttt 120
tttgaagtat ataaaaacaa tttaatagat gaagttatca aggagattaa caaacatgac 180
taa 183

<210> SEQ ID NO 120
<211> LENGTH: 264
<212> TYPE: DNA
<213> ORGANISM: Ureaplasma urealyticum

<400> SEQUENCE: 120
atgaagttat caaggagatt aacaaacatg actaattgag ataaagaaca tgcattaagt 60
gaagaactaa gacaattaaa agatgagttc gaagatttaa tggatgattt agcaagaatt 120
aataaagatt tagattttaa tatctgagaa cgtaaagact tagaatatcg taaagcaagt 180
tatgagacag atatcgaaag tattagatta cgaattaacc aaaaacaaaa tgaaatgatg 240
gagataataa aaaatgacaa atag 264

<210> SEQ ID NO 121
<211> LENGTH: 336
<212> TYPE: DNA
<213> ORGANISM: Ureaplasma urealyticum

<400> SEQUENCE: 121
atgacaaata gtattaaacg tgaaatatta agtgctttaa atgatgaaac aaaaaaagta 60
attagcaaat tacaacaaac aaataattta attaaacaat taagcgatga aaaaaagaca 120
ttagaacaat atttaaaaga taatgttaac aatcatgaaa tcgttgattt agacagtgat 180
ttaaaaatta aaatctatga tttaacatct aaggatagta ttgttttaga ttatgacaaa 240
atcattactg attataaagt tgatacaaaa aaatatgaaa cgattaaaaa aggaacaaca 300
tcaacacgaa taacatgaag tggagcagat aaataa 336

-continued

<210> SEQ ID NO 122
<211> LENGTH: 657
<212> TYPE: DNA
<213> ORGANISM: Ureaplasma urealyticum

<400> SEQUENCE: 122
atggttaaag acgataaatt agtgccaagc attagattat taacaccaaa tgaactaagc 60
gaacaatgag ctaatccaaa tagcgaaatt aatcaaatca cacgtgctgt tttgaccatt 120
caaggaattg atttaaaagc cattgattta aaccaagcag cacaaattat ttatttttgc 180
caagcaaata atttaaatcc actaaacaaa gaagtttatt taattcaaat gggcaatcgt 240
ttagcaccaa ttgttggtat tcatactatg acagaacgtg cttatagaac tgaacgatta 300
gttggtattg tacaaagtta taacgatgtt aacaaaagtg ctaagacaat actaacaatc 360
agatcgccag gtttaaaagg tcttggaact gttgaagctg aagtattttt aagcgaatac 420
agcacgaata aaaacttgtg attaacaaaa cctattacca tgttaaaaaa ggtgtctttg 480
gcccacgcat tgcgtttaag tggcttatta gcgtttaaag gtgatacgcc ttatatttat 540
gaagaaatgc aacaaggcga agcagtgcca aataaaaaaa tgtttacacc accagttgct 600
gaagtaattg aaccagcagt tgaaaatata aagaaagtag attttaatga gttctaa 657

<210> SEQ ID NO 123
<211> LENGTH: 690
<212> TYPE: DNA
<213> ORGANISM: Ureaplasma urealyticum

<400> SEQUENCE: 123
atgagttcta ataactttga taataatatg ccacgtattg aatttaaaaa aatgccacta 60
acttttatta gattaaatac gaaaaaaagt aataacgcac cctttgtttc aggtagtttt 120
tgattagcag ataaagtaaa tgcgaacgtt tattttagtg aatatttaat ggaacgtatt 180
gttccatttg aaaacaataa aactaatatc gttatcttag aaaatgtttc atgttatata 240
aattttaact gagaagaaaa acgaattatt atgcgtgttg tttcatttga taatattttt 300
tacaagcatc aattaagcga acaacaaact attgattttg tgagtgctga aaaagaatat 360
aactatcaaa cacaaacagt taattcttat agtaatagtg atgatgaaat tgaaattatt 420
aactgattag aaagtgatga acaaaaagca tattttgata gtcagttaat gtttattgat 480
tataaaaacc aaggcttttt taaaaataaa acaatgccag ataaactaaa aaataacgct 540
aatgctttag aactttataa acaaattatt aaattagatt tagaagcatt tagtggttta 600
tacaacggct taaaaccatt tgaagcagca aataaattaa ttgaaaaagg ctatataaca 660
cttaacgatt tctttaaata tgcgatctaa 690

<210> SEQ ID NO 124
<211> LENGTH: 462
<212> TYPE: DNA
<213> ORGANISM: Ureaplasma urealyticum

<400> SEQUENCE: 124
atgcgatcta aacaatgaca tttgagcaca caagatgcta atttagcaaa taaaaaatat 60
gattatattt actttagggg tgttaatcaa ctttatttaa aacgtcttaa aaaaagtagt 120
aataagtttt ttgtttataa aaaatgtaaa atcgtaccac gtatgatatc aaaacattta 180
aataacgacc atttaattaa cgttaatgat tatgtaccac taaccaaaga atttattaaa 240
aaaagcgttg aaaaagaagt taaacattat ctaaggttta tatcttatga aaacaaaact 300

```
aaacaaatgc ctgaactaat taattttttta gaaaaatcac ttgaagataa gttatttatt    360

gtcgcaaaag attatgatcc tttattttct gtgtttttac gttattacat tcaaagttta    420

atagaaaaat atattaatga attatgaata aatgagtgat ag                        462
```

<210> SEQ ID NO 125
<211> LENGTH: 678
<212> TYPE: DNA
<213> ORGANISM: Ureaplasma urealyticum

<400> SEQUENCE: 125

```
atgaataaat gagtgatagg aatcgattta tcaacaacaa taacaggagt tgctatttta     60

agaaatgagc agataattaa aacctttgct gttgcttttg ataactttaa tgaaaagaat    120

ttatataaca acgttataag acttattaaa gaaattaatt taaatgtttg attattagct    180

gatgatgatt attatattgg tattgaagtt gctaactttt caaatccaaa actaacacag    240

cgtttttcaa tttatgctgg tatgattatt gcgttaatgt cacaagtttt aagagatttt    300

aacgctgaat ttaaaatgtt taatgcgaat gcttgacagt taaaaatacc acaaatacaa    360

tataacacat tgcgtaaaga tcgtaaatta attactaaaa atttaatgat taaaacattt    420

aatattaaaa gtaatttaaa cgaagacgaa tacgacgcct tagcgattgc ttatttttat    480

gatagtatta attcaacgct agaacaagaa gagataacta aggctaaaaa aatagttaaa    540

atgaataaag ttaaacagca gttatcaatt agtaaaaaga ttaataaact gcttgaaaag    600

aaaagcaaac taaaaaaagc aactgcgata tcaaaagttg atgaacaaat agaagaatta    660

aagaaactaa ataaataa                                                   678
```

<210> SEQ ID NO 126
<211> LENGTH: 444
<212> TYPE: DNA
<213> ORGANISM: Ureaplasma urealyticum

<400> SEQUENCE: 126

```
ctaataatcg cttttaatac gttttaaata ttcgatctct tcttctaatt tgcgttgttt     60

acgtcttgat agataactat gtctgatatc atcaataaac gcctttggat ctaatatacc    120

atccttaatt aatttggcta gcattaatct aaatcttagc attagcatta attcaaatac    180

ttttaatgga attgataacg ctgttattaa atatccaagc actgagaaca ctaaaccaaa    240

taatgcggtt gggtcttgtc agttgatgtg ttttaattta tcaaacaaac tcttaatctt    300

gtcattgaaa ttaaaaaatg gtacaaacac aataatcata gcaaacgcaa ttacaaatat    360

taaaatagca attcataaca tcaagcgttt tttattaaag aaaaataatt ccttagtaat    420

cgctttgaac tcttgttttg tcat                                            444
```

<210> SEQ ID NO 127
<211> LENGTH: 972
<212> TYPE: DNA
<213> ORGANISM: Ureaplasma urealyticum

<400> SEQUENCE: 127

```
ttatttattt tgattaaatc ctttaatcgt ttttaaatat tctaaaactg cttcttgact     60

tccattgcct tttttaatca aaatcttaaa aaccaccgct gttttgttat taacatcagg    120

ttcaacactt tgaatttcat aaataaaacc tgtttggaat ggtaatttaa ataatgtttt    180

ataattttca ataacttctt ttattgtttt ttgttttgtt ttttcatcaa ttaattgtgg    240
```

-continued

```
ttcaagttga tttttatctt gtttaatcgc ttctaaatta gctaaataaa tctttttatc    300

agcttcagaa ataaaaccat taagtgtttt gttataagta atgcttgcta aattttctcc    360

attaccttta ctgattttaa tttcgatatc aatagaatta gcagttttac ttttagtaat    420

ttttagaatt tcatatttta aatcattatt actattgtta atatttaaat aactattttg    480

tcattttaat gcttcatcta ctgttgtttt actaatgtta atacttgaat taactatggg    540

cattaaataa agagtattat ggtttttttc atcttctaaa tatttttat tttctaaaaa    600

taaacgatat tgtttagcat tcttaaaacc ttttaagatt tttttgtaag tgtgcgtttg    660

acctttaaaa tgataacgaa ttattagatc aattacatct tcatctaact cattcaatcg    720

tgcatcatat aattcatatt taatatcttt atttggtgcc aaaaattgaa tattagtttt    780

aataatctta ataaattctg aagctaaaat ctttgaaaaa tcatgttgat cataaccttt    840

aatggttgga taaatttcat tctcttgttt tgattttatt gatgagctgc acgcaacacc    900

acttgttgtt atcaaaccta atagtccaac aattaaacta ctaatgaaaa ctgttttaat    960

tttttattc ac                                                          972
```

<210> SEQ ID NO 128
<211> LENGTH: 549
<212> TYPE: DNA
<213> ORGANISM: Ureaplasma urealyticum

<400> SEQUENCE: 128

```
ttagtaatcg ctttgaactc ttgttttgtc atcttttata atctcctgtt ctaatcgctt     60

aactttttgt tcttgctctt gtatttttaa ttgcttttct tgttgttcta gttttttttaa    120

ttcttcatcc aatgttttgt aattgttaga acttataact gctttaatat tttcaacact    180

aatataacga ttacgtattt gttcaactag tatatctaag gcttcgaact cttctttact    240

taaatccccg tactggtgca ttttagcaac agttcgccat aatgtttttta atgttggtaa    300

aagtgttaac attgaaataa ttaaattaat aaatccaata gtcataaaga atggaaaata    360

aaacttttgt tcttttacaa ataacacaaa tgcgttatca tttggtagtc cagcaattaa    420

ataagtagat aataaagcta atcctaaaaa taaccctgaa ataattgaac ttgttaaata    480

aatcagctgt acttgttttt tagaaaactt ccattctttg tttttaaact tatttttatt    540

gttcatcat                                                             549
```

<210> SEQ ID NO 129
<211> LENGTH: 437
<212> TYPE: DNA
<213> ORGANISM: Ureaplasma urealyticum

<400> SEQUENCE: 129

```
ttattgttca tcatttaaaa tactctcctt attttgcttg tataaatcat tttgagcctt     60

ttttatgctt cttttttgtt cgttaatagc ttttcattca ctttttagtt tgtcttgttc    120

tatgcgagtt tttagatgtc agtttttgcc ttctgttgta aatcgtcaaa agaacggcga    180

tattgcgaaa aaatcaacgc aaccacaaat gatataagca aataaaacaa ctaaaaataa    240

ttgccatttt ttcgtacttc ctagttttgg aaattttgat atcattcagt ctcataatgt    300

ggctttgtct gtatattcgc tttctttacc aaaaaaataca aacgatgtct caccaatttt    360

aataaaaaac gaacaaatta aaaaaatggt tcataatgtg gttagaattc atagtcataa    420

aatacgacga ttaatat                                                    437
```

<210> SEQ ID NO 130
<211> LENGTH: 336
<212> TYPE: DNA
<213> ORGANISM: Ureaplasma urealyticum

<400> SEQUENCE: 130

```
ttattctcct acataaattg ttctaacact tcattcataa tttaatccaa cttcaaagtt     60

tgtagcaaat gttttattta ctatatctat taatcacaaa tcaacattaa caccagattt    120

ttcagcatta acacgaacga ctaaaaattg aggctgatat tgatttcaca acaggatttg    180

ttgttgtgtt tctccactat cagataacat gttattacgg tctgtgtttc tatcaaaaga    240

aaacgttaaa ctataatctt tatcacttca atcaacacta ctgttattaa aatttaatga    300

tagataccat ttaaaaatta cttcatgatt tgccat                              336
```

<210> SEQ ID NO 131
<211> LENGTH: 1374
<212> TYPE: DNA
<213> ORGANISM: Ureaplasma urealyticum

<400> SEQUENCE: 131

```
ttaaattatt ttatttaagt tatccataat ttttcacgga aacctaacat tcctatttag     60

tgcagtgttt ttaaaacttt ctaaattaga tgttaaagca tcaacattag cactatcacc    120

tttttcaccc tttggaccag tttcaccttt tggaccaatt ggaccttgta ttccaggttc    180

gcctttttca cctttaaata caccagatgc tttatcttgc tcataagatg ataaaaccgc    240

ttgtttggct tcattaactt tattttctaa gtttttagtg aatgtatttt ctttagtatc    300

aattgctttt ttaacttcgt ttactttatt atcaacagca tcttgcacgc cttctttaat    360

tttgtttaaa tcaatttgtt gaatattaat taattctcat acattttcgt taatttgctt    420

acttggatct acgatattat gcgtacttac accattgtta actagtgcct tataaacttt    480

aattgtgtta gttttttcat ctaagtcata aactaactca ccagctttat agtcataaat    540

agcatcccag tacattttgg aattaatttt attacaatat tcatacaatt cttggcgtgt    600

aattgcattg ttattatttt gtccatatca tgctaaattt ttaacgtcat gaatatcaac    660

ataattagca atagcattat cataaacttt attgctttta tctgttgtta aatcatttgg    720

tagtgtacaa tcatttaaaa taaagccatt taatgttgct aaattaccag atgcgttaat    780

gctacttacg ttattaatat tgtgatggtt taaatcaaaa ttattattaa caacagggtt    840

atttttagat atataatggt ctcttaattc ttcatgaaca ttattaatcg cattaatttt    900

taattcatca taattaacat aaataccatc atcgttaaag ttagcaaact ttgatttttt    960

atataatcca caaacacgta atttattaat gatatctaat cgcttttttt caaaatcagc   1020

attttcagat ttaaaagata atgataagcc atcaccaata gcagatgtat aatctttatc   1080

gataaaatga ccttgtaatc ataaataatt tgttaatgtt gcaattgctt ctttaaattt   1140

agtttttga taatctgttg tttttaaatc atcaaatcaa ctataaataa aaccagcacc    1200

accatttgat gctacacaat catcaatcat tgattgagca cgcaaaataa acgtagttaa   1260

cgcttgtttt ttacgttcta attgtaattg gttatcttct aaattttcgt ttcgtacaat   1320

tagtggaaac aaacttaaat attcttctac actaagtaat aatctattat tcat         1374
```

<210> SEQ ID NO 132
<211> LENGTH: 783
<212> TYPE: DNA
<213> ORGANISM: Ureaplasma urealyticum

<400> SEQUENCE: 132
ttatttaact ccttcaaaat atttacgaga tgcatcaaat cagtaaatac tttctttttg 60
taagtgaatt aagtttttac gattagcatg gtaaaatatg tttcaaaatg ttgtaccagt 120
tggtgcaaat ttcagcattg tagcaatgcg ttttggaata ttacgtcatg tataacgtgc 180
tagtggatta cgtttggatg gtttcattaa tttaagtgtt aaataaccaa tcttaccaac 240
gccatcactt gcgtatcatg tgccataatc tatccaatgt ttattaaaat caatgtcaac 300
attatcaaca tctttaaact gattttcttt acgcactttt tcaaaattct ttttttcagt 360
tttagatgcg ttatctaatg tatctgttaa atgtttgata atgctatctt tttgttttgt 420
cgtgtattta ctagtttgtt tagcaatatc tttaatcgct tcattaatag catcttttag 480
ttttttagct aaatctttgt tatcttgaat aatttttaat tcttttgagt taaaaatctt 540
ttctaaactt gaattatcaa aaaacttttt taatatgtca tctggtttta aattaaagtc 600
atgaaaaaca gttttacctt ttttcataaa agcaccagtt ttatttttaa acattttaaa 660
aaaatcaaat ttaaacatct ttaacatacg tgaaaataag ttaatcaaag tagatattaa 720
actcttaatt ttagataaca acaagcgacc aacaaagcgt agtattagaa ttagtatacc 780
cat 783

<210> SEQ ID NO 133
<211> LENGTH: 1188
<212> TYPE: DNA
<213> ORGANISM: Ureaplasma urealyticum

<400> SEQUENCE: 133
ttacttgtaa gtacttaaac cccttcaatt tgctttattt acttcagtga ttttagaatc 60
ttcactgatt ggtgttttaa attcagcata tagtgaggga aattgtgaat aaagatttga 120
gcgtgcttta ttgatttcat cttttgttgg tttatcattt aaaatcacaa aatttaaatg 180
tgcaaattgt ggaaagaccg cactgttcat acttcatgag ttatgaatta actggtgtga 240
tttgcttgtt ggactttgaa atgttgttaa cattaattct tgttttaaac aaattgtagt 300
ctcaggcatt gtaataatac cgcttagttt gctaaacttg taatcacgaa ttaaattact 360
tgtgtatttt tgatctgttg attttaaata atcttcgcct aaatatgcag atgagtatat 420
tggcattcct aaataatcac ccatatattg tgaactactt cctaaaccct tagtgctata 480
gtcgctgtat gcttgaccat cacgaatttt ataagtttta gcagttaata caactaatgc 540
tgcatcatct gataaaacga atcgtaattt atttggatca gctcctaaat taaatttagt 600
acgacttttt gttacttgtt ttgctttacg atatattttt tcaacaattt ttaatcgttc 660
atcatctgtt aatgattcaa cacgatcagg actaagttct ggaataataa tataattacc 720
agttgctaaa caagattgat aaatcgcatc aatgttaatt aaattaattt gatcttgttt 780
aacgacttct aaatttgcta atgtcttagc taaaaaatcg tttcattgag cacctgtttt 840
tttatcaaat acactaatac ttacttcttt ttgatagtca ttacttaaat gtaatgttaa 900
tctatcaatt gctggtactt gcttttgtgt aaagtcatca cggtactctt caacttgtcc 960
gattacgcca acttcataaa tagcagttcg catatcatcc ataattttag ttggtgtcat 1020
tgttgcactt cctagaaatt cagcgttaaa ttgattttct agcatatatt tttcaaatcc 1080
acctgcaaca acacgttcat tattagcgtt aacaacatct aaatattgag tgattgtata 1140
tttagcattt ggatctggtc tttttcaagt gttttggtta tcagccat 1188

<210> SEQ ID NO 134
<211> LENGTH: 327
<212> TYPE: DNA
<213> ORGANISM: Ureaplasma urealyticum

<400> SEQUENCE: 134
ttagttaaaa aattttaaaa agtggctatt agcatcttct acgactggtt tttcttgatg 60
aatattaaca aactgttgat tttgttcaag cgttgcgatt ttgtttaata attcttgttc 120
tcgttgctta aacgtatttt ctaagtcttt gatttctttt aacttagctt caactaattt 180
attagcatta tctaattgtt catttgtttt tagataattt tcaaattgtt tttgaatacg 240
tttgtcaatt tcatcatata aagcattttc tttattttct tcagtttctt gtggttgaac 300
ttgatttttt tcaagttcat caaccat 327

<210> SEQ ID NO 135
<211> LENGTH: 699
<212> TYPE: DNA
<213> ORGANISM: Ureaplasma urealyticum

<400> SEQUENCE: 135
ttactccact aattcaattg tttttaattt aatggttttt gatttaatac agttatttgt 60
ctctaattct ttaataacat cgcttaaatc aaatggtgtt gttttaaata aacgtcgttc 120
gttatcttcg cctttaaact catcaattgg tttattattt ttacttattt ctttttcatt 180
acccctatca tcaatataaa tatttgcctt attagcatcg cttaaatcaa atggtttttc 240
aattttataa gttggtaaat aatttgaaac taaacgataa ttaacacgat tagttggctc 300
gatactataa acaatatctt ttgttgtact ttcataatct tttaattcaa ttttaaatgt 360
gttttcatta attttagtta agataatata tttgttttca tttggtttaa cactaacaga 420
tatattctct ttattatcaa caacagaatt aacactaaat tcttgattaa tagctacaag 480
attaaattct aatttatcat caacttcacc taaattaata tgtattgaac tattgtttgg 540
ttttgaaatt agtaaatcat aaacatcagc tttaatacta aatgtactaa ttgttgattt 600
tttatttggt gtgtttaaat ctactgcata attaccacca tattttaatt tattatcttt 660
tgttagttca aaaccaacaa agttattagc tgattgaaa 699

<210> SEQ ID NO 136
<211> LENGTH: 2835
<212> TYPE: DNA
<213> ORGANISM: Ureaplasma urealyticum

<400> SEQUENCE: 136
ttagttcaaa accaacaaag ttattagctg attgaaacta ttatcaacgt taaactgatt 60
tgttcatcct ttctgtatcc aattactttc aatctcaaat gttagtttta aattacgttt 120
tgttttatta actgaaccta aatttaacca ttcacgataa ttaaaatctc atttaaacac 180
aaaactataa gcaataactt tattagcaac aattacatca cttaaattac ttccaccaaa 240
taaataattt agtttattag tatatgaacc ataaccaaat agatttgcta atttagaact 300
gtctggttca taaaaataaa agcgtggttt tctatattgc gtagcactta ataatgaatt 360
atcgcccact ttatataatg tttcattaat tgtttgtaaa cttgcattaa ctccatcatc 420
actatttgtt ttagtatttt ttaaaaaatc agtttcaact ggtggctttg gataacttag 480
tttagttcca actgaattaa tctcatcaag cgttgaaaaa ttaatatagt tgcttcattg 540
actcatatca tcagtatatt ttccattgct ttcaaaaatc gcttcgtaca cgtttttaaa 600

-continued

```
ttcgtctttt aatcgtgcat ctggtgaata aaagccacta aaagctgtta gtttaatatc    660

acacttaccc aagcctttaa tatcaatcgt atcaattaca taaggatatt taacacgatt    720

aacatcttca cgtttaccag acgctatatt aataacagct ggttcataac taagcggtgt    780

gtttggtggt aatgcttcac agaaactatc tcaatataaa ggtttttat cttttcttat     840

atacgtacca tcacgatatg ttgtttgtcc aattagttca gtatcaaata cttttagctc    900

atcatctaca aatttagcaa atctatcagt tatatcaaaa tgataacaac aagcaatggc    960

tggtatgcca agtggactaa atgttttagc tggtttgtta gtgaaaatat ctaaattaat   1020

taaatccgct tttagtttat ttgatacttc taattcaagc ggtaaacatg gtgcaataaa   1080

attaaaacca cgtgtattta atcaaatgtt tgacatgtta taacctgttg cgtcttcaac   1140

tttggttcaa ccaggatata aaatatctac aataccacgt ctaactttac ctaaactaag   1200

tggtgtatta tctattaatt caccaagatt ttgacggatt gtttccttgt atgaatatgg   1260

taaatactta atcaaatcat acataaatgc attgtgattt aaaaacgtat gcaaattagt   1320

accaggtggc attgtaatgt tgtttaatcc aattttagtt gcttctttta tttgttcagc   1380

tttggtttta gcaaatccca tattaaaaga ccataaacct aaattattta aattaaatcc   1440

ttgtgaaaca ttacgtccaa tactttcaaa cactgtactc acaacttcac cagcaacttg   1500

accagttaca acagcatcag ctaacggctt tttttgttct gcattttcag ttaatgatcc   1560

gcccttttgt gctcctgttc cacctaattt aaagttaaaa aagctcgcat gtattttaaa   1620

accttcatct cataatttaa atggataacg attgtcttca taacttagtg cgttattgct   1680

tgcgtctcat ttatgattta ataataatcc accatttaat ttaatattag cgttatggtc   1740

aaatgtaaaa tctttttgtt tttcatactg gtctttataa atcttttcaa tttcaaaaaa   1800

cgcattgtat aaatatacat aattacttgt tggtgctgat acattaaaga atttagatgc   1860

gactggtatt ttagctttat atagtaataa tcgcttatta gcacttaact ctcgtgtgtc   1920

attattataa gttcgtcctg ttattaacat actatttaat gcatatggtc cattagttaa   1980

taattgaata cttttaactc ctaacggttt ttctttacgt tcatcatatg ttaatttacc   2040

attttgaatt actggtcata aataaccatc tccaggttga catggttgaa ttgttgctaa   2100

tatatcatta ccagatgatg ttagtaaatc gttaacgttt gttagtgtaa tttgtgctcc   2160

ttcataacgt tttgatgttg ttgaataaaa aggaatgact tcattaacca ttaatcattg   2220

attagcttgt gcgtgttcat ctggaataat gaataaatat tcttttaaca tatctgtagt   2280

tcattgttta aactttgctt tatgactaac taaattacct tgttcatttt ggtatatttc   2340

atcttcataa acacttggat atttaacaat taaagtaact gttgtaattg ttttaataac   2400

tgtatgttct ttatcattaa aaacaattgt agatacatta tttgcttggg aataattttg   2460

tactcatgct tgaaaataat aaggtttaaa gttgtttttt agcgttgtat tacttggatc   2520

aatacgtgcg taatctttac taatgtaatt taaactacct ttaaagttat acgtaaatga   2580

tttatctcaa tacgcaatga ttggctcatt acttgcttta atatttcaaa cagtgctaaa   2640

atctttgtca tttactaata atgattgttc accggtgttt gtaattttaa taaaaccttt   2700

tagtattcta aatggacata aatgaattgg tttttggttt ggttcaatta aactatcaat   2760

gctgtcttca atattttttt gactataacc ttcaagttca tctaaataaa tattactcat   2820

tttcaaactc tccat                                                    2835
```

<210> SEQ ID NO 137
<211> LENGTH: 360

<212> TYPE: DNA
<213> ORGANISM: Ureaplasma urealyticum

<400> SEQUENCE: 137

```
ttactcattt tcaaactctc cattttctag tttttgttta tgttctaatt cttttactag     60
ttcatcttgt tcggtaggtg taagttctgg atataatttt tgtacagcta aattaagtgg    120
cattaaatta gcaccatata aactaatgac tttttccata ttatcgttgt aatctttaat    180
taaattacta ataattttaa attcaacata ttgatcaaac tcttgacgta ttagtttatt    240
aacttgtttt tgttcaattg agcttaaacg cttgttacca taacgttttg ttttaaatca    300
tgcaatcgca atatttttaa aaaaatctat tcaatcattg gtgtatagtt ctactttcat    360
```

<210> SEQ ID NO 138
<211> LENGTH: 747
<212> TYPE: DNA
<213> ORGANISM: Ureaplasma urealyticum

<400> SEQUENCE: 138

```
ttagtctaaa ttaattttaa tttttttaaa taattgagcc tgttgttcat ttttaccttt     60
actaatcatt atttccacaa ctaattcacg ttgtctttca tctaatggtt caaaatagtt    120
aatgtctatt attttaatat taatatcttt aaattttgag tctactttta attgaggaat    180
taaatcctca ccaaaattaa aagctttttc acctaatgtt ttaatttcaa ccaaacttct    240
tttttgatat tctggtttta ttctaagatt aaaaaaacct attttttgtt tttgatcata    300
atcccaagca cttttaataa tatttaaatt ttgttgaagg attgttttat cttctttttg    360
tttaggagtt aaaaatggtt gaaaataaaa atcataatta attgattctt tatatttttg    420
aattttagca ttaatcgtaa ctttaagaat ttgttctgaa tcctttttaa tatcaacaat    480
tttatactgg acattctttg gatttcttga taaatcataa actagtaggt tatttgatcc    540
gtctttattg atttttactt tttttaaaac atcatcaata gtattgttat cattagcaaa    600
ttcttttgct aatgaaactg ttggacgata agttaaaata acatcctggt taattttaaa    660
ttgcgaacaa gcgctaacga taaggggaat tgccaaaatt ggcaatccca aaaaagacat    720
gattattttt tttaatttta ttttcat                                        747
```

<210> SEQ ID NO 139
<211> LENGTH: 561
<212> TYPE: DNA
<213> ORGANISM: Ureaplasma urealyticum

<400> SEQUENCE: 139

```
ctactttcat ttttgcgttt caaaagttgc tttatttaaa ttagttgctg tttcgctatt     60
ttgatagctt aaactatcgc ccatatttca tacataacca caacctttaa agattaaatt    120
taatttttca gtaatggctt gtaagtgaat actttcgtta aaagtagatt gcataatttc    180
aaatgcgttt ttatctggtg tgtttgtgtt taatatcaga tctgaactca tgtactgtat    240
ttcatcaatt cattgattac gataagtttg tgcgtcattg tgattaataa ttgatccaac    300
gattcgtgtt ttgtttaatt cacgttcttt tttaataaag tttaataaag cattagtatc    360
attgattaaa tcattaactg gatatcaatc tggtaatttc tcattaattt tattttcaaa    420
gtcaataaat gaacgattta aaaactcttt tgtgcacaat acgccgtagt tgtgtacgac    480
gtttttgttt ttaaaaatat ctttaaaata cattggtgta gaaacttcaa attcattaaa    540
aataatttta tatacaccag t                                              561
```

<210> SEQ ID NO 140
<211> LENGTH: 1446
<212> TYPE: DNA
<213> ORGANISM: Ureaplasma urealyticum

<400> SEQUENCE: 140
ttaagtgcca tatcttatag ctcctttttc attaattgca ggtgcttgtg cataaaaata 60
taaatgaaac gcacacatta aatactccaa cgcattaatc gtatgcgtat gctcatgact 120
acgctctttt ttagtatctt ctttaatggt ttttggtaaa acaacgtagc aattttttaa 180
gtccttatat agttttggac acgcattttt actaaatcgc aatttaccac ttgcaagcat 240
gtaattaact aaaacaacac ggtctcaaat agcgtgttta atagcaggtg caaaaacaag 300
ttcagaacca tacatattat attgaaacgc aatgcgttta aatgtagcgt taaatgtttc 360
ataaaaataa cgcaaatgag cattatcaat ataaattaca atcttaacgt ttacttcttg 420
ttgtttttta ataaaccaac gcacaactaa ctcaatttgt tgctcgcttg ttagtggatt 480
aacattgttg ttataaacca tttcatctaa aatctcaatt ccattttctt ttgaaattga 540
accaaataag cacgcagtat ctgatgatga actacttgtt ccatctcccc agtccatacc 600
accaaaaaac tgcattgcat aattatcata ttcgccatat ggttcatgca ttacgcttaa 660
acttcgtgca taaatagcac cttcaacact cccacttaat cccaaactaa ttacacgata 720
tttagaataa tcaatatctt ttcatcattc aaactgctca atttcttgtt gtgatgtaaa 780
tttattcgca cgatatgtac ttcttaaaaa taattttta tctacaacgc tatattcata 840
atatggcttt tgttggattg agaattcgtt ttctgctaaa tgattattaa aattttcaat 900
atatcagtgt tcacttgttc aaggattaga tgcaaaaata gatacgacct gcgtatcttt 960
ggtaccccta agtgattgct gtgagttttt aactaaatta aaatctaatt gtgacgcttc 1020
ttcaaaaaac gcaaaaacat aacgtgcttg cgttcacaaa cgaaatccaa ccttagcacc 1080
tttgttaatg ttattacgtg tctcatttaa tgcttcaaac attacagttc aaccattaat 1140
aataacagta cgttctgaat ggttaatctt agcaaatttt aataattgct tttggtctaa 1200
aaaatttaaa tagtcgctaa aaattttttt cgcatcagat atattctgac gaaaaacata 1260
tattgcgttt tgctgtttaa tcgcaacaag tgatgacaaa aaatctaatg tcgcaaaagt 1320
cttaccacta cttcgtccac ctaataaatt aatttcatta aatggtattg gcaacttttt 1380
ggctacaaac tcaactaaat cactatagaa accaaaacat tctataaaat ctagttttat 1440
tctcat 1446

<210> SEQ ID NO 141
<211> LENGTH: 444
<212> TYPE: DNA
<213> ORGANISM: Ureaplasma urealyticum

<400> SEQUENCE: 141
ttatatcaca tttataagtt ttttaatggt taatttgtta ttatcatcaa ctttttcaa 60 cgttattgtt gtatcttcaa tatctgtact tttttgctca tttgctaact caaaatcta 120 acgtttaaaa tattcttgcg ttctaaactt acgcaatcct tggttgttta tttctttat 180 atacgatgcg tttcgtccca gcaactcatt taaagccatt ctaaggccgt aattagcct 240 ggtaatgtat tcataccttt ttttgttaaa ctcgtctctt tgcgtgctta aattaactc 300 cacgccccaa tttatgccta agaattcaag caaagcactc aaattacata aatctaggt 360 tttagtagtc ataaccaaag tgtaaaagtc attgattttt aactgcagtt cttgtaatt 420

```
ttttagttcg tttcttttca tcat                                          444

<210> SEQ ID NO 142
<211> LENGTH: 600
<212> TYPE: DNA
<213> ORGANISM: Ureaplasma urealyticum

<400> SEQUENCE: 142

ctaaattgct agaaaccaaa caacataagc caaggttcaa taatcaatat tatttttca     60

tttatctttt aaatcaattt ctaaaccatt aggatttaat aattgattct ttgttaacg    120

tttatggaca acttgtgtta ttccgtcttt tttattaatt tcaatatcaa atgttaata    180

aggttgatta tcttgaaaag aatttaatat actaaaattt tgtaatttaa tgttaattt    240

tttattagct ttatcaatta ttgtatttaa ttctgcttgt tgaatatatt ggtttaata    300

ttcttgttgg tcttcttgtt taaaatcaaa tttaatttca ttattattta aagtaaatt    360

tgatatttta tagttaatat tagatgctaa gccatttaat ttacctgtaa gtattttt    420

atttgcatca aatactaatt cagtagcact aatagcagaa gcgtcatcat tagcactat    480

tttaacttct aaaacaaaat ctttttttatt agcatctgct aatttaaatt tactaaatg    540

aacttcaata gtagcagtgc cgttttgaat tttattaatt gttattttat ttgcaatca    600

<210> SEQ ID NO 143
<211> LENGTH: 222
<212> TYPE: DNA
<213> ORGANISM: Ureaplasma urealyticum

<400> SEQUENCE: 143

atgttaatta aacccgcgaa acgcagtgaa aaaatttata caattattgc tataaaaga     60

agtgttgtaa ctttaaaaaa tgattatcaa gacgaaaaaa atattcaaat ttacgagtt    120

gatttgcaga atattattcc agaagttggt aaatttatta atctaattaa atacgatca    180

caaggttgtt cagtatttga agaatatgat aaaaacattt aa                      222

<210> SEQ ID NO 144
<211> LENGTH: 876
<212> TYPE: DNA
<213> ORGANISM: Ureaplasma urealyticum

<400> SEQUENCE: 144

atggataaaa aagctaaaat ttatacttga tcacacatta ttttaattgt ttttagctt     60

gtttgtttgc attggttttt cattttatca atcacaattc ctaaccaaac tggtttttt    120

attaatcgag ttggtcaatg aataaattca tctagtacat atgcttataa aattgatcc    180

cgatcattat tttatttaaa ttatacttta aactttaata ttgctttaaa tgcaagtgg    240

atagctagta ttgttttatt tatttgttat attttaacat ttattttttaa tctaataat    300

attggaatta ttagatcttg aaggccaagt ttattacatt taataattgc tatattaat    360

tgacttgcta ttttatattt atttatcatt attatgatca aaccaaactt taatcagat    420

attaataata gttattatac atgattaaaa aatgttattt ttaatgatca aactttaac    480

cttaataaaa aaaatgtgat tttaaatact tatattaatc actatcattt accaataat    540

aatgatccac aagttgcttt attagatatt agcaaacacc aaattaataa tgaaaattt    600

acatttaatc cttcatacaa ctataatgcc aatctttatt ttacaaaagc aaaattaat    660

tattgtactt atacaattat tggaataatt tttatcatta gttttattta ttatctaag    720
```

-continued

```
gaaattatta aacgatgttt attagttaat gacaattgaa aaattaaaca acacgaacg     780

aaagatggtt taaatataaa aaaaagaaaa aataaacaag aaattgttgc tcctgaccc     840

attttagaag aaatttttaa agaattagat ttataa                              876
```

<210> SEQ ID NO 145
<211> LENGTH: 138
<212> TYPE: DNA
<213> ORGANISM: Ureaplasma urealyticum

<400> SEQUENCE: 145

```
ctaacgtcaa taacatcttt taattctttt tcatatttgt tgttctctaa taattaact      60

aataggcaca aaatatacat tatcatcttt aatatctaag acgttagcac ctgtatcga     120

taaaattgct gttttcat                                                  138
```

<210> SEQ ID NO 146
<211> LENGTH: 225
<212> TYPE: DNA
<213> ORGANISM: Ureaplasma urealyticum

<400> SEQUENCE: 146

```
atgacttata tgctattaac atctagtgac ttacattgcg ggtcatgttc ttcaaattt      60

tataatgtac ttgaaaagat tggcgcacaa aatattagtg taaatatttt aaattcaga     120

tttgcttttg aatttgaaga aaataaaatt gctgatcaag atgtaattaa agaaatcaa     180

aaaaatggtt tcaaaacaaa tattttagaa aaatacatat actaa                    225
```

<210> SEQ ID NO 147
<211> LENGTH: 267
<212> TYPE: DNA
<213> ORGANISM: Ureaplasma urealyticum

<400> SEQUENCE: 147

```
ttaacagttt ataatgatgt taataaccac attatcatca tttaattgtt ttgacaatt      60

ataatatact aaattacgcg cttcatttgc tacacttaaa acattaacaa catcttcat     120

taaatcaatt ttaattacaa aataattacg attaaaatct gataatttgt catttatgt     180

aacactaaaa atcccaggaa cttttaaaat agaggatgta attaaacttt taacaagtt     240

agtatcaaat ttagtttttt ttaacat                                        267
```

<210> SEQ ID NO 148
<211> LENGTH: 639
<212> TYPE: DNA
<213> ORGANISM: Ureaplasma urealyticum

<400> SEQUENCE: 148

```
ttaatacttt ttcaaatttt ttaaatggtt tttaactttt gttgttttta ataaattt      60

taaattttca aatttattaa aggccaaatc aataatatct tcataattat cttttgttg     120

agaatttaaa taaaattttt tcaatacatt tttatcagca aaaagtaata aactatgat     180

tttttgcttt ttatttcttg aaatttcaaa tagtaaaatt tgtggattgg aattattaa     240

caattttttt attgtattat atattaattt atttcacaat tcgtctttaa aatcgtttt     300

tgttaacgta aaattaaact ggttacttaa atatctgctt aaattatttt ttttagtaa     360

atagatttga aataaattaa tataaatatc cttataaata aaattttctt ttaataagt     420

atttttattg atcaaaattt catctcagtt ttttcaacga cgcatttttg aaggtaaat     480

agcattttga ccagataaat aatatatata attatcattt tcaaataaaa taataggaa     540
```

-continued

```
acctccaatc atgttttcaa aaggatcact aacaatataa tttaaatcac tatttctta     600

taaaatctct ttatacatac tttttcagtt gatattcat                           639


<210> SEQ ID NO 149
<211> LENGTH: 2244
<212> TYPE: DNA
<213> ORGANISM: Ureaplasma urealyticum

<400> SEQUENCE: 149

atgaatctaa aaacaaaatt ttttttaaaa gttataagtg ttattgctcc aattgttat      60

attccaacta ttttagctaa ttgtgcacat ataaattcta atgaacttga taatgctaa     120

acaaacttga aaggaagtgt tgaagttgtt aatattaatc cttataaaac aaaacaaat     180

ttagcatcaa atatcaacaa agaacaaatt aattcttatt ttattttat ttttaattt      240

attaaaacaa atcaaaaaat tgaagaaaaa attttagata aaaatgatta tgaaattct     300

aattgagctg ctaatgataa tgatggaacg ttaggtatta acatttacat taaaaccac     360

aaacaaagtt atttaattaa tactaagcct gtttttttaa cagataaaca aaacaatta     420

ctacaagaat taaaatataa aacacctgct gtttatagta ttgatgaaat cttaaaatt     480

tcaaacaacc cttataattt aattcacaat aatccatact atagagaaca attattgcg     540

gcaaaaattt attttaatca aaatgaagct aatgttgatg attctaaact ttatatgaa     600

aaaatcggtt attctgaatt tggtagtgat gtccaaaaaa gattagaaaa cgcctttaa     660

attcgttatg atgagcaaaa tatttatcaa attaattctc cgcaaatttt agctaaaga     720

acaaaaacgc ttacatctta tattgataaa aaaacaaaca acaattatag tattaatat     780

gaattaatca aaaaattaat ccaaattaat cctttttggta aactccccaa aaatttcgc    840

caactaatta atttaattaa aaaagaagaa tatcctaaat tcttgacaat tactaaaaa     900

gaatctgttg acaatattgt tgttaaagat atttattatc ggattattga tcgttatgc     960

aaattagaat ttattttaga aatttataac aaaaaaacaa aacaaaccgt atatttaagt   1020

gctaatttta atcaaaagaa ttcaggatta ttaaaaaatg aagattattt tcaatatatt   1080

tttgatcgta ccatctcact tgatttacta acaacaaaag atggaaaaaa tgttgaatta   1140

aattctggaa ctggttgaat tgttgatcgt attattgacg atagcttacc taaaaataaa   1200

attaaattac ttattgcaac taataatcat gttatgggct gatcgaattt agcaatctca   1260

aaagataaca gaatgaaatc acgctggttt aataaacaag aatatataaa ttatttagaa   1320

aataacgctg gtttcatatc ctcaaacatt tatgaagata aagaccgtta tcaatattta   1380

ctatggggga ctgcgcctct aaaatctcca gtaagtaata aatataattc attaagtggt   1440

attagttttt caaatttagc aaaggtttat aatattacaa atcaaaattt cattaatcga   1500

gcatgatata taccacaatt aagtgctaat ggtataaaaa tcaatgaaaa tttaagaaca   1560

tgatatcaaa ttaatcaaga agatattaaa tcaattaaaa atggaacttt agactttgtt   1620

ttggtcccaa tggtttttga tattgaagat attaaagaaa aattaccaaa ttattataaa   1680

gtattaaata caaaagatga agcaaattga tatattggat taggcaattc aaaaaaatac   1740

ttgccacaat tacaactatt tagtggagga tatcctggtg atgttaatcc taatagttca   1800

gcgattgttt catggcgcgg ttctaaatct tatggttcac taattcaagc atttgatcgt   1860

gaaattaaaa atgaatcaat tttagattat tatggtccaa agcaaattaa taatattgat   1920

ggttatcaaa aggttggcga aggttattta aataaattat ttaatgttgg aacacgagtt   1980
```

-continued attacctctg atgaaatagg tgatttgggt tctggttcat ctggttcaat gattattgat 2040
tctaacttta atttagtagg tattcatttt gcttctttaa attcgcgtgc ttatggtgcg 2100
ccaaatgatt caatgattgg taatttattt gttgctcaat cccaagactt aagtggtgat 2160
attgatgtaa gagctgcggt gataaaaaaa ctaaaagctg aaaatattta cacttataaa 2220
ctaaacccta aagttagttc ttaa 2244

<210> SEQ ID NO 150
<211> LENGTH: 1287
<212> TYPE: DNA
<213> ORGANISM: Ureaplasma urealyticum

<400> SEQUENCE: 150
atgccacgaa taaatacgca agtttttaat gaaaataatg ataaaaatag aattaaaagt 60
aataacaata aaatttgtga tgatattgaa tacactcgct tattagaaac gaaagaatat 120
aatgctggtt tttctcctaa taatgattca caagatatct taattaaaaa acaagacaat 180
attttaaagt taaaaccaac tctaaatttt gatgatagtg atcaattaat ttcaattgtt 240
cctactaaaa attatgaaaa tttaagatta aaagaaattg aaatcgataa aaaaaacact 300
gttgattatc aattaaaaaa agaaataata gatcaggact taacagatga taatcattta 360
tctataagtc aaaaatccaa tggttttgct ttaaaaacta aacaatttat tcctcaaaat 420
atttcagaat ttatttatca taatgaagac gatccaaaaa catacggaag tgaaaataat 480
ttaactttta gtcaactaga agaaaaagtt aatcaaaaaa atacacctga tttttattta 540
aaagaaattc atgcagttcg taacaaaatt atcatttgaa ctattttatt agcaattggc 600
gtaggattaa tattttattt gatttatgaa gttattatta atcattttaa tccatggatt 660
tttttaccaa ttagtattta ttgtgtcttg atgattttct ttttagcttt atcatgtagt 720
aattttataa attttaaaaa agaaatggat tatcaaaaaa accattttga ttgtacaaaa 780
gcaacaaatt ttattgtagg tatatatcgt aaattaatag tagtacatat taatgtaaac 840
tgaatcacag cttatattta tcttactagt ctttttatga tatttggtgt ttttgttgtc 900
agttatttta tgaatttata ttataatgca gctataggaa gtcgttttgg tgatttgatt 960
ataaaaattc ctgttgttat taataatcat ctttcacaaa aaattagttt taacaaaaat 1020
ccattatggg caatgattgg attaggtgct attttaggat taacatttat tattcattta 1080
tggttggttt ttaatgctca tcatcgtatt aatcgtattc atagttatta tgttaatgaa 1140
atcattacta gtgaagaaat aatttcatta aaaaaacaag caaatcgtcg tggtctagtc 1200
atatttttag tgttaactgt tattttaggt ttaatttttt atttgatgta tactatttta 1260
aaaagaaaat acactatcaa aaaataa 1287

<210> SEQ ID NO 151
<211> LENGTH: 1149
<212> TYPE: DNA
<213> ORGANISM: Ureaplasma urealyticum

<400> SEQUENCE: 151
atgaagaaga atcataaaaa atgattatta atgacaacgc caattttatt aattggcgga 60
ttatcaacat tggcattaac aagttgtaaa gacggaaaaa aatctaatcc aaaaccagat 120
aaaccatcaa ctatagaaga atataaatta agtttatcaa gtgttgaaac tggttttaat 180
gaagctaaat taatttttga taataatgat agttttaaaa cattagataa ttttaaagtt 240
attttaaaaa atactcaaaa cactaatgaa gttattgaag caagtaattt atctgcaaca 300

-continued

```
attgaaaatc aaaaattagt tttaaaacta aataatttac aagacggtca aacatataaa    360

attaacaaaa ttttatatca aacaaataaa gaagttattt taagtaataa tcaagtattt    420

actacaaaaa ctaaacctaa aattgaatat gaagtacaag aaaaaatttt gaaacttgat    480

gataaaacat attatgttgt tctaaaagtt aaagaccctc aaaatttaaa tgaaccaaca    540

aaagaaattt taaaatctgt aacttttact tcaaaaatct caaatgttgc aaatcttaaa    600

aatgcaatat tagaaaatca aagaccttac gttaaagaag attattcaga aattcaaatt    660

aaattaccaa gagtacctgt aattagtgaa aaaatagaaa tcactgcaaa caattcctta    720

tttaaatcat tcacaattac tgttggtgaa aaacatatta aaaatgtgga aaaaatcatc    780

gatatcacta aaaaagtttt tggtaatcaa gaattaaaat ctattagtat tacaaaacaa    840

aatagtagca gtgccaatat aacattaagt ttaaaattaa atggtaattc aattattgtt    900

ggtgctaaca aattaattaa taaaaaagac aaagcaataa aatttagctt ctttgttaaa    960

aataaagcaa caaatacagt taaagaattt aatttcaatg aaaaatcaaa acctattgga   1020

agctatcaat tcacattaaa tggattagat gctaatagtg attttgtaat tgaagatatt   1080

agatatgatg ataaatcaat caaaattaca gaagagcttt tagctagctt aagtttttca   1140

acaaaataa                                                           1149
```

<210> SEQ ID NO 152
<211> LENGTH: 318
<212> TYPE: DNA
<213> ORGANISM: Ureaplasma urealyticum

<400> SEQUENCE: 152

```
atgaaaaaat gacaaaaaat tttaacaatt gcactaccaa ctagtttatt agttgctatt     60

ccaattgttg ttgcttcatg ttctactaag agtgaagcac aaaaagaatt tgaaaaaact    120

tataaagaat atttaagttg attagacaaa ttagcttcaa aaatgccagc acttaaagaa    180

gcttttagta ctttgaaaga agaaattaat aaacaaatca ataagagtga aaaattatct    240

gatgaagcgt ataaagcatt aacagcttca ttaaaagttt caattgatgg aatgaaaaaa    300

acattaggac aaaattaa                                                  318
```

<210> SEQ ID NO 153
<211> LENGTH: 1866
<212> TYPE: DNA
<213> ORGANISM: Ureaplasma urealyticum

<400> SEQUENCE: 153

```
atgaataaac aaaaaagaaa aatctcagta ttaacttcaa tatcattatt tttaattatt     60

agtttaagta ttgggttagg tttgggatta ataaaaaata atgaaaattc catcacttct    120

aaagttcaaa aaagtagcaa tttttttatt aatgatttat caaaacaatt gtttttagat    180

gtttttaatc aagataaatt agaattaaat gcttatatgt atgatcaaaa taatgtatca    240

gatcaacaat tattagattt aaaatttgct ttaacattat taaatcctaa cagattagat    300

attaatgatg acgatacaat tgccattatg aaaaataatg ctaaaaaaat tatttttcaa    360

agtttatcta ataattgata ctgattattt accaatttaa agagtttaga attttcttac    420

actccttata aacctaattt ttatgccccc tatataaatg aaaaacaaga ttttactaaa    480

tcatcaattt ttgacaaagt tattaatatt aataaaccct taacaaatta cataaaaatt    540

aagcaaaaat tattcgataa agaaaattat cgtagtgttg atgtttatta tttgcaattt    600
```

-continued

```
ggtgatcact taatcttacg tttattaaaa tttaataaaa aaaatcattt tgatgttcga     660

tttgatacag atctttttca attcaataaa ccaattataa atttggaatt aatagcaaaa     720

gaaatgcaaa caagtattga ttatcatcga gaagataatt ttaaaaaaga tattttagat     780

tataaaaaaa attatgaaga ttatttatat tatgatgaaa agcttaactc aagtatttat     840

caacagggat tagataaaat aaataaagaa tattatgaag tcaataattt taattttttt     900

aatactaaaa aaccactttt tcaaaaattt agttatcaaa tgtttttaga attaaaagat     960

aagttgggtt ttaaacgtta tgttttaaga aatattgatc aaaaagaagt tagagcacgt    1020

gatcatttta atgacaatga aaaaaaacaa caaaataaga attattttag atcttttgat    1080

aaagaattga attattttca aaaatatatt gatcataatt tagatattaa tattaataaa    1140

atttcaaagg aagcatatat tacacaaaaa ataattaaaa atcttttatt agatgctttc    1200

aataataatg atgttcaaat tacaaaatat ctaattcaac aaaatgataa ggaataccaa    1260

aataaattaa ttaaacaatt aatagaattt agtaattatt ttaaaaacca aaaaacacca    1320

agagattcta atgaatataa gcaaaaatta aatgattatg aaaaaatatt ttcacaaaat    1380

tggtatttta ttttaatgaa tttaaagcac tttgaattaa gttttaataa ttgatttact    1440

ttaccaaaac aaataaatcc tattactaaa gagatgttag gaccaagtga aaaatattta    1500

aaaaggttaa aaaaacttaa accatatgag gattattatt tcattaataa ttatttagaa    1560

aaaaaacaag aaggagatac ttcaatgttg attggttcat ttaaggattt atatattaca    1620

aaaaatcaat ctatttttaa tattaagatc gatttttcaa gtagtgaaaa cagattaagt    1680

ttaaatcctt tgatttattt ttttcctaaa actaaaaata aattatcagt tgatttaatc    1740

acatcaattt ttcatcaagc tatatttcac caaaataaag aatactatca attgtttgaa    1800

actgatatga ttgataaata tgaatatggt atcccagccc aaatgttact tttatgaagg    1860

gaatag                                                               1866
```

<210> SEQ ID NO 154
<211> LENGTH: 1296
<212> TYPE: DNA
<213> ORGANISM: Ureaplasma urealyticum

<400> SEQUENCE: 154

```
atgtttattt tttttaaaaa aaatcatcta ctaaaattaa gtttattttt tattcctcta      60

acattaattt caatccttat cacctcatgt agcacatcaa atttaaaaaa acaacagata     120

ttaacaaata atgaaattag tttttttatg gataaatccc aaaattgtta tgttggttta     180

attgttgatc agacattaaa aaatgataaa aaaactattt ttaacgttag tttaattgat     240

gaaaaaaata cgaagttaaa tttattagtt aaagattatc aaattaaaga taacaaaatt     300

ttaattagat taccgcgttt aataaaactt aatgatcatt taattattac aagcaataat     360

gcttcattca tacctattag aaaaaataatt aatattgata atttaattga tttgaatata     420

atcagaacaa ataatcaaac acaagattct tgaatagctt ttttaaataa caaagtgatt     480

aataatcttt taataactat ttttcctaat aaaaaagacc gtgatgaata tattaaatca     540

caacaagaaa ttaaaataga atatgctcat gaaatagcga attgattaaa ttattataac     600

acagtgcaaa atgatgctaa taaagcagca gtatttaatg aaaatacagc tagaagtaaa     660

cttaataaca atctttttaa taatgtatca ttaagcaatc catttgctta tgaacaagca     720

cgtaagtttc acaatacatt atttaataaa aattgattgt gatttttatt taatttaaaa     780

agacaaattt tcatgttata tcctgatgat aatttatttc aagaatcgag cgaggaaaca     840
```

```
gcagaaggat taaaagattc aaaaatcaat aatcgtagtt ctttttatcg tgctcaatcg    900
aatgaattta ttgatgggtt atatgttgta gaaagttcta atttaaataa aaaaccagaa    960
gaattagatg aatatactga ttttagtaaa acagctaaat ttactctgtt gaataatgaa   1020
ggttttgttt ttacaatctc cattgaagaa aattatgata aaaccaaaaa actaatttcg   1080
cgtaaagtta gtttgttgcc atgaattaaa actttaccaa gattaatgtt taatgatcat   1140
gtaataaaac aagaatttaa tttagctaat tatactgaaa attcatacga ttacaatgct   1200
gttaattttc attcacctct tgaaattaaa gtttatgaag atcaatttgg cggaaaagca   1260
attcgttttt catttgttga tattgatcct aattaa                             1296
```

<210> SEQ ID NO 155
<211> LENGTH: 408
<212> TYPE: DNA
<213> ORGANISM: Ureaplasma urealyticum

<400> SEQUENCE: 155

```
atgaacaatt acatacagca agttattgat tatgttaatg ataaaaccta taaaaaataag    60
acatatttta taaagaaata tgcatttgct tttttgactt cattaataat ttttattttt    120
ttattagtat ttggtttatc aaattatttt aatcctttgg ttagtttagt tggtgttgta    180
ttaattttta gtgttttagt tgtcttttgt attcatataa aaattatcaa taattatagt    240
ttaaatttat taaaatgact acgtaatcaa aaagaattat cttataagta tattattaat    300
attcttgatt ttattttaaa taaacaatta tatttaaact taacaattat agaagtccaa    360
caaatttgca tagatttgga agaatttaaa aaaacaaatg tcatttaa                 408
```

<210> SEQ ID NO 156
<211> LENGTH: 1785
<212> TYPE: DNA
<213> ORGANISM: Ureaplasma urealyticum

<400> SEQUENCE: 156

```
ttactctaaa ggattagtta acgcgtattt tttacatatt tcaccaattg ttctctctat    60
tctaaaaaac aatcttgctg tatcatattc atttttttaaa tgattaggaa cttgttttgt   120
taatataaac atttcatcac tatttttaat tttttcacct ttatcatctg ttttatagtc    180
agaataataa taaaaattat ctcttttttg attaaaaggt tcatagatat tagtgtaatg    240
atatttaaaa ttataaagtt cttctaattt tgaaacatcg tttgctgaat cactttttga    300
tttaatttga tcaataatag gtttaattat cttttcttta taatattgaa aaacatctgg    360
taattgattt aaatagtaat tagatcaata cattaattca ccaaattctt cttggggata    420
aaaaccataa ccaacggctt taatatatgg aacaatttgc tcaacatcat ctttgacaac    480
gctatcataa aatctagaaa gtttttgatt agcattacgt gctttttttct caatttcgtt   540
tgttaaatct tttaattttt taattaagag gtagtattta cctttttttg aaagagaatt    600
aggatctatt gatggttgtc aattatctaa cattgaagtt ttggacttaa tagtaaaaaa    660
tagacccgaa aaattggctg cgtctaaact atctctaata agtgcttgac catataattt    720
tcatttttct attaattgtt ttaattctag agatttagtg tttataaatt tttgttttgc    780
taaatcttca atttttaatg ctaatccata tcaaatagca acattagtat tatccattaa    840
agtttgatat ataaactttt tacctaaaat atcttctttt catgtatctc aaaaatcttg    900
attatttttg tggccatttt gtttaatata ttgtgaaact tttttatgtt cttggatttc    960
```

-continued

```
tcttttaata ttatcgattt tattttcaat taattttctg tttaatatac tctgtagtac   1020

tgaagaaata ttttcatgaa gttgattagc ttcatgaaat aattccataa tttctctatt   1080

gtataactta taatattctt caccattatc aatttttttca aaataattat gttttaaatt   1140

tttaacatca gatttaatat ttttgatttt attagcttca tcattaattg ttttttttata   1200

aagaccatcg tatgattcaa tcattttttt atatcttaat ttgatatcat caatattttc   1260

attatcagga atttgattat aattagttaa aatttcttca atattatttt tgatatgatc   1320

gatatcatga ataattttgt ttttattttt aaaatttaaa aaatcggctt gtcttttttt   1380

tattaattta acaaagttat caattttaat taatcatgat tcatattctt gtgtttttttc   1440

ttttaaaaga taattaaaat cttttattaa tttatataat tcataataag taaatgctaa   1500

taattcattc tcactatttt catttaaatt taaattcacc aagtaattaa tataattatt   1560

gattatatct gctttattaa gaagataatt gtatttatga ttatttttaa gaacaaaatc   1620

aactttagaa ctagcttctt ctttaatttt caaataaaga ttaaagaaat ttttattgtc   1680

ttctttttta atttttgtta atgagcaact caaaattata ggaattggtg taactataac   1740

tcctataaat gataataaaa aagttctttt aaaatttatt ttcat                  1785
```

<210> SEQ ID NO 157
<211> LENGTH: 672
<212> TYPE: DNA
<213> ORGANISM: Ureaplasma urealyticum

<400> SEQUENCE: 157

```
atgatcaata aaaacaaaaa atttcatttt cagtatttta aaaaagataa cgatcaatca     60

atttctacta aagaaacatt aaaaagatat tttaatttta ggtctcaaag tgtaaaattg    120

attattttta atttagtttt aacagcattt tttcttgcat tatttttaat tggtcgtttt    180

ttaactaaaa atttagattt tttaaatggt tttagttgac aattgcaaat gggaattttt    240

gttttagcaa tcgtttgtat tcccaatttt tattataaat taatgtatta tattattgcg    300

ccgttagtga tgttagcaat tggttttagt gctgagccct tctttggata tttaatgcca    360

cattatggtt ttggtttaat tttatttacg gatgtcattt taattattgt taaaaagtca    420

tgtcagtcaa ttaaaaagca aatattttta tcctatttat taatttttag cttttcaatc    480

attggttatt ttattgtttg aatgggctat agtattcaag gaacactttt ttacaatact    540

gcttttattc cttctatgat ttataattct ttggtaactt ttggttcaat ggcaattaat    600

tttgtattat atataatttc aattcccgct attgttgcct taaaaaacaa atatttatgt    660

aaattagttt aa                                                        672
```

<210> SEQ ID NO 158
<211> LENGTH: 1374
<212> TYPE: DNA
<213> ORGANISM: Ureaplasma urealyticum

<400> SEQUENCE: 158

```
atgtttatgt ttgatcaaat ctttaaaaaa aggaaacgtc atttaaactt tcaaattttt     60

attttctttt ttgttttaat attaattact tttttgattt tatgaattat ttcaggtaat    120

gttcaaacaa ttattgattt tattaaaaaa aagatttatg atgctagtcc acaattaaaa    180

tatttaacaa atattcagat caaacctttt aaaaatttag aagaaatttt tgattttatt    240

attaaaaata agaatttgat taaagattta caaaacgaac ctgaaatttt agatgttatt    300

aaaaacaatc cacagatctt aaaaacactt aatgataacc gcgaattttt aaaacaaatt    360
```

```
gttgaatata agccatttgc tgaaattctt agcaagcaac ctgaaatttt aaaatttgtt    420

caaaataata aagaattaat taaacagata caaaatttac ctgaattatt agatttaatt    480

aaaaaacacc aaaatttaat tgatcactta aaaactaacg aaaaatatat agaagttatt    540

aaagctaatc ctcaaatgtt aaaagatctc tatcatgtag atgataattt atttaatatt    600

ataaagacaa gcttagaaaa tgataaagaa aataatattt taatgttggc tattaaatat    660

tcagtattaa ttaataattt tactaagaat ttaactttac aagaatgaaa gcaaataata    720

gaattttata aaacagttga tttaaataaa tttatagttg atgataattt gtttaatatt    780

attaaaaata ataatcaatt atttgaagtt tttttaaata attatgacta cataaaaaat    840

cttgaggaca atcaaaaaat tattgatatt attcaacaaa atcctgattt aattgatgat    900

tttaaaaaga ttgattttga tcttttaaca caaaaaagga attttgttcg tgcactaatt    960

aaaataattg attataaaca acccaaagaa attcaattcc ttaacaaaaa agttttttta   1020

gatttcttta aaaataaatc tgaaattacc aatgctttaa acatcacatc tttaattgga   1080

tttgtattgt ttatagtaat ttatacaatt tttatttttg catcttttat ttctcatatt   1140

ctaatgttaa aacaaattaa agattttaat aaaattttta aagaagctaa attaaaaaaa   1200

atatatctta taagcacttt attattacaa tttttatttt taattttatt cattattaat   1260

tttatagtat taattattct agttgtagat tataataaat tgaaagcaat agttttaaat   1320

agtggtataa aaagaaaagt ggaggatagt gatgcaagat tgcatttttt gtaa         1374
```

```
<210> SEQ ID NO 159
<211> LENGTH: 756
<212> TYPE: DNA
<213> ORGANISM: Ureaplasma urealyticum

<400> SEQUENCE: 159

atggaacaaa ttagaaattt aattgattta caaatcaaac taaaaccaat ccaaaaagca     60

ttttatgatg cgtgatcaaa aacatttatt aatggaattg ataataataa agaaactcat    120

gaacaaaaca aaaaaattat tttagaaatt tatatgattt taaaagtttt tttaaacaaa    180

aaccgagata ttatttctaa aattccatta aatcaagtta aaaaaatagc taatgacatt    240

ttagaaaaag aaattatttt agaacagcct ttagttgatt attattacca aagttcatct    300

tgttttattt taatacctta tttgattcaa attctttatc aatcttatca ccttaataaa    360

ccaatttata aaataatgtg taaatttatt attagaaata atttagcatt atttaaagaa    420

tgagatttaa ttgaacgtca aacattggaa attattaaat taaaaacaaa tttaattgaa    480

gataacaata aggcaatcaa tttatttagt tgtgaacaac gagaattaca acacaatcgt    540

tttgtaaaat tatttaataa ttttatttta gtgtattgaa ctaaacgaga agttaaatac    600

atagaggcaa ttcgtttttt gatgtatttt atttgaattc ctatcatttt tattgtttta    660

ttaattttga ttttaggttt atattttggt ttaagtaata gtgaatcctt aaaaagttca    720

acacaattct tactagattt gtttattatt aattaa                              756
```

```
<210> SEQ ID NO 160
<211> LENGTH: 765
<212> TYPE: DNA
<213> ORGANISM: Ureaplasma urealyticum

<400> SEQUENCE: 160

atggccattg ttgctaaaat aaacggaaat gcatcagaat gatatcacgc accaatcgct     60
```

-continued

```
ttagctttct tcttacggtt ttcattaatt aataaaattt ttgcaattat actatcttgt    120

atttttttgcg taagcattta tcgttttcgt aaaaaattag tacaatatga aaattttaat    180

gaaataaaat caattaaaaa taatgcgatt cttactgtaa tttttagtgt tgttgcaata    240

ctttcattaa cactatttat taatttaatg attgttttta ttaatcaaaa ttactattac    300

attaaacgta ttcataattt acttatacca ataagaattg atgaaattaa aattttagaa    360

tatagttaca tttatttatt acgttgtgga ttttatattt tattaacagt atttatagca    420

aaatttattc atgataaaag aagtatgata aaggttttat cattatattt attcgttaat    480

tttatattaa tgattattgg aacttcattt actttttttag aacatacaaa cttttataat    540

ggtatgttaa cttattgaac aacttttagt tgtggattat tatatccaga aattattaat    600

gataattttc agtgaataag tagttttaat tacaatctaa aaaatactat ttatgaaaat    660

aactttattg cttatttacc ttatttttgc tcatttatcg ttttaataat cttaattaaa    720

aaagttagtt gaaaatcaat tactattagt tcaaatagtt attaa                    765
```

<210> SEQ ID NO 161
<211> LENGTH: 546
<212> TYPE: DNA
<213> ORGANISM: Ureaplasma urealyticum

<400> SEQUENCE: 161

```
atgggattaa aaaaagaaaa aaaagatcgt tcaacgattc aattattatt tggaacaatt     60

aaaaaacgca aaattgcgaa ctatttaatt attgcttttg ccttttttaac atttgcctta    120

gcaattatag gaagttttga agctattgca tcaaaatatg ctattggcat tggatcaggg    180

ctttcattat ttattacgat tgcttttagt gtttgacgaa ttttaatgat tcatttagaa    240

aaagaatgaa ataaaagtga aattatttga caatccgtta tgggcgcaat tttagtatta    300

tcaattattt tttgaatatg agcaacaact acaacaacta tacaatattc atcactaaaa    360

gaacatcttt tattgttaaa acaacaagat tcacgcgcta attttgttgt tttaacacaa    420

gcaacagtgg atgaatttgg agttgcttta aaaggcgggt tatgagcttg agttattaca    480

agttgtattt atatttttat caatactttt aataatatgt ttatgaaaga aaaaaattca    540

aaataa                                                               546
```

<210> SEQ ID NO 162
<211> LENGTH: 606
<212> TYPE: DNA
<213> ORGANISM: Ureaplasma urealyticum

<400> SEQUENCE: 162

```
atgattaata aaaagataaa gattaaccca aatataacat attttaaaca aaaaatttct     60

aattatcatg agcatttgtt agtttgaaat gatttatatg ataaattaat ttcattgact    120

aataatatta ttgttgataa aaataacaaa aatatttatc atcaaaacga caaacaaatt    180

tttgatttta ctttatgttt atctggtctt ttgtctaaaa ctttaggttt aaatcataaa    240

tcatcttcgc tttatttaac aaatgatgat gaagtagcgc atcgttttaa gattaaagtt    300

ttgcataatt attttaattt atataatatt gaagaatttt ttacgtttat ggataatcaa    360

attcctttag aaaatgcaaa aaatattgca cgtttaagtt taatttatga tttaaaacaa    420

catgaaaata ttttaaaaac tatatcgaat gaaggtttag aaaatattga tttagaattt    480

gctttcatta attttttaag agcaaaaatc tctattaatt ttgcctatag ttatgatatt    540

tctgaagtaa ttttattgtt gcgaacaggg ctagatttac atttttttag aaaatgagca    600
```

-continued

```
ttttag                                                              606


<210> SEQ ID NO 163
<211> LENGTH: 156
<212> TYPE: DNA
<213> ORGANISM: Ureaplasma urealyticum

<400> SEQUENCE: 163

atgaccgttg catatcataa tttagatatt aatgacccta aaaatgttct tttagcaacg     60

caaaaattct ttaatcatat taatgaaata attattgatt atggtttaga taaacgtgat    120

caatgaatta aaaaaattat tccttttgaa gaataa                              156


<210> SEQ ID NO 164
<211> LENGTH: 591
<212> TYPE: DNA
<213> ORGANISM: Ureaplasma urealyticum

<400> SEQUENCE: 164

ttaatcatta atattattac aagattgata tttctctaat tttttaataa cattatcttt     60

taaaacgtta gttaaaaata ccgccatatc atgaattgat tctttagcac cattttttaa    120

ccattgcatt ctaatattac aaaaaaatcc tgttaaataa ttaattaaat atttatcaat    180

tgaattattt gacatattac ctatagcata aaaaccactt tcagtggtta aatcaacaat    240

taatccacta aaattatttt tatctaagat tagaaaatat tctttgaatt ctaaactaat    300

ttgtaatgaa atttcataaa atttagtaaa accaacttca tcaaaattga tatttaggtt    360

attatttatt aatttactta caactttcca attataaata tttttaataa aataattaat    420

aatcgaaatt ttatcactaa aattacgata atatgaaggt cgcgaaacat ctgcaacctc    480

aataatttgt gaaattttaa ttttgttaaa tgaattggtt ttcaacaaat taaataaagc    540

tgaaacaatt tttaatttaa cttttgaaat tttaattttt tctactgcca t             591


<210> SEQ ID NO 165
<211> LENGTH: 4344
<212> TYPE: DNA
<213> ORGANISM: Ureaplasma urealyticum

<400> SEQUENCE: 165

atgtataatg atcttttaga tagtttattt acaaaattaa gcgataaatc tattttaaat     60

aagttattaa atgatgattt tttatcaatt ggaagtattt taaaagaaat ttttaatata    120

aatcaaccat cacaactaat aaaagttatt gatattttta gtatcaaaga cattactgcc    180

caagattatg taaatgtttt gaatgttatc tttaatgata ttggttttaa taatcaacaa    240

acaaaacaaa atattaccaa tgatcaaaaa tacgatatta atatttactt tgaatattta    300

aaagctttag ttgaacataa ttttagtgag ttaactaaaa caaaattaaa agaaatcgtc    360

aaattattcg ttaaagatgt aatgaatgat gaccatcata accatttatg aaaaaaaatg    420

acatcgttta ttagtcataa attaagtgat ttattaatta aaaaaattca agtattaact    480

ccacagaaaa atgaatatca acaattagtt aacaatttat taaatggtat tgattttaaa    540

aatgttgtcc aaaatttaat tgttgaaggc tttgcaaaaa taattgatca tcaacaacaa    600

ttaaagaact cacaaaattt tggagattta attcaaaaag ttatcaatat agatgatgta    660

tgaattaaaa aacaattaaa acaactccta agtgcaatta caaaagacat aaatttaaca    720

aaagctacat caactactat tattaattcg tatttaaatt attttgaaat taaaaatcta    780
```

-continued

```
acagaagaag ataaaagaaa tttaattaat atctttgaca aaattttaaa gcaaattcct    840
aatttattat atttacaaaa tattgttgat caatcagtag attttttaaa agtaaatatt    900
gaagcattaa ttaatcatca accacttaaa aacacaacat gaaacgattt tattaacaaa    960
aatgttacag atattagtgc tttaagtaac ttattagaaa tttttgaaac taatgaaatt   1020
acaaataatg aatgaaacca attaattacg attttaatta atcatgcacc tattgataaa   1080
attgaagaaa tcattagaaa cataacatca aattcaataa ttaacaataa agcacaaaaa   1140
caagatatta aaaaacaaat tgataaaatt tatctactta ttaaaaaagt tttacaaaca   1200
caaaccttaa ataaaagcca tgccaagact agtgttgtaa aaattaacga aacaattaaa   1260
acattaattg attctttatt tgctaatcaa gaaattaaaa ctttaattag taatacatta   1320
tcaaattgga ttttcagttc gaatttagca aaaattttaa atgttgacga agatcaaaaa   1380
aatagtttaa ttaaaccagt agttgaattt attattagta gtaatgattt aaaaacaatt   1440
ttaaaaacca taacaaatag ctttatttta catgctagtg aattagcgaa cacaaattct   1500
tttgaagaat taattgttaa acttattagt tttgagcaaa ctaatttaaa aagtaattta   1560
aataatttta ttcaaaaaat acttcaaaac gataaaattg atgaattgtt agcgcgtgta   1620
atatttaaac aaatttctcc acaaaaaaaa tatgatcaaa ttcagcaaat aaataaagac   1680
aaagtggtca cttttattaa gaagcttggt gacaatctga caaaatttga tttatataat   1740
aaattactcg ataatttatt tagttcaatt acaaatcaaa caaatttaac aaaattattg   1800
agtgaacagc aagatagtgt aattaatttt attaaaacga tttttgattt tagtgatcct   1860
aaacaaatta tttcactaat tgatgtatta aaagtcaacg agattacaag taatgattat   1920
attgaagtta ttaaatcaat tttagatgaa attgatttta atcatttctt taatcaagct   1980
gtcaaaaaca gtaatctttc aaattatcca ttgaataaac atgaaaatga taatgatagt   2040
aaattagata taaataagta ctatatttat gtaaaaacat tatttgcgca tgaaatggat   2100
tctacatcaa aagaaaaatt aaaaacaatt attgatgaac taacaaaaaa aattgttgaa   2160
aataataata agggcttgtt gtacaatttg ggcaatggat taggtgaaaa actaagtaat   2220
ttaattatta atacattccc tgggttaact aatttaaaac aaaactataa aacactagta   2280
caaaaagtat ttactaatca aaacttgttt gagcaagttc aaaatttgat cacttatgca   2340
atcaatagtt tgattgatca taaaaatgaa tatcaaaatt gtaaaacttt tggtgaatta   2400
ttaacaactt acattaataa gaatcaaaca caaattattg ataaattaaa agaagcaatt   2460
aataaaataa tcagtggttc atcttcatta attgatgaaa tttcaacatc atttgctaat   2520
acaattaaaa catattttaa attagaaaat ttaacagtag aagatatcaa taaactaaag   2580
tcatttatta attttgttat caaaaatatt ttcaatcttg aatatgttaa tgatggttta   2640
gttaaattaa ttacgacttt aagttcaaac gccataaaaa ttgttgatca aaacactaat   2700
tttgtaactg ttatgcaaaa tgatgttatt tcatatttaa catctccgca acaaattgca   2760
aaattacttc aaattgttga tttggataaa aatgatgaca ttttaaattt cttaaaagtt   2820
attttatctc atttgcctca aaacgcatat actattttat ttggtaataa aattaatctt   2880
ataacaaaga acacaaatca aaaaactaat agaagtgtaa ttcaaaaata tacaatatta   2940
gattatgtaa aaactatttt aaattcttct tacttaaaaa aacaagatac aattgtaaaa   3000
attaaacata tttttaaaga tcttttagta actatatcta aatcatcaca attaaataat   3060
tatattggtg agttgattag taatactttc gcacaaaaac tttcaaatct tagtggtgtg   3120
gataaacaat atagtgaatc atttttaaaa gaatcatata aatttattat aagtgatgaa   3180
```

```
aaattaatca agattattga tgaagtagtt aatgatttag ttgatcataa agatgaatat   3240

ttaaaagaaa ttacaaacaa taatcaacca tcaattaata ttattttaaa tatgttaatt   3300

aaacgaaatg ttgatcaaca aaaagttgat tttgtacctt ttataaaacg ttatttagtt   3360

attgattctt caacacaatt tatggctcaa taccttttta aaactttaaa attagaaaat   3420

actaatgatc aagatgtaaa aattgttcaa acatttgtaa aagaattaat taatcaaatt   3480

gatcaattag attttgtaaa tttattcatt gataaaatat ttactttaat aaaagaaaat   3540

ggacttgatt tatttacaaa agaagagggt ataaaaaaag taaatgaagc tatgaaaacg   3600

tttggtttaa ctgaaacaac taatttatta aaaattgcaa aacttgtcga accaaataaa   3660

attaaacccc aaaccatagg tgatctaatt aatttagtat ttgaaaaatc accattagct   3720

gaagatttcg aaagtataac acaagataaa aatcctttat attatggttt aaaaaatctt   3780

aaagaagata gtttaaatgc tgttttattt gctagtggca aaaagaaaat aggagaagca   3840

gcaaaagtta gtgaaattaa tatgttagat gctatccaac atttaattaa taaattatga   3900

tcagctcgtg cagaatacgc taaaaatcat cctaatttag aatatgaaca agataatcca   3960

tatatgcgtt cgctaattca tttaggaatt gtgatgcaat gatatgttca tgaaacatat   4020

tttagaaatg tttcaggtgg gctatgatgg actggttctg attcattatc gggtgaagga   4080

cgtgtctatt tattgctaaa agcagatatg ggatctgaaa gtgaaaaacg agtacgctca   4140

atgattatgg ggaatcgtgg tgcaatgctt tgaaatacac caaaagagtg gaattataat   4200

aaaaatgatt ttttatatat gattacatat tgaaaatgaa gaacaaattc acgttttaac   4260

gattctaaag agaaaaataa agcaacttat attttcaaag ctttaaaacg cggttatggt   4320

gaaaaagtta aaacaatgaa ataa                                          4344
```

<210> SEQ ID NO 166
<211> LENGTH: 606
<212> TYPE: DNA
<213> ORGANISM: Ureaplasma urealyticum

<400> SEQUENCE: 166

```
atgattcaaa aagcaaaatt ttatgctgga tatatttctc gtctgcgttt tattcaaaaa     60

ttaagatatg aaattcaaaa cgaaaaaaaa acattgaata aaataattaa agttgtgaat    120

gatgctgata ttagtacctt atatgatttt aaagataaaa atctaactat ttatacgaaa    180

acattttatt tccataatta tcaatttgtc aatgctaata aaaaaaatta ttttatttct    240

aaaaaaacta ttaaatctgt tattacagaa aatttattag atataggatt tacttgaaca    300

attatttata atgatcaaac aaaaacttat atcaggccaa ctgattttat gaccaaaaat    360

tttattgatt ataaaaaaaa tgaaaataaa attgctactc gttcgaaaat tttatatgat    420

atgattgtta aaaatgaatc attaaatatt aatcatagtg aatatgaatc tttattagtc    480

aataatgaat gaaaaagata ttatgaaaat atgattaata tatttttata tcaatattat    540

aatgaaggta taaaaaacga tattgatttt ttaaatcatt ttttattaaa agatgcacta    600

aaatag                                                               606
```

<210> SEQ ID NO 167
<211> LENGTH: 741
<212> TYPE: DNA
<213> ORGANISM: Ureaplasma urealyticum

<400> SEQUENCE: 167

-continued

```
atgagtaatt acgaattacg aagaagaatt ataatgtcaa atattgatgt aaaaactaat      60

ttttgaaaat taaatcaaaa gaataaaaag attttatttc gtgtgcttgg atattctagt     120

ttatcagtta ctataataac acctttaatt tataagatat catataataa acaatactca     180

tttattacta aaagtatacg agaattaaaa acaattgata ctaattttgt ttcatcttat     240

tcagattttt atattcttca gaaatcaagt atatctaatg acttgtataa ttataatttg     300

attaacaatt atcatgattt tgaaaaatta ataaaaaacg atttgaattt tgataaatat     360

aatagtgctt tgatttatga aaaaataaag gttagtttat tagagaaata taatgaaaat     420

tttttcaaaa ataacgatct gttatatgtt tcttataatt cattagactc aaaatatttt     480

ttaacttcaa ttttgagttt tgattacaat aatttatatt taccattttt aaacactaaa     540

tcgattttta atgatgagta tgataataaa aatttttata cagattcagc tctaagtact     600

actaaaacag aagttaaatt ttttagtatt aataaaaaat ataacataaa acttaaacaa     660

attaaaattt atagtattga aacggcaaag gatttatttc tatacaaaaa ctatgttcga     720

aagaataata aacctattta a                                               741
```

```
<210> SEQ ID NO 168
<211> LENGTH: 303
<212> TYPE: DNA
<213> ORGANISM: Ureaplasma urealyticum

<400> SEQUENCE: 168

atgcagtaca ttaccattaa taatacaaaa tcagggaaga ttttaatctc aaaatcaaat      60

attaaaaagt ttattgaaca aaaatttaat ttgattgtta ataaaaaatt tgtaattaag     120

aatatcgata ttgttcagta tgatgaatcc cttgttgata tatctattat tatttcatta     180

tttgatattc atcaaaaagt tgatcttgat gaagtaagag atgtacaaaa tcatttagct     240

tcttttattt attcaaattt aggcgttgat actaaaagtg taaatatagg gattgattta     300

taa                                                                   303
```

```
<210> SEQ ID NO 169
<211> LENGTH: 363
<212> TYPE: DNA
<213> ORGANISM: Ureaplasma urealyticum

<400> SEQUENCE: 169

atgaagcaac gattaataaa ttatattatt gttttaattg gtattttatg tattgttagt      60

cttgtcgttg gttttgccgt ttgatttagc cctaataaaa attttgatac gttaactcaa     120

aacaaaattg atggtaatga agttaaaaga ttatataacc caaacaatgg catttttttta     180

gaacaattag aagggtttag taaatataat attgctggtt atgtggttcc aattgttttt     240

gttattttat catttatttt attattttta tattattttt taaataaaaa atcacgatct     300

aaagctgatt ttcctattag tgaaaaattt attatcacac ttcaattacc actctttatt     360

tag                                                                   363
```

```
<210> SEQ ID NO 170
<211> LENGTH: 501
<212> TYPE: DNA
<213> ORGANISM: Ureaplasma urealyticum

<400> SEQUENCE: 170

ttgcaagaag gagattttta tgcgacagat agagaccctt ttttaacata ttgaaaagaa      60

ttaaaaccaa gtttttatgc aaaaaaaagt gtttatattg catttttaac tattataatt     120
```

-continued

```
gcttttgctg ttagcatcat tggttttgta aattattttt cattaaaaat tgccttagaa    180
caaacacaaa aagccacttt agaagttcaa aaacaaaaag aagaacaaaa aaatcaatta    240
tcaaatggtg tatattttga tcaggattta aatttattaa atgagtatga taaattagtt    300
ttatatcaaa aaaataattt atcaagtata gtctttttag cgattaatga ccaagaacaa    360
attttgatgc aaaaagatca ggttgtagtt aattctctaa atattgaaca aaaagttaaa    420
tatcgtgaac aagcaacacg aattgttttt gagaaacaag ctgaacataa tgatcatcta    480
gtaacttctg gaaatttcta a                                              501
```

<210> SEQ ID NO 171
<211> LENGTH: 528
<212> TYPE: DNA
<213> ORGANISM: Ureaplasma urealyticum

<400> SEQUENCE: 171

```
ttagttatct tgatttttat tatattttct taaaggacaa taatcatatt ttttagtatc     60
tttatcatta taagattgac tttcatatcc taaatgatga tgatcaataa gtaaaggaaa    120
taaaatatta tcgatttttg agcatattac tctaactgat cttccaaggc ctagttgata    180
aagttctaat tcttcattat catttttcaa taaattagga tggagttttt taattaattt    240
aatatattta ctaaatacat tattttgttt aataggatgg caatgatcgt taattccttt    300
attttttcaa tttttataaa catagggaaa caatgtatta agaatataaa taatattttt    360
taaaaattgg ttttcatcct tagtataagt cgttaaacta tttactcgtt cctctttaac    420
tcaattttca taacgcaaag aaataacaat gtcatcatta tcttttgaaa cattgttatt    480
tttaacttta ttgcgaggag ttttattgtt atttattttc ttagacat                 528
```

<210> SEQ ID NO 172
<211> LENGTH: 561
<212> TYPE: DNA
<213> ORGANISM: Ureaplasma urealyticum

<400> SEQUENCE: 172

```
atgtttgaac aagtattttt tttagcatcc attaacgaca aaaagattat tagatgatta     60
tatgaacgtt atcataaaat ttttttaaaa tatattaatg agcaattgaa ttttaaattt    120
tatactttag agattgaagc aaatgattta aaaactatta tttatgaaat atttttaaaa    180
atatttcaag taactagaat taaaagttta aatcaattta taggatttgt taaacggcaa    240
atttattttt atttagtata tttattacgt aaatctttat ctaataaaaa tttagttaat    300
catttaaata ataataattt tgaaaattat gaattaatta gtaccaattc agatgaagtt    360
ggtgctgaat taaacaacag atttttaatt tatgaatttt taagaagtat tcagaaagaa    420
aatttatttt tatatcattt tactatttta attattaaag gatataatac aaaggaaatt    480
agtgaaattt taaaaattaa ttctgcaaaa atttattatt ataaagcact tttaaaaaaa    540
tatataaaaa aattattata a                                              561
```

<210> SEQ ID NO 173
<211> LENGTH: 381
<212> TYPE: DNA
<213> ORGANISM: Ureaplasma urealyticum

<400> SEQUENCE: 173

```
atgaaaaatt tttcaaaaaa tagaaatatt aataatttta aaaacccttt aagagttatt     60
```

gaaggaattg ttcgtgaaat taaaaataat gaacttcaaa ttgattttgt taatagtcat 120
aaaaaaggag tttgtaagtt tattaatttg acagattatc attgaaatac aatttcttcg 180
cgttttttaa ttaacagtaa acacttattt ttagtttcaa aatttgaccc aattcgtcat 240
gtttattgat taaattataa aattattcat cctattgaaa ttaaaaacaa acgtcgttct 300
taccccactt tatctcatga tagaaattta cggatctttt taaataatct attagaaaaa 360
gaaaatgaat taaaaaacta a 381

<210> SEQ ID NO 174
<211> LENGTH: 252
<212> TYPE: DNA
<213> ORGANISM: Ureaplasma urealyticum

<400> SEQUENCE: 174
atggcaatga aagttaatga aagaacttgt gtttttagta aagaaaaata tcctaaagat 60
catttagttc gctttgttat tattaacggt gagttaattt ttagtttgaa ttatcatcgt 120
gggtattatt taatgattca aaagaataca aacattcaaa aggtgtgtca atttctaaaa 180
aaacgtttta tgattaaaaa cgaagaacaa gtttatcgga ttttagagca attaattcaa 240
tcattaattt aa 252

<210> SEQ ID NO 175
<211> LENGTH: 471
<212> TYPE: DNA
<213> ORGANISM: Ureaplasma urealyticum

<400> SEQUENCE: 175
atgctaatca tattgatgaa ttatttaaaa aaattaaaca acaagaaaat taattatcca 60
atgttaaaaa aacaaaataa aaataaagaa caacactgat tagaaaaaca tttacgacaa 120
aaaacaggtt tgattatttc ttgatcaatt atttttggtg ttttagtttt attatcaatt 180
ggttttggtt taattctaca ttttttttaac tcaaataatt taagtattca attaagcttt 240
attattaatc tcaataaata cttagttaat attactaaaa tattagatta tatcggtttt 300
gctttaattt atttaccaat tattttttta ttaggttgtt gaattactgg aattaatggc 360
gtgcacgaat cattatacta tcatgtgttt atttgattat tttatttcat tagtgttatt 420
ttattaatca ttaccatttg tttaagtatt gcgacacaca tatattatta a 471

<210> SEQ ID NO 176
<211> LENGTH: 360
<212> TYPE: DNA
<213> ORGANISM: Ureaplasma urealyticum

<400> SEQUENCE: 176
atggaaaaga caataattca attggaattt aatgaagaag aattagcatc aataaaaaaa 60
attaaagata aaatggatcc taataataat ttagaattaa atgtattttt aaaagattta 120
attaaggatt tagcgcgtga ttatttaaat ttttcaaacc aatcatttga aagtattgca 180
aagcaaatga atgatttaaa agatctaata ggaaacgtag cgaacgatcc atctagtttc 240
gattttaatt cagtaatgaa tgaattccaa aagtttagta aatcacaaaa ggatgaagaa 300
aaagaaataa aaaacgatac tgaaataaaa actgcgacta aacctactaa aaaatcttaa 360

<210> SEQ ID NO 177
<211> LENGTH: 945
<212> TYPE: DNA
<213> ORGANISM: Ureaplasma urealyticum

<400> SEQUENCE: 177

```
atgaacttaa taaataaaga acttttttta attactggtg acaatcgttt aaaaatggat     60
caaaaaatta atgaaattgc gacctctttt gatgaattag ttaaaattaa tgatcaagaa    120
atttcattaa tttcttttaa aaatcttatt gaacaagatg atttattcaa tagtaataag    180
atctacttat ttaaaaacgt taactgattc gaaaatttag aacatttaaa aaatgttagt    240
gatttaattg attatttttt taataatcat gttgctatta ttattacaat tgaatctaca    300
aaaatttcta cagcaaaaaa aattcaagaa acaattgcaa aatttaatca tcaaattact    360
tttatgacat atacaaatga aaatgctatg gctttcttaa aagaagagtt aaatcagcgt    420
aatttatcat taaataaatc tataatgcaa acgattattc aaaaaacaaa ttttaatatt    480
aattttctta ataatgaatt agataaaata gaattaatta atgatttttt aaaaaatcat    540
ggtatgtttg atattaataa ttttatatgt gattatggtg aatatcaaat ttttagttta    600
ttaaatcttt tgtatcaaca taaaataaat gaatcaataa atttaattaa taaaatgctc    660
attgacaaaa ttgatgaact cacaataatt aatatgttag cgacaataat gagtacacat    720
tacttaatta aattattaca tgaaaaaaaa tataacaaaa acgttatatc tagctcttta    780
aatcaaaaac cttatattat tgatttaaat ttaaaattaa ttagaaatta ttcagctaaa    840
tttttactta aaaaaatgta tgatttatta caattagaaa ttaaagtcaa ggaaaataaa    900
attgataaat attttggatt aattaattga gttttgaatt tttaa                    945
```

<210> SEQ ID NO 178
<211> LENGTH: 1269
<212> TYPE: DNA
<213> ORGANISM: Ureaplasma urealyticum

<400> SEQUENCE: 178

```
atgctaaatg cagaattgtc aagtgcacaa aaagatttat ataaatcaat taaattatat     60
ttaaacacaa tttttttgaa tcaaaaacta aattatgcta ttaaaaatga taatgattat    120
cgaaatcaat taaataaagt aatgaatatt tttgaatatt atgaagataa ttatgaaata    180
gcaaataaaa attttcatag ttattgacag gcttttaagt catatgttca ttatgaaaaa    240
atagttaatg attataacga ttttgatgaa ttaaaagata ttgtaaatgg tttaaaaatt    300
tatgttttaa atacatttca aatagattta gatcaagaat cacaaagaat tgcagatatt    360
gattttaagt atgatgaaaa gacgcaagca tcaatgggtt tttatactcc aagaaatcaa    420
gaaaataata ctagtacaga atatgaaaag gtaagtgctg aatctattag tgatgaagat    480
agtatgaatc atacttatca accaacttct gattttacaa cagcaaatat cgataattta    540
acaaatatgg tatttagtgc tcgggttatg aatggtgaaa tttatttata tgaaacgaaa    600
ccaaaagtta ttcctttctt aaaatatgtt ttttttgctg ttagtttagc tttggttttt    660
tttacaacat taacgtatgc ttttctaatg gattttggca cacatatgtc aagtgttatt    720
aatgttaatg gtattactca tattgttcgt ttagtttcgc caacatttcc aacccagtta    780
gtgatatcaa tattcattat gatttatgct ggaataaatg cttttaaaag aaaaattagt    840
gaaaatgaga agtttcattt taaaaatttt atttgaatta ttttgtttgg agcattatta    900
gtagttgcat tagcaaatat ttttactgga aatttaagat tttcaagtag ttcatttgat    960
gaaatgtttc gtcaagcaca aattaatgat gtattagcta acttagcaag aaataatagt   1020
tttagttttg attattcgta tttacaaagt attttttatg gctatagtat cgcccaaatt   1080
```

-continued

```
ttagtatttg tagttattat tttaggaaca attttaatta ttagtacttt tattttaaat   1140
cctaaacgtg atattcaaag aataaaatta ttattacaag aaattcatga tgatatttta   1200
acaggtaaaa ttgatcctaa tacatattta agaacaaaaa atccctttag agacttgttt   1260
ggtttttag                                                           1269
```

<210> SEQ ID NO 179
<211> LENGTH: 303
<212> TYPE: DNA
<213> ORGANISM: Ureaplasma urealyticum

<400> SEQUENCE: 179

```
ttatttaatt tttttaatat ggtaaaaatc atttttatta gttcgtttag tgtaagaaat     60
aattgtattt gtgtatttat caactaaaaa ataataacct ttatttttag ggtccatgta    120
aatatggaaa ttattgtcta aagaatttaa aggacgaatt cctaaaattc gctcattaat    180
aattggaata atgaatgtac cacttagatt tttaatgtta acatcagttc attcagcacg    240
ttctcgaaaa cgagctaatg catgatctgt aattctaaat ttgcttttat aataatatga    300
cat                                                                  303
```

<210> SEQ ID NO 180
<211> LENGTH: 261
<212> TYPE: DNA
<213> ORGANISM: Ureaplasma urealyticum

<400> SEQUENCE: 180

```
atgatgaatg atagtgttaa acaaaccaat aatattgatg aaaatcaatt aaaaccaact     60
acaaaaagct tttttgatga taaaaacaac caattaacaa aagttttaaa tattcctagc    120
gttgttaaat atacggaatc aaaaattaaa aaaaatggta aaaatttttc aattaattta    180
atcattacaa ttacaacaat gtttattgta attgggatta ttataactat tgctattgct    240
attggtatta aattaagtta g                                              261
```

<210> SEQ ID NO 181
<211> LENGTH: 2043
<212> TYPE: DNA
<213> ORGANISM: Ureaplasma urealyticum

<400> SEQUENCE: 181

```
atgttttata ttaatttaag ggtgaaaaca atgatggaaa aattaaaaaa caacaagact     60
ttgtttttga atgtagaaca agctcaaaaa ctagggatta ataacccttt aacacaagag    120
atttttttag atgatcaaaa gttaaaagtt catttaatta atagtataaa agatgagttt    180
tacttaaaaa aaagtattag taaaggttat gcttatttta atagtttaga acaatttaag    240
actatggagc ttgatgtttt agataactat caatttgcaa aaatagcagc tactaattta    300
gatgagtatg atcaattagt ttacacaaaa actcgtcaat atttaattaa taaagaattt    360
tgaactaatg atggtttaga tgcatttatt ggtgatgatt ttaaaagaaa acaattaacg    420
agcaaagaaa tcgttaatct aaaaaacaaaa tatgatttat gaatacaaga attacatttt   480
aataatgcac gaattagtaa acaaattcat aatttaagta ttcatggtca aaataaatta    540
gattatgaga aattttatga taaaaaagca acccttgaat caaatttaga tattcttcaa    600
attttaattt atttaagatc ttcattactt gagttagatt ttgacgatct ttttaaagat    660
gatcaaaata aaataagtat tcgtcaatta ttagttaatg atttagaata cttgccgttt    720
tcatttcaac gttatgatta tgaatcaaga cgtaatttca ttagaaactc acgtcaatta    780
```

-continued

```
gttgatacct caattgattt tgacgatctt gaatatgatt ttttgcacaa taagaaacca    840
aaacaagaac tagaaaaaaa taatgaatca attaaaatag ctgaattaaa aaaatttgaa    900
aattcacaat taagtgatga acaacaatct aatttagaaa aagagttcta tagtattgga    960
agaattaact gttttgacga agttagcgaa aataaacaag aattaaacaa agaacaatta   1020
gtaatcgata aaaaaaatgg gtatttgaag ccacgtagtt acttacgtca tcatgaaact   1080
ccatttatgg ttgacattga gaaccgggta gactttttaa tggcaggata tgaaattatt   1140
aaaaatgatg atccatatgc aattaaacaa gaaatattaa aaaataccat tttagaacaa   1200
caaaagcttg tcgaacaaga tgatcatgat tttaaagtta aaaatgatga tcaagaagca   1260
aatgaagaat tattggacaa tactgataaa ttagaaaatc aagattctac aagtgctgtt   1320
gaatttaatg attcatctga agttactcaa gtagtaaaaa cggatgaaaa tgttgataat   1380
ttaattaaaa ctaagcaaat aactagtttt aacgatctta aacaagagca atcatctcaa   1440
gaaaatatta ttaaaaatga tctttcatca attcaaattc gtttagatga aattattaat   1500
gtacatgaaa aagatactaa attacaaacc gaactaaatt caattatgat agatagtaat   1560
gaaaaaaata ttgatgatag tttaaataat ttaaatgaac aaatacgaat tcaagatcaa   1620
gaattagaat catcagataa tcaaaatgta attattgaag aagaaattaa taccaaaaat   1680
ttaaataata aagctgatgt tggtgttatg agtgttgaaa aaaaatatga acctgaagag   1740
gaaatggtta attttgaatt tgaaatacct gaaaaccaaa aagaatcagt taaccaagat   1800
gttttaaata gtaatagtat tgataatttt aaagaagaaa aagctaaaga aaatactttc   1860
ttaacaccaa aagaaataga aaataatgat ttatcatcac aaattgaatt aacacctgct   1920
gattttgaac ttaagacaca agaaattaat gacgaaactg aacgtttatt ggatgaatta   1980
aataataata aacctaaaga aaagaagaaa ttttggacat gatttaactc aaaaaaaaga   2040
taa                                                                 2043
```

NUCLEIC ACID PROBES AND METHOD FOR DETECTING *UREAPLASMA UREALYTICUM*

This application claims the benefit of provisional application No. 60/073,189, filed Jan. 30, 1998.

GRANT REFERENCE

The subject invention was made with government support under a grant from the National Institutes of Health, Grant No. NIH-AI28279. The government has certain rights in the invention.

TECHNICAL FIELD

The present invention relates to the determination of the complete DNA sequence of *Ureaplasma urealyticum* (Uu) and to the use of novel genes and sequences as probes and primers for assays for use in the detection and/or quantification of Uu in a sample.

BACKGROUND OF THE INVENTION

*Ureaplasma urealyticum* (Uu) is a Mycoplasma which was first discovered in men with nongonococcal urethritis (NGU) in 1954. Approximately two-thirds of adults have Uu as part of their normal flora. Uu has been associated with and suspected as a pathogen in adverse pregnancy outcomes such as chorioamnionitis, intrauterine infection, and premature births. Uu has also been diagnosed as the causative agent of neonatal diseases such as pneumonia, meningitis, and sepsis. Uu has also been isolated in certain patients suffering from suppurative arthritis, especially those having hypogammaglobulinemia.

The primary mechanism of transmission of Uu is by sexual contact which can then be transmitted to neonates born to infected mothers.

The biology of Uu, which is a member of the Mycoplasma family, is unique. The Mycoplasma family is a family of wall-less bacteria which has descended from low G+C Gram positive bacteria. The Mycoplasma are included among the smallest free-living cells known. Additionally, the Mycoplasma use an alternate genetic code wherein the codon UGA=tryptophan (trp) rather than a stop or termination codon. Additionally, the Mycoplasma are biochemically different in that they possess no TCA cycle and most Mycoplasma require cholesterol for growth.

*Ureaplasma urealyticum* infections are commonly asymptomatic, it is important to have specific and sensitive methods for detecting their presence in a patient. Mycoplasmas including *Ureaplasma urealyticum* are somewhat atypical organisms and are difficult and are complex to culture. It is difficult for clinical laboratories to perform culture isolation of Mycoplasmas and consequently there are no relatively easy and inexpensive methods for diagnosing the presence of this bacterium.

Genetic probes and detection methods for detecting Mycoplasmas including *Ureaplasma urealyticum* have been developed. U.S. Pat. No. 5,843,667 to Weisburg et al. discloses various nucleic acid sequences which are capable of hybridizing to rRNA and rDNA of Mycoplasma etiological agents including *Ureaplasma urealyticum.* The nucleic acid probes disclosed in the Weisburg et al. patent specifically hybridize to 16S rRNA or 16S rDNA of *Ureaplasma urealyticum.* Similarly, U.S. Pat. No. 5,728,522 to Del Vecchio et al. discloses a method for detecting *Ureaplasma urealyticum* involving in vitro nucleic acid amplification by contacting *Ureaplasma urealyticum* target nucleic acids with an oligonucleotide fragment consisting of a contiguous nucleotide of *Ureaplasma urealyticum* DNA inserted into the plasmid pCU3900 having ATCC Accession No. 97424.

Neither U.S. Pat. No. 5,843,667 nor U.S. Pat. No. 5,728,522 disclose the entire DNA sequence of *Ureaplasma urealyticum* serovar 3 and, in fact, only disclose small DNA and/or RNA sequences from *Ureaplasma urealyticum.*

Therefore, in order to better understand the nature and effects of *Ureaplasma urealyticum,* as well as to more accurately and consistently detect and diagnose the presence of *Ureaplasma urealyticum* in a potential carrier and to better develop antibiotic drugs specifically effective against *Ureaplasma urealyticum,* which, consequently, has no current antibiotic directed specifically against it, it would be advantageous to isolate and determine the gene sequences and functions which are unique to *Ureaplasma urealyticum* and utilize these sequences as a basis for detecting *Ureaplasma urealyticum* in a patient and thereby be able to more effectively treat those patients infected with *Ureaplasma urealyticum* as well as to develop new and improved drug therapies against *Ureaplasma urealyticum.*

SUMMARY OF THE INVENTION

A method of detecting a nucleic acid sequence in *Ureaplasma urealyticum* serovar 3 includes the steps of isolating a specimen containing nucleic acid; and analyzing the specimen with an assay such as in situ hybridization, Southern blotting, single strand conformational polymorphism, restriction endonuclease fingerprinting (REF), PCR amplification, 5' nuclease assay (such as the TAQMAN PCR method for quantification of PCR), and DNA-chip analysis using the unique nucleic acid sequence SEQ ID Nos:1–181.

DETAILED DESCRIPTION OF THE INVENTION

The present invention provides the sequence of the genome of the bacterium *Ureaplasma urealyticum* serovar 3 (Uu). Uu is an opportunistic pathogen of the human urogenital tract that is a significant cause of adverse pregnancy outcome, neonatal disease, and suppurative arthritis. Uu contains a single circular chromosome having 751,719 base pairs designated SEQ ID No:182. Of these base pairs, only 25.5% of the bases are G or C. The Uu chromosome codes for approximately 600 genes. As discussed above, Ureaplasmas use an unusual genetic code in which TGA codes for tryptophan instead of for translation termination. Although 62 codons for amino acid are represented in the Uu genome, only 30 tRNAs are coded for by the Uu genome. There are only two rRNA operons.

The present invention also consists of purified, isolated, and cloned nucleic acid sequences encoding novel genes designated SEQ ID Nos:1–181. The nucleic acid can be genomic DNA, cDNA, or mRNA.

The invention further provides purified protein sequences as encoded by the novel Uu genes and analogs and mutations thereof.

The present invention further includes the recombinant proteins encoded by the genes. These recombinant proteins are isolated and purified by techniques known to those skilled in the art.

As used herein, the term "analog" is used to define a compound or molecule which will be generally at least 70% homologous over any portion that is functionally relevant. In more preferred embodiments, the homology will be at least 80% and can approach 95% homology to the native protein. The amino acid sequence of any analog may differ from that of the native protein when at least one residue is deleted, inserted, or substituted but the protein remains functional. Differences in glycosylation can provide analogs.

As defined herein, the term "nucleotide" is used to define a subunit of nucleic acid consisting of a phosphate group, a 5' carbon sugar, and a nitrogen containing base. In DNA, the 5' carbon sugar is a 2-deoxyribose. For RNA, the 5' carbon sugar is a ribose.

As used herein, the term "oligonucleotide" is defined as a nucleotide polymer (at least two nucleotides linked by a phosphodiester bond).

As defined herein, the terms "nucleic acid probe" and "primer" are used to define a single stranded nucleic acid sequence that will combine with a complementary single stranded target nucleic acid sequence to form a double-stranded molecule or hybrid. In the case of the primer, the hybrid can be used to initiate replication such as with PCR.

As used herein, the term "hybrid" is used to define the complex formed between two single stranded nucleic acid sequences by standard base pairing.

As used herein, the term "hybridization" defines the process by which two complementary strands of nucleic acids combine to form a double stranded molecule or hybrid.

As used herein, the term "stringency" is used to define the temperature and solvent composition existing during hybridization and the subsequent processing steps at which a hybrid comprised of two complementary nucleic acid sequences will form. Stringency also defines the amount of homology, the conditions necessary, and the stability of hybrids formed between target sequences and nontarget sequences.

The present invention also provides vectors comprising an expression control sequence operatively linked to the nucleic acid sequences of the Uu genes and portions thereof as well as mutant sequences. The present invention further provides host cells, selected from suitable eukaryotic and prokaryotic cells, which are transformed with these vectors.

Using the present invention, it is possible to transform host cells including *E. coli,* using the appropriate vectors so that they carry recombinant DNA sequences derived from Uu genes. Such transformed cells allow the study of the function and regulation of the particular genes. Use of recombinantly transformed host cells allows for the study of the mechanisms of Uu gene function and, in particular, it will allow for the study of gene function and can be used in the development of antibiotics or other drug therapies useful against Uu.

Vectors are known or can be constructed by those skilled in the art and should contain all expression elements necessary to achieve the desired transcription of the sequences. Other beneficial characteristics can also be contained within the vector such as mechanisms for recovery of the nucleic acids in a different form. Phagemids are a specific example of such beneficial vectors because they can be used either as plasmids or bacteriophage vectors. Examples of other vectors include viruses such as bacteriophages, baculoviruses and retroviruses, DNA viruses, cosmids, plasmids and other recombination vectors. The vectors can also contain elements for use in either prokaryotic or eukaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual,* Cold Springs Harbor Laboratory, New York (1992). Also, nucleic acids can be introduced by, for example, stable or transient transfection, lipofection, electroporation and infection with recombinant viral vectors. Introduction of nucleic acids by infection offers several advantages over the other listed methods. Higher efficiency can be obtained due to their infectious nature. See also U.S. Pat. Nos. 5,487,992 and 5,464,764. Moreover, viruses are very specialized and typically infect and propagate in specific cell types. Thus, their natural specificity can be used to target the vectors to a specific cell type in vivo or within a tissue or mixed culture of cells. Viral vectors can also be modified with specific receptors or ligands to alter target specificity through receptor mediated events.

Recombinant methods known in the art can also be used to achieve the sense, anti-sense or triplex inhibition of target nucleic acid. For example, vectors containing anti-sense nucleic acids can be employed to express protein or anti-sense messages to reduce the expression of the target nucleic acid and therefore its activity.

According to the present invention, there is also provided a method for diagnosing and detecting Uu in a subject. Carrier detection is especially important in diagnosing and treating those individuals or patients which may be infected with Uu. Identifying those infected by the presence of Uu specific nucleic acid sequences can lead to earlier diagnosis and treatment.

The methods for diagnosing and detecting Uu in a subject generally comprise the steps of obtaining a sample from a test subject, isolating the appropriate test material from the sample and assaying the sample for the target nucleic acid sequences or gene products. The sample can be tissue or bodily fluids from which genetic material and/or proteins are isolated using methods standard in the art. For example, DNA can be isolated from fluid or cells obtained from a vaginal swab.

More specifically, the method of Uu detection is carried out by first obtaining a sample of either cells or bodily fluid from a subject. Convenient methods for obtaining a cellular sample can include swabbing or fluid collection. Crude DNA samples can be isolated from the cells (or alternatively proteins isolated) by techniques well known to those skilled in the art. This isolated target DNA is then used for PCR analysis (or alternatively, Western blot analysis for proteins) with appropriate primers derived from selected Uu gene sequences such as SEQ ID Nos:1–173 by techniques well known in the art. The PCR product would then be tested for the presence of Uu specific sequences or variations thereof in order to diagnose and detect Uu in the subject.

The specimen can be assayed for polypeptides/proteins by immunohistochemical and immunocytochemical staining, ELISA, RIA, immunoblots, Western blotting, immunoprecipitation, functional assays and protein truncation tests. In preferred embodiments, Western blotting, functional assays, and protein truncation tests will be used. mRNA complementary to the target nucleic acid sequences can be assayed by in situ hybridization, Northern blotting and reverse transcriptase-polymerase chain reaction. Nucleic acid sequences can be identified by in situ hybridization, Southern blotting, single strand conformational polymorphism, PCR amplification and DNA-chip analysis using specific primers.

ELISA assays are well known to those skilled in the art. Both polygonal and monoclonal antibodies can be used in the assays. Where appropriate, other immunoassays, such as radioimmunoassays (RIA) can be used as are known to those in the art. Available immunoassays are extensively described in the patent and scientific literature. See, for example, U.S. Pat. Nos. 3,791,932, 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771; and 5,281,521 as well as Sambrook et al., 1992. The Uu gene sequences SEQ ID Nos:1–173 can be expressed using protein expression technology such as generally described in Sambrook et al., 1992. Those Uu proteins expressed using recombinant DNA technology can be used in ELISA or Western blot assays for serological based detection of Uu in patient samples. The aforementioned Uu proteins can also be used to generate monoclonal antibodies that could be used in the detection of Uu.

In order to use the method of the present invention for diagnostic applications, it is advantageous to include a mechanism for identifying the presence or absence of target polynucleotide sequences (or alternatively proteins). In many hybridization based diagnostic or experimental procedures, a label or tag is used to detect or visualize for the presence or absence of a particular polynucleotide sequence. Typically, oligomer probes are labeled with radioisotopes such as $^{32}$P or $^{35}$S (Sambrook, 1992) which can be detected by methods well known in the art such as autoradiography. Oligomer probes can also be labeled with non-radioactive methods such as chemiluminescent materials which can be detected by autoradiography (Sambrook, 1992). Also, enzyme-substrate based labeling and detection methods can be used. Labeling can be accomplished by mechanisms well known in the art such as end labeling (Sambrook, 1992), chemical labeling, or by hybridization with another labeled oligonucleotide. These methods of labeling and detection are provided merely as examples and are not meant to provide a complete and exhaustive list of all of the methods known in the art.

The introduction of a label for detection purposes can be accomplished by attaching the label to the probe prior to hybridization.

An alternative method for practicing the method of the present invention includes the step of binding the target DNA to a solid support prior to the application of the probe. The solid support can be any material capable of binding the target DNA, such as beads or a membranous material such as nitrocellulose or nylon. After the target DNA is bound to the solid support, the probe oligomers are applied.

The present invention also provides a kit for diagnosis and detection of Uu in a subject. The kit can include a molecular probe complementary to specific genetic sequences found only in Uu and suitable labels for detecting hybridization of the molecular probe and the specific Uu gene thereby indicating the presence of Uu. The molecular probe has a DNA sequence complementary to the targeted Uu sequence. Alternatively, the kit can contain reagents and antibodies for detection of specific Uu proteins. The above discussion provides the factual basis for the use and identification of Uu, Uu genes, and Uu gene products and the identification and detection of those infected with Uu.

Materials and Methods

General Methods in Molecular Biology:

Standard molecular biology techniques known in the art and not specifically described were generally followed as in Sambrook et al., *Molecular Cloning: A Laboratory Manual,* Cold Springs Harbor Laboratory, New York (1992).

*Ureaplasma urealyticum* serovar 3 reference strain was obtained from E. A. Freundt (Institute of Medical Microbiology, University of Aarhus, Aarhus, Denmark). Uu was grown in 10B medium until the media pH became alkaline, the cells were concentrated in a phosphate buffered saline solution by a combination of filtration and high speed centrifugation. Uu genomic DNA was extracted from the cell suspension using an Invitrogen EZ DNA kit according to the manufacturer's instructions for isolating DNA from Gram positive bacteria.

The Uu genomic sequence was obtained by a process developed for this project that is referred to as CROSS (Complete Random+Ordered Shotgun Sequencing). In preparation for the complete random phase of the sequence analysis three different clonal libraries were prepared. To make a large insert library in lambda bacteriophage, Uu DNA was partially digested using the restriction enzyme Sau 3A and fragments containing between 7,000 and 11,000 base pairs were ligated into a Novagen Bluestar lambda vector according to the Novagen Lambda Bluestar Vector System instructions. Individual phage clones grown in *E. coli* were collected in to a TM solution to stabilize the phage. The inserts contained in more than 1,500 individual Uu-lambda bacteriophage clones were amplified using XL-PCR according to the manufacturer's instructions (Perkin Elmer XL-PCR kit) using universal T3 and T7 primers. The ends of the XL-PCR amplicons were sequenced by performing reactions in a Applied Biosystems 877 Catalyst Robotic Workstation and analyzing the reactants using either an Applied Biosystems 373 or 377 Prism DNA Sequencing apparatus. Two small insert libraries containing Uu DNA inserts were made by ligating Uu fragments sheared to between 1,000 and 2,000 base pairs using nebulization or digested using either Rsa I, Alu I or Sau 3A I to between 1,000 and 2,000 base pairs. Inserts were ligated into the cloning vector pUC18. The plasmids were then ligated into *E. coli.* Sequencing templates were generated from bacteria containing Uu inserts in plasmids by the method of colony PCR. The ends of those DNA templates were then sequenced using M13-40 forward and reverse primers by performing reactions in a Applied Biosystems 877 Catalyst Robotic Workstation and analyzing the reactants using either an Applied Biosystems 373 or 377 Prism DNA Sequencing apparatus. After obtaining approximately 2,400 DNA sequencing reads from the large insert lambda bacteriophage library and 7,600 DNA sequencing reads from the small insert plasmid libraries, the data were assembled using the DNA sequence assembly software Autoassembler 1.4 (PE-Applied Biosystems). Gaps remaining in the genomic sequence were filled by an ordered phase which was a mix of "genomic walking" and "ordered shotgun sequencing". Those gaps in the sequence that were small were closed by either making a PCR amplicon that crossed the gap to use as a DNA sequencing template, or were closed by sequencing using whole genomic DNA as a template (the last method was developed as part of the Uu genome sequencing project, and is described in Heiner C. R., K. L. Hunkapiller, S. Chen, J. I. Glass, and E. Y. Chen. Sequencing multimegabase-template DNA with BigDye™ terminator chemistry PCR Methods & Applications. 8(5):557–6 (1998). Large gaps or areas containing many small gaps were completed using a method developed for "ordered shotgun sequencing" (Chen, E. Y., Schlessinger, D. and Kere, J. Ordered shotgun sequencing, a strategy for integrated mapping and sequencing of YAC clones. Genomics 17, 651–656 (1993);Chen, C., Su, Y., Baybayan, P., Siruno, A., Nagaraja, R., Mezzarella, R., Schlessinger, D, and Chen, E. Y. Ordered Shotgun Sequencing of a 135 kb Xq25 YAC containing ANT-2 and four possible genes, including three confirmed by EST matches. Nucleic Acids Res. 24, 4034–4041 (1996).) Briefly, a XL-PCR amplified insert from a large Uu insert bacteriophage clone that spanned the gap or region of low sequence quality was sonicated to generate Uu genome fragments between 1,000 and 2,000 base pairs in length. Using colony PCR sequencing as described earlier in this paragraph, 48 clones containing Uu inserts were sequenced and the new data was added to the assembly. All the assembled sequences were edited to remove low quality data and correct incorrect base calls made by the Applied Biosystems 373 and 377 Prism DNA sequencing software. Each of the 751,719 bases in the final assembly was sequenced by at least two different high quality sequencing reactions.

Data checking and functional annotation of the Uu sequence was performed using a system based upon compiling the results from Genemark searches (Borodovsky, M., McIninch, J., Koonin, E., Rudd, K., Medigue, C. and A. Danchin 1995. Detection of New Genes in the Bacterial Genome Using Markov Models for Three Gene Classes. Nucleic Acids Research, 23, 3554–3562) for potential protein-coding genes, followed by BLAST sequence homology searches (Altschul, S. F., Madden, T. L., Schaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389–3402) to determine matches to existing genes and identify genes unique to Uu. This information was then loaded into a Microsoft SQL Server database that we have developed that contains all Uu sequence and annotation information. The front-end for this database is a web page that directly accesses the SQL Server data, and allows users to develop individualized queries that can be constructed by setting desired options on a web form. This system is not only used to query the similarity and alignment data, but is also used in the direct annotation of the sequence. Web forms have been developed that allow us to directly enter coordinate data along with gene identification and similarity data into our annotation database.

The unique genes isolated, purified, and cloned which were derived from *Ureaplasma urealyticum serovar* 3. These sequences, designated SEQ ID Nos:1–173, can be specifically utilized as probes or primers in the detection and diagnosis of Uu infection in a subject by the methods described above. SEQ ID Nos:174–181 designate genes associated with the urease complex of *Ureaplasma urealyticum.* In terms of developing or designing an antibiotic specifically targeted at *Ureaplasma urealyticum,* the most logical genetic target or gene product target would be some component associated with the urease gene complex.

Throughout this application, various publications and patents are referenced by citation or number. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A vector comprising nucleotide sequence SEQ ID No: 60.

2. A prokaryotic or eukaryotic host cell stably transformed or transfected by a vector comprising nucleotide sequence SEQ ID No: 60.

* * * * *